US 11,732,011 B2

United States Patent
King et al.

(10) Patent No.: US 11,732,011 B2
(45) Date of Patent: Aug. 22, 2023

(54) SELF-ASSEMBLING PROTEIN NANOSTRUCTURES DISPLAYING PARAMYXOVIRUS AND/OR PNEUMOVIRUS F PROTEINS AND THEIR USE

(71) Applicants: UNIVERSITY OF WASHINGTON, Seattle, WA (US); INSTITUTE FOR RESEARCH IN BIOMEDICINE, Bellinzona (CH)

(72) Inventors: Neil P. King, Seattle, WA (US); David Baker, Seattle, WA (US); Brooke Fiala, Seattle, WA (US); Lance Joseph Stewart, Seattle, WA (US); Laurent Perez, Bellinzona (CH); Antonio Lanzavecchia, Bellinzona (CH); Jessica Marcandalli, Bellinzona (CH)

(73) Assignees: University of Washington, Seattle, WA (US); Institute for Research in Biomedicine, Bellinzona (CH)

( * ) Notice: Subject to any disclaimer, the term of this patent is extended or adjusted under 35 U.S.C. 154(b) by 27 days.

(21) Appl. No.: 17/523,174

(22) Filed: Nov. 10, 2021

(65) Prior Publication Data
US 2022/0169681 A1    Jun. 2, 2022

Related U.S. Application Data

(62) Division of application No. 16/500,331, filed as application No. PCT/US2018/025880 on Apr. 3, 2018, now Pat. No. 11,192,926.

(60) Provisional application No. 62/481,331, filed on Apr. 4, 2017.

(51) Int. Cl.
| | |
|---|---|
| C12N 7/00 | (2006.01) |
| C12N 1/15 | (2006.01) |
| C12N 15/45 | (2006.01) |
| A61K 39/12 | (2006.01) |
| A61K 39/155 | (2006.01) |
| C07K 14/005 | (2006.01) |
| A61P 31/14 | (2006.01) |
| B82Y 5/00 | (2011.01) |
| A61K 39/00 | (2006.01) |

(52) U.S. Cl.
CPC ............ *C07K 14/005* (2013.01); *A61K 39/12* (2013.01); *A61P 31/14* (2018.01); *B82Y 5/00* (2013.01); *C12N 7/00* (2013.01); *A61K 2039/575* (2013.01); *C07K 2319/735* (2013.01); *C12N 2760/18022* (2013.01); *C12N 2760/18322* (2013.01); *C12N 2760/18522* (2013.01)

(58) Field of Classification Search
CPC ............ A61K 39/12; A61K 2039/5256; A61K 2039/70; A61K 39/155; C12N 2760/18511
See application file for complete search history.

(56) References Cited

U.S. PATENT DOCUMENTS

| | | |
|---|---|---|
| 6,929,933 B1 | 8/2005 | Revuelta Doval et al. |
| 8,563,002 B2 | 10/2013 | Baudoux et al. |
| 8,969,521 B2 | 3/2015 | Baker et al. |
| 9,441,019 B2 | 9/2016 | Nabel et al. |
| 9,487,593 B2 | 11/2016 | Powell et al. |
| 9,630,994 B2 | 4/2017 | Baker et al. |
| 9,738,689 B2 | 8/2017 | Kwong et al. |
| 9,856,313 B2 | 1/2018 | Zheng et al. |
| 9,913,894 B2 | 3/2018 | Tous et al. |
| 9,950,058 B2 | 4/2018 | Che et al. |
| 10,017,543 B2 | 7/2018 | Kwong et al. |
| 10,022,437 B2 | 7/2018 | Pushko et al. |
| 10,040,828 B2 | 8/2018 | Weiner et al. |
| 10,351,603 B2 | 7/2019 | Baker et al. |
| 2011/0200560 A1 | 8/2011 | Zhang |
| 2013/0122032 A1 | 5/2013 | Smith et al. |
| 2014/0248314 A1 | 9/2014 | Swanson et al. |
| 2014/0302079 A1 | 10/2014 | Nabel et al. |
| 2015/0110825 A1 | 4/2015 | Sasisekharan et al. |
| 2015/0356240 A1 | 12/2015 | Baker et al. |
| 2016/0046675 A1 | 2/2016 | Kwong et al. |
| 2016/0122392 A1 | 5/2016 | Baker et al. |
| 2017/0182151 A1 | 6/2017 | Che et al. |

(Continued)

FOREIGN PATENT DOCUMENTS

| | | |
|---|---|---|
| EP | 1 010 760 | 6/2000 |
| WO | WO 2006/033679 | 3/2006 |

(Continued)

OTHER PUBLICATIONS

Georgiev et al., "Two-Component Ferritin Nanoparticles for Multimerization of Diverse Trimeric Antigens." ACS Infect Dis. May 11, 2018;4(5):788-796. doi: 10.1021/acsinfecdis.7b00192. Epub Mar. 6, 2018. PMID: 29451984—Abstract provided.

(Continued)

*Primary Examiner* — Barry A Chestnut
(74) *Attorney, Agent, or Firm* — McDonnell Boehnen Hulbert & Berghoff

(57) ABSTRACT

Disclosed herein are nanostructures and their use, where the nanostructures include (a) a plurality of first assemblies, each first assembly comprising a plurality of identical first polypeptides; (b) a plurality of second assemblies, each second assembly comprising a plurality of identical second polypeptides, wherein the second polypeptide differs from the first polypeptide; wherein the plurality of first assemblies non-covalently interact with the plurality of second assemblies to form a nanostructures; and wherein the nanostructure displays multiple copies of one or more paramyxovirus and/or pneumovirus F proteins or antigenic fragments thereof, on an exterior of the nanostructure.

30 Claims, 16 Drawing Sheets
Specification includes a Sequence Listing.

(56) References Cited

U.S. PATENT DOCUMENTS

| | | |
|---|---|---|
| 2017/0202948 A1 | 7/2017 | Smith et al. |
| 2017/0298101 A1 | 10/2017 | Kwong et al. |
| 2017/0326228 A1 | 11/2017 | Cheminay et al. |
| 2018/0021258 A1 | 1/2018 | Graham et al. |
| 2018/0194808 A1 | 7/2018 | Langedijk et al. |
| 2018/0200360 A1 | 7/2018 | Langedijk et al. |
| 2018/0237476 A1 | 8/2018 | Swanson et al. |
| 2018/0256704 A1 | 9/2018 | Nicosia et al. |
| 2019/0330279 A1 | 10/2019 | Kwong et al. |

FOREIGN PATENT DOCUMENTS

| | | |
|---|---|---|
| WO | WO 2010/019725 | 2/2010 |
| WO | WO 2010/035009 | 4/2010 |
| WO | WO 2011/019585 | 2/2011 |
| WO | WO 2013/044203 | 3/2013 |
| WO | WO 2013/056122 | 4/2013 |
| WO | 2014/124301 A1 | 8/2014 |
| WO | 2015/048149 A9 | 4/2015 |
| WO | 2015/177312 A1 | 11/2015 |
| WO | WO 2016/138525 | 9/2016 |
| WO | WO 2016/160166 | 10/2016 |
| WO | WO 2017/005844 | 1/2017 |
| WO | 2017/040387 A2 | 3/2017 |
| WO | WO 2017/075125 | 5/2017 |
| WO | WO 2017/172890 | 10/2017 |
| WO | WO 2017/174568 | 10/2017 |
| WO | WO 2017/207477 | 12/2017 |
| WO | WO 2017/207480 | 12/2017 |
| WO | WO 2018/005558 | 1/2018 |
| WO | WO 2018/109220 | 6/2018 |

OTHER PUBLICATIONS

Kanekiyo et al., "Self-assembling influenza nanoparticle vaccines elicit broadly neutralizing H1N1 antibodies" Nature. Jul. 4, 2013,499(7456):102-6. doi: 10.1038/nature12202. Epub May 22, 2013. PMID: 23698367.

Olsen, "Gene transfer vectors derived from equine infectious anemia virus," Gene Therapy, vol. 5, No. 11, pp. 1481-1487, 1998.

Otwinowski, et al., "[20] Processing of X-ray diffraction data collected in oscillation mode," Methods in Enzymology, vol. 276, pp. 307-326, 1997.

Oubridge, et al., "Crystal structure at 1.92 A resolution of the RNA-binding domain of the U1A spliceosomal protein complexed with an RNA hairpin," Nature, vol. 372, No. 6505, pp. 432-438, 1994.

Pancera, et al., "Structure and immune recognition of trimeric pre-fusion HIV-1 Env.," Nature, vol. 514, No. 7523, pp. 455-461, 2014.

Parent, et al., "Positionally independent and exchangeable late budding functions of the Rous Sarcoma Virus and Human Immunodeficiency Virus Gag proteins," Journal of Virology, vol. 69, No. 9, pp. 5455-5460, 1995.

Patterson, et al., "Characterization of a highly flexible self-assembling protein system designed to form nanocages," Protein Science, vol. 23, No. 2, pp. 190-199, 2014.

Pesarrodona, et al., "Intracellular targeting of CD44+ cells with self-assembling, protein only nanoparticles," International Journal of Pharmaceutics, vol. 473, No. 1-2, pp. 286-295, 2014.

Puglisi, et al., "Solution structure of a bovine immunodeficiency virus Tat-TAR peptide-RNA complex," Science, vol. 270, No. 5239, pp. 1200-1203, 1995.

Resh, "Covalent lipid modifications of proteins," Current Biology, vol. 23, No. 10, pp. R431-R435, 2013.

Resh, "Fatty acylation of proteins: new insights into membrane targeting of myristoylated and palmitoylated proteins," Biochimica et Biophysica Acta, vol. 1451, No. 1, pp. 1-16, 1999.

Rosa, et al., "HIV-1 Nef promotes infection by excluding SERINC5 from virion incorporation," Nature, vol. 526, No. 1572, pp. 212-217, 2015.

Salgado, et al., "Controlling protein-protein interactions through metal coordination: assembly of a 16-helix bundle protein," Journal of the American Chemical Society, vol. 129, No. 44, pp. 13374-13375, 2007.

Schneidman-Duhovny et al., "Accurate SAXS Profile Computation and its Assessment by Contrast Variation Experiements," Biophysical Journal, Aug. 2013, pp. 962-974, vol. 105.

Schneidman-Duhovny et al., "FoXS: a web server for rapid computation and fitting of SAXS profiles," Nucleic Acids Research, 2010, pp. W540-W544, vol. 38.

Schrodinger, LLC, "The PyMOL Molecular Graphics System, Version 1.4," available online at: http://www.pymol.org, 2011.

Schuck, "Size-distribution analysis of macromolecules by sedimentation velocity ultracentrifugation and lamm equation modeling," Biophysical Journal, vol. 78, No. 3, pp. 1606-1619, 2000.

Stahelin, "Lipid binding domains: more than simple lipid effectors," Journal of Lipid Research, vol. 50, Suppl S299-S304, 2009.

Sun, et al., "Cyclic GMP-AMP synthase is a cytosolic DNA sensor that activates the type I interferon pathway," Science, vol. 339, No. 6121, pp. 786-791, 2013.

Thery, et al., "Isolation and Characterization of Exosomes from Cell and Culture Supernatants and Biological Fluids," Current Protocols in Cell Biology, Chapter 3, Unit 3.22, pp. 3.22.1-3.22.19, 2006.

Tobiume, et al., "Nef does not affect the efficiency of human immunodeficiency virus type 1 fusion with target cells," Journal of Virology, vol. 77, No. 19, pp. 10645-10650, 2003.

Tsai, et al., "Analysis of lattice-translocation disorder in the layered hexagonal structure of carboxysome shell protein CsoS1C," Acta Crystallographica, Section D: Biological Crystallography, vol. 65, Pt 9, pp. 980-988, 2009.

Tsvetkova, et al., "Cutting edge: an NK cell-independent role for Slamf4 in controlling humoral autoimmunity," Protein Cages, Methods in Molecular Biology, 1252:1-15, 2014.

Usami, et al., "SERINC3 and SERINC5 restrict HIV-1 infectivity and are counteracted by Nef," Nature, vol. 526, No. 1572, pp. 218-223, 2015.

Votteler, et al., "Virus budding the ESCRT pathway," Cell Host & Microbe, vol. 14, No. 3, pp. 232-241, 2013.

Wang, et al., "Expanding the genetic code of *Escherichia coli*," Science, vol. 292, No. 5516, pp. 498-500, 2001.

Whitehead, et al., "Optimization of Affinity, Specificity and Function of Designed Influenza Inhibitors Using Deep Sequencing," Nature Biotechnology, vol. 30, No. 6, pp. 543-548, 2012.

Winn, et al., "Macromolecular TLS refinement in REFMAC at moderate resolutions," Methods in Enzymology, vol. 374, pp. 300-321, 2003.

Wu, et al., "Cyclic GMP-AMP is an endogenous second messenger in innate immune signaling by cytosolic DNA," Science, vol. 339, No. 6121, pp. 826-830, 2013.

Yeates et al., "Bacterial microcompailment organelles: protein shell structure and evolution," Annual Review of Biophysics, vol. 39, pp. 185-205, 2010.

Yee et al., "Generation of high-titer pseudotyped retroviral vectors with very broad host range," Methods in Cell Biology, vol. 43, Pt A, pp. 99-112, 1994.

Zaccai, et al., "A de novo peptide hexamer with a mutable channel," Nature Chemical Biology, vol. 7, No. 12, pp. 935-941, 2011.

Zacharias, et al., "Partitioning of lipid-modified GFPs into membrane microdomains in live cells," Science, vol. 296, No. 5569, pp. 913-916, 2002.

Zhang, "Fabrication of novel biomaterials through molecular self-assembly," Nature Biotechnology, vol. 21, No. 10, pp. 1171-1178, 2003.

Zhao, et al., "A simple guide to biochemical approaches for analyzing lipid-protein interactions," Molecular Biology of the Cell, vol. 23, No. 15, pp. 2823-2830, 2012.

Zheng, et al., "From molecular to macroscopic via the rational design of a self-assembled 3D DNA crystal," Nature, vol. 461, No. 7260, pp. 74-77, 2009.

PCT/US2014/015371 International Search Report and Written Opinion, dated 2014.

PCT/US2016/020090, International Search Report and Written Opinion, 10 pages, dated 2016.

(56) References Cited

OTHER PUBLICATIONS

Adams et al., PHENIX: a comprehensive Python-based system for macromolecular structure solution. Acta Crystallogr. D Biol. Crystallogr. 66, 213-221 (2010).
Arnold & Volkov, Directed evolution of biocatalysts. Curr. Opin. Chem. Biol. 3, 54-59 (1999).
Bale et al., Structure of a designed tetrahedral protein assembly variant engineered to have improved soluble expression, Protein Sci. 24:1695-1701 (2015).
Boyle et al., Squaring the circle in peptide assembly: from fibers to discrete nanostructures by de novo design. J. Am Chem. Soc. 134, 15457-15467 (2012).
Bradley & Baker, Improved beta-protein structure prediction by multilevel optimization of nonlocal strand pairings and local backbone conformation. Proteins 65, 922-929 (2006).
Brodin et al., et al. Metal-directed, chemically tunable assembly of one-, two- and three-dimensional crystalline protein arrays. Nature Chem. 4, 375-382 (2012).
Burkhard et al., Malaria vaccine based on Self-Assembling Protein Nanoparticles, Expert Rev. Vaccines 14 (12):1525-27 (2015).
Caspar & Klug, The Principles in the Contstruction of Regular Viruses, Cold Spring Harb. Symp. Quant. Biol. 27, 1-24 (1962).
Chan et al. Structure and function of P19, a high-affinity iron transporter of the human pathogen Campylobacter jejuni. J. Mol. Biol. 401, 590-604 (2010).
Colovos & Yeates, Verification of protein structures: patterns of nonbonded atomic interactions. Protein Sci. 2, 1511-1519 (1993).
Correia et al., Proof of principle for epitope-focused vaccine design, Nature 507(7491):201-06 (2014).
Davis et al. MolProbity: all-atom contacts and structure validation for proteins and nucleic acids. Nucleic Acids Res. 35, W375-383 (2007).
Dempsey et al., C3d of Complement as a Molecular Adjuvant: Bridging Innate and Acquired Immunity, Science, 271:348-50 (Jan. 1996).
Der et al., Metal-mediated affinity and orientation specificity in a computationally designed protein homodimer. J. Am. Chem. Soc. 134, 375-385 (2012).
DiMaio et al., Modeling symmetric macromolecular structures in Rosetta3. PLoS ONE 6, e20450 (2011).
Douglas & Young, Viruses: making friends with old foes. Science 312, 873-875 (2006).
Dyer et al., High-Throughput SAXS for the Characterization of Biomolecules in Solution: A Practical Approach, Methods Mol. Biol. 1091:245-58 (2014).
Emsley et al., Features and development of Coot. Acta Crystallogr. D Biol. Crystallogr. 66, 486-501 (2010).
Fallas et al., Computational Design of Self-Assembling Cyclic Protein Homo-oligomers, Nat. Chem. 9(4):353-60 (Apr. 2017).
Fleishman et al., Computational design of proteins targeting the conserved stem region of influenza hemagglutinin. Science 332, 816-821 (2011).
Fleishman et al. Community-wide assessment of protein-interface modeling suggests improvements to design methodology. J. Mol. Biol. 414, 289-302 (2011).
Fleishman et al. RosettaScripts: a scripting language interface to the Rosetta macromolecular modeling suite. PLoS One 6, e20161 (2011).
Fleishman et al., Restricted sidechain plasticity in the structures of native proteins and complexes. Protein Sci. 20, 753-757 (2011).
Fletcher et al. Self-assembling cages from coiled-coil peptide modules. Science 340, 595-599 (2013).
Frank et al. SPIDER and WEB: processing and visualization of images in 3D electron microscopy and related fields. J. Struct. Biol. 116, 190-199 (1996).
Gibson et al. Enzymatic assembly of DNA molecules up to several hundred kilobases. Nat. Methods 6, 343-345 (2009).
Glen et al., A Randomized, Blinded, Controlled, Dose-Ranging Study of a Respiratory Syncytial Virus Recombinant Fusion, J. Infect. Dis. 213(3):411-22 (2016).
Gonen et al., Design of ordered two-dimensional arrays mediated by noncovalent protein-protein interfaces, Science 348:1365-68 (2015).
Goodsell & Olson, Structural symmetry and protein function. Annu. Rev. Biophys. Biomol. Struct. 29, 105-153 (2000).
Grigoryan et al. Computational design of virus-like protein assemblies on carbon nanotube surfaces. Science 332, 1071-1076 (2011).
Grueninger et al. Designed protein-protein association. Science 319, 206-209 (2008).
Han et al. DNA gridiron nanostructures based on four-arm junctions. Science 339, 1412-1415 (2013).
Howorka, Rationally engineering natural protein assemblies in nanobiotechnology. Curr. Opin. Biotechnol. 22, 485-491 (2011).
Hsia et al., Design of a hyperstable 60-subunit protein icosahedron, Nature 535:136-39 (2016).
Huang et al., A de novo designed protein protein interface. Protein Sci. 16, 2770-2774 (2007).
Jackel et al., Protein design by directed evolution. Annu. Rev. Biophys. 37, 153-173 (2008).
Janin et al., Protein-protein interaction and quaternary structure. Q. Rev. Biophys. 41, 133-180 (2008).
Jha et al., Computational design of a PAK1 binding protein. J. Mol. Biol. 400, 257-270 (2010).
Kabsch, Xds. Acta Crystallogr. D Biol. Crystallogr. 66, 125-132 (2010).
Karanicolas et al., A de novo protein binding pair by computational design and directed evolution. Mol. Cell 42, 250-260 (2011).
Ke, Three-dimensional structures self-assembled from DNA bricks. Science 338, 1177-1183 (2012).
Khare & Fleishman, Emerging themes in the computational design of novel enzymes and protein-protein interfaces. FEBSLett. 587, 1147-1154(2013).
King & Lai, Practical approaches to designing novel protein assemblies. Curr. Opin. Struct. Biol. 23, 632-638 (2013).
King et al. Computational design of self-assembling protein nanomaterials with atomic level accuracy. Science 336, 1171-1174 (2012).
King et al., "Accurate design of coassembling multi-component protein nanomaterials" Nature 510(7503):103-108 (Jun. 2014). With supplementary data.
Krissinel & Henrick, Inference of macromolecular assemblies from crystalline state. J. Mol. Biol. 372, 774-797 (2007).
Kuhlman & Baker, Native protein sequences are close to optimal for their structures. Proc. Natl Acad. Sci. USA 97, 10383-10388 (2000).
Lai et al., Structure of a Designed Protein Cage that Self-Assembles into a Highly Porous Cube, Nat. Chem. 6:1065-71 (2014).
Lai et al., Principles for designing ordered protein assemblies. Trends Cell Biol. 22, 653-661 (2012).
Lai et al., Structure of a 16-nm cage designed by using protein oligomers. Science 336:1129-30 (Jun. 2012).
The International Search Report (ISR) with Written Opinion for PCT/US2018025880 dated Jun. 29, 2018, pp. 1-19.
Bale, Jacob B. et al. "Accurate design of megadalton-scale two-component icosahedral protein complexes" Science (2016) vol. 353(6297), pp. 389-394.
McLellan, Jason S. et al. "Structure-Based Design of a Fusion Glycoprotein Vaccine for Respiratory Syncytial Virus" Science (2013) vol. 342(6158), pp. 592-598.
Website: http://www.genisphere.com/, 1 page retrieved on Sep. 12, 2016.
AfosrApan, "Computational design of self- and co-assembling protein nanomaterials with atomic level accuracy" available online at: https://community.apan.org/afosr/w/researchareas/7659.human-performance-and-biosystems.aspx, 2014.
Andersen, et al., "Self-assembly of a nanoscale DNA box with a controllable lid," Nature, vol. 459, No. 7243, pp. 73-76, 2009.
Apolonia, et al., "Promiscuous RNA binding ensures effective encapsidation of APOBEC3 proteins by HIV-1," PLoS Pathogens, vol. 11, No. 1, e1004609, 2015.
Bagby, et al., "[2]—Optimization of Protein Solubility and Stability for Protein Nuclear Magnetic Resonance," Methods in Enzymology, vol. 339, pp. 20-41, 2001.
Ballister, et al., "In vitro self-assembly of tailorable nanotubes from a simple protein building block," Proceedings of the National Academy of Sciences USA, vol. 105, No. 10, pp. 3733-3738, 2008.

(56) References Cited

OTHER PUBLICATIONS

Bieniasz, "Late budding domains and host proteins in enveloped virus release," Virology, vol. 344, No. 1, pp. 55-63, 2006.
Biswas, et al., "The human immunodeficiency virus type 1 ribosomal frameshifting site is an invariant sequence determinant and an important target for antiviral therapy," Journal of Virology, vol. 78, No. 4, pp. 2082-2087, 2004.
Blanc, et al., "Refinement of severely incomplete structures with maximum likelihood in BUSTER-TNT," Acta Carystallographica, Section D: Biological Crystallography, vol. 60, Pt 12, Pt 1, pp. 2210-2221, 2004.
Bondos, et al., "Detection and Prevention of Protein Aggregation Before, During, and After Purification," Analytical Biochemistry, vol. 316, No. 2, pp. 223-231, 2003.
Bridgeman, et al., "Viruses transfer the antiviral second messenger cGAMP between cells," Science, vol. 349, No. 6253, pp. 1228-1232, 2015.
Cavrois, et al., "A sensitive and specific enzyme-based-assay detecting HIV-1 virion fusion in primary T lymphocytes," Nature Biotechnology, vol. 20, No. 11, pp. 1151-1154, 2002.
Chao, et al., "Isolating and Engineering Human Antibodies Using Yeast Surface Display," Nature Protocols, vol. 1, No. 2, pp. 755-768, 2016.
Chao, et al., "Structural basis for the coevolution of a viral RNA-protein complex," Nature Structural & Molecular Biology, vol. 15, No. 1, pp. 103-105, 2008.
Cooper, et al., "Predicting protein structures with a multiplayer online game," Nature, vol. 466, No. 7307, pp. 756-760, 2010.
Crowley, et al., "Structural insight into the mechanisms of transport across the *Salmonella enterica* Pdu microcompartment shell," Journal of Biological Chemistry, vol. 285, No. 48, pp. 37838-37846, 2010.
Das, et al., "Simultaneous prediction of protein folding and docking at high resolution," Proceedings of the National Academy of Sciences USA, vol. 106, No. 45, pp. 18978-18983, 2009.
De Guzman, et al., "Structure of the HIV-1 nucleocapsid protein bound to the SL3 psi-RNA recognition element," Science, vol. 279, No. 5349, pp. 384-388, 1998.
Fleishman, et al., "Hotspot-centric de novo design of protein binders," Journal of Molecular Biology, vol. 413, No. 5, pp. 1047-1062, 2011.
Freed, et al., "Single amino acid changes in the human immunodeficiency virus type 1 matrix block virus particle production," Journal of Virology, vol. 68, No. 8, pp. 5311-5320, 1994.
Gentili, et al., "Transmission of innate immune signaling by packaging of cGAMP in viral particles," Science, vol. 349, No. 6253, pp. 1232-1236, 2015.
Golovanov, et al., "A Simple Method for Improving Protein Solubility and Long-Term Stability," Journal of the American Chemical Society, vol. 126, No. 29, pp. 8933-8939, 2004.
Gosser, et al., "Peptide-triggered conformational switch in HIV-1 RRE RNA complexes," Nature Structural Biology, vol. 3, No. 2, pp. 146-150, 2001.
Gray et al., "Cutting Edge: cGAS is Required for Lethal Autoimmune Disease in the Trexl-Deficient Mouse Model of Aicardi-Goutieres Syndrome," Journal of Immunology, vol. 195, No. 5, pp. 1939-1943, 2015.
Gribbon, et al., "MagicWand: a single, designed peptide that assembles to stable, ordered alpha-helical fibers," Biochemistry, vol. 47, No. 39, pp. 10365-10371, 2008.
Griffith, et al., "Cloning, isolation and characterization of the Thermotoga maritima KDPG aldolase," Bioorganic & Medicinal Chemistry, vol. 10, No. 3, pp. 545-550, 2002.
Grigorieff, "FREALIGN: high-resolution refinement of single particle structures," Journal of Structural Biology, vol. 157, No. 1, pp. 117-125, 2007.
Harbury, et al., "High-resolution protein design with backbone freedom," Science, vol. 282, No. 5393, pp. 1462-1467, 1998.
Hurley, et al., "Membrane Budding and Scission by the ESCRT Machinery: It's All in the Neck," Nature Reviews Molecular Cell Biology, vol. 11, No. 8, pp. 556-566, 2010.
Ishikawa, et al., "STING is an endoplasmic reticulum adaptor that facilitates innate immune signalling," Nature, vol. 155, No. 7213, pp. 674-678, 2008.
Jacak, et al., "Computational Protein Design with Explicit Consideration of Surface Hydrophobic Patches," Proteins Structure, Function, and Bioinformatics, vol. 80, No. 3, pp. 825-838, 2012.
Jackel, et al., "Consensus Protein Design Without Phylogenetic Bias," Journal of Molecular Biology, vol. 399, No. 4, pp. 541-546, 2010.
Julien, et al., "Crystal structure of a soluble cleaved HIV-1 envelope trimer," Science, vol. 342, No. 6165, pp. 1477-1483, 2013.
Koder, et al., "Design and engineering of an O(2) transport protein," Nature, vol. 458, No. 7236, pp. 305-309, 2009.
Kortemme, et al., "Computational redesign of protein-protein interaction specificity," Nature Structural & Molecular Biology, vol. 11, No. 4, pp. 371-379, 2004.
Kremer, et al., "Computer visualization of three-dimensional image data using IMOD," Journal of Structural Biology, vol. 116, No. 1, pp. 71-76, 1996.
Kumar, et al., "Crystal structure analysis of icosahedral lumazine synthase from *Salmonella typhimurium*, an antibacterial drug target," Acta Crystallographica, Section D: Biological Crystallography, vol. 67, Pt 2, pp. 131-139, 2011.
Laskowski, et al., "PROCHECK: a program to check the stereochemical quality of protein structures," Journal of Applied Crystallography, 26:283-291, 1993.
Lemmon, "Membrane recognition by phospholipid-binding domains." Nature Reviews Molecular Cell Biology, vol. 9, No. 2, pp. 99-111, 2008.
Levy, et al., "3D complex: a structural classification of protein complexes," PLoS Computational Biology, vol. 2, No. 11, 3155, pp. 1395-1406, 2006.
Lovejoy, et al., "Crystal structure of a synthetic triple-stranded alpha-helical bundle," Science, vol. 259, No. 5099, pp. 1288-1293, 1993.
Lyumkis, et al., "Cryo-EM structure of a fully glycosylated soluble cleaved HIV-1 envelope timer," Science, vol. 342, No. 6165, pp. 1484-1490, 2013.
Mangeot, et al., "Protein transfer into human cells by VSV-G-induced nanovesicles," Molecular Therapy, vol. 19, No. 9, pp. 1656-1666, 2011.
McCullough, et al., "Membrane Fission Reactions of the Mammalian ESCRT Pathway," Annual Review of Biochemistry, vol. 82, pp. 663-692, 2013.
McDonald, et al., "No strings attached: the ESCRT machinery in viral budding and cytokinesis," Journal of Cell Science, vol. 122, Pt 13, pp. 2167-2177, 2009.
Mindell, et al., "Accurate determination of local defocus and specimen tilt in electron microscopy," Journal of Structural Biology, vol. 142, No. 3, pp. 334-347, 2003.
Murshudov, et al., "Refinement of macromolecular structures by the maximum-likelihood method," Acta Crystallographica, Section D: Biological Crystallography, vol. 53, Pt 3, pp. 240-255, 1997.
Nam, et al., "Molecular basis for interaction of let-7 microRNAs with Lin28," Cell, vol. 147, No. 5, pp. 1080-1091, 2011.
Ni, et al., "Crystal structure of the MS2 coat protein dimer: implication for RNA binding and virus assembly," Structure, vol. 3, No. 3, pp. 255-263, 1995.
Ohi, et al., "Negative staining and image classification-powerful tools in modem electron microscopy," Biological Procedures Online, vol. 6, pp. 23-34, 2004.
U.S. Appl. No. 16/427,493, filed May 31, 2019, Baker et al.
Lanci et al. Computational design of a protein crystal. Proc. Natl Acad. Sci. USA 109, 7304-7309 (2012).
Lawrence & Colman, Shape complementarity at protein/protein interfaces. J. Mol. Biol. 234, 946-950 (1993).
Lawrence et al., Supercharging Proteins Can Impart Unusual Resilience, J. Am. Chem. Soc. 129, 10110-10112 (2007).

(56) References Cited

OTHER PUBLICATIONS

Leaver-Fay et al., Rosetta3: an object-oriented software suite for the simulation and design of macromolecules. Methods Enzymol. 487, 545-574 (2011).
Leaver-Fay et al. Scientific benchmarks for guiding macromolecular energy function improvement. Methods Enzymol. 523, 109-143 (2013).
Lin et al., Structural Fingerprinting: Subgrouping of Comoviruses by Structural Studies of Red Clover Mottle Virus to 2.4-Å Resolution and Comparisons with Other Comoviruses J. Virol. 74, 493-504 (2000).
Lin et al., The Refined Crystal Structure of Cowpea Mosaic Virus at 2.8 Å Resolution, Virology 265, 20-34 (1999).
Ludtke et al., EMAN: semiautomated software for high-resolution single-particle reconstructions. J. Struct. Biol. 128, 82-97 (1999).
Lüthy et al., Assessment of protein models with three-dimensional profiles. Nature 356, 83-85 (1992).
McCoy et al. Phaser crystallographic software. J. Appl. Crystallogr. 40, 658-674 (2007).
Nannenga et al., Overview of electron crystallography of membrane proteins: crystallization and screening strategies using negative stain electron microscopy. Curr. Protoc. Protein Sci. Chapter 17, Unit17.15 (2013).
Nivon et al., Automating human intuition for protein design. Proteins (2013). doi: 10.1002/prot.24463.
Padilla et al., Nanohedra: using symmetry to design self assembling protein cages, layers, crystals, and filaments. Proc. Natl Acad. Sci. USA 98, 2217-2221 (2001).
Painter & Merritt, Optimal description of a protein structure in terms of multiple groups undergoing TLS motion. Acta Crystallogr. D Biol. Crystallogr. 62, 439-450 (2006).
Painter, J. & Merritt, TLSMD web server for the generation of multi-group TLS models. Journal of Applied Crystallography 39, 109-111 (2006).
Pettersen et al. UCSF Chimera—a visualization system for exploratory research and analysis. J. Comput. Chem. 25, 1605-1612 (2004).
Prodromou & Pearl,Recursive PCR: a novel technique for total gene synthesis. Protein Eng. 5, 827-829 (1992).
Raman et al., Design of Peptide Nanoparticles Using Simple Protein Oligomerization Domains, The Open Nanomedicine Journal, 2:15-26 (2009).
Raman et al., Materials Science: Structure-based design of peptides that self-assemble into regular polyhedral nanoparticles, Nanomedicine: Nanotechnology, Biology, and Medicine 2:95-102 (2006).
Ringler & Schulz, Self-Assembly of Proteins into Designed Networks, Science 302:106-09 (2003).
Rothemund, Folding DNA to create nanoscale shapes and patterns. Nature 440, 297-302 (2006).
Salgado et al., Metal-directed protein self-assembly. Acc. Chem. Res. 43, 661-672 (2010).
Schindelin et al. Fiji: an open-source platform for biological-image analysis. Nat. Methods 9, 676-682 (2012).
Seeman, Nanomaterials based on DNA. Annu. Rev. Biochem. 79, 65-87 (2010).
Sheffler & Baker, RosettaHoles2: a volumetric packing measure for protein structure refinement and validation. Protein Sci 19, 1991-1995 (2010).
Sinclair et al., Generation of protein lattices by fusing proteins with matching rotational symmetry. Nature Nanotechnol. 6, 558-562 (2011).
Sinclair, Constructing arrays of proteins. Curr. Opin. Chem. Biol. 17, 946-951 (2013).
Smith, Ximdisp—A visualization tool to aid structure determination from electron microscope images. J. Struct. Biol. 125, 223-228 (1999).
Stranges et al., Computational design of a symmetric homodimer using beta-strand assembly. Proc. Natl Acad. Sci. USA 108, 20562-20567 (2011).
Tinberg et al. Computational design of ligand-binding proteins with high affinity and selectivity. Nature 501, 212-216 (2013).
Usui et al. Nanoscale elongating control of the self-assembled protein filament with the cysteine-introduced building blocks. Protein Sci. 18, 960-969 (2009).
Van Heel et al., A new generation of the IMAGIC image processing system. J. Struct. Biol. 116, 17-24 (1996).
Van Kooten & Banchereau, CD40-CD40 Ligand, J. Leukoc. Biol. 67:2-17 (Jan. 2000).
Voet et al., Computational design of a self-assembling symmetrical β-propeller protein, Proc. Natl. Acad. Sci. U.S.A. 111:15102-107 (2014).
Worsdorfer et al., Directed evolution of a protein container. Science 331, 589-592 (2011).
Worsdorfer et al., Efficient in vitro encapsulation of protein cargo by an engineered protein container. J.Am.Chem. Soc. 134,909-911(2012).
Zakeri et al., Peptide tag forming a rapid covalent bond to a protein, through engineering a bacterial adhesin, Proc. Natl. Acad. Sci. U.S.A. 109(12):E690-E697 (Mar. 2012).
Zandi et al., Origin of icosahedral symmetry in viruses, Proc. Natl. Acad. Sci. U.S.A. 101(44):15556-560 (Nov. 2004).
Zhou et al., Genetically encoded short peptide tags for orthogonal protein labeling by Sfp and AcpS phosphopantetheinyl transferases ACS Chem. Biol. 2, 337-346 (2007).
Zlotnick et al., A Theoretical Model Successfully Identifies Features of Hepatitis B Virus Capsid Assembly, Biochemistry 38:14644-652 (1999).
Zlotnick et al., Mechanism of Capsid Assembly for an Icosahedral Plant Virus, Virology 277:450-56 (2000).
Zschoche & Hilvert, Diffusion-Limited Cargo Loading of an Engineered Protein Container, Am. Chem. Soc. 137:16121-132 (2015).

SELF-ASSEMBLING PROTEIN NANOSTRUCTURES DISPLAYING PARAMYXOVIRUS AND/OR PNEUMOVIRUS F PROTEINS AND THEIR USE

CROSS REFERENCE

This application is a divisional of U.S. patent application Ser. No. 16/500,331, filed Oct. 2, 2019, which is a U.S. national phase of International Application No. PCT/US2018/025880, filed on Apr. 3, 2018, which claims priority to U.S. Provisional Application No. 62/481,331, filed Apr. 4, 2017, all of which are incorporated by reference herein in their entirety

BACKGROUND

Molecular self- and co-assembly of proteins into highly ordered, symmetric supramolecular complexes is an elegant and powerful means of patterning matter at the atomic scale. Recent years have seen advances in the development of self-assembling biomaterials, particularly those composed of nucleic acids. DNA has been used to create, for example, nanoscale shapes and patterns, molecular containers, and three-dimensional macroscopic crystals. Methods for designing self-assembling proteins have progressed more slowly, yet the functional and physical properties of proteins make them attractive as building blocks for the development of advanced functional materials.

SUMMARY OF THE INVENTION

In one aspect, nanostructures are provided comprising:
(a) a plurality of first assemblies, each first assembly comprising a plurality of identical first polypeptides;
(b) a plurality of second assemblies, each second assembly comprising a plurality of identical second polypeptides, wherein the second polypeptide differs from the first polypeptide;
wherein the plurality of first assemblies non-covalently interact with the plurality of second assemblies to form a nanostructure; and
wherein the nanostructure displays multiple copies of one or more paramyxovirus and/or pneumovirus F proteins, or antigenic fragments thereof, on an exterior of the nanostructure.

In one embodiment, (a) the first polypeptides comprise a polypeptide having at least 70%, 75%, 80%, 85%, 90%, 91%, 92%, 93%, 94%, 95%, 96%, 97%, 98%, 99%, or 100% identity along its full length to the amino acid sequence of a polypeptide selected from the group consisting of SEQ ID NOS:1-51; and
(b) the second polypeptides comprise a polypeptide having at least 70%, 75%, 80%, 85%, 90%, 91%, 92%, 93%, 94%, 95%, 96%, 97%, 98%, 99%, or 100% identity along its full length to the amino acid sequence of a polypeptide selected from the group consisting of SEQ ID NOS:1-51.

In another embodiment, the one or more paramyxovirus and/or pneumovirus F proteins, or antigenic fragments thereof, comprise a polypeptide having at least 75%, 80%, 85%, 90%, 91%, 92%, 93%, 94%, 95%, 96%, 97%, 98%, 99%, or 100% identity along its full length to the amino acid sequence of a polypeptide selected from the group consisting of SEQ ID NOS: 53, 61-68, and 101.

In various embodiments:
(a) the first polypeptide comprises a polypeptide having at least 75%, 80%, 85%, 90%, 91%, 92%, 93%, 94%, 95%, 96%, 97%, 98%, 99%, or 100% identity along its full length to the amino acid sequence of T33-31A (SEQ ID NO:51) and the second polypeptide comprises a polypeptide having at least 75%, 80%, 85%, 90%, 91%, 92%, 93%, 94%, 95%, 96%, 97%, 98%, 99%, or 100% identity along its full length to the amino acid sequence of T33-09B/T33-31B (SEQ ID NO:44);
(b) the first polypeptide comprises a polypeptide having at least 75%, 80%, 85%, 90%, 91%, 92%, 93%, 94%, 95%, 96%, 97%, 98%, 99%, or 100% identity along its full length to the amino acid sequence of T33-15B (SEQ ID NO:46) and the second polypeptide comprises a polypeptide having at least 75%, 80%, 85%, 90%, 91%, 92%, 93%, 94%, 95%, 96%, 97%, 98%, 99%, or 100% identity along its full length to the amino acid sequence of T33-15A (SEQ ID NO:45);
(c) the first polypeptide has at least 75%, 80%, 85%, 90%, 91%, 92%, 93%, 94%, 95%, 96%, 97%, 98%, 99%, or 100% identity along its full length to the amino acid sequence of a polypeptide selected from the group consisting of I53-50A (SEQ ID NO:7), I53-50A.1 (SEQ ID NO:29), I53-50A.1NegT2 (SEQ ID NO:30), and I53-50A.1PosT1 (SEQ ID NO:31), and the second polypeptide has at least 75%, 80%, 85%, 90%, 91%, 92%, 93%, 94%, 95%, 96%, 97%, 98%, 99%, or 100% identity along its full length to the amino acid sequence of a polypeptide selected from the group consisting of I53-50B (SEQ ID NO:8), I53-50B.1 (SEQ ID NO:32), I53-50B.1NegT2 (SEQ ID NO:33), and I53-50B.4PosT1 (SEQ ID NO:34); or
(d) the first polypeptide comprises a polypeptide having at least 75%, 80%, 85%, 90%, 91%, 92%, 93%, 94%, 95%, 96%, 97%, 98%, 99%, or 100% identity along its full length to the amino acid sequence of I32-28A (SEQ ID NO:21) and the second polypeptide comprises a polypeptide having at least 75%, 80%, 85%, 90%, 91%, 92%, 93%, 94%, 95%, 96%, 97%, 98%, 99%, or 100% identity along its full length to the amino acid sequence of I32-28B (SEQ ID NO:22).

In one embodiment, the one or more paramyxovirus and/or pneumovirus F proteins, or antigenic fragments thereof, are expressed as a fusion protein with the first polypeptides. In one such embodiment, the plurality of first assemblies each comprise identical first polypeptides; in another such embodiment, the plurality of first assemblies in total comprise two or more paramyxovirus and/or pneumovirus F proteins, or antigenic fragments thereof. In another embodiment, only a subset of the first polypeptides comprise a fusion protein with an F protein or antigenic fragment thereof. In a further embodiment, each first assembly comprises a homotrimer of the first polypeptide.

In another embodiment, the fusion protein comprises an amino acid linker positioned between the first polypeptide and the paramyxovirus and/or pneumovirus F proteins, or antigenic fragment thereof. In one such embodiment, the fusion protein comprises an amino acid linker positioned between the first polypeptide and the paramyxovirus F proteins, or antigenic fragment thereof.

In one embodiment the amino acid linker sequence comprises one or more trimerization domain; in another embodiment the amino acid linker sequence comprises a Gly-Ser linker.

In various embodiments, the first polypeptides comprise or consist of first polypeptides having at least 75%, 80%, 85%, 90%, 91%, 92%, 93%, 94%, 95%, 96%, 97%, 98%, 99%, or 100% identity along their full length to the amino acid sequence of a polypeptide selected from the group consisting of DS-Cav1-foldon-T33-31A (SEQ ID NO:69), DS-Cav1-T33-31A (SEQ ID NO:70), DS-Cav1-foldon-T33-15B (SEQ ID NO:71), DS-Cav1-T33-15B (SEQ ID NO:72), DS-Cav1-foldon-I53-50A (SEQ ID NO:73), DS-Cav1-I53-50A (SEQ ID NO:74), and DS-Cav1-I32-28A (SEQ ID NO:75).

In other embodiments, (a) when each first polypeptide has at least 75%, 80%, 85%, 90%, 91%, 92%, 93%, 94%, 95%, 96%, 97%, 98%, 99%, or 100% identity along its full length to the amino acid sequence of DS-Cav1-foldon-T33-31A (SEQ ID NO:69) or DS-Cav1-T33-31A (SEQ ID NO:70), each second polypeptide has at least 75%, 80%, 85%, 90%, 91%, 92%, 93%, 94%, 95%, 96%, 97%, 98%, 99%, or 100% identity along its full length to the amino acid sequence of T33-31B (SEQ ID NO:44);

(b) when each first polypeptide has at least 75%, 80%, 85%, 90%, 91%, 92%, 93%, 94%, 95%, 96%, 97%, 98%, 99%, or 100% identity along its full length to the amino acid sequence of DS-Cav1-foldon-T33-15B (SEQ ID NO:71) or DS-Cav1-T33-15B (SEQ ID NO:72), each second polypeptide has at least 75%, 80%, 85%, 90%, 91%, 92%, 93%, 94%, 95%, 96%, 97%, 98%, 99%, or 100% identity along its full length to the amino acid sequence of T33-15A (SEQ ID NO:45);

(c) when each first polypeptide has at least 75%, 80%, 85%, 90%, 91%, 92%, 93%, 94%, 95%, 96%, 97%, 98%, 99%, or 100% identity along its full length to the amino acid sequence of DS-Cav1-foldon-I53-50A (SEQ ID NO:73) or DS-Cav1-I53-50A (SEQ ID NO:74), each second polypeptide has at least 75%, 80%, 85%, 90%, 91%, 92%, 93%, 94%, 95%, 96%, 97%, 98%, 99%, or 100% identity along its full length to the amino acid sequence of a polypeptide selected from the group consisting of I53-50B (SEQ ID NO:8), I53-50B.1 (SEQ ID NO:32), I53-50B.1NegT2 (SEQ ID NO:33), or I53-50B.4PosT1 (SEQ ID NO:34); or (d) when each first polypeptide has at least 75%, 80%, 85%, 90%, 91%, 92%, 93%, 94%, 95%, 96%, 97%, 98%, 99%, or 100% identity along its full length to the amino acid sequence of DS-Cav1-I32-28A (SEQ ID NO:75), each second polypeptide has at least 75%, 80%, 85%, 90%, 91%, 92%, 93%, 94%, 95%, 96%, 97%, 98%, 99%, or 100% identity along its full length to the amino acid sequence of I32-28B.

In one embodiment, the one or more paramyxovirus and/or pneumovirus F proteins, or antigenic fragments thereof comprises a polypeptide having at least 75%, 80%, 85%, 90%, 91%, 92%, 93%, 94%, 95%, 96%, 97%, 98%, 99%, or 100% identity along its full length to the amino acid sequence of DS-Cav1 (SEQ ID NO:53). In one such embodiment, each first polypeptide comprises a fusion polypeptide of a polypeptide having at least 75%, 80%, 85%, 90%, 91%, 92%, 93%, 94%, 95%, 96%, 97%, 98%, 99%, or 100% identity along its full length to the amino acid sequence of DS-Cav1 linked via an amino acid linker to a polypeptide having at least 75%, 80%, 85%, 90%, 91%, 92%, 93%, 94%, 95%, 96%, 97%, 98%, 99%, or 100% identity along its full length to the amino acid sequence of SEQ ID NO:7 (I53-50A). In another embodiment, the amino acid linker comprises a Gly-Ser linker. In a further embodiment, each fusion protein comprises a polypeptide having at least 75%, 80%, 85%, 90%, 91%, 92%, 93%, 94%, 95%, 96%, 97%, 98%, 99%, or 100% identity along its full length to the amino acid sequence selected from the group consisting of SEQ ID NOS:69-100. In a specific embodiment, each fusion protein comprises a polypeptide having at least 75%, 80%, 85%, 90%, 91%, 92%, 93%, 94%, 95%, 96%, 97%, 98%, 99%, or 100% identity along its full length to the amino acid sequence of SEQ ID NO:76 (F10). In other embodiments, each second polypeptide comprises a polypeptide having at least 75%, 80%, 85%, 90%, 91%, 92%, 93%, 94%, 95%, 96%, 97%, 98%, 99%, or 100% identity along its full length to the amino acid sequence selected from the group consisting of I53-50B (SEQ ID NO:8), I53-50B.1 (SEQ ID NO:32), I53-50B.1NegT2 (SEQ ID NO:33), or I53-50B.4PosT1 (SEQ ID NO:34). In a specific embodiment, each second polypeptide comprises a polypeptide having at least 75%, 80%, 85%, 90%, 91%, 92%, 93%, 94%, 95%, 96%, 97%, 98%, 99%, or 100% identity along its full length to the amino acid sequence of I53-50B.4PosT1 (SEQ ID NO:34).

In other aspects, recombinant expression nucleic acids expressing the first polypeptide fusions, recombinant expression vectors comprising the recombinant nucleic acids linked to a promoter, and recombinant host cells comprising the recombinant expression vectors are provided.

Also provided are immunogenic compositions comprising the nanostructure of any embodiment or combination of embodiments disclosed herein, and a pharmaceutically acceptable carrier. In one embodiment, the immunogenic compositions may further comprise an adjuvant.

In other aspects, methods for generating an immune response to RSV F protein in a subject, or for treating or limiting a RSV infection in a subject are provided, comprising administering to the subject in need thereof an effective amount of the nanostructure or immunogenic composition of embodiment or combination of embodiments disclosed herein to generate the immune response or to treat or prevent RSV infection in the subject.

Also provided are processes assembling the nanostructures of any embodiment or combination of embodiments disclosed herein, comprising mixing two or more nanostructures components in aqueous conditions to drive spontaneous assembly of the desired nanostructures.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
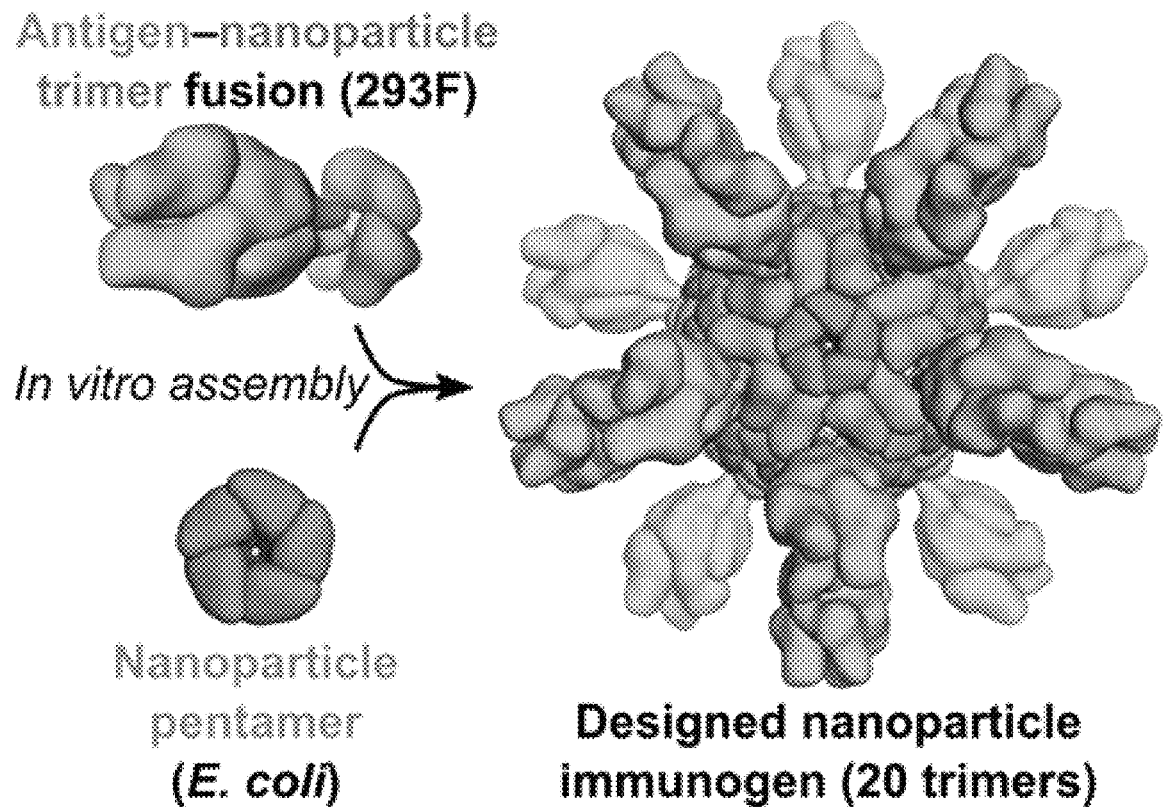
FIG. 1 shows a schematic diagram of the production of antigen-bearing nanostructures by in vitro assembly. The two components or building blocks of a given nanostructure can be expressed and purified individually, which allows assembly of the nanostructure to be initiated by mixing the purified components in vitro, a process referred to as in vitro assembly. In some embodiments, the two components of the nanostructure may be expressed in different expression hosts (e.g., human HEK293F cells or bacterial E. coli cells). The figure schematically depicts assembly of a 120-subunit nanostructure bearing 20 trimeric antigens (60 antigen subunits) via in vitro assembly of an antigen-nanostructure trimer fusion protein produced in HEK293F cells and a nanostructure pentamer protein produced in E. coli.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used herein, "about" means+/−5% of the recited parameter.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the disclosure provides nanostructures, comprising:

(a) a plurality of first assemblies, each first assembly comprising a plurality of identical first polypeptides;

(b) a plurality of second assemblies, each second assembly comprising a plurality of identical second polypeptides, wherein the second polypeptide differs from the first polypeptide;

wherein the plurality of first assemblies non-covalently interact with the plurality of second assemblies to form a nanostructure; and wherein the nanostructure displays multiple copies of one or more paramyxovirus and/or pneumovirus F proteins, or antigenic fragments thereof, on an exterior of the nanostructure.

Self-assembling polypeptide nanostructures are disclosed herein that multivalently display paramyxovirus and/or pneumovirus F proteins on the nanostructure exteriors. Multiple copies of pairs of first and second polypeptides are able to self-assemble to form nanostructures, such as icosahedral nanostructures. The nanostructures include symmetrically repeated, non-natural, non-covalent polypeptide-polypeptide interfaces that orient a first assembly and a second assembly into a nanostructure, such as one with an icosahedral symmetry.

The nanostructures of the invention are synthetic, in that they are not naturally occurring. The first polypeptides and the second polypeptides are non-naturally occurring proteins that can be produced by any suitable means, including recombinant production or chemical synthesis. Each member of the plurality of first polypeptides is identical to each other (though when the first polypeptide is present as a fusion polypeptide with one or more paramyxovirus and/or pneumovirus F proteins, or antigenic fragments thereof, the F protein or antigenic fragment thereof may differ from one first polypeptide to another), and each member of the plurality of second polypeptides is identical to each other. The first proteins and the second proteins are different. There are no specific primary amino acid sequence requirements for the first and second polypeptides. US published patent application 20160122392 and published PCT application WO2014/124301 describe methods for designing synthetic nanostructures, where the nanostructures are not dependent on specific primary amino acid sequences of the first and second polypeptides.

A plurality (2, 3, 4, 5, 6, or more) of first polypeptides self-assemble to form a first assembly, and a plurality (2, 3, 4, 5, 6, or more) of second polypeptides self-assemble to form a second assembly. A plurality of these first and second assemblies then self-assemble non-covalently via the designed interfaces to produce the nanostructures.

The number of first polypeptides in the first assemblies may be the same or different than the number of second polypeptides in the second assemblies. In one exemplary embodiment, the first assembly comprises trimers of the first polypeptides, and the second assembly comprises dimers of the second polypeptides. In a further exemplary embodiment, the first assembly comprises trimers of the first polypeptides, and the second assembly comprises trimers of the second polypeptides. In a further exemplary embodiment, the first assembly comprises trimers of the first polypeptides, and the second assembly comprises pentamers of the second polypeptides.

The first and second polypeptides may be of any suitable length for a given purpose of the resulting nanostructure. In one embodiment, the first polypeptides and the second polypeptides are typically between 30-250 amino acids in length; the length of the first polypeptides and the second polypeptides may be the same or different. In various further embodiments, the first polypeptides and the second polypeptides are between 30-225, 30-200, 30-175, 50-250, 50-225, 50-200, 50-175, 75-250, 75-225, 75-200, 75-175, 100-250, 100-225, 100-200, 100-175, 125-250, 125-225, 125-200, 125-175, 150-250, 150-225, 150-200, and 150-175 amino acids in length.

The isolated polypeptides of SEQ ID NOS:1-51 were designed for their ability to self-assemble in pairs to form nanostructures, such as icosahedral nanostructures. The design involved design of suitable interface residues for each member of the polypeptide pair that can be assembled to form the nanostructure. The nanostructures so formed include symmetrically repeated, non-natural, non-covalent polypeptide-polypeptide interfaces that orient a first assembly and a second assembly into a nanostructure, such as one with an icosahedral symmetry. Thus, in one embodiment the first and second polypeptides are selected from the group SEQ ID NOS:1-51. In each case, the N-terminal methionine residue is optional.

TABLE 1

| Name | Amino Acid Sequence | Identified interface residues |
|------|---------------------|-------------------------------|
| I53-34A SEQ ID NO: 1 | (M)EGMDPLAVLAESRLLPLLTVRGGEDLAGLATVLELMGV GALEITLRTEKGLEALKALRKSGLLLGAGTVRSPKEAEAAL EAGAAFLVSPGLLEEVAALAQARGVPYLPGVLTPTEVERAL ALGLSALKFFPAEPFQGVRVLRAYAEVFPEVRFLPTGGIKE EHLPHYAALPNLLAVGGSWLLQGDLAAVMKKVKAAKALLSP QAPG | I53-34A: 28, 32, 36, 37, 186, 188, 191, 192, 195 |
| I53-34B SEQ ID NO: 2 | (M)TKKVGIVDTTFARVDMAEAAIRTLKALSPNIKIIRKTV PGIKDLPVACKKLLEEEGCDIVMALGMPGKAEKDKVCAHEA SLGLMLAQLMTNKHIIEVFVHEDEAKDDDELDILALVRAIE HAANVYYLLFKPEYLTRMAGKGLRQGREDAGPARE | I53-34B: 19, 20, 23, 24, 27, 109, 113, 116, 117, 120, 124, 148 |

TABLE 1-continued

| Name | Amino Acid Sequence | Identified interface residues |
|---|---|---|
| I53-40A SEQ ID NO: 3 | (M)TKKVGIVDTTFARVDMASAAILTLKMESPNIKIIRKTV PGIKDLPVACKKLLEEEGCDIVMALGMPGKAEKDKVCAHEA SLGLMLAQLMTNKHIIEVFVHEDEAKDDAELKILAARRAIE HALNVYYLLFKPEYLTRMAGKGLRQGFEDAGPARE | I53-40A: 20, 23, 24, 27, 28, 109, 112, 113, 116, 120, 124 |
| I53-40B SEQ ID NO: 4 | (M)STINNQLKALKVIPVIAIDNAEDIIPLGKVLAENGLPA AEITFRSSAAVKAIMLLRSAQPEMLIGAGTILNGVQALAAK EAGATFVVSPGFNPNTVRACQIIGIDIVPGVNNPSTVEAAL EMGLITLKFFPAEASGGISMVKSLVGPYGDIRLMPTGGITP SNIDNYLAIPQVLACGGTWMVDKKLVTNGEWDEIARLTREI VEQVNP | I53-40B: 47, 51, 54, 58, 74, 102 |
| I53-47A SEQ ID NO: 5 | (M)PIFTLNTNIKATDVPSDFLSLTSRLVGLILSKPGSYVA VHINTDQQLSFGGSTNPAAFGTLMSIGGIEPSKNRDHSAVL FDHLNAMLGIPKNRMYIHFVNLNGDDVGWNGTTF | I53-47A: 22, 25, 29, 72, 79, 86, 87 |
| I53-47B SEQ ID NO: 6 | (M)NQHSHKDYETVRIAVVRARWHADIVDACVEAFEIAMAA IGGDRFAVDVFDVPGAYEIPLHARTLAETGRYGAVLGTAFV VNGGIYRHEFVASAVIDGMMNVQLSTGVPVLSAVLTPHRYR DSAEHHRFFAAHFAVKGVEAARACIEILAAREKIAA | I53-47B: 28, 31, 35, 36, 39, 131, 132, 135, 139, 146 |
| I53-50A SEQ ID NO: 7 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHTILKLFPGEVVGPQFVKAMKGPFPNVKFVPTGGVNLD NVCEWFKAGVLAVGVGSALVKGTPDEVREKAKAFVEKIRGC TE | I53-50A: 25, 29, 33, 54, 57 |
| I53-50B SEQ ID NO: 8 | (M)NQHSHKDYETVRIAVVRARWHAEIVDACVSAFEAAMAD IGGDRFAVDVFDVPGAYEIPLHARTLAETGRYGAVLGTAFV VNGGIYRHEFVASAVIDGMMNVQLSTGVPVLSAVLTPHRYR DSDAHILLFLALFAVKGMEAARACVEILAAREKIAA | I53-50B: 24, 28, 36, 124, 125, 127, 128, 129, 131, 132, 133, 135, 139 |
| I53-51A SEQ ID NO: 9 | (M)FIKSGDDGNINVINKRVGKDSPLVNFLGDLDELNSFIG FAISKIPWEDMKKDLERVQVELFEIGEDLSTQSSKKKIDES YVLWLLAATAIYRIESGPVKLFVIPGGSEEASVLHVTRSVA RRVERNAVKYTKELPEINRMIIVYLNRLSSLLFAMALVANK RRNQSEKIYEIGKSW | I53-51A: 80, 83, 86, 87, 88, 90, 91, 94, 166, 172, 176 |
| I53-51B SEQ ID NO: 10 | (M)NQHSHKDYETVRIAVVRARWHADIVDQCVRAFEEAMAD AGGDRFAVDVFDVPGAYEIPLHARTLAETGRYGAVLGTAFV VNGGIYRHEFVASAVIDGMMNVQLSTGVPVLSAVLTPHRYR SSREHHEFFREHFMVKGVEAAAACITILAAREKIAA | I53-51B: 31, 35, 36, 40, 122, 124, 128, 131, 135, 139, 143, 146, 147 |
| I52-03A SEQ ID NO: 11 | (M)GHTKGPTPQQHDGSALRIGIVHARWNKTIIMPLLIGTI AKLLECGVKASNIVVQSVPGSWELPIAVQRLYSASQLQTPS SGPSLSAGDLLGSSTTDLTALPTTTASSTGPFDALIAIGVL IKGETMHFEYIADSVSHGLMRVQLDTGVPVIFGVLTVLTDD QAKARAGVIEGSHNHGEDWGLAAVEMGVRRRDWAAGKTE | I52-03A: 28, 32, 36, 39, 44, 49 |
| I52-03B SEQ ID NO: 12 | (M)YEVDHADVYDLFYLGRGKDYAAEASDIADLVRSRTPEA SSLLDVACGTGTHLEHFTKEFGDTAGLELSEDMLTHARKRL PDATLHQGDMRDFQLGRKFSAVVSMFSSVGYLKTVAELGAA VASFAEHLEPGGVVVVEPWWFPETFADGWVSADVVRRDGRT VARVSHSVREGNATRMEVHFTVADPGKGVRHFSDVHLITLF HQREYEAAFMAAGLRVEYLEGGPSGRGLFVGVPA | I52-03B: 94, 115, 116, 206, 213 |
| I52-32A SEQ ID NO: 13 | (M)GMKEKFVLIITHGDFGKGLLSGAEVIIGKQENVHTVGL NLGDNIEKVAKEVMRIIIAKLAEDKEIIIVVDLFGGSPFNI ALEMMKTFDVKVITGINMPMLVELLTSINVYDTTELLENIS KIGKDGIKVIEKSSLKM | I52-32A: 47, 49, 53, 54, 57, 58, 61, 83, 87, 88 |
| I52-32B SEQ ID NO: 14 | (M)KYDGSKLRIGILHARWNLEIIAALVAGAIKRLQEFGVK AENIIETVPGSFELPYGSKLFVEKQKRLGKPLDAIIPIGV LIKGSTMHFEYICDSTTHQLMKLNFELGIPVIFGVLTCLTD EQAEARAGLIEGKMHNHGEDWGAAAVEMATKFN | I52-32B: 19, 20, 23, 30, 40 |
| I52-33A SEQ ID NO: 15 | (M)AVKGLGEVDQKYDGSKLRIGILHARWNRKIILALVAGA VLRLLEFGVKAENIIIETVPGSFELPYGSKLFVEKQKRLGK PLDAIIPIGVLIKGSTMHFEYICDSTTHQLMKLNFELGIPV IFGVLTCLTDEQAEARAGLIEGKMHNHGEDWGAAAVEMATK FN | I52-33A: 33, 41, 44, 50 |
| I52-33B SEQ ID NO: 16 | (M)GANWYLDNESSRLSFTSTKNADIAEVHRFLVLHGKVDP KGLAEVEVETESISTGIPLRDMLLRVLVFQVSKFPVAQINA QLDMRPINNLAPGAQLELRLPLTVSLRGKSHSYNAELLATR | I52-33B: 61, 63, 66, 67, 72, 147, 148, 154, 155 |

TABLE 1-continued

| Name | Amino Acid Sequence | Identified interface residues |
|---|---|---|
| | LDERRFQVVTLEPLVIHAQDFDMVRAFNALRLVAGLSAVSL SVPVGAVLIFTAR | |
| I32-06A SEQ ID NO: 17 | (M)TDYIRDGSAIKALSFAIILAEADLRHIPQDLQRLAVRV IHACGMVDVANDLAFSEGAGKAGRNALLAGAPILCDARMVA EGITRSRLPADNRVIYTLSDPSVPELAKKIGNTRSAAALDL WLPHIEGSIVAIGNAPTALFRLFELLDGAPKPALIIGMPV GFVGAAESKDELAANSRGVPYVIVRGRRGGSAMTAAAVNAL ASERE | I32-06A: 9, 12, 13, 14, 20, 30, 33, 34 |
| I32-06B SEQ ID NO: 18 | (M)ITVFGLKSKLAPRREKLAEVIYSSLHLGLDIPKGKHAI RFLCLEKEDFYYPFDRSDDYTVIEINLMAGRSEETKMLLIF LLFIALERKLGIRAHDVEITIKEQPAHCWGFRGRTGDSARD LDYDIYV | I32-06B: 24, 71, 73, 76, 77, 80, 81, 84, 85, 88, 114, 118 |
| I32-19A SEQ ID NO: 19 | (M)GSDLQKLQRFSTCDISDGLLNVYNIPIGGYFPNLTAIS PPQNSSIVGTAYTVLFAPIDDPRPAVNYIDSVPPNSILVLA LEPHLQSQFHPFIKITQAMYGGLMSTRAQYLKSNGTVVFGR IRDVDEHRTLNHPVFAYGVGSCAPKAVVKAVGTNVQLKILT SDGVTQTICPGDYIAGDNNGIVRIPVQETDISKLVTYIEKS IEVDRLVSEAIKNGLPAKAAQTARRMVLKDYI | I32-19A: 208, 213, 218, 222, 225, 226, 229, 233 |
| I32-19B SEQ ID NO: 20 | (M)SGMRVYLGADHAGYELKQAIIAFLKMTGHEPIDCGALR YDADDDYPAFCIAAATRTVADPGSLGIVLGGSGNGEQIAAN KVPGARCALAWSVQTAALAREHNNAQLIGIGGRMHTLEEAL RIVKAFVTTPWSKAQRHQRRIDILAEYERTHEAPPVPGAPA | I32-19B: 20, 23, 24, 27, 117, 118, 122, 125 |
| I32-28A SEQ ID NO: 21 | (M)GDDARIAAIGDVDELNSQIGVLLAEPLPDDVRAALSAI QHDLFDLGGELCIPGHAAITEDHLLRLALWLVHYNGQLPPL EEFILPGGARGAALAHVCRTVCRRAERSIKALGAsEPLNIA PAAYVNLLSDLLFVLARVLNRAAGGADVLWDRTRAH | I32-28A: 60, 61, 64, 67, 68, 71, 110, 120, 123, 124, 128 |
| I32-28B SEQ ID NO: 22 | (M)ILSAEQSFTLRHPHGQAAALAFVREPAAALAGVQRLRG LDSDGEQVWGELLVRVPLLGEVDLPFRSEIVRTPQGAELRP LTLTGERAWVAVSGQATAAEGGEMAFAFQFQAHLATPEAEG EGGAAFEVMVQAAAGVTLLLVAMALPQGLAAGLPPA | I32-28B: 35, 36, 54, 122, 129, 137, 140, 141, 144, 148 |
| I53-40A.1 SEQ ID NO: 23 | (M)TKKVGIVDTTFARVDMASAAILTLKMESPNIKIIRKTV PGIKDLPVACKKLLEEEGCDIVMALGMPGKKEKDKVCAHEA SLGLMLAQLMTNKHIIEVFVHEDEAKDDAELKILAARRAIE HALNVYYLLFKPEYLTRMAGKGLRQGFEDAGPARE | I53-40A: 20, 23, 24, 27, 28, 109, 112, 113, 116, 120, 124 |
| I53-40B.1 SEQ ID NO: 24 | (M)DDINNQLKRLKVIPVIAIDNAEDIIPLGKVLAENGLPA AEITFRSSAAVKAIMLLRSAQPEMLIGAGTILNGVQALAAK EAGADFVVSPGFNPNTVRACQIIGIDIVPGVNNPSTVEQAL EMGLTTLKFFPAEASGGISMVKSLVGPYGDIRLMPTGGITP DNIDNYLAIPQVLACGGTWMVDKKLVRNGEWDEIARLTREI VEQVNP | I53-40B: 47, 51, 54, 58, 74, 102 |
| I53-47A.1 SEQ ID NO: 25 | (M)PIFTLNTNIKADDVPSDFLSLTSRLVGLILSKPGSYVA VHINTDQQLSFGGSTNPAAFGTLMSIGGIEPDKNRDHSAVL FDHLNAMLGIPKNRMYIHFVNLNGDDVGWNGTTF | I53-47A: 22, 25, 29, 72, 79, 86, 87 |
| I53-47A.1NegT2 SEQ ID NO: 26 | (M)PIFTLNTNIKADDVPSDFLSLTSRLVGLILSEPGSYVA VHINTDQQLSFGGSTNPAAFGTLMSIGGIEPDKNEDHSAVL FDHLNAMLGIPKNRMYIHFVDLDGDDVGWNGTTF | I53-47A: 22, 25, 29, 72, 79, 86, 87 |
| I53-47B.1 SEQ ID NO: 27 | (M)NQHSHKDHETVRIAVVRARWHADIVDACVEAFEIAMAA IGGDRFAVDVFDVPGAYEIPLHARTLAETGRYGAVLGTAFV VNGGIYRHEFVASAVIDGMMNVQLDTGVPVLSAVLTPHRYR DSDEHHRFFAAHFAVKGVEAARACIEILNAREKIAA | I53-47B: 28, 31, 35, 36, 39, 131, 132, 135, 139, 146 |
| I53-47B.1NegT2 SEQ ID NO: 28 | (M)NQHSHKDHETVRIAVVRARWHADIVDACVEAFEIAMAA IGGDRFAVDVFDVPGAYEIPLHARTLAETGRyGAVLGTAFV VDGGIYDHEFVASAVIDGMMNVQLDTGVPVLSAVLTPHEYE DSDEDHEFFAAHFAVKGVEAARACIEILNAREKIAA | I53-47B: 28, 31, 35, 36, 39, 131, 132, 135, 139, 146 |
| I53-50A.1 SEQ ID NO: 29 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPQFVKAMKGPFPNVKFVPTGGVNLD NVCEWFKAGVLAVGVGDALVKGDPDEVREKAKKFVEKIRGC TE | I53-50A: 25, 29, 33, 54, 57 |

TABLE 1-continued

| Name | Amino Acid Sequence | Identified interface residues |
|---|---|---|
| I53-50A.1NegT2 SEQ ID NO: 30 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPEFVEAMKGPFPNVKFVPTGGVDLD DVCEWFDAGVLAVGVGDALVEGDPDEVREDAKEFVEEIRGC TE | I53-50A: 25, 29, 33, 54, 57 |
| I53-50A.1PosT1 SEQ ID NO: 31 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPQFVKAMKGPFPNVKFVPTGGVNLD NVCKWFKAGVLAVGVGKALVKGKPDEVREKAKKFVKKIRGC TE | I53-50A: 25, 29, 33, 54, 57 |
| I53-50B.1 SEQ ID NO: 32 | (M)NQHSHKDHETVRIAVVRARWHAEIVDACVSAFEAAMRD IGGDRFAVDVFDVPGAYEIPLHARTLAETGRYGAVLGTAFV VNGGIYRHEFVASAVIDGMMNVQLDTGVPVLSAVLTPHRYR DSDAHILLFLALFAVKGMEAARACVEILAAREKIAA | I53-50B: 24, 28, 36, 124, 125, 127, 128, 129, 131, 132, 133, 135, 139 |
| I53-50B.1NegT2 SEQ ID NO: 33 | (M)NQHSHKDHETVRIAVVRARWHAEIVDACVSAFEAAMRD IGGDRFAVDVFDVPGAYEIPLHARTLAETGRYGAVLGTAFV VDGGIYDHEFVASAVIDGMMNVQLDTGVPVLSAVLTPHEYE DSDADTLLFLALFAVKGMEAARACVEILAAREKIAA | I53-50B: 24, 28, 36, 124, 125, 127, 128, 129, 131, 132, 133, 135, 139 |
| I53-50B.4PosT1 SEQ ID NO: 34 | (M)NQHSHKDHETVRIAVVRARWHAEIVDACVSAFEAAMRD IGGDRFAVDVFDVPGAYEIPLHARTLAETGRYGAVLGTAFV VNGGIYRHEFVASAVINGMMNVQLNTGVPVLSAVLTPHNYD KSKAHTLLFLALFAVKGMEAARACVEILAAREKIAA | I53-50B: 24, 28, 36, 124, 125, 127, 128, 129, 131, 132, 133, 135, 139 |

I53-40A genus
(SEQ ID NO: 35)
(M)TKKVGIVDTTFARVDMASAAILTLKMESPNIKIIRKTVPGIKDLPVACKKLLEEEGCDIVMA

LGMPGK(A/K)EKDKVCAHEASLGLMLAQLMTNKHIIEVFVHEDEAKDDAELKILAARRAIEHAL

NVYYLLFKPEYLTRMAGKGLRQGFEDAGPARE

I53-40B genus
(SEQ ID NO: 36)
(M)

(S/D)(T/D)INNQLK(A/R)LKVIPVIAIDNAEDIIPLGKVLAENGLPAAEITFRSSAAVKAIM

LLRSAQPEMLIGAGTILNGVQALAAKEAGA(T/D)FVVSPGFNPNTVRACQIIGIDIVPGVNNPS

TVE(A/Q)ALEMGLTTLKFFPAEASGGISMVKSLVGPYGDIRLMPTGGITP(S/D)NIDNYLAIP

QVLACGGTWMVDKKLV(T/R)NGEWDEIARLTREIVEQVNP

I53-47A genus
(SEQ ID NO: 37)
(M)PIFTLNTNIKA(T/D)DVPSDFLSLTSRLVGLILS(K/E)PGSYVAVHINTDQQLSFGGSTN

PAAFGTLMSIGGIEP(S/D)KN(R/E)DHSAVLFDHLNAMLGIPKNRMYIHFV(N/D)L(N/D)G

DDVGWNGTTF

I53-47B genus
(SEQ ID NO: 38)
(M)NQHSHKD(Y/H)ETVRIAVVRARWHADIVDACVEAFEIAMAAIGGDRFAVDVFDVPGAYEIP

LHARTLAETGRYGAVLGTAFVV(N/D)GGIY(R/D)HEFVASAVIDGMMNVQL(S/D)TGVPVLS

AVLTPH(R/E)Y(R/E)DS(A/D)E(H/D)H(R/E)FFAAHFAVKGVEAARACIEIL(A/N)ARE

KIAA

I53-50A genus
(SEQ ID NO: 39)
(M)KMEELFKKHKIVAVLRANSVEEAIEKAVAVFAGGVHLIEITFTVPDADTVIKALSVLKEKGA

IIGAGTVISVEQCRKAVESGAEFIVSPHLDEEISQFCKEKGVFYMPGVMTPTELVKAMKLGH(T/

-continued

D)ILKLFPGEVVGP(Q/E)FV(K/E)AMKGPFPNVKFVPTGGV(N/D)LD(N/D)VC(E/K)WF (K/D)AGVLAVGVG(S/K/D)ALV(K/E)G(T/D/K)PDEVRE(K/D)AK(A/E/K)FV(E/K)

(K/E)IRGCTE

I53-50B genus
(SEQ ID NO: 40)
(M)NQHSHKD(Y/H)ETVRIAVVRARWHAEIVDACVSAFEAAM(A/R)DIGGDRFAVDVFDVPGA

YEIPLHARTLAETGRYGAVLGTAFVV(N/D)GGIY(R/D)HEFVASAVI(D/N)GMMNVQL(S/

D/N)TGVPVLSAVLTPH(R/E/N)Y(R/D/E)(D/K)S(D/K)A(H/D)TLLFLALFAVKGMEAA

RACVEILAAREKIAA

T32-28A
(SEQ ID NO: 41)
(M)GEVPIGDPKELNGMEIAAVYLQPIEMEPRGIDLAASLADIHLEADIHALKNNPNGFPEGFWM

PYLTIAYALANADTGAIKTGTLMPMVADDGPHYGANIAMEKDKKGGFGVGTYALTFLISNPEKQG

FGRHVDEETGVGKWFEPFVVTYFFKYTGTPK

T32-28B
(SEQ ID NO: 42)
(M)SQAIGILELTSIAKGMELGDAMLKSANVDLLVSKTISPGKFLLMLGGDIGAIQQAIETGTSQ

AGEMLVDSLVLANIHPSVLPAISGLNSVDKRQAVGIVETWSVAACISAADLAVKGSNVTLVRVHM

AFGIGGKCYMVVAGDVLDVAAAVATASLAAGAKGLLVYASIIPRPHEAMWRQMVEG

T33-09A
(SEQ ID NO: 43)
(M)EEVVLITVPSALVAVKIAHALVEERLAACVNIVPGLTSIYRWQGSVVSDHELLLLVKTTTHA

FPKLKERVKALHPYTVPEIVALPIAEGNREYLDWLRENTG

T33-09B
(SEQ ID NO: 44)
(M)VRGIRGAITVEEDTPAAILAATIELLLKMLEANGIQSYEELAAVIFTVTEDLTSAFPAEAAR

LIGMHRVPLLSAREVPVPGSLPRVIRVLALWNTDTPQDRVRHVYLNEAVRLRPDLESAQ

T33-15A
(SEQ ID NO: 45)
(M)SKAKIGIVTVSDRASAGITADISGKAIILALNLYLTSEWEPIYQVIPDEQDVIETTLIKMAD

EQDCCLIVTIGGIGPAKRDVTPEATEAVCDRMMPGFGELMRAESLKEVPTAILSRQTAGLRGDSL

IVNLPGDPASISDCLLAVFPAIPYCIDLMEGPYLECNEAMIKPFRPKAK

T33-15B
(SEQ ID NO: 46)
(M)VRGIRGAITVNSDTPTSIIIATILLLEKMLEANGIQSYEELAAVIFTVTEDLTSAFPAEAAR

QIGMHRVPLLSAREVPVPGSLPRVIRVLALWNTDTPQDRVRHVYLSEAVRLRPDLESAQ

T33-21A
(SEQ ID NO: 47)
(M)RITTKVGDKGSTRLFGGEEVWKDSPIIEANGTLDELTSFIGEAKHYVDEEMKGILEEIQNDI

YKIMGEIGSKGKIEGISEERIAWLLKLILRYMEMVNLKSFVLPGGTLESAKLDVCRTIARRALRK

VLIVTREFGIGAEAAAYLLALSDLLFLLARVIEIEKNKLKEVRS

T33-21B
(SEQ ID NO: 48)
(M)PHLVIEATANLRLETSPGELLEQANKALFASGQFGEADIKSRFVTLEAYRQGTAAVERAYLH

ACLSILDGRDIATRTLLGASLCAVLAEAVAGGGEEGVQVSVEVREMERLSYAKRVVARQR

T33-28A
(SEQ ID NO: 49)
(M)ESVNTSFLSPSLVTIRDFDNGQFAVLRIGRTGFPADKGDIDLCLDKMIGVRAAQIFLGDDTE

DGFKGPHIRIRCVDIDDKHTYNAMVYVDLIVGTGASEVERETAEEEAKLALRVALQVDIADEHSC

VTQFEMKLREELLSSDSFHPDKDEYYKDFL

```
T33-28B
                                                  (SEQ ID NO: 50)
(M)PVIQTFVSTPLDHHKRLLLAIIYRIVTRVVLGKPEDLVMMTFHDSTPMHFFGSTDPVACVRV

EALGGYGPSEPEKVTSIVTAAITAVCGIVADRIFVLYFSPLHCGWNGTNF

T33-31A
                                                  (SEQ ID NO: 51)
(M)EEVVLITVPSALVAVKIAHALVEERLAACVNIVPGLTSIYREEGSVVSDHELLLLVKITTDA

FPKLKERVKELHPYEVPEIVALPIAEGNREYLDWLRENTG
```

Table 1 provides the amino acid sequence of the first and second polypeptides; the right hand column in Table 1 identifies the residue numbers in each exemplary polypeptide that were identified as present at the interface of resulting assembled nanostructures (i.e.: "identified interface residues"). As can be seen, the number of interface residues for the exemplary polypeptides of SEQ ID NO:1-34 range from 4-13. In various embodiments, the first and second polypeptides comprise an amino acid sequence that is at least 75%, 80%, 85%, 90%, 91%, 92%, 93%, 94%, 95%, 96%, 97%, 98%, or 99% identical over its length, and identical at least at 1, 2, 3, 4, 5, 6, 7, 8, 9, 10, 11, 12, or 13 identified interface positions (depending on the number of interface residues for a given polypeptide), to the amino acid sequence of a polypeptide selected from the group consisting of SEQ ID NOS: 1-34. In other embodiments, the first and second polypeptides comprise an amino acid sequence that is at least 75%, 80%, 85%, 90%, 91%, 92%, 93%, 94%, 95%, 96%, 97%, 98%, or 99% identical over its length, and identical at least at 20%, 25%, 33%, 40%, 50%, 60%, 70%, 75%, 80%, 90%, or 100% of the identified interface positions, to the amino acid sequence of a polypeptide selected from the group consisting of SEQ ID NOS:1-51.

As is the case with proteins in general, the polypeptides are expected to tolerate some variation in the designed sequences without disrupting subsequent assembly into nanostructures: particularly when such variation comprises conservative amino acid substitutions. As used here, "conservative amino acid substitution" means that: hydrophobic amino acids (Ala, Cys, Gly, Pro, Met, See, Sme, Val, Ile, Leu) can only be substituted with other hydrophobic amino acids; hydrophobic amino acids with bulky side chains (Phe, Tyr, Trp) can only be substituted with other hydrophobic amino acids with bulky side chains; amino acids with positively charged side chains (Arg, His, Lys) can only be substituted with other amino acids with positively charged side chains; amino acids with negatively charged side chains (Asp, Glu) can only be substituted with other amino acids with negatively charged side chains; and amino acids with polar uncharged side chains (Ser, Thr, Asn, Gln) can only be substituted with other amino acids with polar uncharged side chains.

Table 2 lists surface amino acid residue numbers for each exemplary polypeptide of the invention denoted by SEQ ID NOS: 1-34. Thus, in various embodiments, 1 or more (at least 1, 2, 3, 4, 5, 6, 7, 8, 9, 10, 11, 12, 13, 14, 15, 16, 17, 18, 19, 20, 21, 22, 23, 24, 25, 26, 27 28, 29, 30, 31, 32, 33, 34, 35, 36, 37, 38, 39, 40, 41, 42, 43, 44, 45, 46, 47, 48, 49, 50, or more) of these surface residues may be modified in the polypeptides of the invention. Residues in parentheses are optional.

TABLE 2

| Name | Amino Acid Sequence | Surface residues not near interface |
|---|---|---|
| I53-34A SEQ ID NO: 1 | (m)EGMDPLAVLAESRLLPLLTVRGGEDLAGLATVLELMGV GALEITLRTEKGLEALKALRKSGLLLGAGTVRSPKEAEAAL EAGAAFLVSPGLLEEVAALAQARGVPYLPGVLTPTEVERAL ALGLSALKFFPAEPFQGVRVLRAYAEVFPEVRFLPTGGIKE EHLPHYAALPNLLAVGGSWLLQGDLAAVMKKVKAAKALLSP QAPG | I53-34A: 6, 8, 9, 12, 14, 22, 25, 48, 49, 50, 52, 53, 56, 73, 74, 81, 94, 95, 101, 102, 103, 104, 119, 122, 137, 140, 143, 147, 150, 151, 153, 161, 162, 163, 164, 166, 167, 170, 172, 184, 193, 198, 199, 200, 202 |
| I53-34B SEQ ID NO: 2 | (m)TKKVGIVDTTFARVDMAEAAIRTLKALSPNIKIIRKTV PGIKDLPVACKKLLEEEGCDIVMALGMPGKAEKDKVCAHEA SLGLMLAQLMTNKHIIEVFVHEDEAKDDDELDILALVRAIE HAANVYYLLFKPEYLTRMAGKGLRQGREDAGPARE | I53-34B: 3, 12, 31, 33, 35, 36, 51, 54, 55, 56, 59, 69, 70, 71, 74, 93, 103, 106, 107, 108, 131, 132, 133, 134, 138, 142, 153 |
| I53-40A SEQ ID NO: 3 | (m)TKKVGIVDTTFARVDMASAAILTLKMESPNIKIIRKTV PGIKDLPVACKKLLEEEGCDIVMALGMPGKAEKDKVCAHEA SLGLMLAQLMTNKHIIEVFVHEDEAKDDAELKILAARRAIE HALNVYYLFKPEYLTRMAGKGLRQGFEDAGPARE | I53-40A: 3, 4, 31, 33, 35, 36, 37, 51, 54, 55, 56, 57, 59, 69, 70, 71, 74, 93, 103, 106, 118, 127, 128, 131, 132, 133, 134, 135, 138, 139, 142, 150, 153 |
| I53-40B SEQ ID NO: 4 | (M)STINNQLKALKVIPVIAIDNAEDIIPLGKVLAENGLPA AEITFRSSAAVKAIMLLRSAQPEMLIGAGTILNGVQALAAK EAGATFVVSPGFNPNTVRACQIIGIDIVPGVNNPSTVEAAL EMGLTTLKFFPAEASGGISMVKSLVGPYGDIRLMPTGGITP SNIDNYLAIPQVLACGGTWMVDKKLVINGEWDEIARLTREI VEQVNP | I53-40B: 2, 3, 7, 9, 10, 12, 20, 21, 23, 26, 27, 30, 34, 38, 45, 60, 62, 75, 85, 94, 95, 122, 124, 126, 134, 139, 143, 151, 153, 161, 163, 166, 167, 170, 172, 180, 184, 185, 186, 189, 190, 192, 193, |

TABLE 2-continued

| Name | Amino Acid Sequence | Surface residues not near interface |
|---|---|---|
| | | 194, 195, 198, 201, 202, 205, 208, 209 |
| I53-47A SEQ ID NO: 5 | (M)PIFTLNTNIKATDVPSDFLSLTSRLVGLILSKPGSYVA VHINTDQQLSFGGSTNPAAFGTLMSIGGIEPSKNRDHSAVL FDHLNAMLGIPKNRMYIHFVNLNGDDVGWNGTTF | I53-47A: 11, 13, 14, 17, 34, 36, 37, 45, 47, 54, 55, 56, 65, 69, 70, 71, 74, 91, 92, 93, 101, 103, 105, 109, 110, 112, 114 |
| I53-47B SEQ ID NO: 6 | (m)NQHSHKDYETVRIAVVRARWHADIVDACVEAFEIAMAA IGGDRFAVDVFDVPGAYEIPLHARTLAETGRYGAVLGTAFV VNGGIYRHEFVASAVIDGMMNVQLSTGVPVLSAVLTPHRYR DSAEHHRFFAAHFAVKGVEAARACIEILAAREKIAA | I53-47B: 6, 7, 8, 9, 10, 11, 13, 18, 20, 21, 24, 43, 44, 51, 63, 67, 70, 85, 87, 101, 105, 122, 123, 124, 125, 126, 147, 152, 153, 154 |
| I53-50A SEQ ID NO: 7 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHTILKLFPGEVVGPQFVKAMKGPFPNVKFVPTGGVNLD NVCEWFKAGVLAVGVGSALVKGTPDEVREKAKAFVEKIRGC TE | I53-50A: 4, 5, 6, 8, 9, 11, 17, 19, 23, 37, 46, 47, 59, 74, 77, 78, 81, 94, 95, 98, 101, 102, 103, 106, 119, 122, 126, 139, 142, 145, 149, 150, 152, 160, 161, 162, 163, 166, 169, 179, 183, 185, 188, 191, 192, 194, 198, 199 |
| I53-50B SEQ ID NO: 8 | (M)NQHSHKDYETVRIAVVRARWHAEIVDACVSAFEAAMAD IGGDRFAVDVFDVPGAYEIPLHARTLAETGRYGAVLGTAFV VNGGIYRHEFVASAVIDGMMNVQLSTGVPVLSAVLTPHRYR DSDAHILLFLALFAVKGMEAARACVEILAAREKIAA | I53-50B: 6, 7, 8, 9, 10, 11, 13, 18, 20, 21, 34, 38, 39, 40, 43, 44, 48, 51, 63, 67, 70, 87, 101, 105, 118, 143, 147, 152, 153, 154 |
| I53-51A SEQ ID NO: 9 | (M)FIKSGDDGNINVINKRVGKDSPLVNFLGDLDELNSFIG FAISKIPWEDMKKDLERVQVELFEIGEDLSTQSSKKKIDES YVLWLLAATAIYRIESGPVKLFVIPGGSEEASVLHVTRSVA RRVERNAVKYTKELPEINRMIIVYLNRLSSLLFAMALVANK RRNQSEKIYEIGKSW | I53-51A: 19, 20, 24, 28, 46, 47, 51, 70, 71, 73, 74, 75, 76, 102, 122, 130, 133, 134, 135, 136, 137, 140, 162, 163, 164, 165, 169, 175, 177 |
| I53-51B SEQ ID NO: 10 | (M)NQHSHKDYETVRIAVVRARWHADIVDQCVRAFEEAMAD AGGDRFAVDVFDVPGAYEIPLHARTLAETGRYGAVLGTAFV VNGGIYRHEFVASAVIDGMMNVQLSTGVPVLSAVLTPHRYR SSREHHEFFREHFMVKGVEAAAACITILAAREKIAA | I53-51B: 6, 7, 8, 9, 10, 11, 13, 18, 21, 27, 34, 38, 43, 48, 63, 67, 70, 85, 87, 101, 118, 125, 126, 129, 152, 153, 154 |
| I52-03A SEQ ID NO: 11 | (M)GHTKGPTPQQHDGSALRIGIVHARWNKTIIMPLLIGTI AKLLECGVKASNIVVQSVPGSWELPIAVQRLYSASQLQTPS SGPSLSAGDLLGSSTTDLTALPTTTASSTGPFDALIAIGVL IKGETMHFEYIADSVSHGLMRVQLDTGVPVIFGVLTVLTDD QAKARAGVIEGSHNHGEDWGLAAVEMGVRRRDWAAGKTE | I52-03A: 6, 9, 10, 11, 13, 15, 16, 26, 48, 69, 75, 76, 78, 79, 111, 125, 127, 142, 146, 159, 160, 161, 162, 171, 175, 193, 194, 196, 197, 199, 200 |
| I52-03B SEQ ID NO: 12 | (M)YEVDHADVYDLFYLGRGKDYAAEASDIADLVRSRTPEA SSLLDVACGTGTHLEHFTKEFGDTAGLELSEDMLTHARKRL PDATLHQGDMRDFQLGRKFSAVVSMFSSVGYLKTVAELGAA VASFAEHLEPGGVVVVEPWWFPETFADGWVSADVVRRDGRT VARVSHSVREGNATRMEVHFTVADPGKGVRHFSDVHLITLF HQREYEAAFMAAGLRVEYLEGGPSGRGLFVGVPA | I52-03B: 2, 3, 5, 6, 8, 15, 17, 20, 22, 23, 26, 27, 30, 33, 34, 35, 37, 38, 40, 54, 55, 57, 58, 59, 61, 62, 68, 70, 71, 74, 77, 78, 79, 81, 82, 84, 86, 87, 91, 96, 97, 98, 111, 127, 130, 131, 132, 141, 144, 145, 148, 150, 154, 157, 158, 159, 160, 161, 171, 172, 173, 174, 177, 187, 189, 192, 198, 199, 222, 223, 224, 236 |
| I52-32A SEQ ID NO: 13 | (M)GMKEKFVLIITHGDFGKGLLSGAEVIIGKQENVHTVGL NLGDNIEKVAKEVMRIIAKLAEDKEIIIVVDLFGGSPFNI ALEMMKTFDVKVITGINMPMLVELLTSINVYDTTELLENIS KIGKDGIKVIEKSSLKM | I52-32A: 3, 5, 15, 18, 30, 32, 35, 40, 41, 42, 44, 45, 65, 73, 79, 91, 103, 106, 109, 110, 111, 112, 114, 115, 118, 122, 123, 125, 126, 129, 131 |
| I52-32B SEQ ID NO: 14 | (M)KYDGSKLRIGILHARWNLEIIAALVAGAIKRLQEFGVK AENIIIETVPGSFELPYGSKLFVEKQKRLGKPLDAIIPIGV LIKGSTMHFEYICDSTTHQLMKLNFELGIPVIFGVLTCLTD | I52-32B: 4, 6, 7, 9, 17, 32, 35, 42, 59, 63, 64, 66, |

TABLE 2-continued

| Name | Amino Acid Sequence | Surface residues not near interface |
|---|---|---|
| | EQAEARAGLIEGKMHNHGEDWGAAAVEMATKFN | 67, 68, 69, 70, 71, 73, 83, 85, 90, 106,<br>119, 120, 121, 122, 125, 131, 133, 134, 135, 136, 154 |
| I52-33A<br>SEQ ID<br>NO: 15 | (M)AVKGLGEVDQKYDGSKLRIGILHARWNRKIILALVAGA<br>VLRLLEFGVKAENIIIETVPGSFELPYGSKLFVEKQKRLGK<br>PLDAIIPIGVLIKGSTMHFEYICDSTTHQLMKLNFELGIPV<br>IFGVLTCLTDEQAEARAGLIEGKMHNHGEDWGAAAVEMATK<br>FN | I52-33A:<br>12, 14, 16, 17, 19, 26, 27, 46, 69<br>73, 74, 76, 77, 78, 80, 81, 83, 93,<br>95, 100, 116, 129, 130, 131,<br>132, 145, 164 |
| I52-33B<br>SEQ ID<br>NO: 16 | (M)GANWYLDNESSRLSFTSTKNADIAEVHRFLVLHGKVDP<br>KGLAEVEVETESISTGIPLRDMLLRVLVFQVSKFPVAQINA<br>QLDMRPINNLAPGAQLELRLPLTVSLRGKSHSYNAELLATR<br>LDERRFQVVTLEPLVIHAQDFDMVRAFNALRLVAGLSAVSL<br>SVPVGAVLIFTAR | I52-33B:<br>4, 6, 10, 20, 21, 23, 24, 31, 32,<br>34, 36,<br>39, 40, 42, 44, 46, 48, 56, 73, 77,<br>81, 83, 85, 88, 89, 91, 92, 96, 97,<br>99,<br>101, 103, 109, 110, 111, 112, 114,<br>124, 125, 138, 140, 143, 158, 175 |
| I32-06A<br>SEQ ID<br>NO: 17 | (M)TDYIRDGSAIKALSFAIILAEADLRHIPQDLQRLAVRV<br>IHACGMVDVANDLAFSEGAGKAGRNALLAGAPILCDARMVA<br>EGITRSRLPADNRVIYTLSDPSVPELAKKIGNTRSAAALDL<br>WLPHIEGSIVAIGNAPTALFRLFELLDAGAPKPALIIGMPV<br>GFVGAAESKDELAANSRGVPYVIVRGRRGGSAMTAAAVNAL<br>ASERE | I32-06A:<br>24, 26, 27, 41, 47, 50, 51, 56, 60,<br>63, 64, 67, 68, 77, 84, 85, 86, 91,<br>93, 98, 99,<br>100, 101, 102, 105, 108, 109, 114,<br>123, 124, 125, 127, 135, 142, 145,<br>148, 149, 152, 153, 169, 172, 173,<br>176, 177, 180, 187, 189 |
| I32-06B<br>SEQ ID<br>NO: 18 | (M)ITVFGLKSKLAPRREKLAEVIYSSLHLGLDIPKGKHAI<br>RFLCLEKEDFYYPFDRSDDYTVIEINLMAGRSEETKMLLIF<br>LLFIALERKLGIRAHDVEITIKEQPAHCWGFRGRTGDSARD<br>LDYDIYV | I32-06B:<br>8, 9, 10, 13, 14, 15, 16, 17, 20,<br>34, 36,<br>45, 46, 47, 50, 51, 53, 54, 57, 67,<br>70, 91, 93, 95, 105, 112 |
| I32-19A<br>SEQ ID<br>NO: 19 | (M)GSDLQKLQRFSTCDISDGLLNVYNIPIGGYFPNLTAIS<br>PPQNSSIVGTAYTVLFAPIDDPRPAVNYIDSVPPNSILVLA<br>LEPHLQSQFHPFIKITQAMYGGLMSTRAQYLKSNGTVVFGR<br>IRDVDEHRTLNHPVFAYGVGSCAPKAVVKAVGTNVQLKILT<br>SDGVTQTICPGDYIAGDNNGIVRIPVQETDISKLVTYIEKS<br>IEVDRLVSEAIKNGLPAKAAQTARRMVLKDYI | I32-19A:<br>3, 4, 6, 7, 9, 10, 25, 27, 36, 40,<br>42, 43, 44, 49, 58, 59, 61, 62, 63,<br>70, 72, 73, 74,<br>82, 84, 88, 89, 109, 110, 112, 126,<br>127, 129, 130, 132, 146, 155,<br>156, 157,<br>159, 166, 169, 172, 189, 190, 192,<br>194, 195, 198, 201, 204, 215, 232 |
| I32-19B<br>SEQ ID<br>NO: 20 | (M)SGMRVYLGADHAGYELKQAIIAFLKMTGHEPIDCGALR<br>YDADDDYPAFCIAAATRTVADPGSLGIVLGGSGNGEQIAAN<br>KVPGARCALAWSVQTAALAREHNNAQLIGIGGRMHTLEEAL<br>RIVKAFVTTPWSKAQRHQRRIDILAEYERTHEAPPVPGAPA | I32-19B:<br>4, 5, 31, 33, 38, 41, 42, 43, 55,<br>56, 59,<br>61, 62, 83, 93, 94, 101, 104, 113,<br>119, 129, 131, 134, 136, 137,<br>139, 140,<br>143, 144, 146, 147, 150, 152, 153,<br>156, 158, 159 |
| I32-28A<br>SEQ ID<br>NO: 21 | (M)GDDARIAAIGDVDELNSQIGVLLAEPLPDDVRAALSAI<br>QHDLFDLGGELCIPGHAAITEDHLLRLALWLVHYNGQLPPL<br>EEFILPGGARGAALAHVCRTVCRRAERSIKALGASEPLNIA<br>PAAYVNLLSDLLFVLARVLNRAAGGADVLWDRTRAH | I32-28A:<br>4, 6, 7, 10, 14, 27, 30, 31, 33, 34,<br>41, 44, 45, 51, 52, 53, 54, 55, 56,<br>59, 76, 78, 79, 80, 81, 82, 83, 90,<br>103, 111, 115, 116, 131, 134,<br>142, 145, 147, 150 |
| I32-28B<br>SEQ ID<br>NO: 22 | (M)ILSAEQSFTLRHPHGQAAALAFVREPAAALAGVQRLRG<br>LDSDGEQVWGELLRVPLLGEVDLPFRSEIVRTPQGAELRP<br>LTLTGERAWVAVSGQATAAEGGEMAFAFQFQAHLATPEAEG<br>EGGAAFEVMVQAAAGVTLLLVAMALPQGLAAGLPPA | I32-28B:<br>3, 4, 6, 8, 12, 15, 17, 18, 22, 26,<br>28, 32,<br>38, 39, 41, 43, 45, 46, 48, 50, 60,<br>66, 68, 71, 73, 74, 79, 81, 82, 83,<br>84, 86, 87,<br>95, 100, 103, 105, 109, 111, 113,<br>151, 152, 155, 156, 157 |
| I53-<br>40A.1<br>SEQ ID<br>NO: 23 | (M)TKKVGIVDTTFARVDMASAAILTLKMESPNIKIIRKTV<br>PGIKDLPVACKKLLEEEGCDIVMALGMPGKKEKDKVCAHEA<br>SLGLMLAQLMTNKHIIEVFVHEDEAKDDAELKILAARRAIE<br>HALNVYYLLFKPEYLTRMAGKGLRQGFEDAGPARE | I53-40A:<br>3, 4, 31, 33, 35, 36, 37, 51, 54,<br>55, 56,<br>57, 59, 69, 70, 71, 74, 93, 103,<br>106,<br>118, 127, 128, 131, 132, 133, 134,<br>135, 138, 139, 142, 150, 153 |

TABLE 2-continued

| Name | Amino Acid Sequence | Surface residues not near interface |
|---|---|---|
| I53-40B.1 SEQ ID NO: 24 | (M)DDINNQLKRLKVIPVIAIDNAEDIIPLGKVLAENGLPA AEITFRSSAAVKAIMLLRSAQPEMLIGAGTILNGVQALAAK EAGADFVVSPGFNPNTVRACQIIGIDIVPGVNNPSTVEQAL EMGLTTLKFFPAEASGGISMVKSLVGPYGDIRLMPTGGITP DNIDNYLAIPQVLACGGTWMVDKKLVRNGEWDEIARLTREI VEQVNP | I53-40B: 2, 3, 7, 9, 10, 12, 20, 21, 23, 26, 27, 30, 34, 38, 45, 60, 62, 75, 85, 94, 95, 122, 124, 126, 134, 139, 143, 151, 153, 161, 163, 166, 167, 170, 172, 180, 184, 185, 186, 189, 190, 192, 193, 194, 195, 198, 201, 202, 205, 208, 209 |
| I53-47A.1 SEQ ID NO: 25 | (M)PIFTLNTNIKADDVPSDFLSLTSRLVGLILSKPGSYVA VHINTDQQLSFGGSTNPAAFGTLMSIGGIEPDKNRDHSAVL FDHLNAMLGIPKNRMYIHFVNLNGDDVGWNGTTF | I53-47A: 11, 13, 14, 17, 34, 36, 37, 45, 47, 54, 55, 56, 65, 69, 70, 71, 74, 91, 92, 93, 101, 103, 105, 109, 110, 112, 114 |
| I53-47A.1NegT2 SEQ ID NO: 26 | (M)PIFTLNTNIKADDVPSDFLSLTSRLVGLILSEPGSYVA VHINTDQQLSFGGSTNPAAFGTLMSIGGIEPDKNEDHSAVL FDHLNAMLGIPKNRMYIHFVDLDGDDVGWNGTTF | I53-47A: 11, 13, 14, 17, 34, 36, 37, 45, 47, 54, 55, 56, 65, 69, 70, 71, 74, 91, 92, 93, 101, 103, 105, 109, 110, 112, 114 |
| I53-47B.1 SEQ ID NO: 27 | (M)NQHSHKDHETVRIAVVRARWHADIVDACVEAFEIAMAA IGGDRFAVDVEDVPGAYEIPLHARTLAETGRYGAVLGTAFV VNGGIYRHEFVASAVIDGMMNVQLDTGVPVLSAVLTPHRYR DSDEHHRFFAAHFAVKGVEAARACIEILNAREKIAA | I53-47B: 6, 7, 8, 9, 10, 11, 13, 18, 20, 21, 24, 43, 44, 51, 63, 67, 70, 85, 87, 101, 105, 122, 123, 124, 125, 126, 147, 152, 153, 154 |
| I53-47B.1NegT2 SEQ ID NO: 28 | (M)NQHSHKDHETVRIAVVRARWHADIVDACVEAFEIAMAA IGGDRFAVDVEDVPGAYEIPLHARTLAETGRYGAVLGTAFV VDGGIYDHEFVASAVIDGMMNVQLDTGVPVLSAVLTPHEYE DSDEDHEFFAAHFAVKGVEAARACIEILNAREKIAA | I53-47B: 6, 7, 8, 9, 10, 11, 13, 18, 20, 21, 24, 43, 44, 51, 63, 67, 70, 85, 87, 101, 105, 122, 123, 124, 125, 126, 147, 152, 153, 154 |
| I53-50A.1 SEQ ID NO: 29 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPQFVKAMKGPFPNVKFVPTGGVNLD NVCEWFKAGVLAVGVGDALVKGDPDEVREKAKKFVEKIRGC TE | I53-50A: 4, 5, 6, 8, 9, 11, 17, 19, 23, 37, 46, 47, 59, 74, 77, 78, 81, 94, 95, 98, 101, 102, 103, 106, 119, 122, 126, 139, 142, 145, 149, 150, 152, 160, 161, 162, 163, 166, 169, 179, 183, 185, 188, 191, 192, 194, 198, 199 |
| I53-50A.1NegT2 SEQ ID NO: 30 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPEFVEAMKGPFPNVKFVPTGGVDLD DVCEWFDAGVLAVGVGDALVEGDPDEVREDAKEFVEEIRGC TE | I53-50A: 4, 5, 6, 8, 9, 11, 17, 19, 23, 37, 46, 47, 59, 74, 77, 78, 81, 94, 95, 98, 101, 102, 103, 106, 119, 122, 126, 139, 142, 145, 149, 150, 152, 160, 161, 162, 163, 166, 169, 179, 183, 185, 188, 191, 192, 194, 198, 199 |
| I53-50A.1PosT1 SEQ ID NO: 31 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPQFVKAMKGPFPNVKFVPTGGVNLD NVCKWFKAGVLAVGVGKALVKGKPDEVREKAKKFVKKIRGC TE | I53-50A: 4, 5, 6, 8, 9, 11, 17, 19, 23, 37, 46, 47, 59, 74, 77, 78, 81, 94, 95, 98, 101, 102, 103, 106, 119, 122, 126, 139, 142, 145, 149, 150, 152, 160, 161, 162, 163, 166, 169, 179, 183, 185, 188, 191, 192, 194, 198, 199 |
| I53-50B.1 SEQ ID NO: 32 | (M)NQHSHKDHETVRIAVVRARWHAEIVDACVSAFEAAMRD IGGDRFAVDVEDVPGAYEIPLHARTLAETGRYGAVLGTAFV VNGGIYRHEFVASAVIDGMMNVQLDTGVPVLSAVLTPHRYR DSDAHILLFLALFAVKGMEAARACVEILAAREKIAA | I53-50B: 6, 7, 8, 9, 10, 11, 13, 18, 20, 21, 34, 38, 39, 40, 43, 44, 48, 51, 63, 67, 70, 87, 101, 105, 118, 143, 147, 152, 153, 154 |
| I53-50B.1NegT2 SEQ ID NO: 33 | (M)NQHSHKDHETVRIAVVRARWHAEIVDACVSAFEAAMRD IGGDRFAVDVEDVPGAYEIPLHARTLAETGRYGAVLGTAFV VDGGIYDHEFVASAVIDGMMNVQLDTGVPVLSAVLTPHEYE DSDADTLLFLALFAVKGMEAARACVEILAAREKIAA | I53-50B: 6, 7, 8, 9, 10, 11, 13, 18, 20, 21, 34, 38, 39, 40, 43, 44, 48, 51, 63, 67, 70, 87, 101, 105, 118, 143, 147, 152, 153, 154 |
| I53-50B.4PosT1 | (M)NQHSHKDHETVRIAVVRARWHAEIVDACVSAFEAAMRD IGGDRFAVDVEDVPGAYEIPLHARTLAETGRYGAVLGTAFV | I53-50B: 6, 7, 8, 9, 10, 11, 13, 18, 20, 21, |

TABLE 2-continued

| Name | Amino Acid Sequence | Surface residues not near interface |
|---|---|---|
| SEQ ID NO: 34 | VNGGIYRHEEVASAVINGMMNVQLNTGVPVLSAVLTPHNYD KSKAHTLLFLALFAVKGMEAARACVEILAAREKIAA | 34, 38, 39, 40, 43, 44, 48, 51, 63, 67, 70, 87, 101, 105, 118, 143, 147, 152, 153, 154 |

In various embodiments of the nanostructure of the invention, the first polypeptides and the second polypeptides comprise polypeptides with the amino acid sequence selected from the following pairs, or modified versions thereof (i.e.: permissible modifications as disclosed for the polypeptides of the invention: isolated polypeptides comprising an amino acid sequence that is at least 75% 80%, 85%, 90%, 91%, 92%, 93%, 94%, 95%, 96%, 97%, 98%, 99%, or 100% identical over its length, and/or identical at least at one identified interface position, to the amino acid sequence indicated by the SEQ ID NO.):

SEQ ID NO:1 and SEQ ID NO:2 (I53-34A and I53-34B);
SEQ ID NO:3 and SEQ ID NO:4 (I53-40A and I53-40B);
SEQ ID NO:3 and SEQ ID NO:24 (I53-40A and I53-40B.1);
SEQ ID NO:23 and SEQ ID NO:4 (I53-40A.1 and I53-40B);
SEQ ID NO:35 and SEQ ID NO:36 (I53-40A genus and I53-40B genus);
SEQ ID NO:5 and SEQ ID NO:6 (I53-47A and I53-47B);
SEQ ID NO:5 and SEQ ID NO:27 (I53-47A and I53-47B.1);
SEQ ID NO:5 and SEQ ID NO:28 (I53-47A and I53-47B.1NegT2);
SEQ ID NO:25 and SEQ ID NO:6 (I53-47A.1 and I53-47B);
SEQ ID NO:25 and SEQ ID NO:27 (I53-47A.1 and I53-47B.1);
SEQ ID NO:25 and SEQ ID NO:28 (I53-47A.1 and I53-47B.1NegT2);
SEQ ID NO:26 and SEQ ID NO:6 (I53-47A.1NegT2 and I53-47B);
SEQ ID NO:26 and SEQ ID NO:27 (I53-47A.1NegT2 and I53-47B.1);
SEQ ID NO:26 and SEQ ID NO:28 (I53-47A.1NegT2 and I53-47B.1NegT2);
SEQ ID NO:37 and SEQ ID NO:38 (I53-47A genus and I53-47B genus);
SEQ ID NO:7 and SEQ ID NO:8 (I53-50A and I53-50B);
SEQ ID NO:7 and SEQ ID NO:32 (I53-50A and I53-50B.1);
SEQ ID NO:7 and SEQ ID NO:33 (I53-50A and I53-50B.1NegT2);
SEQ ID NO:7 and SEQ ID NO:34 (I53-50A and I53-50B.4PosT1);
SEQ ID NO:29 and SEQ ID NO:8 (I53-50A.1 and I53-50B);
SEQ ID NO:29 and SEQ ID NO:32 (I53-50A.1 and I53-50B.1);
SEQ ID NO:29 and SEQ ID NO:33 (I53-50A.1 and I53-50B.1NegT2);
SEQ ID NO:29 and SEQ ID NO:34 (I53-50A.1 and I53-50B.4PosT1);
SEQ ID NO:30 and SEQ ID NO:8 (I53-50A.1NegT2 and I53-50B);
SEQ ID NO:30 and SEQ ID NO:32 (I53-50A.1NegT2 and I53-50B.1);
SEQ ID NO:30 and SEQ ID NO:33 (I53-50A.1NegT2 and I53-50B.1NegT2);
SEQ ID NO:30 and SEQ ID NO:34 (I53-50A.1NegT2 and I53-50B.4PosT1);
SEQ ID NO:31 and SEQ ID NO:8 (I53-50A.1PosT1 and I53-50B);
SEQ ID NO:31 and SEQ ID NO:32 (I53-50A.1PosT1 and I53-50B.1);
SEQ ID NO:31 and SEQ ID NO:33 (I53-50A.1PosT1 and I53-50B.1NegT2);
SEQ ID NO:31 and SEQ ID NO:34 (I53-50A.1PosT1 and I53-50B.4PosT1);
SEQ ID NO:39 and SEQ ID NO:40 (I53-50A genus and I53-50B genus);
SEQ ID NO:9 and SEQ ID NO:10 (I53-51A and I53-51B);
SEQ ID NO:11 and SEQ ID NO:12 (I52-03A and I52-03B);
SEQ ID NO:13 and SEQ ID NO:14 (I52-32A and I52-32B);
SEQ ID NO:15 and SEQ ID NO:16 (I52-33A and I52-33B)
SEQ ID NO:17 and SEQ ID NO:18 (I32-06A and I32-06B);
SEQ ID NO:19 and SEQ ID NO:20 (I32-19A and I32-19B);
SEQ ID NO:21 and SEQ ID NO:22 (I32-28A and I32-28B);
SEQ ID NO:23 and SEQ ID NO:24 (I53-40A.1 and I53-40B.1);
SEQ ID NO:41 and SEQ ID NO:42 (T32-28A and T32-28B);
SEQ ID NO:43 and SEQ ID NO:44 (T33-09A and T33-09B);
SEQ ID NO:45 and SEQ ID NO:46 (T33-15A and T33-15B);
SEQ ID NO:47 and SEQ ID NO:48 (T33-21A and T33-21B);
SEQ ID NO:49 and SEQ ID NO:50 (T33-28A and T32-28B); and
SEQ ID NO:51 and SEQ ID NO:44 (T33-31A and T33-09B (also referred to as T33-31B))

In one embodiment, the one or more paramyxovirus and/or pneumovirus F proteins, or antigenic fragments thereof, are expressed as a fusion protein with the first and/or second polypeptides. In these embodiments, it is preferred that the one or more paramyxovirus and/or pneumovirus F proteins, or antigenic fragments thereof are present at the N terminus of the fusion protein, whenever this configuration can facilitate presentation of the one or more paramyxovirus and/or pneumovirus F proteins, or antigenic fragments thereof on an exterior of the nanostructure. This preference for the presence of the paramyxovirus and/or pneumovirus F protein at the N terminus of the fusion protein derives from the location of the C terminus of the paramyxovirus and/or pneumovirus F proteins at one extreme (the "bottom") of the F protein trimer; by locating the genetic fusion at this point, the majority of the F protein structure will be displayed and accessible on the nanostructure exterior. In a further embodiment, the nanostructures comprise one or more copies of a fusion protein comprising at least two domains—a paramyxovirus and/or pneumovirus F protein, or an antigenic fragment thereof, and a trimeric assembly domain (i.e.: each first assembly is a homotrimer of the first polypeptide)—and one or more copies of a second oligomeric block (i.e.: each second assembly is an oligomer of two or more copies of the second polypeptide). In another embodiment, the first and or second polypeptides may be modified to permit the one or more paramyxovirus and/or pneumovirus F proteins, or antigenic fragments thereof, to be covalently linked to the first and/or second polypeptides. In one non-limiting example, the first and/or second polypeptides can be modified, such as by introduction of various cysteine residues at defined positions to facilitate linkage one or more paramyxovirus and/or pneumovirus F proteins, or antigenic fragments thereof.

In other embodiments, the one or more paramyxovirus and/or pneumovirus F proteins, or antigenic fragments thereof are attached to the first or second polypeptides via any suitable technique, including but not limited to covalent chemical cross-linking (via any suitable cross-linking technique) and non-covalent attachment including engineered electrostatic interactions.

Trimeric Assembly Domains

In one embodiment of a trimeric assembly that comprises a trimeric paramyxovirus and/or pneumovirus F protein, or antigenic fragments thereof, the paramyxovirus and/or pneumovirus F protein, or antigenic fragment thereof is genetically fused to the first polypeptides that self-assemble into the trimeric assembly. The trimeric assembly comprises a protein-protein interface that induces three copies of the first polypeptides to self-associate to form trimeric building blocks. Each copy of the first polypeptides further comprises a surface-exposed interface that interacts with a complementary surface-exposed interface on a second assembly domain. As described in King et al. (Nature 510, 103-108, 2014), Bale et al. (Science 353, 389-394, 2016), and patent publications WO2014124301 A1 and US20160122392 A1, the complementary protein-protein interface between the trimeric assembly domain and second assembly domain drives the assembly of multiple copies of the trimeric assembly domain and second assembly domain to a target nanostructure. In some embodiments, each copy of the trimeric assembly domains of the nanostructure bears a paramyxovirus and/or pneumovirus F proteins, or antigenic fragment thereof, as a genetic fusion; these nanostructures display the F proteins at full valency. In other embodiments, the nanostructures of the invention comprise one or more copies of trimeric assembly domains bearing paramyxovirus and/or pneumovirus F proteins, or antigenic fragments thereof as genetic fusions as well as one or more trimeric assembly domains that do not bear F proteins as genetic fusions; these nanostructures display the F proteins at partial valency. The trimeric assembly domain can be any polypeptide sequence that forms a trimer and interacts with a second assembly domain to drive assembly to a target nanostructure.

In one specific embodiment, the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-31A (SEQ ID NO:51) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-09B/T33-31B (SEQ ID NO:44) (residues in parentheses are optional)

```
T33-31A
                                        (SEQ ID NO: 51)
(M)EEVVLITVPSALVAVKIAHALVEERLAACVNIVPGLTSIYREEGSV
VSDHELLLLVKITTDAFPKLKERVKELHPYEVPEIVALPIAEGNREYLD
WLRENTG

>T33-31B
                                        (SEQ ID NO: 44)
(M)VRGIRGAITVEEDTPAAILAATIELLLKMLEANGIQSYEELAAVIF
TVTEDLTSAFPAEAARLIGMHRVPLLSAREVPVPGSLPRVIRVLALWNT
DTPQDRVRHVYLNEAVRLRPDLESAQ
```

In another specific embodiment, the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-15A (SEQ ID NO:45) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-15B (SEQ ID NO:46).

In various further specific embodiments, the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of a polypeptides selected from the group consisting of I53-50A (SEQ ID NO:7), I53-50A.1 (SEQ ID NO:29), I53-50A.1NegT2 (SEQ ID NO:30), and I53-50A.1PosT1 (SEQ ID NO:31), and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of a polypeptide selected from the group consisting of I53-50B (SEQ ID NO:8), I53-50B.1 (SEQ ID NO:32), I53-50B.1NegT2 (SEQ ID NO:33), and I53-50B.4PosT1 (SEQ ID NO:34).

In another specific embodiment, the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of I32-28A (SEQ ID NO:21) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of I32-28B (SEQ ID NO:22).

The nanostructures of the invention display multiple copies (i.e.: 2, 3, or more) of one or more paramyxovirus and/or pneumovirus F proteins, or antigenic fragments thereof, on an exterior of the nanostructure. Exemplary paramyxovirus and/or pneumovirus include, but are not limited to, respiratory syncytial virus (RSV) and Human metapneumovirus (hMPV). (C. L. Afonso et al., Taxonomy of the order Mononegavirales: update 2016. Arch. Virol. 161, 2351-2360 (2016)).

As used herein, "on an exterior of the nanostructure" means that an antigenic portion of the one or more paramyxovirus and/or pneumovirus F proteins, or antigenic fragments thereof, must be accessible for binding by B cell receptors, antibodies, or antibody fragments and not buried within the nanostructure.

The one or more paramyxovirus and/or pneumovirus F proteins, or antigenic fragments thereof, may comprise any suitable native F proteins, post-fusion, or pre-fusion (preF)

antigens, or mutants thereof capable of inducing an immune response that will generate antibodies that bind to paramyxovirus and/or pneumovirus F proteins. A nanostructure may display more than one F protein; thus, in some embodiments the one or more paramyxovirus and/or pneumovirus F proteins, or antigenic fragments thereof comprise 1, 2, 3, 4, or more F proteins or antigenic fragments thereof. In one embodiment, the one or more paramyxovirus and/or pneumovirus F proteins, or antigenic fragments thereof may be as defined in patent publication number US 2016/0046675 A1. In some embodiments, the one or more paramyxovirus and/or pneumovirus F proteins, or antigenic fragments thereof, are selected from the group consisting of SEQ ID NOS: 1-350, 370-382, 389-693, 698-1026, 1429-1442, 1456-1468, and 1474-1478 as disclosed in US published patent application 2016/0046675. In other embodiments, the one or more paramyxovirus and/or pneumovirus F proteins, or antigenic fragments thereof may be as defined in WO2012158613, US 20160102123, US20140141037, WO2014079842, WO2014160463, US20140271699, EP2970393, WO2014174018, US20140271699, US20160176932, US20160122398, WO2017040387, WO2017109629, WO2017172890, WO2017207477, Krarup et al. (2015) Nature Communications 6:8143, and WO2017207480.

In a specific embodiment, the one or more paramyxovirus and/or pneumovirus F proteins, or antigenic fragments thereof, comprise a polypeptide having at least 75%, 80%, 85%, 90%, 91%, 92%, 93%, 94%, 95%, 96%, 97%, 98%, 99%, or 100% identity along its full length to the amino acid sequence of DS-Cav1 shown below (residues in parentheses are optional; note that the N-terminal residues in parentheses are cleaved from the protein during secretion—the mature N terminus begins with QNITEEF . . . (SEQ ID NO:52)). DS-Cav1 comprises a prefusion-stabilized form of the fusion (F) glycoprotein, which elicits improved protective responses against respiratory syncytial virus (RSV) in mice and macaques compared to postfusion RSV F (McLellan et al. (2013) Science 342:592-8).

DS-Cav1 (SEQ ID NO: 53):
(MELLILKANAITTILTAVTFCFASG)QNITEEFYQSTCSAVSKGYLSA

LRTGWYTSVITIELSNIKENKCNGTDAKVKLIKQELDKYKNAVTELQLL

MQSTPATNNRARRELPRFMNYTLNNAKKTNVTLSKKRKRRFLGFLLGVG

SAIASGVAVCKVLHLEGEVNKIKSALLSTNKAVVSLSNGVSVLTFKVLD

LKNYIDKQLLPILNKQSCSISNIETVIEFQQKNNRLLEITREFSVNAGV

TTPVSTYMLTNSELLSLINDMPITNDQKKLMSNNVQIVRQQSYSIMCII

KEEVLAYVVQLPLYGVIDTPCWKLHTSPLCTINTKEGSNICLTRTDRGW

YCDNAGSVSFFPQAETCKVQSNRVFCDTMNSLTLPSEVNLCNVDIFNPK

YDCKIMTSKTDVSSSVITSLGAIVSCYGKTKCTASNKNRGIIKTFSNGC

DYVSNKGVDTVSVGNTLYYVNKQEGKSLYVKGEPIINFYDPLVFPSDEF

DASISQVNEKINQSLAFIR(KSDELL)

In other embodiments, the F protein may comprise a polypeptide having at least 75%, 80%, 85%, 90%, 91%, 92%, 93%, 94%, 95%, 96%, 97%, 98%, 99%, or 100% identity along its full length to a polypeptide selected from:

RSV F
sc9-10 DS-Cav1 A149C Y458C
(SEQ ID NO: 61)
(MELLILKANAITTILTAVTFCFASG)QNITEEFYQSTCSAVSKGYLSA

LRTGWYTSVITIELSNIKENKCNGTDAKVKLIKQELDKYKNAVTELQLL

MQSTPATGSGSAICSGVAVCKVLHLEGEVNKIKSALLSTNKAVVSLSNG

VSVLTFKVLDLKNYIDKQLLPILNKQSCSISNIETVIEFQQKNNRLLEI

TREFSVNAGVTTPVSTYMLTNSELLSLINDMPITNDQKKLMSNNVQIVR

QQSYSIMCIIKEEVLAYVVQLPLYGVIDTPCWKLHTSPLCTTNTKEGSN

ICLTRTDRGWYCDNAGSVSFFPQAETCKVQSNRVFCDTMNSRTLPSEVN

LCNVDIFNPKYDCKIMTSKTDVSSSVITSLGAIVSCYGKTKCTASNKNR

GIIKTFSNGCDYVSNKGVDTVSVGNTLYCVNKQEGKSLYVKGEPIINFY

DPLVFPSDEFDASISQVNEKINQSLAFIR(KSDELL)

sc9-10 DS-Cav1 A149C Y458C S46G K465Q S215P E92D
(SEQ ID NO: 62)
(MELLILKANAITTILTAVTFCFASG)QNITEEFYQSTCSAVSKGYLGA

LRTGWYTSVITIELSNIKENKCNGTDAKVKLIKQELDKYKNAVTDLQLL

MQSTPATGSGSAICSGVAVCKVLHLEGEVNKIKSALLSTNKAVVSLSNG

VSVLTFKVLDLKNYIDKQLLPILNKQSCSIPNIETVIEFQQKNNRLLEI

TREFSVNAGVTTPVSTYMLTNSELLSLINDMPITNDQKKLMSNNVQIVR

QQSYSIMCIIKEEVLAYVVQLPLYGVIDTPCWKLHTSPLCTTNTKEGSN

ICLTRTDRGWYCDNAGSVSFFPQAETCKVQSNRVFCDTMNSRTLPSEVN

LCNVDIFNPKYDCKIMTSKTDVSSSVITSLGAIVSCYGKTKCTASNKNR

GIIKTFSNGCDYVSNKGVDTVSVGNTLYCVNKQEGQSLYVKGEPIINFY

DPLVFPSDEFDASISQVNEKINQSLAFIR(KSDELL)

SEQ ID NO:61-62 represent second-generation stabilized DS-Cav1 immunogens; mutations relative to DS-Cav1 are noted and it should be noted that the present disclosure contemplates the use of DS-Cav1 mutants that differ by a single one of the noted amino acid substitutions in SEQ ID NO:61 or 62 above, or two or more of the amino acid substitutions noted. In other embodiments, the F protein may comprise one or more of the following, each of which may additionally include 1, 2, or more of the noted amino acid substitutions in SEQ ID NO:61 or 62 above:

RSV F SC-DM (N67I, S215P)
(SEQ ID NO: 63)
(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

-continued

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDEFDASISQVNEKINQSLAFIR(KSDELLSAIGGYIPEAPRDGQAYVRKDGEWVL

LSTFL)

SC-TM (N671, S215P, and E487Q)
(SEQ ID NO: 64)
(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDQFDASISQVNEKINQSLAFIR(KSDELLSAIGGYIPEAPRDGQAYVRKDGEWVL

LSTFL)

HMPV F protein, strain CAN97-83 (A2)

(SEQ ID NO: 65)

(MSWKVVIIFSLLITPQHG)LKESYLEESCSIITEGYLSVLRTGWYTNVFTLEVGDVENLICSDG

PSLIKTELDLTKSALRELKTVSADQLAREEQIENPRQSRFVLGAIALGVATAAAVTAGVAIAKTI

RLESEVTAIKNALKTTNEAVSTLGNGVRVLATAVRELKDFVSKNLTRAINKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNIG

HMPVF with A113C, A339C, T160F, I177L (SEQ ID NO: 66)

(MSWKVVIIFSLLITPQHG)LKESYLEESCSIITEGYLSVLRTGWYTNVFTLEVGDVENLICSDG

PSLIKTELDLTKSALRELKTVSADQLAREEQIENPRQSRFVLGAIALGVCTAAAVTAGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNIG

HMPV F with A113C, A120C, A339C, T160F, I177L, and Q426C (SEQ ID NO: 67)

(MSWKVVIIFSLLITPQHG)LKESYLEESCSTITEGYLSVLRTGWYTNVFTLEVGDVENLICSDG

PSLIKTELDLTKSALRELKTVSADQLAREEQIENPRQSRFVLGAIALGVCTAAAVTCGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

-continued

```
SCSIGSNRVGIIKQLNKGCSYITNQDADTVTIDNTVYCLSKVEGEQHVIKGRPVSSSFDPIKFPE

DQFNVALDQVFENIENSQALVDQSNRILSSAEKGNIG
```

HMPV F >AAK62968.2 fusion protein metapneumovirus (SEQ ID NO: 101)

```
(MSWKVVIIFSLLITPQHG)LKESYLEESCSTITEGYLSVLRTGWYTNVFTLEVGDVENLICADG

PSLIKTELDLIKSALRELRIVSADQLAREEQIENPRQSRFVLGAIALGVATAAAVTAGVAIAKTI

RLESEVTAIKNALKKTNEAVSTLGNGVRVLATAVRELKDFVSKNLTRAINKNKCDIADLKMAVSF

SQFNRRFLNVVRQFSDNAGITPAISLDLMTDAELARAVSNMPTSAGQIKLMLENRAMVRRKGFGF

LIGVYGSSVIYMVQLPIFGVIDTPCWIVKAAPSCSGKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPVKFPE

DQFNVALDQVFESIENSQALVDQSNRILSSAEKGNIG
```

115-BV (A185P)

(SEQ ID NO: 68)

```
(MSWKVVIIFSLLITPQHG)LKESYLEESCSTITEGYLSVLRTGWYTNVFTLEVGDVENLICADG

PSLIKTELDLIKSALRELRIVSADQLAREEQIENPRRRRFVLGAIALGVATAAAVTAGVAIAKTI

RLESEVTAIKNALKKTNEAVSTLGNGVRVLATAVRELKDFVSKNLTRAINKNKCDIPDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSEKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPVKFPE

DQFNVALDQVFESIENSQALVDQSNRILSSAEKGNT(SGRENLYFQGGGGSGYIPEAPRDGQAYV

RKDGEWVLLSTFLGGIEGRHHHHHH)
```

In other embodiments, the one or more paramyxovirus and/or pneumovirus F proteins, or antigenic fragments thereof, may comprise a polypeptide having at least 75%, 80%, 85%, 90%, 91%, 92%, 93%, 94%, 95%, 96%, 97%, 98%, 99%, or 100% identity along its full length to an RSV F protein or mutant thereof selected from the group consisting of SEQ ID NO:53 and 61-64, wherein the polypeptide includes one or more of the following residues: 67I, 149C, 458C, 46G, 465Q, 215P, 92D, and 487Q.

In other embodiments, the one or more paramyxovirus and/or pneumovirus F proteins, or antigenic fragments thereof, may comprise a polypeptide having at least 75%, 80%, 85%, 90%, 91%, 92%, 93%, 94%, 95%, 96%, 97%, 98%, 99%, or 100% identity along its full length to an MPV F protein or mutant thereof selected from the group consisting of SEQ ID NO:65-68 and 101, wherein the polypeptide includes one or more of the following residues: 113C, 120C, 339C, 160F, 177L, 185P, and 426C.

Linker Between F Proteins and Trimeric Assembly Domains and Geometric Requirements In the nanostructures of the invention, the F protein and the trimeric assembly domain may be genetically fused such that they are both present in a single polypeptide. Preferably, the linkage between the F protein and the trimeric assembly domain allows the F protein, or antigenic fragment thereof, to be displayed on the exterior of the nanostructures of the invention. As such, the point of connection to the trimeric assembly domain should be on the exterior of the nanostructure formed by the trimeric assembly domain and the second assembly domain in the absence of any F protein. As will be understood by those of skill in the art, a wide variety of polypeptide sequences can be used to link the paramyxovirus and/or pneumovirus F proteins, or antigenic fragments thereof and the trimeric assembly domain. These polypeptide sequences are referred to as linkers. Any suitable linker can be used; there is no amino acid sequence requirement to serve as an appropriate linker. There is no requirement that the linker impose a rigid relative orientation of the F protein or antigenic fragment thereof to the trimeric assembly domain beyond enabling the F protein or antigenic fragment thereof to be displayed on the exterior of the nanostructures of the invention. In some embodiments, the linker includes additional trimerization domains (e.g., the foldon domain of T4 fibritin) that assist in stabilizing the trimeric form of the F protein.

T4 Fibritin Foldon Domain (Optional in the Linker Region) (SEQ ID NO:54) GYIPEAPRDGQAYVRKDGEWVLL-STFL In other embodiments, the linker may comprise a Gly-Ser linker (i.e.: a linker consisting of glycine and serine residues) of any suitable length. In various embodiments, the Gly-Ser linker may be 3, 4, 5, 6, 7, 8, 9, 10, 11, 12, 13, 14, 15, 16, 17, 18, 19, 20, or more amino acids in length. In various embodiments, the Gly-Ser linker may comprise or consist of the amino acid sequence of GSGGSGSGSGGSGSG (SEQ ID NO:55), GGSGGSGS (SEQ ID NO:56) or GSGGSGSG (SEQ ID NO:57).

In further embodiments the linker may comprise a helical extension domain that may serve to extend the N-terminal helix of the first polypeptide, when expressed as a fusion polypeptide with the one or more paramyxovirus and/or pneumovirus F proteins, or antigenic fragments thereof, so that it is located at the exterior of the nanostructure surface. The helical extension may be present in combination with the other linker components described herein, or may be absent. The helical extension may be of any suitable length (i.e.: 7, 8, 9, 10, 11, 12, or more amino acids) and comprise any suitable primary amino acid sequence. In one embodiment, the helical extension may comprise or consist of the amino acid sequence EKAAKAEEAAR (SEQ ID NO:58).

Thus, in various non-limiting embodiments in which the F protein is present as a fusion protein with the first polypeptide and a linker is used, the F protein-linker sequence may comprise the following (exemplified by DS-Cav1 as the F protein in these non-limiting embodiments). Residues in parentheses are optional and the amino acid sequence MELLILKANAITTILTAVTFCFASG (SEQ ID NO:59) represents the N-terminal DS-Cav1 signal peptide that is cleaved during processing:

```
DS-Cav1-foldon (SEQ ID NO: 60):
(MELLILKANAITTILTAVTFCFASG)QNITEEFYQSTCSAVSKGYLSA
```

```
-continued
LRTGWYTSVITIELSNIKENKCNGTDAKVKLIKQELDKYKNAVTELQLL

MQSTPATNNRARRELPRFMNYTLNNAKKTNVTLSKKRKRRFLGFLLGVG

SAIASGVAVCKVLHLEGEVNKIKSALLSTNKAVVSLSNGVSVLTFKVLD

LKNYIDKQLLPILNKQSCSISNIETVIEFQQKNNRLLEITREFSVNAGV

TTPVSTYMLTNSELLSLINDMPITNDQKKLMSNNVQIVRQQSYSIMCII

KEEVLAYVVQLPLYGVIDTPCWKLHTSPLCTINTKEGSNICLTRTDRGW

YCDNAGSVSFFPQAETCKVQSNRVFCDTMNSLTLPSEVNLCNVDIFNPK

YDCKIMTSKTDVSSSVITSLGAIVSCYGKTKCTASNKNRGIIKTFSNGC

DYVSNKGVDTVSVGNTLYYVNKQEGKSLYVKGEPIINFYDPLVFPSDEF

DASISQVNEKINQSLAFIRKSDELLGYIPEAPRDGQAYVRKDGEWVLLS

TFL
```

In various further embodiments, the first polypeptides comprise or consist of fusion polypeptides of first polypeptides fused to an F protein, where the fusion protein has a sequence selected from the following (optional residues in parentheses):

```
DS-Cav1-foldon-T33-31A
                                            (SEQ ID NO: 69)
(MELLILKANVIATILTAVTFCFASS)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRKSDELLGYIPE

APRDGQAYVRKDGEWVLLSTFLGGSMEEVVLITVPSALVAVKIAHALVEERLAACVNIVPGLTSI

YREEGSVVSDHELLLLVKITTDAFPKLKERVKELHPYEVPEIVALPIAEGNREYLDWLRENTG

DS-Cav1-T33-31A
                                            (SEQ ID NO: 70)
(MELLILKANVIATILTAVTFCFASS)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRKSDELLGGSME

EVVLITVPSALVAVKIAHALVEERLAACVNIVPGLTSIYREEGSVVSDHELLLLVKITTDAFPKL

KERVKELHPYEVPEIVALPIAEGNREYLDWLRENTG

DS-Cav1-foldon-T33-15B
                                            (SEQ ID NO: 71)
(MELLILKANVIATILTAVTFCFASS)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT
```

-continued

LSKKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRKSDELLGYIPE

APRDGQAYVRKDGEWVLLSTFLGGSMVRGIRGAITVNSDTPTSIIIATILLLEKMLEANGIQSYE

ELAAVIFTVTEDLTSAFPAEAARQIGMHRVPLLSAREVPVPGSLPRVIRVLALWNTDTPQDRVRH

VYLSEAVRLRPDLESAQ

DS-Cav1-T33-15B
(SEQ ID NO: 72)
(MELLILKANVIATILTAVTFCFASS)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRKSDELLGGSMV

RGIRGAITVNSDTPTSIIIATILLLEKMLEANGIQSYEELAAVIFTVTEDLTSAFPAEAARQIGM

HRVPLLSAREVPVPGSLPRVIRVLALWNTDTPQDRVRHVYLSEAVRLRPDLESAQ

DS-Cav1-foldon-I53-50A
(SEQ ID NO: 73)
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGYIPEAPRDGQ

AYVRKDGEWVLLSTFLGSGSHHHHHHHGGSGGGSGSEKAAKAEEEAARKMEELFKKHKIVAVLRAN

SVEEAIEKAVAVFAGGVHLIEITFTVPDADTVIKALSVLKEKGAIIGAGTVTSVEQCRKAVESGA

EFIVSPHLDEEISQFCKEKGVFYMPGVMTPTELVKAMKLGHTILKLFPGEVVGPQFVKAMKGPFP

NVKFVPTGGVNLDNVCEWFKAGVLAVGVGSALVKGTPDEVREKAKAFVEKIRGCTE

DS-Cav1-I53-50A
(SEQ ID NO: 74)
(MELLILKANVIATILTAVTFCFASS)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

-continued

NTLYYVNKQEGKSLYVKGEPIINFYDPLVFPSDEFDASISQVNEKINQSLAFIRGGSGGSGSEKA

AKAEEAARKMEELFKKHKIVAVLRANSVEEAIEKAVAVFAGGVHLIEITFTVPDADTVIKALSVL

KEKGAIIGAGTVTSVEQCRKAVESGAEFIVSPHLDEEISQFCKEKGVFYMPGVMTPTELVKAMKL

GHTILKLFPGEVVGPQFVKAMKGPFPNVKFVPTGGVNLDNVCEWFKAGVLAVGVGSALVKGTPDE

VREKAKAFVEKIRGCTE

DS-Cav1-I32-28A
(SEQ ID NO: 75)
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRKSDELLGGSGG

SGSDDARIAAIGDVDELNSQIGVLLAEPLPDDVRAALSAIQHDLFDLGGELCIPGHAAITEDHLL

RLALWLVHYNGQLPPLEEFILPGGARGAALAHVCRTVCRRAERSIKALGASEPLNIAPAAYVNLL

SDLLFVLARVLNRAAGGADVLWDRTRAH

DS-Cav1-8GS-HelExt-I53-50A (F10)
(SEQ ID NO: 76)
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGSGGSGSGEKA

AKAEEAARKMEELFKKHKIVAVLRANSVEEAIEKAVAVFAGGVHLIEITFTVPDADTVIKALSVL

KEKGAIIGAGTVTSVEQCRKAVESGAEFIVSPHLDEEISQFCKEKGVFYMPGVMTPTELVKAMKL

GHTILKLFPGEVVGPQFVKAMKGPFPNVKFVPTGGVNLDNVCEWFKAGVLAVGVGSALVKGTPDE

VREKAKAFVEKIRGCTE

DS-Cav1-foldon-15GS-HelExt-I53-50A (F14)
(SEQ ID NO: 77)
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGYIPEAPRDGQ

AYVRKDGEWVLLSTFLGSGGSGSGSGGSGSGEKAAKAEEAARKMEELFKKHKIVAVLRANSVEEA

-continued

IEKAVAVFAGGVHLIEITFTVPDADTVIKALSVLKEKGAIIGAGTVTSVEQCRKAVESGAEFIVS

PHLDEEISQFCKEKGVFYMPGVMTPTELVKAMKLGHTILKLFPGEVVGPQFVKAMKGPFPNVKFV

PTGGVNLDNVCEWFKAGVLAVGVGSALVKGTPDEVREKAKAFVEKIRGCTE

HMPV F wt_CAN97-83 strain-I53-50A
(SEQ ID NO: 78)
(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVATAAAVTAGVAIAKTI

RLESEVTAIKNALKTTNEAVSTLGNGVRVLATAVRELKDFVSKNLTRAINKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNTGFIIVIILIAVLGSSMILVSIFIIIKKTK

KPTGAPPELSGVTNNGFIPHSGSGSHHHHHHHHGGSGGSGSEKAAKAEEAARKMEELFKKHKIVA

VLRANSVEEAIEKAVAVFAGGVHLIEITFTVPDADTVIKALSVLKEKGAIIGAGTVTSVEQCRKA

VESGAEFIVSPHLDEEISQFCKEKGVFYMPGVMTPTELVKAMKLGHTILKLFPGEVVGPQFVKAM

KGPFPNVKFVPTGGVNLDNVCEWFKAGVLAVGVGSALVKGTPDEVREKAKAFVEKIRGCTE

HMPV F A113C_A339C_T160F_I177L-I53-50A
(SEQ ID NO: 79)
(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVCTAAAVTAGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNTGGSGSHHHHHHHHGGSGGSGSEKAAKAEE

AARKMEELFKKHKIVAVLRANSVEEAIEKAVAVFAGGVHLIEITFTVPDADTVIKALSVLKEKGA

IIGAGTVTSVEQCRKAVESGAEFIVSPHLDEEISQFCKEKGVFYMPGVMTPTELVKAMKLGHTIL

KLFPGEVVGPQFVKAMKGPFPNVKFVPTGGVNLDNVCEWFKAGVLAVGVGSALVKGTPDEVREKA

KAFVEKIRGCTE

HMPV F A113C_A339C_T160F_I177L_A120C, Q426C mutations-I53-50A (SEQ ID NO: 80)

(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVCTAAAVTCGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYCLSKVEGEQHVIKGRPVSSSFDPIKFPE

DQFNVALDQVFENIENSQALVDQSNRILSSAEKGNTGGSGSHHHHHHHHGGSGGSGSEKAAKAEE

AARKMEELFKKHKIVAVLRANSVEEAIEKAVAVFAGGVHLIEITFTVPDADTVIKALSVLKEKGA

IIGAGTVTSVEQCRKAVESGAEFIVSPHLDEEISQFCKEKGVFYMPGVMTPTELVKAMKLGHTIL

KLFPGEVVGPQFVKAMKGPFPNVKFVPTGGVNLDNVCEWFKAGVLAVGVGSALVKGTPDEVREKA

KAFVEKIRGCTE sc-DS2-I53-50A (SEQ ID NO: 81)
(MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATGSGSCIASGVAVCKVLHLEGEVNKI
KSALLSTNKAVVSLSNGVSVLTFKVLDLKNYIDKQLLPILNKQSCSISNIETVIEFQQKNNRLLE
ITREFSVNAGVTTPVSTYMLINSELLSLINDMPITNDQKKLMSNNVQIVRQQSYSIMCIIKEEVL
AYVVQLPLYGVIDTPCWKLHTSPLCTTNTKEGSNICLTRTDRGWYCDNAGSVSFFPQAETCKVQS
NRVFCDTMNSLTLPSEVNLCNVDIFNPKYDCKIMTSKTDVSSSVITSLGAIVSCYGKTKCTASNK
NRGIIKTFSNGCDYVSNKGVDTVSVGNTLYCVNKQEGKSLYVKGEPIINFYDPLVFPSDEFDASI
SQVNEKINQSLAFIRGSGSHHHHHHHGGSGGSGSEKAAKAEEAARKMEELFKKHKIVAVLRANS
VEEAIEKAVAVFAGGVHLIEITFTVPDADTVIKALSVLKEKGAIIGAGTVTSVEQCRKAVESGAE
FIVSPHLDEEISQFCKEKGVFYMPGVMTPTELVKAMKLGHTILKLFPGEVVGPQFVKAMKGPFPN
VKFVPTGGVNLDNVCEWFKAGVLAVGVGSALVKGTPDEVREKAKAFVEKIRGCTE tc-DS2-I53-50A (SEQ ID NO: 82)
(MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSCIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL
SLINDMPITNDQKKLMSNNVQIVRQQSYSIMCIIKEEVLAYVVQLPLYGVIDTPCWKLHTSPLCT
INTKEGSNICLTRTDRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGCDYVSNKGVDTVSVG
NTLYCVNKQEGKSLYVKGEPIINFYDPLVFPSDEFDASISQVNEKINQSLAFIRGSGSHHHHHH
HGGSGGSGSEKAAKAEEAARKMEELFKKHKIVAVLRANSVEEAIEKAVAVFAGGVHLISITFTVP
DADTVIKALSVLKEKGAIIGAGTVTSVEQCRKAVESGAEFIVSPHLDEEISQFCKEKGVFYMPGV
MTPTELVKAMKLGHTILKLFPGEVVGPQFVKAMKGPFPNVKFVPTGGVNLDNVCEWFKAGVLAVG
VGSALVKGTPDEVREKAKAFVEKIRGCTE

DS-Cav1-12GS-HelExt-I53-50A (F11)

(SEQ ID NO: 83)
(MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSAIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL
SLINDMPITNDQKKLMSNNVQIVRQQSYSIMCIIKEEVLAYVVQLPLYGVIDTPCWKLHTSPLCT
INTKEGSNICLTRTDRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGCDYVSNKGVDTVSVG
NTLYYVNKQEGKSLYVKGEPIINFYDPLVFPSDEFDASISQVNEKINQSLAFIRGSGGSGSGSGG
SEKAAKAEEAARKMEELFKKHKIVAVLRANSVEEAIEKAVAVFAGGVHLIEliFTVPDADTVIKA
LSVLKEKGAIIGAGTVTSVEQCRKAVESGAEFIVSPHLDEEISQFCKEKGVFYMPGVMTPTELVK
AMKLGHTILKLFPGEVVGPQFVKAMKGPFPNVKFVPTGGVNLDNVCEWFKAGVLAVGVGSALVKG
TPDEVREKAKAFVEKIRGCTE

DS-Cav1-16GS-HelExt-I53-50A (F12)

(SEQ ID NO: 84)

-continued (MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSAIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL
SLINDMPITNDQKKLMSNNVQIVRQQSYSIMCIIKEEVLAYVVQLPLYGVIDTPCWKLHTSPLCT
INTKEGSNICLTRTDRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGCDYVSNKGVDTVSVG
NTLYYVNKQEGKSLYVKGEPIINFYDPLVFPSDEFDASISQVNEKINQSLAFIRGSGGGSGSGG
SGSGGEKAAKAEEAARKMEELFKKHKIVAVLRANSVEEAIEKAVAVFAGGVHLIEliFTVPDADT
VIKALSVLKEKGAIIGAGTVTSVEQCRKAVESGAEFIVSPHLDEEISQFCKEKGVFYMPGVMTPT
ELVKAMKLGHTILKLFPGEVVGPQFVKAMKGPFPNVKFVPTGGVNLDNVCEWFKAGVLAVGVGSA
LVKGTPDEVREKAKAFVEKIRGCTE DS-Cav1-foldon-10GS-HelExt-I53-50A (F13
(SEQ ID NO: 85)
(MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSAIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL
SLINDMPITNDQKKLMSNNVQIVRQQSYSIMCIIKEEVLAYVVQLPLYGVIDTPCWKLHTSPLCT
INTKEGSNICLTRTDRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGCDYVSNKGVDTVSVG
NTLYYVNKQEGKSLYVKGEPIINFYDPLVFPSDEFDASISQVNEKINQSLAFIRGYIPEAPRDGQ
AYVRKDGEWVLLSTFLGSGGSGSGSGEKAAKAEEAARKMEELFKKHKIVAVLRANSVEEAIEKAV
AVFAGGVHLIEITFTVPDADTVIKALSVLKEKGAIIGAGTVTSVEQCRKAVESGAEFIVSPHLDE
EISQFCKEKGVFYMPGVMTPTELVKAMKLGHTILKLFPGEVVGPQFVKAMKGPFPNVKFVPTGGV
NLDNVCEWFKAGVLAVGVGSALVKGTPDEVREKAKAFVEKIRGCTE DS-Cav1-foldon-20GS-HelExt-I53-50A (F15)
(SEQ ID NO: 86)
(MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSAIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL
SLINDMPITNDQKKLMSNNVQIVRQQSYSIMCIIKEEVLAYVVQLPLYGVIDTPCWKLHTSPLCT
INTKEGSNICLTRTDRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGCDYVSNKGVDTVSVG
NTLYYVNKQEGKSLYVKGEPIINFYDPLVFPSDEFDASISQVNEKINQSLAFIRGYIPEAPRDGQ
AYVRKDGEWVLLSTFLGSGGSGSGSGGSGSGGSSGSEKAAKAEEAARKMEELFKKHKIVAVLRAN
SVEEAIEKAVAVFAGGVHLIEITFTVPDADTVIKALSVLKEKGAIIGAGTVTSVEQCRKAVESGA
EFIVSPHLDEEISQFCKEKGVFYMPGVMTPTELVKAMKLGHTILKLFPGEVVGPQFVKAMKGPFP
NVKFVPTGGVNLDNVCEWFKAGVLAVGVGSALVKGTPDEVREKAKAFVEKIRGCTE sc9-10 DS-Cav1 A149C Y458C-foldon-I53-50A embodiment
(SEQ ID NO: 87)
(MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATGSGSAICSGVAVCKVLHLEGEVNKI -continued

KSALLSTNKAVVSLSNGVSVLTFKVLDLKNYIDKQLLPILNKQSCSISNIETVIEFQQKNNRLLE

ITREFSVNAGVTTPVSTYMLINSELLSLINDMPITNDQKKLMSNNVQIVRQQSYSIMCIIKEEVL

AYVVQLPLYGVIDTPCWKLHTSPLCTINTKEGSNICLTRTDRGWYCDNAGSVSFFPQAETCKVQS

NRVFCDTMNSRTLPSEVNLCNVDIFNPKYDCKIMTSKTDVSSSVITSLGAIVSCYGKTKCTASNK

NRGIIKTFSNGCDYVSNKGVDTVSVGNTLYCVNKQEGKSLYVKGEPIINFYDPLVFPSDEFDASI

SQVNEKINQSLAFIR(KSDELL)GYIPEAPRDGQAYVRKDGEWVLLSTFLGSGSHHHHHHHGGS

GGSGSEKAAKAEEAARKMEELFKKHKIVAVLRANSVEEAIEKAVAVFAGGVHLIEITFTVPDADT

VIKALSVLKEKGAIIGAGTVTSVEQCRKAVESGAEFIVSPHLDEEISQFCKEKGVFYMPGVMTPT

ELVKAMKLGHTILKLFPGEVVGPQFVKAMKGPFPNVKFVPTGGVNLDNVCEWFKAGVLAVGVGSA

LVKGTPDEVREKAKAFVEKIRGCTE sc9-10 DS-Cav1 A149C Y458C-I53-50A-F10 embodiment (SEQ ID NO: 88)

(MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATGSGSAICSGVAVCKVLHLEGEVNKI
KSALLSTNKAVVSLSNGVSVLTFKVLDLKNYIDKQLLPILNKQSCSISNIETVIEFQQKNNRLLE
ITREFSVNAGVTTPVSTYMLINSELLSLINDMPITNDQKKLMSNNVQIVRQQSYSIMCIIKEEVL
AYVVQLPLYGVIDTPCWKLHTSPLCTINTKEGSNICLTRTDRGWYCDNAGSVSFFPQAETCKVQS
NRVFCDTMNSRTLPSEVNLCNVDIFNPKYDCKIMTSKTDVSSSVITSLGAIVSCYGKTKCTASNK
NRGIIKTFSNGCDYVSNKGVDTVSVGNTLYCVNKQEGKSLYVKGEPIINFYDPLVFPSDEFDASI
SQVNEKINQSLAFIR(KSDELL)GSGGSGSGEKAAKAEEAARKMEELFKKHKIVAVLRANSVEEA
IEKAVAVFAGGVHLIEITFTVPDADTVIKALSVLKEKGAIIGAGTVTSVEQCRKAVESGAEFIVS
PHLDEEISQFCKEKGVFYMPGVMTPTELVKAMKLGHTILKLFPGEVVGPQFVKAMKGPFPNVKFV
PTGGVNLDNVCEWFKAGVLAVGVGSALVKGTPDEVREKAKAFVEKIRGCTE sc9-10 DS-Cav1 A149C Y458C S46G K465Q S215P E92D-foldon-I53-50A embodiment (SEQ ID NO: 89)

(MELLILKANAITTILTAVTFCFASG)QNITEEFYQSTCSAVSKGYLGALRTGWYTSVITIELSN
IKENKCNGTDAKVKLIKQELDKYKNAVTDLQLLMQSTPATGSGSAICSGVAVCKVLHLEGEVNKI
KSALLSTNKAVVSLSNGVSVLTFKVLDLKNYIDKQLLPILNKQSCSIPNIETVIEFQQKNNRLLE
ITREFSVNAGVTTPVSTYMLINSELLSLINDMPITNDQKKLMSNNVQIVRQQSYSIMCIIKEEVL
AYVVQLPLYGVIDTPCWKLHTSPLCTTNTKEGSNICLTRTDRGWYCDNAGSVSFFPQAETCKVQS
NRVFCDTMNSRTLPSEVNLCNVDIFNPKYDCKIMTSKTDVSSSVITSLGAIVSCYGKTKCTASNK
NRGIIKTFSNGCDYVSNKGVDTVSVGNTLYCVNKQEGQSLYVKGEPIINFYDPLVFPSDEFDASI
SQVNEKINQSLAFIR(KSDELL)GYIPEAPRDGQAYVRKDGEWVLLSTFLGSGSHHHHHHHHGGS
GGSGSEKAAKAEEAARKMEELFKKHKIVAVLRANSVEEAIEKAVAVFAGGVHLIEliFTVPDADT
VIKALSVLKEKGAIIGAGTVTSVEQCRKAVESGAEFIVSPHLDEEISQFCKEKGVFYMPGVMTPT
ELVKAMKLGHTILKLFPGEVVGPQFVKAMKGPFPNVKFVPTGGVNLDNVCEWFKAGVLAVGVGSA
LVKGTPDEVREKAKAFVEKIRGCTE sc9-10 DS-Cav1 A149C Y458C S46G K465Q S215P E92D-I53-50A-F10 embodiment (SEQ ID NO: 90)

(MELLILKANAITTILTAVTFCFASG)QNITEEFYQSTCSAVSKGYLGALRTGWYTSVITIELSN
IKENKCNGTDAKVKLIKQELDKYKNAVTDLQLLMQSTPATGSGSAICSGVAVCKVLHLEGEVNKI
KSALLSTNKAVVSLSNGVSVLTFKVLDLKNYIDKQLLPILNKQSCSIPNIETVIEFQQKNNRLLE

-continued

```
ITREFSVNAGVTTPVSTYMLINSELLSLINDMPITNDQKKLMSNNVQIVRQQSYSIMCIIKEEVL

AYVVQLPLYGVIDTPCWKLHTSPLCTTNTKEGSNICLTRTDRGWYCDNAGSVSFFPQAETCKVQS

NRVFCDTMNSRTLPSEVNLCNVDIFNPKYDCKIMTSKTDVSSSVITSLGAIVSCYGKTKCTASNK

NRGIIKTFSNGCDYVSNKGVDTVSVGNTLYCVNKQEGQSLYVKGEPIINFYDPLVFPSDEFDASI

SQVNEKINQSLAFIR(KSDELL)GSGSGSGSEKAAKAEEAARKMEELFKKHKIVAVLRANSVEEA

IEKAVAVFAGGVHLIEITFTVPDADTVIKALSVLKEKGAIIGAGTVTSVEQCRKAVESGAEFIVS

PHLDEEISQFCKEKGVFYMPGVMTPTELVKAMKLGHTILKLFPGEVVGPQFVKAMKGPFPNVKFV

PTGGVNLDNVCEWFKAGVLAVGVGSALVKGTPDEVREKAKAFVEKIRGCTE
```

SC-DM (N67I, S215P)-foldon-I53-50A embodiment
(SEQ ID NO: 91)

```
(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDEFDASISQVNEKINQSLAFIR(KSDELL)GYIPEAPRDGQAYVRKDGEWVLLST

FLGSGSHHHHHHHGGSGGSGSEKAAKAEEAARKMEELFKKHKIVAVLRANSVEEAIEKAVAVFA

GGVHLIEITFTVPDADTVIKALSVLKEKGAIIGAGTVTSVEQCRKAVESGAEFIVSPHLDEEISQ

FCKEKGVFYMPGVMTPTELVKAMKLGHTILKLFPGEVVGPQFVKAMKGPFPNVKFVPTGGVNLDN

VCEWFKAGVLAVGVGSALVKGTPDEVREKAKAFVEKIRGCTE
```

SC-DM (N67I, S215P) 453-50A-F10 embodiment
(SEQ ID NO: 92)

```
(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDEFDASISQVNEKINQSLAFIR(KSDELL)GSGGSGSGEKAAKAEEAARKMEELF

KKHKIVAVLRANSVEEAIEKAVAVFAGGVHLIEITFTVPDADTVIKALSVLKEKGAIIGAGTVTS

VEQCRKAVESGAEFIVSPHLDEEISQFCKEKGVFYMPGVMTPTELVKAMKLGHTILKLFPGEVVG

PQFVKAMKGPFPNVKFVPTGGVNLDNVCEWFKAGVLAVGVGSALVKGTPDEVREKAKAFVEKIRG

CTE
```

SC-TM (N67I, S215P, and E487Q)-foldon-I53-50A embodiment
(SEQ ID NO: 93)

```
(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL
```

GAIVSCYGKTKCTASNKNRGIIKTFSNGCDYVSNKGVDTVSVGNTLYYVNKQEGKSLYVKGEPII

NFYDPLVFPSDQFDASISQVNEKINQSLAFIR(KSDELL)GYIPEAPRDGQAYVRKDGEWVLLST

FLGSGSHHHHHHHHGGSGGSGSEKAAKAEEAARKMEELFKKHKIVAVLRANSVEEAIEKAVAVFA

GGVHLIEITFTVPDADTVIKALSVLKEKGAIIGAGTVTSVEQCRKAVESGAEFIVSPHLDEEISQ

FCKEKGVFYMPGVMTPTELVKAMKLGHTILKLFPGEVVGPQFVKAMKGPFPNVKFVPTGGVNLDN

VCEWFKAGVLAVGVGSALVKGTPDEVREKAKAFVEKIRGCTE

SC-TM (N67I, S215P, and E487Q) 453-50A-F10 embodiment
(SEQ ID NO: 94)
(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDQFDASISQVNEKINQSLAFIR(KSDELL)GSGGSGSGEKAAKAEEAARKMEELF

KKHKIVAVLRANSVEEAIEKAVAVFAGGVHLIEITFTVPDADTVIKALSVLKEKGAIIGAGTVTS

VEQCRKAVESGAEFIVSPHLDEEISQFCKEKGVFYMPGVMTPTELVKAMKLGHTILKLFPGEVVG

PQFVKAMKGPFPNVKFVPTGGVNLDNVCEWFKAGVLAVGVGSALVKGTPDEVREKAKAFVEKIRG

CTE

HMPV-F with A113C, A339C, T160F, I177L-foldon-I53-50A embodiment (SEQ ID NO: 95)

(MSWKVVIIFSLLITPQHG)LKESYLEESCSTITEGYLSVLRTGWYTNVFTLEVGDVENLICSDG

PSLIKTELDLTKSALRELKTVSADQLAREEQIENPRQSRFVLGAIALGVCTAAAVTAGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNTGGYIPEAPRDGQAYVRKDGEWVLLSTFLG

SGSHHHHHHHHGGSGGSGSEKAAKAEEAARKMEELFKKHKIVAVLRANSVEEAIEKAVAVFAGGV

HLIEITFTVPDADTVIKALSVLKEKGAIIGAGTVTSVEQCRKAVESGAEFIVSPHLDEEISQFCK

EKGVFYMPGVMTPTELVKAMKLGHTILKLFPGEVVGPQFVKAMKGPFPNVKFVPTGGVNLDNVCE

WFKAGVLAVGVGSALVKGTPDEVREKAKAFVEKIRGCTE

HMPV-F with A113C, A339C, T160F, I177L-I53-50A F10 embodiment (SEQ ID NO: 96)

(MSWKVVIIFSLLITPQHG)LKESYLEESCSTITEGYLSVLRTGWYTNVFTLEVGDVENLICSDG

PSLIKTELDLTKSALRELKTVSADQLAREEQIENPRQSRFVLGAIALGVCTAAAVTAGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

-continued

DQFNVALDQVFENIENSQALVDQSNRILSSAEKGNTGGSGGSGSGEKAAKAEEAARKMEELFKKH

KIVAVLRANSVEEAIEKAVAVFAGGVHLIEITFTVPDADTVIKALSVLKEKGAIIGAGTVTSVEQ

CRKAVESGAEFIVSPHLDEEISQFCKEKGVFYMPGVMTPTELVKAMKLGHTILKLFPGEVVGPQF

VKAMKGPFPNVKFVPTGGVNLDNVCEWFKAGVLAVGVGSALVKGTPDEVREKAKAFVEKIRGCTE

HMPV-F with A113C, A120C, A339C, T160F, I177L, and Q426C-foldon-I53-50A
embodiment
(SEQ ID NO: 97)
(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVCTAAAVTCGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYCLSKVEGEQHVIKGRPVSSSFDPIKFPE

DQFNVALDQVFENIENSQALVDQSNRILSSAEKGNTGGYIPEAPRDGQAYVRKDGEWVLLSTFLG

SGSHHHHHHHHGGSGGSGSEKAAKAEEAARKMEELFKKHKIVAVLRANSVEEAIEKAVAVFAGGV

HLIEITFTVPDADTVIKALSVLKEKGAIIGAGTVTSVEQCRKAVESGAEFIVSPHLDEEISQFCK

EKGVFYMPGVMTPTELVKAMKLGHTILKLFPGEVVGPQFVKAMKGPFPNVKFVPTGGVNLDNVCE

WFKAGVLAVGVGSALVKGTPDEVREKAKAFVEKIRGCTE

HMPV-F with A113C, A120C, A339C, T160F, I177L, and Q426C-F10 embodiment
(SEQ ID NO: 98)
(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVCTAAAVTCGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYCLSKVEGEQHVIKGRPVSSSFDPIKFPE

DQFNVALDQVFENIENSQALVDQSNRILSSAEKGNTGGSGGSGSGEKAAKAEEAARKMEELFKKH

KIVAVLRANSVEEAIEKAVAVFAGGVHLIEITFTVPDADTVIKALSVLKEKGAIIGAGTVTSVEQ

CRKAVESGAEFIVSPHLDEEISQFCKEKGVFYMPGVMTPTELVKAMKLGHTILKLFPGEVVGPQF

VKAMKGPFPNVKFVPTGGVNLDNVCEWFKAGVLAVGVGSALVKGTPDEVREKAKAFVEKIRGCTE

HMPV-F 115-BV (A185P)-foldon-I53-50A embodiment
(SEQ ID NO: 99)
(MSWKVVIIFSLLITPQHG)LKESYLEESCSTITEGYLSVLRTGWYINVFTLEVGDVENLICADG

PSLIKTELDLIKSALRELRIVSADQLAREEQIENPRRRRFVLGAIALGVATAAAVTAGVAIAKTI

RLESEVTAIKNALKKTNEAVSTLGNGVRVLATAVRELKDFVSKNLTRAINKNKCDIPDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSEKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPVKFPE

DQFNVALDQVFESIENSQALVDQSNRILSSAEKGNTGYIPEAPRDGQAYVRKDGEWVLLSTFLGS

GSHHHHHHHHGGSGGSGSEKAAKAEEAARKMEELFKKHKIVAVLRANSVEEAIEKAVAVFAGGVH

LIEITFTVPDADTVIKALSVLKEKGAIIGAGTVTSVEQCRKAVESGAEFIVSPHLDEEISQFCKE

```
KGVFYMPGVMTPTELVKAMKLGHTILKLFPGEVVGPQFVKAMKGPFPNVKFVPTGGVNLDNVCEW

FKAGVLAVGVGSALVKGTPDEVREKAKAFVEKIRGCTE

HMPV-F 115-BV (A185P)-I53-50A-F10 embodiment
                                                                  (SEQ ID NO: 100)
(MSWKVVIIFSLLITPQHG)LKESYLEESCSTITEGYLSVLRTGWYINVFTLEVGDVENLICADG

PSLIKTELDLIKSALRELRIVSADQLAREEQIENPRRRRFVLGAIALGVATAAAVTAGVAIAKTI

RLESEVTAIKNALKKTNEAVSTLGNGVRVLATAVRELKDFVSKNLTRAINKNKCDIPDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSEKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPVKFPE

DQFNVALDQVFESIENSQALVDQSNRILSSAEKGNTGSGGSGSGEKAAKAEEAARKMEELFKKHK

IVAVLRANSVEEAIEKAVAVFAGGVHLIEITFTVPDADTVIKALSVLKEKGAIIGAGTVTSVEQC

RKAVESGAEFIVSPHLDEEISQFCKEKGVFYMPGVMTPTELVKAMKLGHTILKLFPGEVVGPQFV

KAMKGPFPNVKFVPTGGVNLDNVCEWFKAGVLAVGVGSALVKGTPDEVREKAKAFVEKIRGCTE
```

Second Assemblies

The nanostructures of the invention may comprise multiple copies of a trimeric first assembly and multiple copies of a second assembly. The second assembly comprises a protein-protein interface that induces multiple copies of the second polypeptide to self-associate to form the second assemblies. Multiple oligomeric states of the second assembly may be compatible with nanostructure formation, including dimeric (two copies), trimeric (three copies), tetrameric (four copies), pentameric (five copies), hexameric (six copies), or higher oligomeric states. Each copy of the second assembly further comprises a surface-exposed interface that interacts with a complementary surface-exposed interface on a trimeric assembly domain. As described in King et al., Bale et al., and patent publications WO2014124301 A1 and US20160122392 A1, the complementary interface between the trimeric assembly domain and second assembly domain drives the assembly of multiple copies of the trimeric assembly domain and second assembly domain to a target nanostructure. In various specific embodiments:

(a) when each first polypeptide is DS-Cav1-foldon-T33-31A (SEQ ID NO:69) or DS-Cav1-T33-31A (SEQ ID NO:70), each second polypeptide is T33-31B (SEQ ID NO:44);

(b) when each first polypeptide is DS-Cav1-foldon-T33-15B (SEQ ID NO:71) or DS-Cav1-T33-15B (SEQ ID NO:72), each second polypeptide is T33-15A (SEQ ID NO:45);

(c) when each first polypeptide is DS-Cav1-foldon-I53-50A (SEQ ID NO:73) or DS-Cav1-I53-50A (SEQ ID NO:74), each second polypeptide is I53-50B (SEQ ID NO:8), I53-50B.1 (SEQ ID NO:32), I53-50B.1NegT2 (SEQ ID NO:33), or I53-50B.4PosT1 (SEQ ID NO:34);

(d) when each first polypeptide is DS-Cav1-I32-28A (SEQ ID NO:75), each second polypeptide is I32-28B.

Assembly of Full Valency Nanostructures by In Vitro Assembly of Two Components In some embodiments, each trimeric first assembly of the nanostructure bears an identical F protein as a genetic fusion; these nanostructures display the F protein at full (100%) valency. Such nanostructures are produced from purified first polypeptides and second polypeptides in a process called in vitro assembly. Purified trimeric first polypeptides comprising an F protein, are mixed with appropriate second polypeptides in an approximately 1:1 molar ratio in aqueous conditions (see FIG. 1). The second assembly interacts with the trimeric first assembly in order to drive assembly of the target nanostructure. Successful assembly of the target nanostructure can be confirmed by analyzing the in vitro assembly reaction by common biochemical or biophysical methods used to assess the physical size of proteins or protein assemblies, including but not limited to size exclusion chromatography, native (non-denaturing) gel electrophoresis, dynamic light scattering, multi-angle light scattering, analytical ultracentrifugation, negative stain electron microscopy, cryo-electron microscopy, or X-ray crystallography. If necessary, the assembled nanostructure can be purified from other species or molecules present in the in vitro assembly reaction using preparative techniques commonly used to isolate proteins by their physical size, including but not limited to size exclusion chromatography, preparative ultracentrifugation, tangential flow filtration, or preparative gel electrophoresis. The presence of the F protein in the nanostructure can be assessed by techniques commonly used to determine the identity of protein molecules in aqueous solutions, including but not limited to SDS-PAGE, mass spectrometry, protein sequencing, or amino acid analysis. The accessibility of the F protein on the exterior of the particle, as well as its conformation or antigenicity, can be assessed by techniques commonly used to detect the presence and conformation of an antigen, including but not limited to binding by monoclonal antibodies, conformation-specific monoclonal antibodies, or antisera specific to the antigen.

In Vitro Assembly of Partial Valency Nanostructures

In other embodiments, the nanostructures of the invention comprise one or more copies of trimeric first assemblies bearing F proteins as genetic fusions as well as one or more trimeric first assemblies that do not bear F proteins as genetic fusions; these nanostructures display the F proteins at partial valency. These partial valency nanostructures are produced by performing in vitro assembly with mixtures of first polypeptides in which the fraction of trimeric first assemblies bearing an F protein as a genetic fusion is equal to the desired valency of the antigen in the resulting nanostructure. The in vitro assembly reaction typically contains an approximately 1:1 molar ratio of total first polypeptides to total second polypeptides. By way of non-limiting example, performing an in vitro assembly reaction with a mixture of trimeric assemblies in which one half of the first polypeptides bear an F protein as a genetic fusion would yield an assembled nanostructure with an F protein valency of 50%. That is, 50% of the possible sites for F protein display on the nanostructure would be occupied. By way of non-limiting example, if the nanostructure is a 120-subunit assembly with icosahedral symmetry, the nanostructure comprises 20 total trimeric building blocks, and a 50% valency nanostructure displays 10 of the possible 20 F protein trimers. In this way, the ratio of F protein-bearing first polypeptides to first polypeptides lacking F proteins in an in vitro assembly reaction can be used to precisely tune the F protein valency of the resulting nanostructures. It will be understood by those of skill in the art that it is the average valency that can be tuned in this manner; the valency of individual nanostructures in the mixture will be a distribution centered around the average. Successful assembly of such partial valency nanostructures can be assessed using the techniques described above for evaluating full-valency nanostructures, and, if necessary, the partial valency nanostructures can be purified using the methods described for purifying full-valency nanostructures. The average valency of F protein-bearing first polypeptides in a given sample can be assessed by quantitative analysis using the techniques described above for evaluating the presence of F proteins in full-valency nanostructures.

In Vitro Assembly of Nanostructures Co-Displaying Multiple F Proteins

In other embodiments, the nanostructures of the invention comprise two or more distinct first polypeptides bearing different F proteins as genetic fusions; these nanostructures co-display multiple different F proteins on the same nanostructure. These multi-antigen nanostructures are produced by performing in vitro assembly with mixtures of first polypeptides in which each first polypeptide bears one of two or more distinct F proteins as a genetic fusion. The fraction of each first polypeptide in the mixture determines the average valency of each F protein in the resulting nanostructures. The in vitro assembly reaction typically contains an approximately 1:1 molar ratio of total trimeric first polypeptides to total second polypeptides. The presence and average valency of each F protein-bearing first polypeptides in a given sample can be assessed by quantitative analysis using the techniques described above for evaluating the presence of F proteins in full-valency nanostructures.

In various embodiments, the nanostructures are between about 20 nanometers (nm) to about 40 nm in diameter, with interior lumens between about 15 nm to about 32 nm across and pore sizes in the protein shells between about 1 nm to about 14 nm in their longest dimensions.

In one embodiment, the nanostructure has icosahedral symmetry. In this embodiment, the nanostructure may comprise 60 copies of the first polypeptide and 60 copies of the second polypeptide. In one such embodiment, the number of identical first polypeptides in each first assembly is different than the number of identical second polypeptides in each second assembly. For example, in one embodiment, the nanostructure comprises twelve first assemblies and twenty second assemblies; in this embodiment, each first assembly may, for example, comprise five copies of the identical first polypeptide, and each second assembly may, for example, comprise three copies of the identical second polypeptide. In another embodiment, the nanostructure comprises twelve first assemblies and thirty second assemblies; in this embodiment, each first assembly may, for example, comprise five copies of the identical first polypeptide, and each second assembly may, for example, comprise two copies of the identical second polypeptide. In a further embodiment, the nanostructure comprises twenty first assemblies and thirty second assemblies; in this embodiment, each first assembly may, for example, comprise three copies of the identical first polypeptide, and each second assembly may, for example, comprise two copies of the identical second polypeptide. All of these embodiments are capable of forming synthetic nanomaterials with regular icosahedral symmetry. In various further embodiments, oligomeric states of the first and second polypeptides are as follows:

I53-34A: trimer+I53-34B: pentamer;
I53-40A: pentamer+I53-40B: trimer;
I53-47A: trimer+I53-47B: pentamer;
I53-50A: trimer+I53-50B: pentamer;
I53-51A: trimer+I53-51B: pentamer;
I32-06A: dimer+I32-06B: trimer;
I32-19A: trimer+I32-19B: dimer;
I32-28A: trimer+I32-28B: dimer;
I52-03A: pentamer+I52-03B: dimer;
I52-32A: dimer+I52-32B: pentamer; and
I52-33A: pentamer+I52-33B: dimer In another embodiment, the nanostructure of any embodiment or combination of embodiments of the invention has one or more of the following characteristics, each as demonstrated in the examples that follow:

(a) binds prefusion F-specific antibodies including but not limited to monoclonal antibody D25;

(b) forms a symmetrical structure, including but not limited to an icosahedral structure;

(c) is stable at 50° C.; and/or (d) is stable in 2.25M guanidine hydrochloride.

In another aspect, the present invention provides isolated nucleic acids encoding a fusion protein of the present invention. The isolated nucleic acid sequence may comprise RNA or DNA. As used herein, “isolated nucleic acids” are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the proteins of the invention.

In a further aspect, the present invention provides recombinant expression vectors comprising the isolated nucleic acid of any embodiment or combination of embodiments of the invention operatively linked to a suitable control sequence. “Recombinant expression vector” includes vectors that operatively link a nucleic acid coding region or gene to any control sequences capable of effecting expression of the gene product. “Control sequences” operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides host cells that have been transfected with the recombinant expression vectors disclosed herein, wherein the host cells can be either prokaryotic or eukaryotic, such as mammalian cells. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2nd Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide.

In a further aspect, the invention provides an immunogenic composition comprising an effective amount of the nanostructure of any embodiment or combination of embodiments of the invention and a pharmaceutically acceptable carrier. The composition may comprise (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The composition may also include a lyoprotectant, e.g. sucrose, sorbitol or trehalose. In certain embodiments, the composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the composition includes a bulking agent, like glycine. In yet other embodiments, the composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the composition additionally includes a stabilizer, e.g., a molecule which substantially prevents or reduces chemical and/or physical instability of the nanostructure, in lyophilized or liquid form. Exemplary stabilizers include sucrose, sorbitol, glycine, inositol, sodium chloride, methionine, arginine, and arginine hydrochloride.

The nanostructure may be the sole active agent in the composition, or the composition may further comprise one or more other agents suitable for an intended use, including but not limited to adjuvants to stimulate the immune system generally and improve immune responses overall. Any suitable adjuvant can be used. The term "adjuvant" refers to a compound or mixture that enhances the immune response to an antigen. Exemplary adjuvants include, but are not limited to, Adju-Phos™, Adjumer™ albumin-heparin microparticles, Algal Glucan, Algammulin, Alum, Antigen Formulation, AS-2 adjuvant, autologous dendritic cells, autologous PBMC, Avridine™, B7-2, BAK, BAY R1005, Bupivacaine, Bupivacaine-HCl, BWZL, Calcitriol, Calcium Phosphate Gel, CCR5 peptides, CFA, Cholera holotoxin (CT) and Cholera toxin B subunit (CTB), Cholera toxin A1-subunit-Protein A D-fragment fusion protein, CpG, CRL1005, Cytokine-containing Liposomes, D-Murapalmitine, DDA, DHEA, Diphtheria toxoid, DL-PGL, DMPC, DMPG, DOC/Alum Complex, Fowlpox, Freund's Complete Adjuvant, Gamma Inulin, Gerbu Adjuvant, GM-CSF, GMDP, hGM-CSF, hIL-12 (N222L), hTNF-alpha, IFA, IFN-gamma in pcDNA3, IL-12 DNA, IL-12 plasmid, IL-12/GMCSF plasmid (Sykes), IL-2 in pcDNA3, IL-2/Ig plasmid, IL-2/Ig protein, IL-4, IL-4 in pcDNA3, Imiquimod™, ImmTher™, Immunoliposomes Containing Antibodies to Costimulatory Molecules, Interferon-gamma, Interleukin-1 beta, Interleukin-12, Interleukin-2, Interleukin-7, ISCOM(s)™, Iscoprep 7.0.3™, Keyhole Limpet Hemocyanin, Lipid-based Adjuvant, Liposomes, Loxoribine, LT(R192G), LT-OA or LT Oral Adjuvant, LT-R192G, LTK63, LTK72, MF59, MONTANIDE ISA 51, MONTANIDE ISA 720, MPL™, MPL-SE, MTP-PE, MTP-PE Liposomes, Murametide, Murapalmitine, NAGO, nCT native Cholera Toxin, Non-Ionic Surfactant Vesicles, non-toxic mutant E112K of Cholera Toxin mCT-E112K, p-Hydroxybenzoique acid methyl ester, pCIL-10, pCIL12, pCMVmCAT1, pCMVN, Peptomer-NP, Pleuran, PLG, PLGA, PGA, and PLA, Pluronic L121, PMMA, PODDS™, Poly rA: Poly rU, Polysorbate 80, Protein Cochleates, QS-21, Quadri A saponin, Quil-A, Rehydragel HPA, Rehydragel LV, RIBI, Ribilike adjuvant system (MPL, TMD, CWS), S-28463, SAF-1, Sclavo peptide, Sendai Proteoliposomes, Sendai-containing Lipid Matrices, Span 85, Specol, Squalane 1, Squalene 2, Stearyl Tyrosine, Tetanus toxoid (TT), Theramide™, Threonyl muramyl dipeptide (TMDP), Ty Particles, and Walter Reed Liposomes. Selection of an adjuvant depends on the subject to be treated. Preferably, a pharmaceutically acceptable adjuvant is used.

In another aspect, the invention provides methods for generating an immune response to paramyxovirus and/or pneumovirus F protein in a subject, comprising administering to the subject an effective amount of the immunogenic composition of any embodiment or combination of embodiments of the invention to generate the immune response. In a further aspect, the invention provides methods for treating or preventing a paramyxovirus and/or pneumovirus infection in a subject, comprising administering to the subject an effective amount of the immunogenic composition of any embodiment or combination of embodiments of the invention, thereby treating or preventing paramyxovirus and/or pneumovirus infection in the subject.

In one embodiment, the paramyxovirus and/or pneumovirus comprises respiratory syncytial virus. "Respiratory Syncytial Virus" and "RSV" refer to a negative-sense, single-stranded RNA virus that causes a respiratory disease, especially in children. When the method comprises treating an RSV infection, the immunogenic compositions are administered to a subject that has already been infected with the RSV, and/or who is suffering from symptoms (including but not limited to lower respiratory tract infections, upper respiratory tract infections, bronchiolitis, pneumonia, fever, listlessness, diminished appetite, recurrent wheezing, and asthma) indicating that the subject is likely to have been infected with the RSV. As used herein, "treat" or "treating" includes, but is not limited to accomplishing one or more of the following: (a) reducing paramyxovirus and/or pneumovirus titer in the subject; (b) limiting any increase of paramyxovirus and/or pneumovirus titer in the subject; (c) reducing the severity of paramyxovirus and/or pneumovirus symptoms; (d) limiting or preventing development of paramyxovirus and/or pneumovirus symptoms after infection; (e) inhibiting worsening of paramyxovirus and/or pneumovirus symptoms; (f) limiting or preventing recurrence of paramyxovirus and/or pneumovirus symptoms in subjects that were previously symptomatic for paramyxovirus and/or pneumovirus infection; and/or promoting maternal transmission of paramyxovirus and/or pneumovirus antibodies to infants (after maternal immunization).

When the method comprises limiting a paramyxovirus and/or pneumovirus infection, the immunogenic compositions are administered prophylactically to a subject that is not known to be infected, but may be at risk of exposure to the paramyxovirus and/or pneumovirus. As used herein, "limiting" means to limit RSV infection in subjects at risk of RSV infection. Groups at particularly high risk include children under age 18 (particularly infants 3 years or younger), adults over the age of 65, and individuals suffering from any type of immunodeficiency.

As used herein, an "effective amount" refers to an amount of the immunogenic composition that is effective for treating and/or limiting RSV infection. The immunogenic compositions are typically formulated as a pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Polypeptide compositions may also be administered via microspheres, liposomes, immune-stimulating complexes (ISCOMs), or other microparticulate delivery systems or sustained release formulations introduced into suitable tissues (such as blood). Dosage regimens can be adjusted to provide the optimum desired response (e.g., a therapeutic or prophylactic response). A suitable dosage range may, for instance, be 0.1 ug/kg-100 mg/kg body weight of the F protein or antigenic fragment thereof. The composition can be delivered in a single bolus, or may be administered more than once (e.g., 2, 3, 4, 5, or more times) as determined by attending medical personnel.

In one embodiment, the administering results in production of paramyxovirus and/or pneumovirus neutralizing antibodies in the subject. In another embodiment, the neutralizing antibodies are present in sera of the subject at a titer ($1/ID_{50}$) of at least 1,000; in other embodiments, the neutralizing antibodies are present in sera of the subject at a titer of 2,000 or 5,000.

EXAMPLES

Methods

Expression and Screening of Trimeric Building Blocks Comprising an F Protein and a Trimeric Assembly Domain Human codon-optimized sequences for trimeric building blocks including and lacking DS-Cav1 fusions were ordered from Genscript. Building blocks for single-component nanostructures (i.e., I3-01) were cloned into the pcDNA3.1 vector (ThermoFisher Scientific) containing one CMV promoter, while building blocks for two-component nanostructures (e.g., I53-50) were cloned into the pBudCE4.1™ vector (ThermoFisher Scientific) containing both CMV and EF-1α promoters. Recombinant proteins were expressed by transient transfection of Expi293F™ cells (ThermoFisher Scientific) using polyethylenimine (PEI). Cell cultures were harvested five days post-transfection by centrifugation. Secreted proteins were analyzed by ELISA, using either direct coating of the cell supernatants or by sandwich ELISA. Briefly, 96-well MaxiSorp™ plates (Nunc) were coated with cell supernatant for direct ELISA or murine anti-His tag monoclonal antibody (ThermoFisher Scientific) for sandwich ELISA. Secreted proteins were detected using the human Palivizumab, MPE8, RSD5, and D25 monoclonal antibodies. Transfected Expi293F cells were fixed and permeabilized with BD cytofix/cytoperm (BD Biosciences), incubated with human Palivizumab, MPE8, and D25 monoclonal antibodies, and stained with Alexa Fluor 647-conjugated anti-human IgG antibody (Jackson ImmunoResearch). Stained cells were counted with a FACS Fortessa™ flow cytometer (BD Biosciences). Analysis was performed with FlowJo™ software. Cell lines were routinely tested for mycoplasma contamination.

Expression and Purification of DS-Cav1-I53-50A

Lentivirus was produced by transient transfection of 293T (ATCC) cells using linear 25-kDa polyethyleneimine (PEI; Polysciences). Briefly, $4\times10^6$ cells were plated onto 10 cm tissue culture plates. After 24 h, 3 μg of psPAX2, 1.5 μg of pMD2G (Addgene™ plasmid #12260 and #12259, respectively) and 6 μg of lentiviral vector plasmid were mixed in 500 μl diluent (5 mM HEPES, 150 mM NaCl, pH=7.05) and 42 μl of PEI (1 mg/ml) and incubated for 15 min. The DNA/PEI complex was then added to the plate drop-wise. Lentivirus was harvested 48 h post-transfection and concentrated 100-fold by low-speed centrifugation at 8000 g for 18 h. Transduction of the target cell line was carried out in 125 mL shake flasks containing 10×10⁶ cells in 10 mL of growth media. 100 uL of 100× lentivirus was added to the flask and the cells were incubated with shaking (225 rpm) at 37° C., in 8% $CO_2$ for 4-6 h. 20 mL of growth media was added to the shake flask after 4-6 h.

Transduced cells were expanded every other day to a density of 1×10⁶ cells/ml until a final culture size of 4 L was reached. The media was harvested after 17 days of total incubation after measuring final cell concentration (~5×10⁶ cells/mL) and viability (~90% viable). Culture supernatant was harvested by low-speed centrifugation to remove cells from the supernatant. NaCl and $NaN_3$ were added to final concentrations of 250 mM and 0.02%, respectively. The supernatant was loaded over one 5 mL HisTrap™ FF Crude column (GE Healthsciences) at 5 ml/min by an AKTA Pure™ (GE Healthsciences). The nickel elution was applied to a HiLoad™ 16/600 Superdex 200 pg column (GE Healthsciences) to further purify the target protein by size-exclusion chromatography. The size-exclusion purified target protein was snap frozen in liquid nitrogen and stored at −80° C.

In Vitro Assembly of DS-Cav1-bearing Nanostructures

100% valency particles (20 DS-Cav1 trimers per icosahedral nanostructure) were prepared by mixing DS-Cav1-foldon-I53-50A trimers and I53-50B.4PT1 pentamers at 50 µM each and incubating with rocking overnight at 4° C. In some cases, assembled nanostructures were purified from excess components remaining in the in vitro assembly reaction using a GE Sephacryl S-500 HR 16/60 column in a buffer comprising 25 mM Tris pH 8, 250 mM NaCl, 5% glycerol. Sample load and SEC fractions were analyzed by SDS-PAGE in the presence and absence of reducing agent. Peak fractions were pooled, concentrated using a GE Vivaspin™ 20 30 kDa MWCO centrifugal filter, and quantified using an Agilent 8454 spectrophotometer.

66% valency particles (~14 DS-Cav1 trimers per icosahedral nanostructure) were prepared by mixing DS-Cav1-foldon-I53-50A trimers, I53-50A trimers, and I53-50B.4PosT1 pentamers at 50, 25, and 75 µM, respectively. 33% valency particles (~7 DS-Cav1 trimers per icosahedral nanostructure) were prepared by mixing DS-Cav1-foldon-I53-50A trimers, I53-50A trimers, and I53-50B.4PosT1 pentamers at 25, 50, and 75 µM, respectively. The in vitro assembly reactions were allowed to incubate with rocking overnight at 4° C. In some cases, assembled nanostructures were purified from excess components remaining in the in vitro assembly reaction using a GE Sephacryl™ S-500 HR 16/60 column in a buffer comprising 25 mM Tris pH 8, 250 mM NaCl, 5% glycerol. Sample load and SEC fractions were analyzed by SDS-PAGE in the presence and absence of reducing agent. Peak fractions were pooled, concentrated using a GE Vivaspin™ 20 30 kDa MWCO centrifugal filter, and quantified using an Agilent 8454 spectrophotometer after centrifuging at ~21,000 g for 10 minutes at 4° C. Samples were then transferred to cryogenic tubes in 1 mL aliquots at 1.1 mg/mL for the 33% valency particles and 0.6 mg/mL for the 66% valency particles, flash frozen in liquid nitrogen, and stored at −80° C.

Electron Microscopy of DS-Cav1-Bearing Nanostructures

Samples were prepared for negative stain EM by diluting to 0.01 mg/mL using 25 mM Tris pH 8, 250 mM NaCl, 5% glycerol, and 3.5 µL was incubated on a glow-discharged, copper, carbon-coated grid for 20 seconds before blotting away the liquid with a piece of Whatman No. 1 filter paper. Within seconds of blotting away the sample, a 3.5 µL droplet of stain (2% w/v uranyl formate) was deposited and blotted away immediately, and then a second cycle of staining/blotting was performed.

Circular Dichroism (CD) Spectropolarimetry

CD spectra from F proteins (0.5 mg ml⁻¹) were recorded on a Chirascan™ spectropolarimeter (Applied Photophysics) over the wavelength range of 195 to 260 nm at a bandwidth of 1 nm, step size of 0.5 nm, and 1 s per step. The spectra in the far-ultraviolet region required an average of three scans and were subtracted from blank spectra performed with buffer. Thermal denaturation was monitored by performing scans at intervals of 1° C., after equilibration for 1 min at each temperature. Data were fitted to a simple first order curve. The values of ΔA222 are represented on the y axis as the percentage of the values recorded at 20° C.

Enzyme-linked Immunosorbent Assay (ELISA)

To test specific binding of antibody or sera, 96-well MaxiSorp™ plates (Nunc) were coated with serial dilutions of tissue culture supernatants from cells expressing trimeric building blocks comprising F proteins and a trimeric assembly domain or 2 µg ml⁻¹ of the following purified proteins: Ds-Cav1 with foldon, Ds-Cav1 fused to a trimeric first polypeptide or DS-Cav1-displaying nanostructures. Plates were blocked with 1% bovine serum albumin (BSA) and incubated with titrated antibodies (D25, MPE8, Palivizumab, RSD5) or murine sera followed by AP-conjugated goat anti-human IgG (Southern Biotech, 2040-04) or goat anti-mouse IgG (Southern Biotech, 1030-04). Plates were then washed with PBS buffer (Gibco, Invitrogen), 0.05% Tween-20 and substrate (p-NPP, Sigma) was added and plates were read at 405 nm.

Surface Plasmon Resonance (SPR)

The experiments were carried out at 25° C. on a ProteON™ XPR-36 instrument (Bio-Rad Laboratories) in a PBS buffer (Gibco, Invitrogen), 0.05% Tween-20. The D25 mAb was immobilized on a GLM sensor chip surface through amine coupling at 1000 response units (RU) and a blank surface with no protein was created under identical coupling conditions for use as a reference. Monoclonal antibodies (D25, MPE8, Palivizumab and 131-2a) were injected at a flow rate of 100 µl/min, at concentrations of 50 nM in different sensor channels. The data were processed using Proteon software and double referenced by subtraction of the blank surface and buffer only injection before local fitting of the data.

Vaccination and Serological Analysis

Female BALB/c mice 6-9 weeks of age were obtained from ENVIGO Laboratories (Italy). All proteins were formulated with AddaVax™ adjuvant (Invivogen) according to the manufacturer's instruction. Mice were immunized subcutaneously (s.c) with a total protein dose corresponding to 5 µg of the DS-Cav1 antigen equivalent on day 0, 14, and 28 in 50% AddaVax™ in PBS. Mice were bled on day 24 and 40. Recovered sera were used to measure binding and neutralizing titers. Binding titers were measured by coating 3 µg/ml of DS-Cav1, I53-50 nanostructures or I53-50 nanostructure subunits.

Virus Neutralization Assay and Microscopy Analysis

Neutralization of RSV infection by sera was measured using a micro-neutralization flow cytometry-based assay. Serial dilutions of sera were pre-incubated with RSV for 1 hour at 37° C. and added to 10000 HEp-2 (ATCC® CCL-23™) cells/well in 96-well flat-bottom plates (MOI of 1). After 24 hours, cells were washed, detached and fixed with 2% formaldehyde. Percentage of GFP positive cells were measured by High throughput FACS with an Intellicyt coupled to an automated platform. The Tissue Culture Inhibiting Dilution (TCID) neutralizing 50% of the Infection (TCID$_{50}$) was calculated by nonlinear regression with Prism 7 (GraphPad Software).

Non-Human Primate (NHP) Immunization

Rhesus macaques were immunized i.m. (right quadriceps) at weeks 0 and 4 with trimeric DS-Cav1 (50 μg; n=4) or DS-Cav1-foldon-I53-50 nanostructures (96 μg, comprising 50 μg of displayed DS-Cav1; n=5) formulated in the MF59-like adjuvant SWE. Sera were obtained at weeks 6 and 16 for serological analysis.

Stability of DS-Cav1-bearing Nanostructures by Relative Binding to D25

Experiments were carried out at 20° C. on a ProteON™ XPR-36 instrument (Bio-Rad Laboratories) in a PBS buffer (Gibco, Thermo Fisher Scientific) and 0.05% Tween-20 (Sigma). 100 nM D25 antibody was immobilized on a GLM sensor chip surface through amine coupling (EDC/NHS chemistry) and a blank surface with no antibody was created under identical coupling conditions for use as a reference. Analyte proteins (soluble DS-Cav1, soluble DS-Cav1-I53-50A and DS-Cav1-foldon-I53-50 nanostructures), heat stressed at different temperatures (20, 50, 70 or 80° C.) for 1 h, were injected at a flow rate of 100 μl/min, at a concentration of 50 nM in the different sensor channels. Data were processed using Proteon software and double referenced by subtraction of the blank surface and buffer-only injection before local fitting of the data.

Chemical Denaturation of Nanostructure-Related Proteins

Trimeric DS-Cav1, DS-Cav1-I53-50A, DS-Cav1-I53-50, I53-50, trimeric I53-50A, or pentameric I53-50B.4PT1 was diluted to a final concentration of 2.5 μM in 25 mM Tris pH 8, 250 mM NaCl, 5% glycerol with varying concentrations of guanidine hydrochloride, ranging from 0 M to 6.5 M, increasing in 0.25 M increments. Samples were prepared in triplicate and incubated for 16 hours at ambient temperature. On a Cary Eclipse Fluorescence Spectrophotometer, intrinsic fluorescence was measured for each guanidine hydrochloride concentration of each protein and of each replicate. A Peltier controller was used in the cell holder to maintain a temperature of 25° C. throughout all experiments. Using a 10 mm cell (Agilent Cuvette, part #6610021600), fluorescence spectra were collected, exciting at 290 nm and scanning emission from 310 nm to 510 nm at a rate of 60 nm/minute with a bandpass of 1 nm.

Statistical Analysis

No statistical methods were used to predetermine sample size. Data were analyzed with Prism 6 (GraphPad™ Software) using the two-tailed non-parametric Mann-Whitney U test for two groups' comparison, or Kruskall-Wallis test (and Dunn's posttest) when three or more groups were compared.

Results

Trimeric Building Blocks Comprising an F Protein and a Trimeric Assembly Domain

Figure 2:
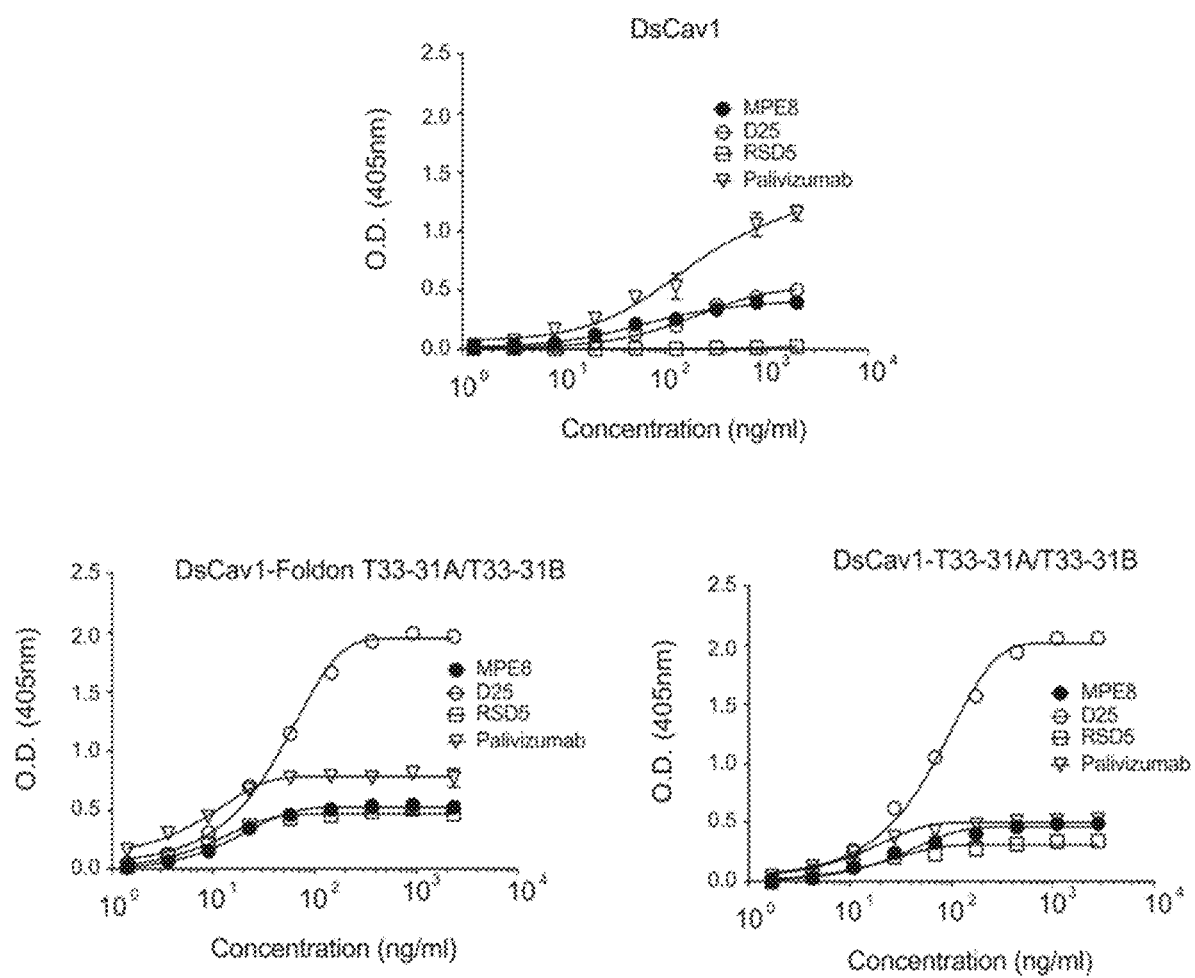
FIG. 2 shows graphs illustrating detection of secreted DS-Cav1, DS-Cav1-foldon-T33-31A, and DS-Cav1-T33-31A fusion proteins in tissue culture supernatants. ELISA assays were performed on tissue culture supernatants from cells expressing DS-Cav1 (top), DS-Cav-1-foldon-T33-31A/T33-31B (bottom left), and DS-Cav-1-T33-31A/T33-31B (bottom right). Four different monoclonal antibodies that bind RSV F were used to evaluate the presence of DS-Cav1 or DS-Cav1 fusion proteins in the supernatants. The results confirm the secretion of proteins comprising well-folded RSV F antigen.

Several trimeric building blocks, each comprising an F protein genetically fused to a trimeric assembly domain, were found to be secreted from HEK293F cells with their F proteins in a well-folded, prefusion conformation as judged by prefusion-specific monoclonal antibody binding in ELISA assays. FIG. 2 shows an example of ELISA data analyzing the supernatant of HEK293F cells expressing DS-Cav1-foldon, DS-Cav1-foldon-T33-31B, and DS-Cav1-T33-31A. Several other trimeric building blocks yielded detectable secretion of well-folded, prefusion F proteins.

Expression and Purification of DS-Cav1-foldon-I53-50A

Figure 3:
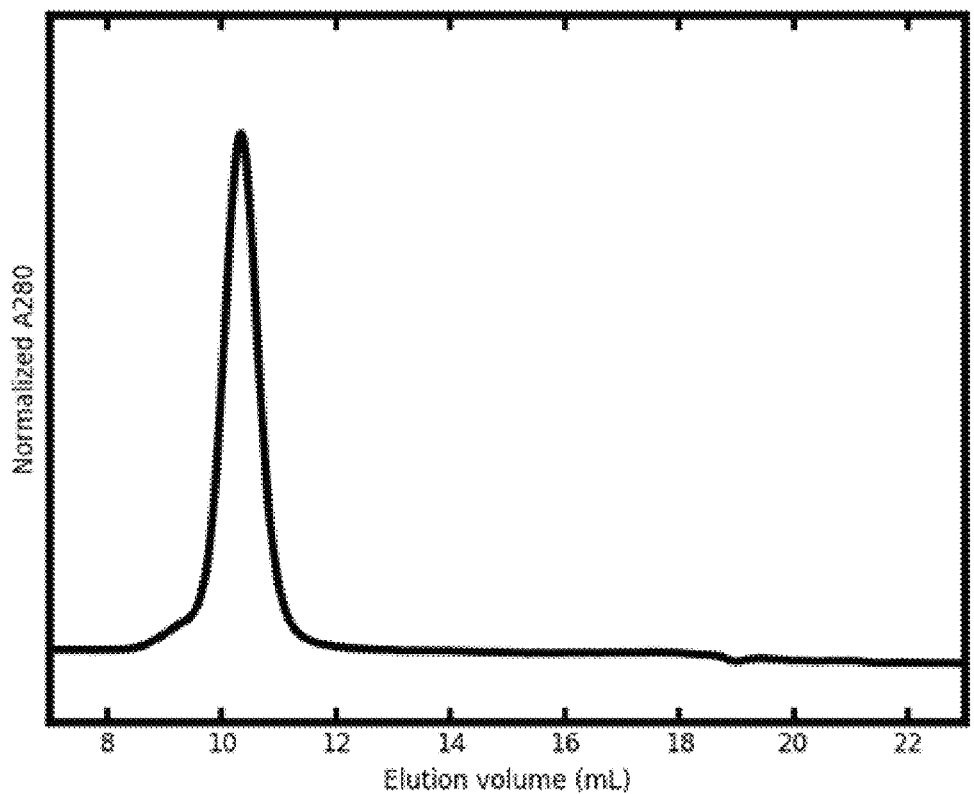
FIG. 3 shows size-exclusion chromatography of DS-Cav1-I53-50A. Protein purified from tissue culture supernatants by immobilized metal affinity chromatography was applied to a Superose™ 6 10/300 GL size exclusion column. The protein eluted as a single, monodisperse species.

A lentiviral vector encoding DS-Cav1-foldon-I53-50A was used to transduce HEK293F cells for large-scale expression. The secreted protein was purified from tissue culture supernatants by immobilized metal affinity chromatography and size exclusion chromatography. Size exclusion chromatograms (FIG. 3) indicated that the purified protein formed a single, monodisperse species.

Expression and Purification of I53-50B.4PT1

I53-50B.4PT1, a pentameric protein comprising a second assembly domain that interacts with the trimeric assembly domain in I53-50A or DS-Cav1-foldon-I53-50A to drive assembly of icosahedral I53-50-based nanostructures, was expressed and purified as described in Bale et al. and patent publication US20160122392 A1.

In Vitro Assembly and Characterization of DS-Cav1-bearing I53-50 Nanostructures

Figure 4:
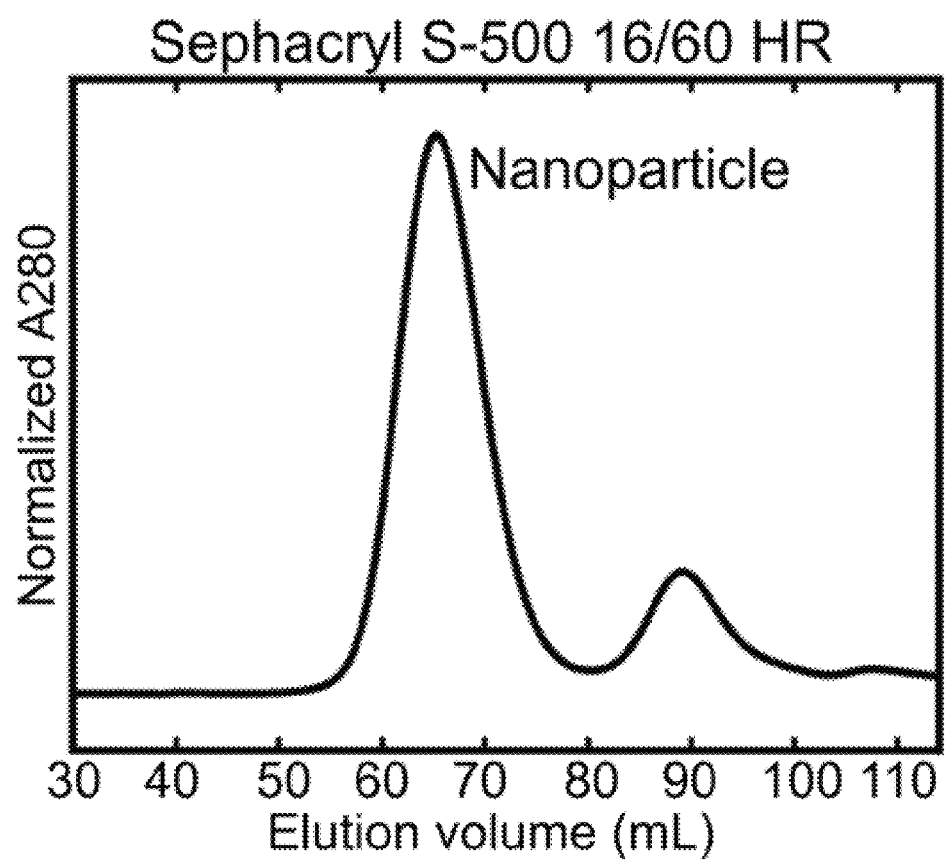
FIG. 4 shows size exclusion chromatography of in vitro-assembled DS-Cav1-I53-50 nanostructures. Purified DS-Cav1-I53-50A and I53-50B.4PT1 proteins were mixed at an approximately 1:1 molar ratio, incubated overnight at 4° C., and then applied to a Sephacryl S-500 16/60 HR size exclusion column. The assembled nanostructure eluted as a single, monodisperse peak around 65 mL, while excess DS-Cav1-I53-50A trimeric component eluted around 90 mL.
Figure 5:
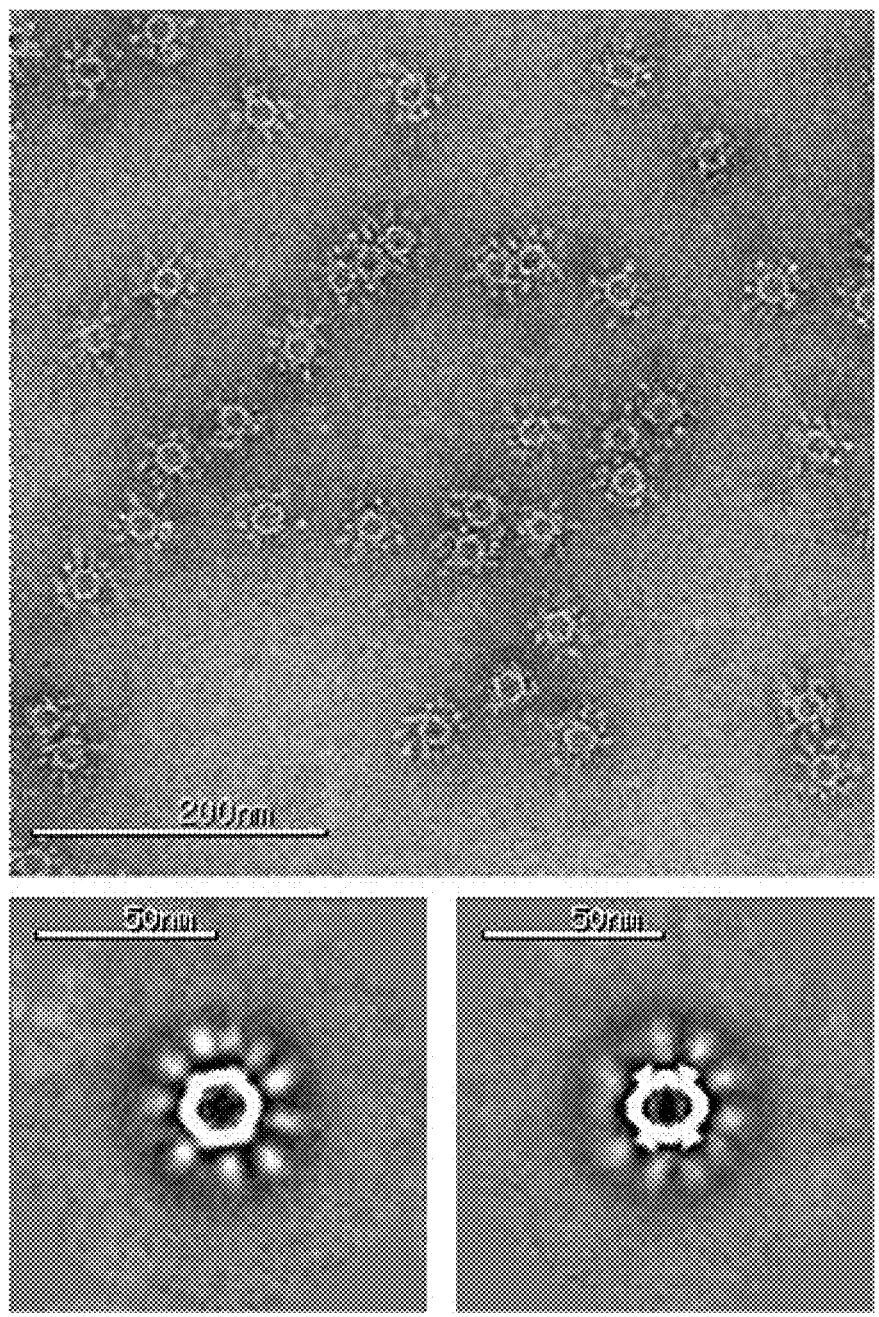
FIG. 5 shows a negative stain electron micrograph and two-dimensional class averages of in vitro-assembled DS-Cav1-I53-50 nanostructures. In vitro-assembled DS-Cav1-I53-50 nanostructures, purified by size exclusion chromatography, were imaged by negative stain electron microscopy (top). Averaging many nanostructures yielded two-dimensional class averages (bottom) that indicate that the I53-50 portion of the nanostructures is highly ordered and consistent, while the precise three-dimensional position of the displayed antigen varies slightly due to the flexible nature of the linker between the DS-Cav1 and I53-50A domains of the DS-Cav1-I53-50A fusion protein.
Figure 6A:
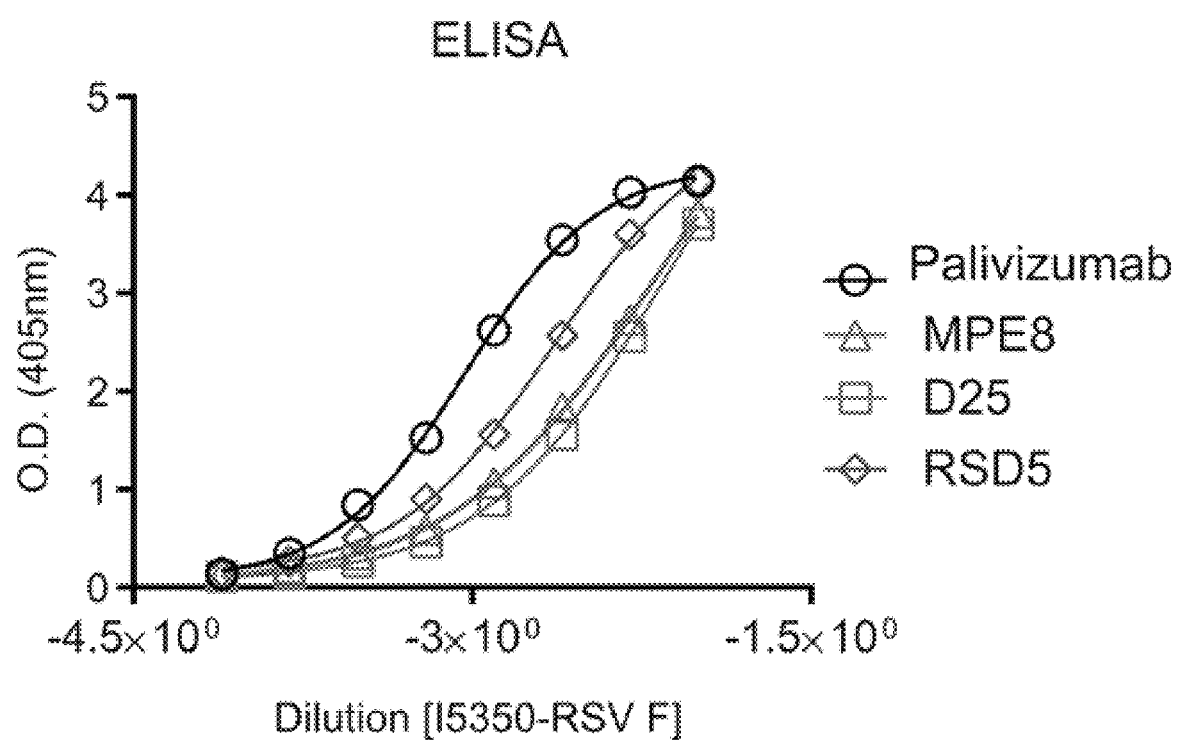
FIG. 6A-6C show a series of graphs depicting the antigenicity of DS-Cav1-I53-50 nanostructures. Analysis of purified DS-Cav1-I53-50 nanostructures by ELISA (FIG. 6A) using four RSV F-specific monoclonal antibodies, including the prefusion-specific antibodies MPE8, D25, and RSD5, indicated that the DS-Cav1 antigen is correctly folded and maintained in the prefusion state when multivalently displayed on DS-Cav1-I53-50 nanostructures. This finding was confirmed by surface plasmon resonance measurements using multiple RSV F-specific antibodies (FIG. 6B-6C), which, when compared to trimeric DS-Cav1, further suggested that multivalent display of DS-Cav1 results in an avidity effect that reduces the dissociation rate of the antibodies.
Figure 6B:
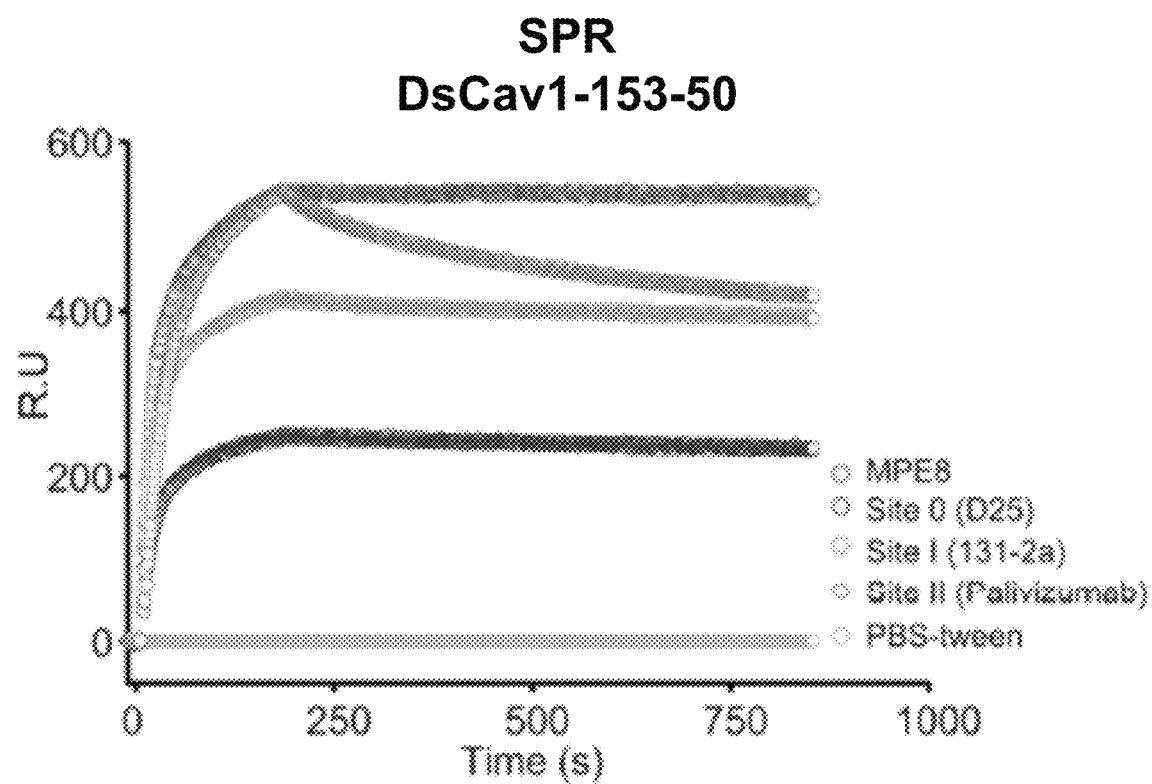
Figure 6C:
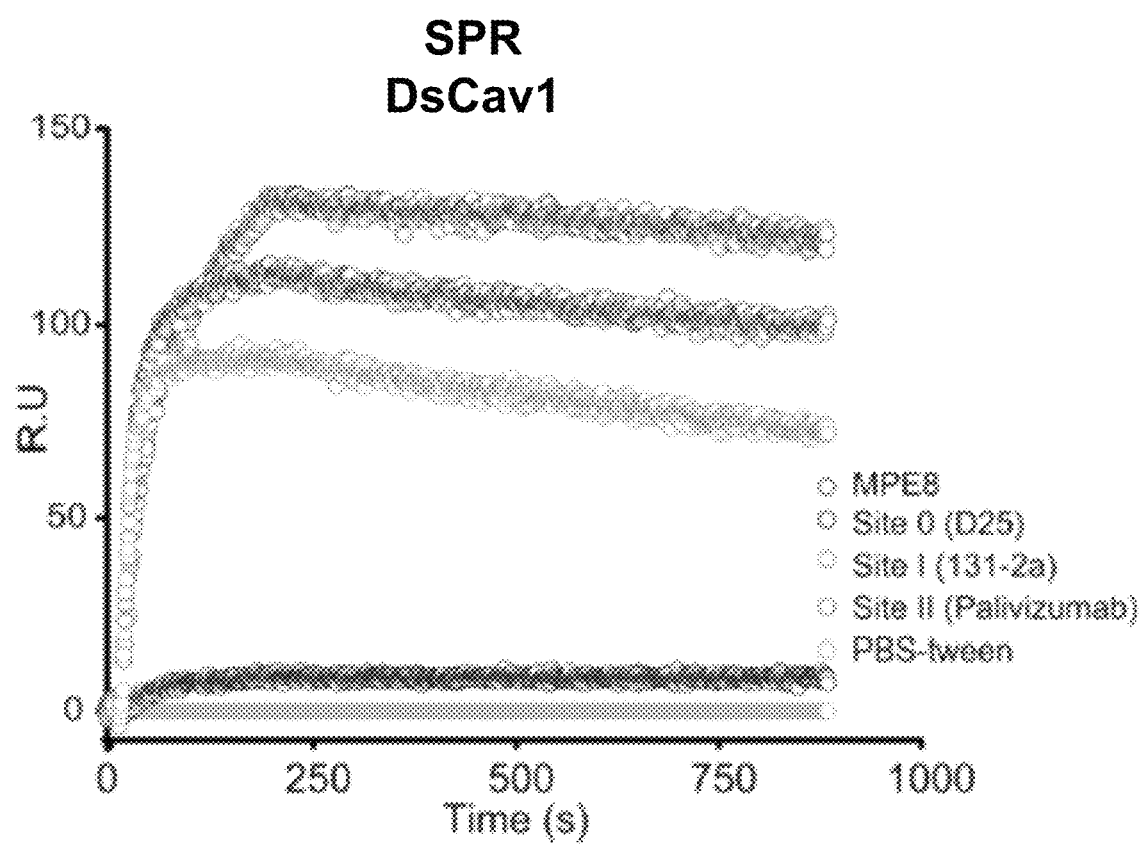

I53-50 is a 120-subunit two-component nanostructure with icosahedral symmetry comprising 20 trimeric (I53-50A) and 12 pentameric (I53-50B) building blocks, as recently described by Bale et al. The N terminus of I53-50A is exposed on the exterior of the I53-50 nanostructure, which enables the display of antigens on the nanostructure exterior through genetic fusion to the I53-530A N terminus. Purified DS-Cav1-foldon-I53-50A and I53-50B.4PT1 were assembled in vitro to form 120-subunit icosahedral nanostructures displaying various amounts of DS-Cav1 on the nanostructure exteriors by mixing the two purified proteins in various molar ratios. In separate preparations, nanostructures displaying DS-Cav1 at valencies of 100% (20 trimers), 66% (~14 trimers), and 33% (~7 trimers) were prepared as described above. The species present in the in vitro assembly reactions after overnight incubation were assessed by several techniques, including size exclusion chromatography-multi-angle light scattering (SEC-MALS), dynamic light scattering, and UV/vis spectroscopy. Assembled, 120-subunit nanostructures were purified from the in vitro assembly reactions using size exclusion chromatography (an example chromatogram obtained using the 100% valency nanostructures is presented in FIG. 4). The purified nanostructures were characterized by negative stain electron microscopy, which revealed fields of monodisperse particles in which DS-Cav1 was clearly visible as spikes projecting outward from the core icosahedral I53-50 assembly (an example micrograph obtained using the 100% valency particles is presented in FIG. 5). ELISA assays using monoclonal antibodies specific to the prefusion conformation confirmed that the DS-Cav1 thus displayed on the nanostructure exteriors was well-folded and antigenically intact (FIG. 6). Surface plasmon resonance experiments evaluating the kinetics of monoclonal antibody binding revealed that antibody dissociation from the 100% valency DS-Cav1-foldon-I53-50 nanostructures was slower than from DS-Cav1-foldon trimers, likely due to avidity effects deriving from the multivalent presentation of DS-Cav1 on the nanostructure exterior (FIG. 6). Together, these experiments confirmed that the DS-Cav1-foldon-I53-50 nanostructures formed monodisperse, icosahedral nanostructures that display well-folded, antigenically intact DS-Cav1 trimers on their exteriors. These findings motivated experiments to evaluate the utility of the DS-Cav1-foldon-I53-50 nanostructures as immunogens for inducing humoral immune responses against DS-Cav1 in animals.

Immunogenicity of DS-Cav1-foldon-I53-50 Nanostructures

Figure 7:
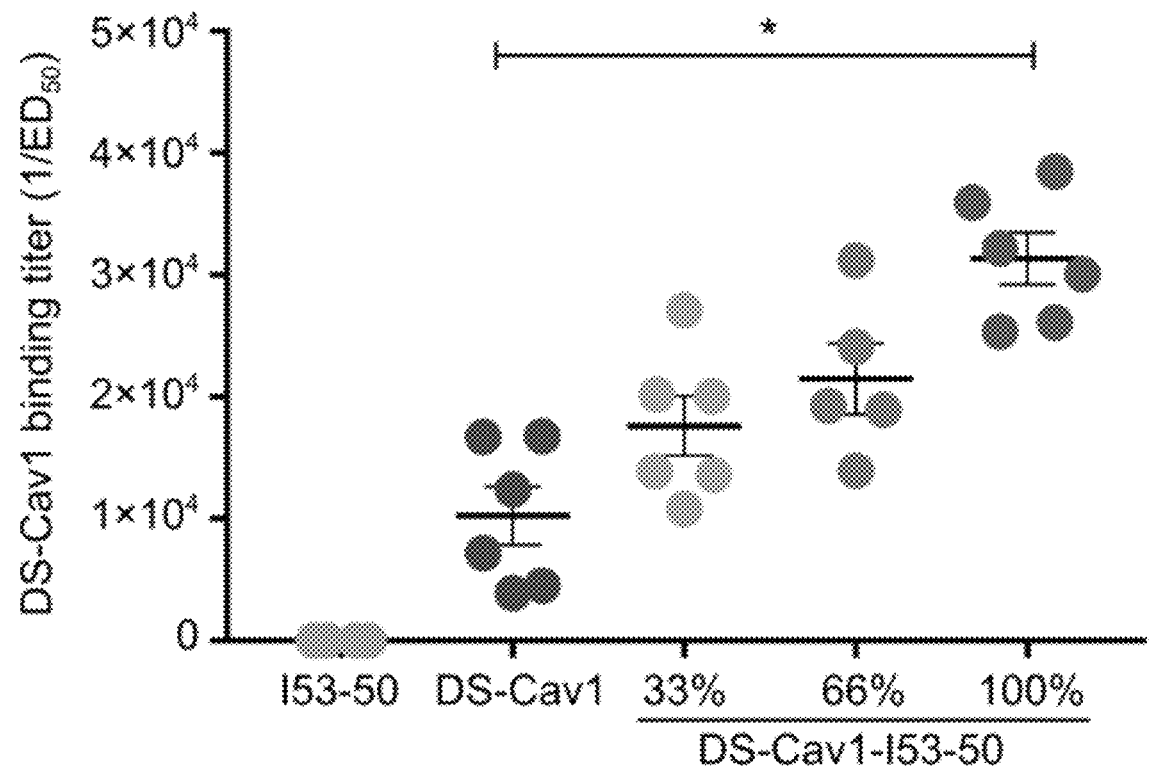
FIG. 7 is a graph depicting DS-Cav1-specific serum antibody titers from mice immunized with DS-Cav1-I53-50 nanostructures. Groups of mice were immunized with I53-50 nanostructures lacking additional antigen, trimeric DS-Cav1, or I53-50 nanostructures bearing DS-Cav1 antigen at 33%, 66%, or 100% valency. DS-Cav1-specific serum antibody titers were measured by ELISA on plates coated with DS-Cav1. Serum antibody titers for each mouse are plotted as circles, with the geometric mean within each group plotted as a horizontal line.

The DS-Cav1-foldon-I53-50 nanostructures displaying DS-Cav1 at 33%, 66%, and 100% valency were injected into mice using a prime-boost strategy as described above. Additional groups of mice were injected with trimeric DS-Cav1-foldon as a benchmark for the humoral immune response induced against DS-Cav1 by the nanostructures or I53-50 nanostructures lacking displayed DS-Cav1 as negative controls for a DS-Cav1 specific response. ELISA assays of serum extracted from the mice at defined time points after the injections were used to measure DS-Cav1 specific antibody titers present in the sera of the injected animals (FIG. 7). As expected, sera from animals injected with the I53-50 nanostructures lacking displayed DS-Cav1 did not contain antibodies specific to DS-Cav1. Trimeric DS-Cav1-foldon induced DS-Cav1-specific antibodies, in accordance with previous results (McClellan et al.). The 33%, 66%, and 100% valency DS-Cav1 nanostructures all induced higher DS-Cav1-specific antibody titers than trimeric DS-Cav1-foldon, with the antibody titers increasing with increasing DS-Cav1 valency. DS-Cav1-specific titers were roughly 2.5-fold higher on average in mice injected with 100% valency DS-Cav1-foldon-I53-50 nanostructures compared to DS-Cav1. These results demonstrate that immunogens in which paramyxovirus F proteins are multivalently displayed on self-assembling protein nanostructures can induce higher humoral immune responses when injected into animals.

Figure 8:
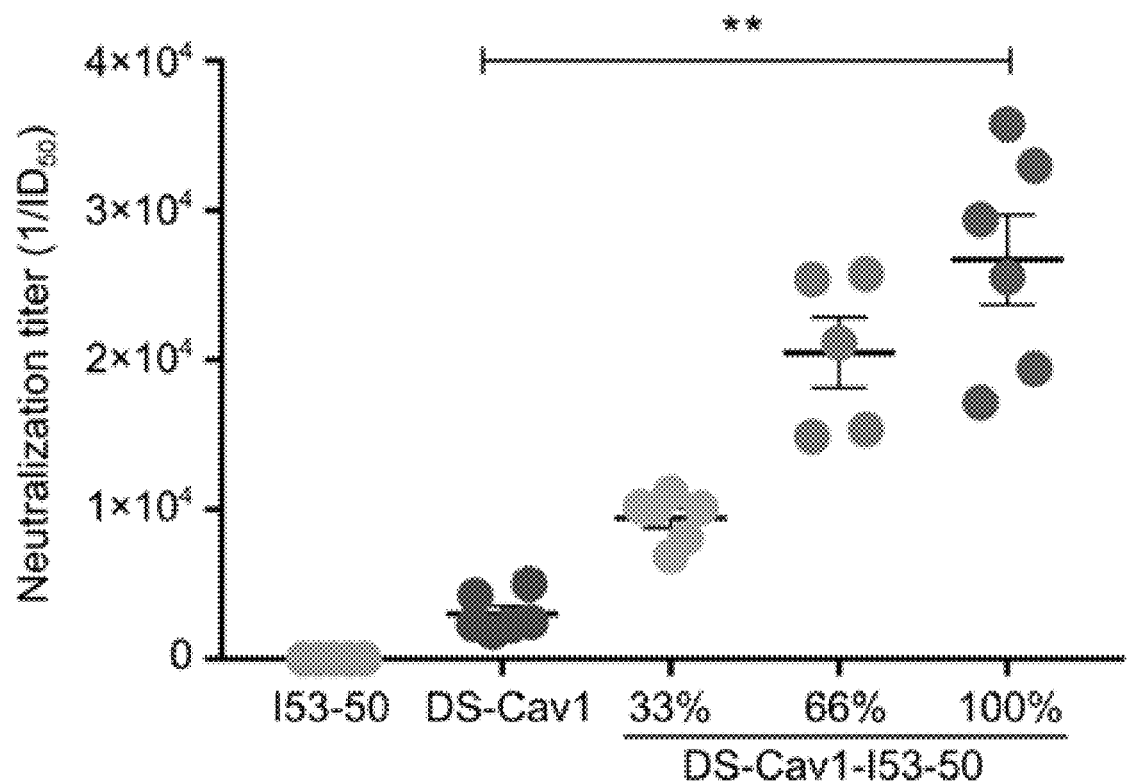
FIG. 8 is a graph depicting serum neutralization activity elicited by immunization with DS-Cav1-I53-50 nanostructures. Groups of mice were immunized with I53-50 nanostructures lacking additional antigen, trimeric DS-Cav1, or I53-50 nanostructures bearing DS-Cav1 antigen at 33%, 66%, or 100% valency. Neutralization titers for each mouse are plotted as circles, with the geometric mean within each group plotted as a horizontal line.

The sera from the mice injected with the series of immunogens described above was also evaluated for the presence of neutralizing antibody titers using the standard neutralization assay in HEp-2 cells (FIG. 8). The trend in serum neutralizing antibody titers correlated highly with the trend observed in DS-Cav1-specific binding antibody titers. Sera from animals injected with the I53-50 nanostructures lacking displayed DS-Cav1 did not neutralize virus, consistent with the lack of DS-Cav1-specific antibodies in these sera. The sera from animals injected with trimeric DS-Cav-1-foldon neutralized virus with an average titer ($1/ID_{50}$) of 3,030. The 33%, 66%, and 100% valency DS-Cav1-I53-50 nanostructures induced higher neutralizing antibody titers than trimeric DS-Cav1-foldon, with average titers of 9,400, 20,000, and 30,500, respectively. These results demonstrate that the higher humoral response induced by immunogens in which paramyxovirus F proteins are multivalently displayed on self-assembling protein nanostructures result in more effective virus neutralization.

Figure 9A:
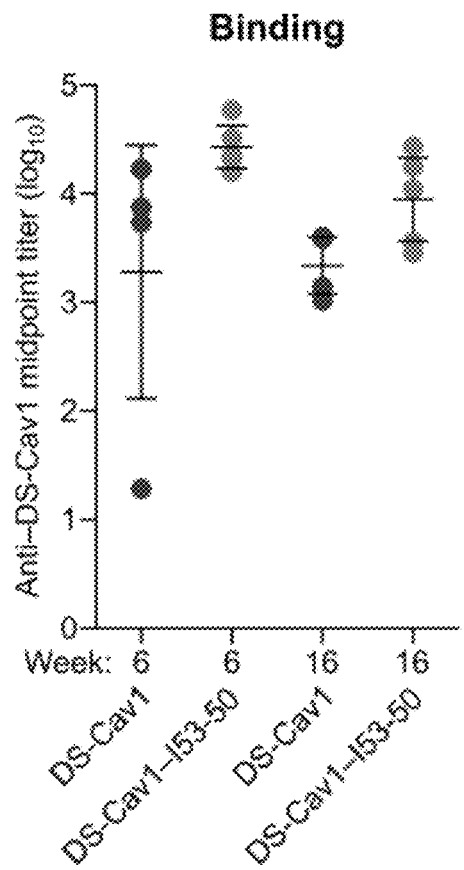
FIG. 9A-9B are graphs depicting immunogenicity in a primate immune system elicited by immunization with DS-Cav1-foldon I53-50 nanostructures. Rhesus macaques were injected at weeks 0 and 4 with either free DS-Cav1 trimer or DS-Cav1-foldon-I53-50 nanostructures displaying DS-Cav1 at 100% valency. In both cases, the dose of DS-Cav1 antigen was 50 μg, and the immunogens were formulated with the MF59-like, squalene-based oil-in-water emulsion adjuvant SWE. Sera obtained from the animals at weeks 6 and 16 were evaluated for anti-DS-Cav1 antibody titers (FIG. 9A) and RSV-neutralizing antibody titers (FIG. 9B).
Figure 9B:
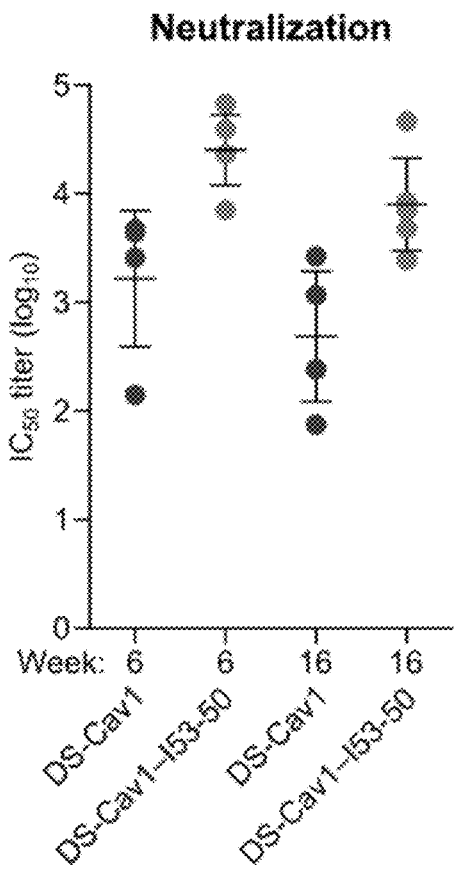

The DS-Cav1-foldon-I53-50 nanostructures were also injected into Rhesus macaques to evaluate their immunogenicity in a primate immune system. The animals were injected intramuscularly at weeks 0 and 4 with either free DS-Cav1 trimer or DS-Cav1-foldon-I53-50 nanostructures displaying DS-Cav1 at 100% valency. In both cases, the dose of DS-Cav1 antigen was 50 µg, and the immunogens were formulated with the MF59-like, squalene-based oil-in-water emulsion adjuvant SWE. Sera obtained from the animals at weeks 6 and 16 were evaluated for anti-DS-Cav1 antibody titers and RSV-neutralizing antibody titers (FIG. 9). The results mirrored those obtained in mice. At week 16, the mean anti-DS-Cav1 antibody titer was 4-fold higher in animals injected with the DS-Cav1-foldon-I53-50 nanostructure compared to animals injected with trimeric DS-Cav1. The mean RSV-neutralizing antibody titer at week 16 was 16-fold higher in animals injected with the DS-Cav1-foldon-I53-50 nanostructure compared to animals injected with trimeric DS-Cav1. These results demonstrate, in a primate immune system, that immunogens in which paramyxovirus F proteins are multivalently displayed on self-assembling protein nanostructures induce more robust humoral immune responses, including high levels of virus-neutralizing antibodies, than the trimeric paramyxovirus F proteins alone.

Physical Stabilization of DS-Cav1 by Fusion to I53-50A

Figure 10:
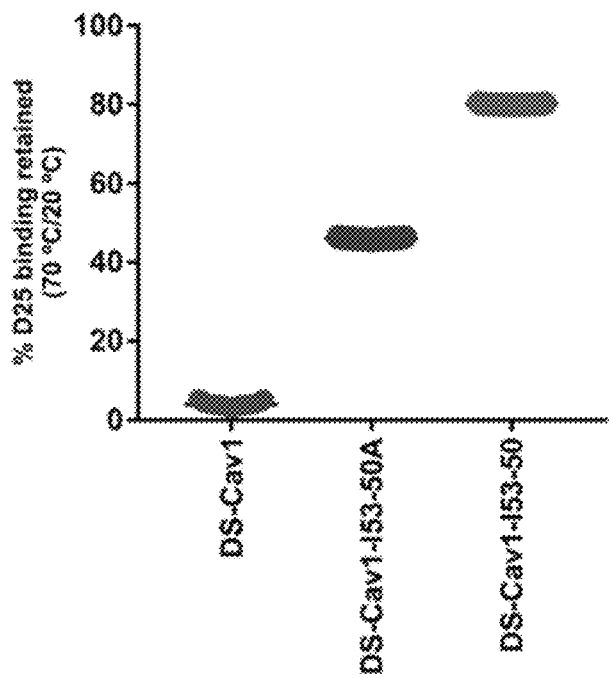
FIG. 10 is a graph depicting the physical stability of DS-Cav1 when fused to I53-50A and/or when further assembled into the icosahedral nanostructure. Samples of trimeric DS-Cav1, trimeric DS-Cav1-foldon-I53-50A, and DS-Cav1-foldon-I53-50 nanostructures containing equivalent concentrations of DS-Cav1 were split into four aliquots and incubated at 20, 50, 70 or 80° C. for 1 hour. After cooling to room temperature, D25 binding was assayed by surface plasmon resonance (SPR).
Figure 11A:
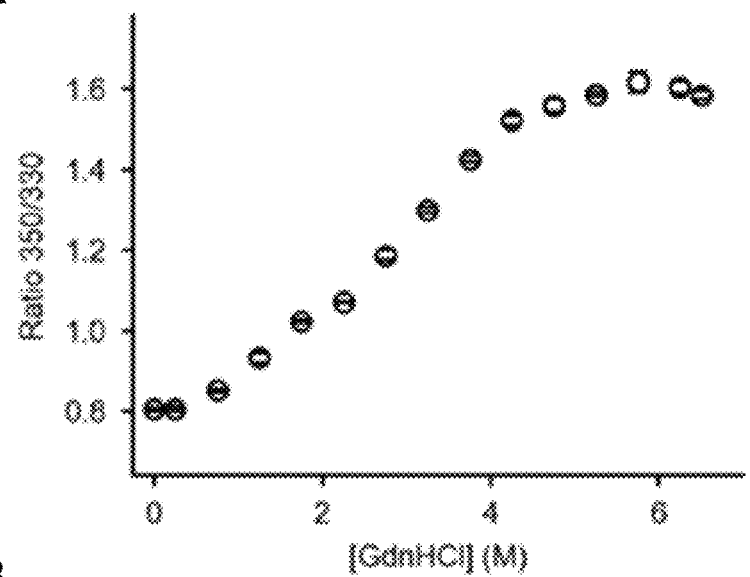
FIGS. 11A-11J are graphs depicting physical stability of the nanostructures. Chemical denaturation in guanidine hydrochloride (GdnHCl), monitored by intrinsic tryptophan fluorescence, was used as a second, antibody-independent technique to evaluate physical stability of trimeric DS-Cav1 (FIGS. 11A-11B), DS-Cav1-foldon-I53-50A (FIGS. 11C-11D), DS-Cav1-foldon-I53-50 (FIGS. 11E-11F), I53-50 (FIGS. 11G-11H), and I53-50A (FIGS. 11-11J). The data indicate superior physical stability of the DS-Cav1 antigen when genetically fused to the I53-50A nanostructure component.
Figure 11B:
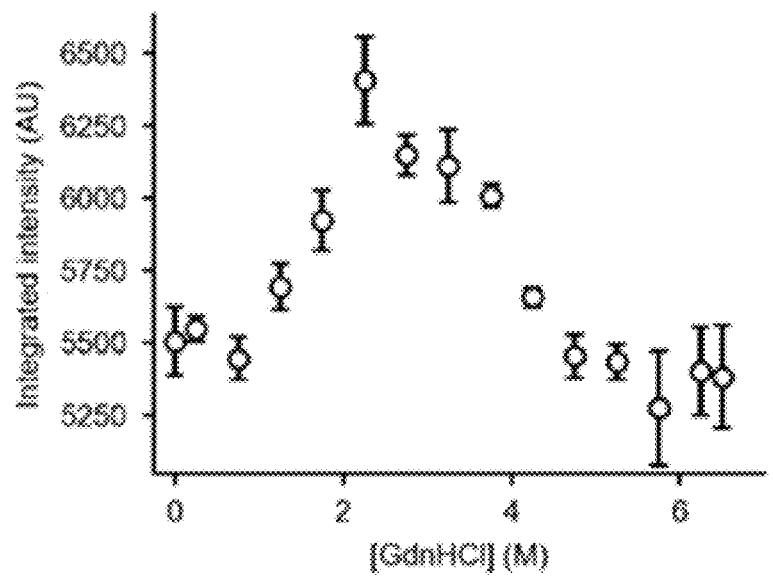
Figure 11C:
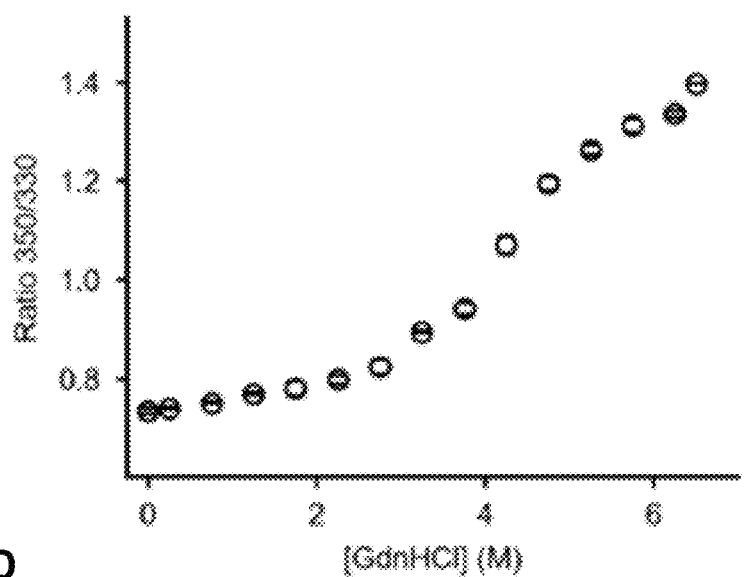
Figure 11D:
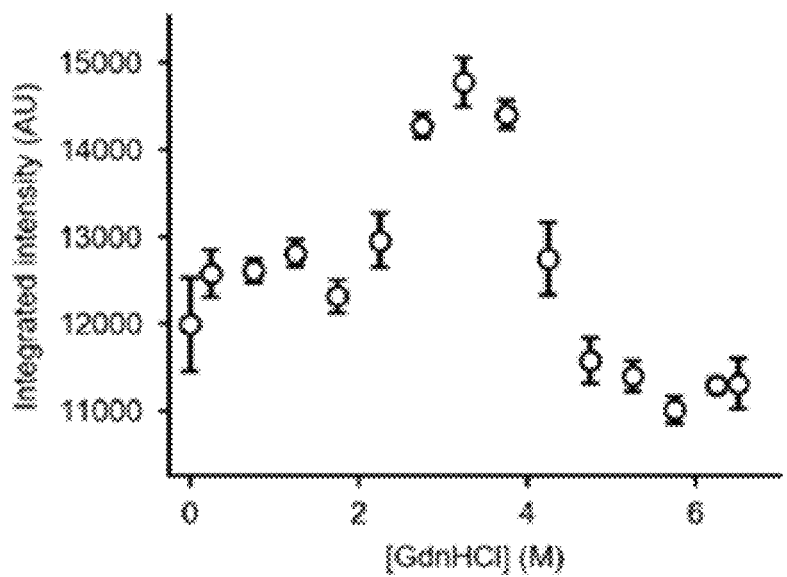
Figure 11E:
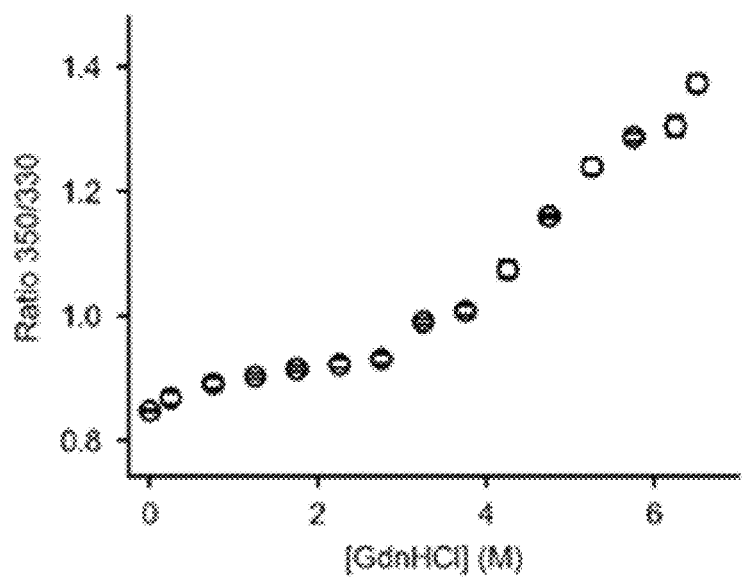
Figure 11F:
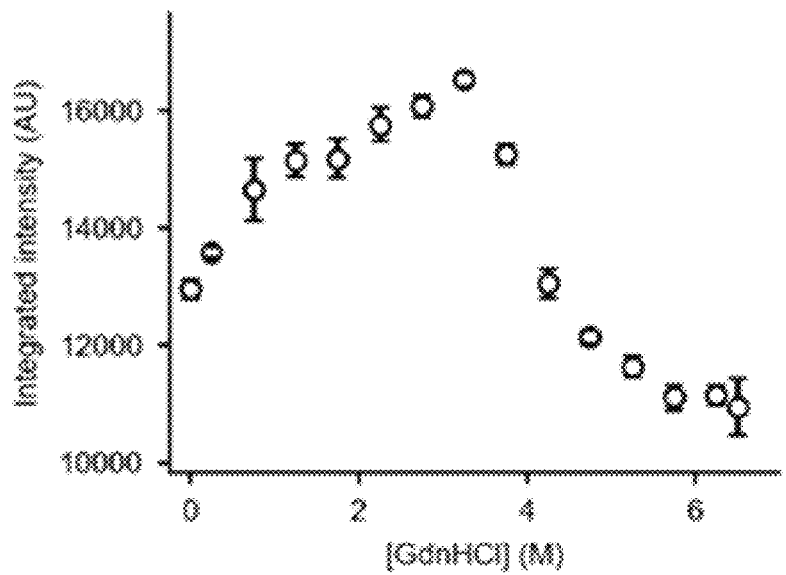
Figure 11G:
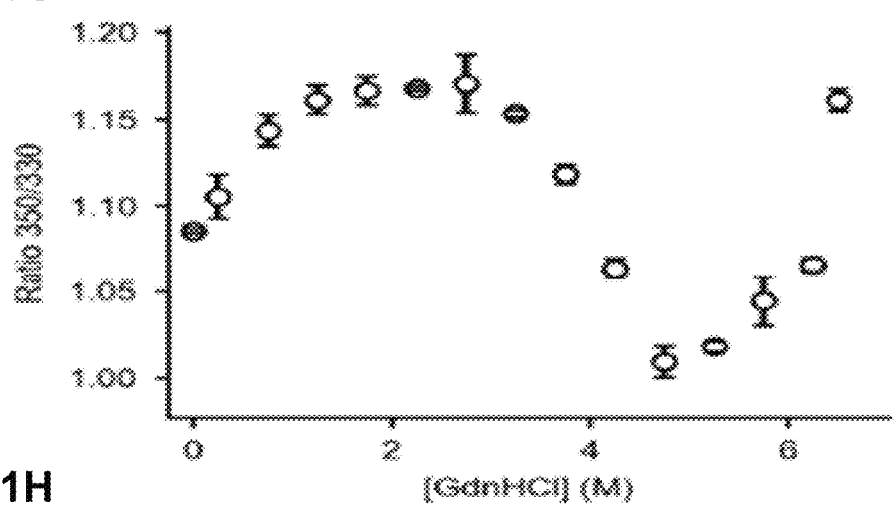
Figure 11H:
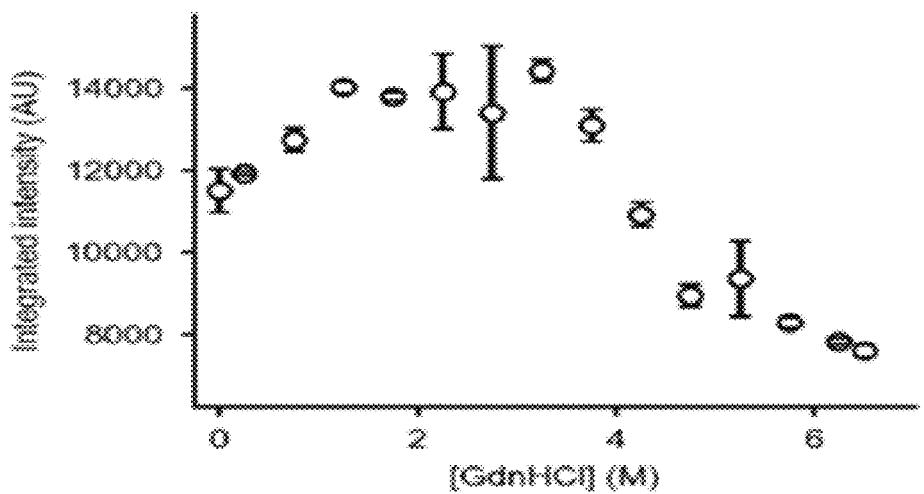
Figure 11I:
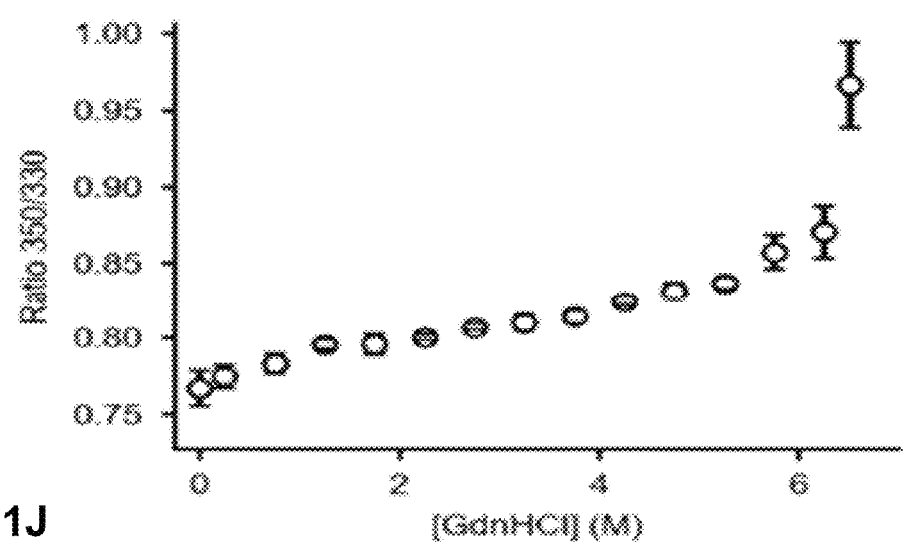
Figure 11J:
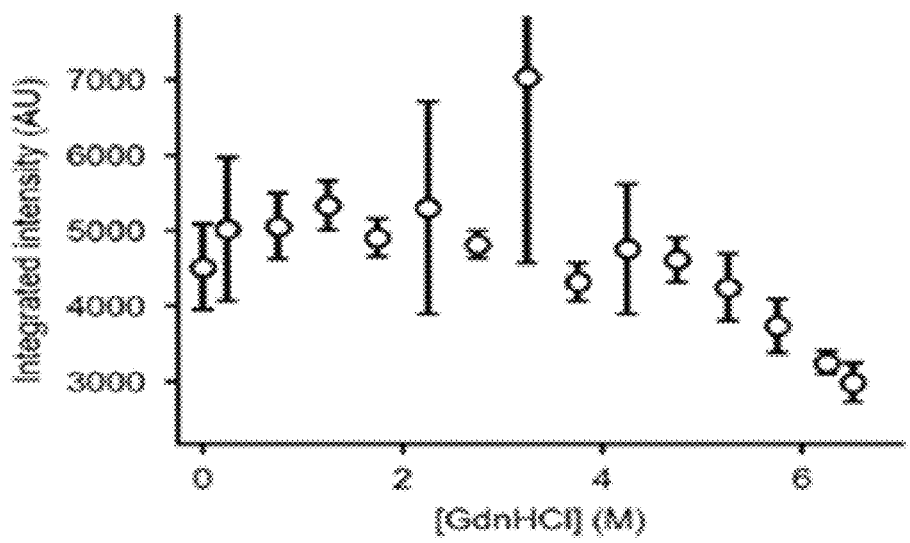

Given the key antigenic properties of prefusion F, we used two orthogonal approaches to measure the physical stability of DS-Cav1 when fused to I53-50A and/or when further assembled into the icosahedral nanostructure. The first assay measured the retention of binding by a prefusion-specific mAb (D25) after thermal stress, an approach that has been used previously to characterize prefusion F stability (McLellan et al. 2013; Joyce et al. 2016; Krarup et al. 2015). Samples of trimeric DS-Cav1, trimeric DS-Cav1-I53-50A, and DS-Cav1-I53-50 nanostructures containing equivalent concentrations (50 nM) of DS-Cav1 were split into four aliquots and incubated at 20, 50, 70 or 80° C. for 1 hour. After cooling to room temperature, D25 binding was assayed by surface plasmon resonance (SPR). We found that all samples bound D25 equivalently at 20 and 50° C., but lost most of their reactivity to D25 after 1 hour at 80° C. as previously reported for DS-Cav1 (McLellan et al. 2013; Joyce et al. 2016) (FIG. 10). Interestingly, while D25 was also unable to bind trimeric DS-Cav1 incubated at 70° C. for 1 hour, trimeric DS-Cav1-I53-50A and the DS-Cav1-I53-50 nanostructures retained 50 and 80% of their respective binding signals (FIG. 10). While the multivalent nature of the DS-Cav1-I53-50 nanostructures complicates direct quantitative comparisons to trimeric DS-Cav1, these results indicate that genetic fusion to the I53-50A trimer further stabilizes the prefusion conformation of DS-Cav1, and suggest that this increased stability is maintained in the context of the assembled nanostructure immunogen.

We used chemical denaturation in guanidine hydrochloride (GdnHCl), monitored by intrinsic tryptophan fluorescence, as a second, antibody-independent technique to evaluate physical stability. Analyzing fluorescence emission from DS-Cav1 incubated in 0-6.5 M GdnHCl revealed that the protein undergoes two subtly distinct transitions, one between 0.25 and 2.25 M GdnHCl and another between 2.25 and 5.75 M (FIG. 11). In contrast, only a single transition is apparent for trimeric DS-Cav1-I53-50A, occurring between 2.25 and 6.25 M GdnHCl (FIG. 11). It is unclear at present whether the transition at lower [GdnHCl] observed for DS-Cav1 is absent from trimeric DS-Cav1-I53-50A or simply shifted to higher [GdnHCl]. However, it is clear that the native conformation of DS-Cav1 is stabilized by genetic fusion to trimeric I53-50A, mirroring the results obtained by measuring D25 binding after thermal stress. Comparing the data for the DS-Cav1-I53-50 nanostructure and the I53-50 nanostructure alone (lacking fused DS-Cav1) indicated that the stabilization is maintained upon assembly to the icosahedral nanostructure (FIG. 11). The source of this effect is likely the extreme stability of the I53-50A trimer. I53-50A is derived from the KDPG aldolase of the hyperthermophilic bacterium *T. maritima* and only began to exhibit changes in fluorescence at very high (≥5.75 M) GdnHCl concentrations (FIG. 11).

We made addition constructs to assess the number of GS repeats and the need for a stabilization domain such as the Foldon moiety.

Sequence Information

| IPD Name | MS (Da) | Construct Information |
| --- | --- | --- |
| RSV_F-10 | 74005.38 | DS-Cav1-8GS-HelExt-50A |
| RSV_F-11 | 74293.64 | DS-Cav1-12GS-HelExt-50A |
| RSV_F-12 | 74551.87 | DS-Cav1-16GS-HelExt-50A |
| RSV_F-13 | 77212.97 | DS-Cav1-foldon-10GS-HelExt-50A |

| IPD Name | MS (Da) | Construct Information |
|---|---|---|
| RSV_F-14 | 77558.28 | DS-Cav1-foldon-15GS-HelExt-50A |
| RSV_F-15 | 77933.62 | DS-Cav1-foldon-20GS-HelExt-50A |

Studies were based on expression yield in a small-scale transient transfection. Plasmids capable of expressing the relevant constructs were transformed into NEB 5α *E. coli* cells and selected on LB+carbenicillin agar plates. 1 mL cultures were prepared by inoculating TB media with a bacterial colony and again selecting with 50 ug/mL carbenicillin. A Qiagen Mini Prep kit was used to purify plasmid from the *E. coli* cultures in accordance with their protocol. Expi293F™ Cells (ThermoFisher) were cultured in Expi293™ Expression Medium (ThermoFisher) supplemented with penicillin (100 u/mL) and streptomycin (100 μg/mL) at 8% $CO_2$, 37° C., and 125 rpm shaking.

On the day prior to transfection, cells were seeded at a concentration of 2E6 cells/mL. On the day of transfection, cells were counted by a Countess II (ThermoFisher) with trypan blue to determine cell viability. Cell concentration was adjusted to 2.5E6 cells/mL, and cells where plated into untreated 12-well plates (Corning) in 1 mL volumes. 1 μg of DNA plasmid were transfected per each well using Expifectamine™ (ThermoFisher), following the manufacturer's directions. Enhancers, components of ThermoFisher's Expifectamine™ Transfection Kit, were added 18 hours after transfection. The 1 mL cultures were harvested 5 days post-transfection, and the cells were pelleted from the supernatant by centrifugation at 1,500×g for 5 minutes at 4° C. Supernatants were filtered through a 0.45 μM filter with a PVDF membrane.

Filtered supernatants containing DS-Cav1-I53-50A constructs were denatured and boiled for 10 minutes at 95° C. for 10 minutes in 2× Laemmli buffer with 2-mercaptoethanol. SDS-PAGE separated the sample fractions, which were then transferred to a nitrocellulose membrane and probed with palivizumab, followed with a secondary antibody, anti-human conjugated to HRP. Blot was imaged using Clarity Western ECL Blotting Substrate (Bio-Rad).

Filtered supernatants containing DS-Cav1-I53-50A constructs were bound to Nunc MaxiSorp™ 96-well plates in a two-fold dilution series. The pre-fusion conformation-specific antibody D25 was used to detect DS-Cav1-I53-50A, followed by a secondary anti-human antibody conjugated to HRP. Protein yield was determined colorimetrically via the substrate TMB and absorbances were collected at 450 nm.

The expression yields and binding of the prefusion-specific mAb D25 (data not shown) indicate that all constructs express well and are in the prefusion conformation. Those of skill in the art would have expected that a heterologous trimerization domain (such as the foldon) would be required for proper expression and folding of prefusion F constructs. Our results indicate that the I53-50A nanostructure component can support the expression and proper folding of DS-Cav1 without the use of a trimerization domain like the foldon. Binding of D25 to these constructs suggests that they are antigenically intact and would be expected to induce potent immune responses, including neutralizing antibodies, similarly to nanostructures comprising the DS-Cav1-foldon-I53-50 fusion polypeptide.

We claim:

1. A nanostructure, comprising:
   (a) a plurality of first assemblies, each first assembly comprising a plurality of identical first polypeptides, wherein the first polypeptides comprise polypeptides having at least 75%, 80%, 85%, 90%, 91%, 92%, 93%, 94%, 95%, 96%, 97%, 98%, 99%, or 100% identity to the amino acid sequence of a polypeptide selected from the group consisting of SEQ ID NOS:1-51;
   (b) a plurality of second assemblies, each second assembly comprising a plurality of identical second polypeptides, wherein the second polypeptides comprise polypeptides having at least 75%, 80%, 85%, 90%, 91%, 92%, 93%, 94%, 95%, 96%, 97%, 98%, 99%, or 100% identity to the amino acid sequence of a polypeptide selected from the group consisting of SEQ ID NOS:1-51,
   wherein the second polypeptide differs from the first polypeptide;
   wherein the plurality of first assemblies non-covalently interact with the plurality of second assemblies to form a nanostructure; and
   wherein the nanostructure displays multiple copies of one or more paramyxovirus and/or pneumovirus F proteins, or antigenic fragments thereof, on an exterior of the nanostructure.

2. The nanostructure of claim 1, wherein the one or more paramyxovirus and/or pneumovirus F proteins, or antigenic fragments thereof, comprise a polypeptide having at least 75%, 80%, 85%, 90%, 91%, 92%, 93%, 94%, 95%, 96%, 97%, 98%, 99%, or 100% identity to an RSV F protein or mutant thereof selected from the group consisting of SEQ ID NO:53 and 61-64, wherein the polypeptide includes one or more of the following residues: 67I, 149C, 458C, 46G, 465Q, 215P, 92D, and 487Q.

3. The nanostructure of claim 1, wherein the first polypeptides and the second polypeptides comprise polypeptides having at least 75%, 80%, 85%, 90%, 91%, 92%, 93%, 94%, 95%, 96%, 97%, 98%, 99%, or 100% identity to the amino acid sequences selected from the following pairs:

SEQ ID NO:1 and SEQ ID NO:2 (I53-34A and I53-34B);
SEQ ID NO:3 and SEQ ID NO:4 (I53-40A and I53-40B);
SEQ ID NO:3 and SEQ ID NO:24 (I53-40A and I53-40B.1);
SEQ ID NO:23 and SEQ ID NO:4 (I53-40A.1 and I53-40B);
SEQ ID NO:35 and SEQ ID NO:36 (I53-40A genus and I53-40B genus);
SEQ ID NO:5 and SEQ ID NO:6 (I53-47A and I53-47B);
SEQ ID NO:5 and SEQ ID NO:27 (I53-47A and I53-47B.1);
SEQ ID NO:5 and SEQ ID NO:28 (I53-47A and I53-47B.1NegT2);
SEQ ID NO:25 and SEQ ID NO:6 (I53-47A1 and I53-47B);
SEQ ID NO:25 and SEQ ID NO:27 (I53-47A1 and I53-47B.1);
SEQ ID NO:25 and SEQ ID NO:28 (I53-47A1 and I53-47B.1NegT2);
SEQ ID NO:26 and SEQ ID NO:6 (I53-47A.1NegT2 and I53-47B);
SEQ ID NO:26 and SEQ ID NO:27 (I53-47A.1NegT2 and I53-47B.1);
SEQ ID NO:26 and SEQ ID NO:28 (I53-47A.1NegT2 and I53-47B.1NegT2);
SEQ ID NO:37 and SEQ ID NO:38 (I53-47A genus and I53-47B genus);
SEQ ID NO:7 and SEQ ID NO:8 (I53-50A and I53-50B);
SEQ ID NO:7 and SEQ ID NO:32 (I53-50A and I53-50B.1);
SEQ ID NO:7 and SEQ ID NO:33 (I53-50A and I53-50B.1NegT2);
SEQ ID NO:7 and SEQ ID NO:34 (I53-50A and I53-50B.4PosT1);
SEQ ID NO:29 and SEQ ID NO:8 (I53-50A.1 and I53-50B);
SEQ ID NO:29 and SEQ ID NO:32 (I53-50A.1 and I53-50B.1);
SEQ ID NO:29 and SEQ ID NO:33 (I53-50A.1 and I53-50B.1NegT2);
SEQ ID NO:29 and SEQ ID NO:34 (I53-50A.1 and I53-50B.4PosT1);
SEQ ID NO:30 and SEQ ID NO:8 (I53-50A.1NegT2 and I53-50B);
SEQ ID NO:30 and SEQ ID NO:32 (I53-50A.1NegT2 and I53-50B.1);
SEQ ID NO:30 and SEQ ID NO:33 (I53-50A.1NegT2 and I53-50B.1NegT2);
SEQ ID NO:30 and SEQ ID NO:34 (I53-50A.1NegT2 and I53-50B.4PosT1);
SEQ ID NO:31 and SEQ ID NO:8 (I53-S0A.1PosT1 and I53-50B);
SEQ ID NO:31 and SEQ ID NO:32 (I53-50A.1PosT1 and I53-50B.1);
SEQ ID NO:31 and SEQ ID NO:33 (I53-50A.1PosT1 and I53-50B.1NegT2);
SEQ ID NO:31 and SEQ ID NO:34 (I53-50A.1PosT1 and I53-50B.4PosT1);
SEQ ID NO:39 and SEQ ID NO:40 (I53-50A genus and I53-50B genus);
SEQ ID NO:9 and SEQ ID NO:10 (I53-51A and I53-51B);
SEQ ID NO:11 and SEQ ID NO:12 (I52-03A and I52-03B);
SEQ ID NO:13 and SEQ ID NO:14 (I52-32A and I52-32B);
SEQ ID NO:15 and SEQ ID NO:16 (I52-33A and I52-33B)
SEQ ID NO:17 and SEQ ID NO:18 (I32-06A and I32-06B);
SEQ ID NO:19 and SEQ ID NO:20 (I32-19A and I32-19B);
SEQ ID NO:21 and SEQ ID NO:22 (I32-28A and I32-28B);
SEQ ID NO:23 and SEQ ID NO:24 (I53-40A.1 and I53-40B.1);
SEQ ID NO:41 and SEQ ID NO:42 (T32-28A and T32-28B);
SEQ ID NO:43 and SEQ ID NO:44 (T33-09A and T33-09B);
SEQ ID NO:45 and SEQ ID NO:46 (T33-15A and T33-15B);
SEQ ID NO:47 and SEQ ID NO:48 (T33-21A and T33-21B);
SEQ ID NO:49 and SEQ ID NO:50 (T33-28A and T32-28B); and
SEQ ID NO:51 and SEQ ID NO:44 (T33-31B and T33-09B (also referred to as T33-31B)).

4. The nanostructure of claim 1, wherein the first polypeptides comprise polypeptides having at least 75%, 80%, 85%, 90%, 91%, 92%, 93%, 94%, 95%, 96%, 97%, 98%, 99%, or 100% identity to the amino acid sequence selected from the group consisting of I53-50A (SEQ ID NO:7), I53-50A.1 (SEQ ID NO:29), I53-50A.1NegT2 (SEQ ID NO:30), and I53-50A.1PosT1 (SEQ ID NO:31), and the second polypeptides comprise polypeptides having at least 75%, 80%, 85%, 90%, 91%, 92%, 93%, 94%, 95%, 96%, 97%, 98%, 99%, or 100% identity to the amino acid sequence selected from the group consisting of I53-50B (SEQ ID NO:8), I53-50B.1 (SEQ ID NO:32), I53-50B.1NegT2 (SEQ ID NO:33), and I53-50B.4PosT1 (SEQ ID NO:34).

5. The nanostructure of claim 1, wherein the one or more paramyxovirus and/or pneumovirus F proteins, or antigenic fragments thereof, are expressed as a fusion protein with the first polypeptides.

6. The nanostructure of claim 1, wherein each first assembly comprises a homotrimer of the first polypeptide.

7. The nanostructure of claim 1, wherein the one or more paramyxovirus and/or pneumovirus F proteins, or antigenic fragments thereof comprise polypeptides having at least 75%, 80%, 85%, 90%, 91%, 92%, 93%, 94%, 95%, 96%, 97%, 98%, 99%, or 100% identity to the amino acid sequence of DS-Cav1 (SEQ ID NO:53).

8. The nanostructure of claim 5, wherein each fusion protein comprises an amino acid linker positioned between the first polypeptide and the one or more paramyxovirus and/or pneumovirus F proteins, or antigenic fragments thereof.

9. The nanostructure of claim 8, wherein the amino acid linker sequence comprises one or more trimerization domains.

10. The nanostructure of claim 8, wherein the amino acid linker sequence comprises a Gly-Ser linker.

11. The nanostructure of claim 5, wherein the fusion protein comprises polypeptides having at least 75%, 80%, 85%, 90%, 91%, 92%, 93%, 94%, 95%, 96%, 97%, 98%, 99%, or 100% identity to the amino acid sequence selected from the group consisting of SEQ ID NOS:69-100.

12. The nanostructure of claim 11, wherein DS-Cav1-I53-50A (SEQ ID NO:74), and each second polypeptide is I53-50B (SEQ ID NO:8), I53-50B.1 (SEQ ID NO:32), I53-50B.1NegT2 (SEQ ID NO:33), or I53-50B.4PosT1 (SEQ ID NO:34).

13. The nanostructure of claim 7, wherein each first polypeptide comprises a fusion protein of DS-Cav1 (SEQ ID NO:53) linked to SEQ ID NO:7 (I53-50A) via an amino acid linker.

14. The nanostructure of claim 13, wherein the amino acid linker comprises a Gly-Ser linker and/or a helical extension domain.

15. The nanostructure of claim 13, wherein each second polypeptide comprises the amino acid sequence of I53-50B.4PosT1 (SEQ ID NO:34).

16. A recombinant nucleic acid encoding the first polypeptide fusion protein of claim 5.

17. A recombinant expression vector comprising the recombinant nucleic acid of claim 16 operatively linked to a promoter.

18. A recombinant host cell, comprising the recombinant expression vector of claim 17.

19. A recombinant host cell, comprising one or more recombinant expression vectors capable of expressing the first polypeptides and the second polypeptides of claim 1.

20. An immunogenic composition comprising the nanostructure of claim 1, and a pharmaceutically acceptable carrier.

21. The immunogenic composition of claim 20, further comprising an adjuvant.

22. A process for assembling the nanostructures of claim 1 in vitro, comprising mixing two or more nanostructure components in aqueous conditions to drive spontaneous assembly of the desired nanostructure.

23. The process of claim 22, wherein the mixing comprises
(a) mixing first assemblies comprising first polypeptides each comprising an F protein or antigenic fragment thereof with appropriate second assemblies comprising second polypeptides in an approximately 1:1 molar first polypeptide: second polypeptide ratio under conditions and for a time suitable to permit interaction of the first assemblies and the second assemblies to form the nanostructure;
(b) mixing first assemblies comprising first polypeptides, wherein fewer than all first polypeptides comprise an F protein with appropriate second assemblies comprising second polypeptides in an approximately 1:1 first polypeptide: second polypeptide molar ratio under conditions and for a time suitable to permit interaction of the first assemblies and the second assemblies to form the nanostructure; or
(c) mixing first assemblies comprising first polypeptides each comprising an F protein, wherein in total the first polypeptides comprise multiple different F proteins with appropriate second assemblies comprising second polypeptides in an approximately 1:1 molar first polypeptide: second polypeptide ratio under conditions and for a time suitable to permit interaction of the first assemblies and the second assemblies to form the nanostructure comprising multiple F proteins, or antigenic fragments thereof.

24. The nanostructure of claim 14, wherein the helical extension domain comprises the sequence of SEQ ID NO: 58.

25. The nanostructure of claim 1, wherein the first polypeptides comprise polypeptides having at least 95% identity to the amino acid sequence of I53-50A (SEQ ID NO:7), and the second polypeptides comprise polypeptides having at least 95% identity to the amino acid sequence of I53-50B.4PosT1 (SEQ ID NO:34).

26. The nanostructure of claim 1, wherein the first polypeptides comprise polypeptides comprising the amino acid sequence of I53-50A (SEQ ID NO:7), and the second polypeptides comprise polypeptides comprising the amino acid sequence of I53-50B.4PosT1 (SEQ ID NO:34).

27. The nanostructure of claim 25, wherein the one or more paramyxovirus and/or pneumovirus F proteins, or antigenic fragments thereof comprises polypeptides having at least 95% identity to the amino acid sequence of DS-Cav1 (SEQ ID NO:53).

28. The nanostructure of claim 26, wherein the one or more paramyxovirus and/or pneumovirus F proteins, or antigenic fragments thereof comprises polypeptides having at least 95% identity to the amino acid sequence of DS-Cav1 (SEQ ID NO:53).

29. The nanostructure of claim 25, wherein the one or more paramyxovirus and/or pneumovirus F proteins, or antigenic fragments thereof comprises polypeptides comprising the amino acid sequence of DS-Cav1 (SEQ ID NO:53).

30. The nanostructure of claim 26, wherein the one or more paramyxovirus and/or pneumovirus F proteins, or antigenic fragments thereof comprise polypeptides comprising the amino acid sequence of DS-Cav1 (SEQ ID NO:53).

* * * * *

SEQUENCE LISTING

```
<160> NUMBER OF SEQ ID NOS: 101

<210> SEQ ID NO 1
<211> LENGTH: 207
<212> TYPE: PRT
<213> ORGANISM: Artificial Sequence
<220> FEATURE:
<223> OTHER INFORMATION: I53-34A
<220> FEATURE:
<221> NAME/KEY: MISC_FEATURE
<222> LOCATION: (1)..(1)
<223> OTHER INFORMATION: optionally absent

<400> SEQUENCE: 1

Met Glu Gly Met Asp Pro Leu Ala Val Leu Ala Glu Ser Arg Leu Leu
1               5                   10                  15

Pro Leu Leu Thr Val Arg Gly Gly Glu Asp Leu Ala Gly Leu Ala Thr
            20                  25                  30

Val Leu Glu Leu Met Gly Val Gly Ala Leu Glu Ile Thr Leu Arg Thr
        35                  40                  45

Glu Lys Gly Leu Glu Ala Leu Lys Ala Leu Arg Lys Ser Gly Leu Leu
    50                  55                  60

Leu Gly Ala Gly Thr Val Arg Ser Pro Lys Glu Ala Glu Ala Ala Leu
65                  70                  75                  80

Glu Ala Gly Ala Ala Phe Leu Val Ser Pro Gly Leu Leu Glu Glu Val
                85                  90                  95

Ala Ala Leu Ala Gln Ala Arg Gly Val Pro Tyr Leu Pro Gly Val Leu
            100                 105                 110

Thr Pro Thr Glu Val Glu Arg Ala Leu Ala Leu Gly Leu Ser Ala Leu
        115                 120                 125
```

-continued

```
Lys Phe Phe Pro Ala Glu Pro Phe Gln Gly Val Arg Val Leu Arg Ala
            130                 135                 140
Tyr Ala Glu Val Phe Pro Glu Val Arg Phe Leu Pro Thr Gly Gly Ile
145                 150                 155                 160
Lys Glu Glu His Leu Pro His Tyr Ala Ala Leu Pro Asn Leu Leu Ala
                165                 170                 175
Val Gly Gly Ser Trp Leu Leu Gln Gly Asp Leu Ala Ala Val Met Lys
            180                 185                 190
Lys Val Lys Ala Ala Lys Ala Leu Leu Ser Pro Gln Ala Pro Gly
            195                 200                 205

<210> SEQ ID NO 2
<211> LENGTH: 156
<212> TYPE: PRT
<213> ORGANISM: Artificial Sequence
<220> FEATURE:
<223> OTHER INFORMATION: I53-34B
<220> FEATURE:
<221> NAME/KEY: MISC_FEATURE
<222> LOCATION: (1)..(1)
<223> OTHER INFORMATION: optionally absent

<400> SEQUENCE: 2

Met Thr Lys Lys Val Gly Ile Val Asp Thr Thr Phe Ala Arg Val Asp
1               5                   10                  15
Met Ala Glu Ala Ala Ile Arg Thr Leu Lys Ala Leu Ser Pro Asn Ile
            20                  25                  30
Lys Ile Ile Arg Lys Thr Val Pro Gly Ile Lys Asp Leu Pro Val Ala
            35                  40                  45
Cys Lys Lys Leu Leu Glu Glu Glu Gly Cys Asp Ile Val Met Ala Leu
        50                  55                  60
Gly Met Pro Gly Lys Ala Glu Lys Asp Lys Val Cys Ala His Glu Ala
65                  70                  75                  80
Ser Leu Gly Leu Met Leu Ala Gln Leu Met Thr Asn Lys His Ile Ile
                85                  90                  95
Glu Val Phe Val His Glu Asp Glu Ala Lys Asp Asp Asp Glu Leu Asp
            100                 105                 110
Ile Leu Ala Leu Val Arg Ala Ile Glu His Ala Ala Asn Val Tyr Tyr
        115                 120                 125
Leu Leu Phe Lys Pro Glu Tyr Leu Thr Arg Met Ala Gly Lys Gly Leu
    130                 135                 140
Arg Gln Gly Arg Glu Asp Ala Gly Pro Ala Arg Glu
145                 150                 155

<210> SEQ ID NO 3
<211> LENGTH: 156
<212> TYPE: PRT
<213> ORGANISM: Artificial Sequence
<220> FEATURE:
<223> OTHER INFORMATION: I53-40A
<220> FEATURE:
<221> NAME/KEY: MISC_FEATURE
<222> LOCATION: (1)..(1)
<223> OTHER INFORMATION: optionally absent

<400> SEQUENCE: 3

Met Thr Lys Lys Val Gly Ile Val Asp Thr Thr Phe Ala Arg Val Asp
1               5                   10                  15
Met Ala Ser Ala Ala Ile Leu Thr Leu Lys Met Glu Ser Pro Asn Ile
            20                  25                  30
```

Lys Ile Ile Arg Lys Thr Val Pro Gly Ile Lys Asp Leu Pro Val Ala
            35                  40                  45

Cys Lys Lys Leu Leu Glu Glu Glu Gly Cys Asp Ile Val Met Ala Leu
 50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
                    100                 105                 110

Ile Leu Ala Ala Arg Arg Ala Ile Glu His Ala Leu Asn Val Tyr Tyr
            115                 120                 125

Leu Leu Phe Lys Pro Glu Tyr Leu Thr Arg Met Ala Gly Lys Gly Leu
            130                 135                 140

Arg Gln Gly Phe Glu Asp Ala Gly Pro Ala Arg Glu
145                 150                 155

<210> SEQ ID NO 4
<211> LENGTH: 209
<212> TYPE: PRT
<213> ORGANISM: Artificial Sequence
<220> FEATURE:
<223> OTHER INFORMATION: I53-40B
<220> FEATURE:
<221> NAME/KEY: MISC_FEATURE
<222> LOCATION: (1)..(1)
<223> OTHER INFORMATION: optionally absent

<400> SEQUENCE: 4

Met Ser Thr Ile Asn Asn Gln Leu Lys Ala Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
            35                  40                  45

Ala Val Lys Ala Ile Met Leu Leu Arg Ser Ala Gln Pro Glu Met Leu
 50                  55                  60

Ile Gly Ala Gly Thr Ile Leu Asn Gly Val Gln Ala Leu Ala Ala Lys
65                  70                  75                  80

Glu Ala Gly Ala Thr Phe Val Val Ser Pro Gly Phe Asn Pro Asn Thr
                85                  90                  95

Val Arg Ala Cys Gln Ile Ile Gly Ile Asp Ile Val Pro Gly Val Asn
                100                 105                 110

Asn Pro Ser Thr Val Glu Ala Ala Leu Glu Met Gly Leu Thr Thr Leu
            115                 120                 125

Lys Phe Phe Pro Ala Glu Ala Ser Gly Gly Ile Ser Met Val Lys Ser
            130                 135                 140

Leu Val Gly Pro Tyr Gly Asp Ile Arg Leu Met Pro Thr Gly Gly Ile
145                 150                 155                 160

Thr Pro Ser Asn Ile Asp Asn Tyr Leu Ala Ile Pro Gln Val Leu Ala
                165                 170                 175

Cys Gly Gly Thr Trp Met Val Asp Lys Lys Leu Val Thr Asn Gly Glu
                180                 185                 190

Trp Asp Glu Ile Ala Arg Leu Thr Arg Glu Ile Val Glu Gln Val Asn
            195                 200                 205

Pro

```
<210> SEQ ID NO 5
<211> LENGTH: 114
<212> TYPE: PRT
<213> ORGANISM: Artificial Sequence
<220> FEATURE:
<223> OTHER INFORMATION: I53-47A
<220> FEATURE:
<221> NAME/KEY: MISC_FEATURE
<222> LOCATION: (1)..(1)
<223> OTHER INFORMATION: optionally absent

<400> SEQUENCE: 5

Met Pro Ile Phe Thr Leu Asn Thr Asn Ile Lys Ala Thr Asp Val Pro
1               5                   10                  15

Ser Asp Phe Leu Ser Leu Thr Ser Arg Leu Val Gly Leu Ile Leu Ser
            20                  25                  30

Lys Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Ser Lys Asn Arg Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asn Leu Asn Gly Asp Asp Val Gly Trp Asn Gly Thr
            100                 105                 110

Thr Phe

<210> SEQ ID NO 6
<211> LENGTH: 157
<212> TYPE: PRT
<213> ORGANISM: Artificial Sequence
<220> FEATURE:
<223> OTHER INFORMATION: I53-47B
<220> FEATURE:
<221> NAME/KEY: MISC_FEATURE
<222> LOCATION: (1)..(1)
<223> OTHER INFORMATION: optionally absent

<400> SEQUENCE: 6

Met Asn Gln His Ser His Lys Asp Tyr Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Asp Ser Ala Glu His His Arg
        115                 120                 125

Phe Phe Ala Ala His Phe Ala Val Lys Gly Val Glu Ala Ala Arg Ala
    130                 135                 140
```

Cys Ile Glu Ile Leu Ala Ala Arg Glu Lys Ile Ala Ala
145                 150                 155

<210> SEQ ID NO 7
<211> LENGTH: 205
<212> TYPE: PRT
<213> ORGANISM: Artificial Sequence
<220> FEATURE:
<223> OTHER INFORMATION: I53-50A
<220> FEATURE:
<221> NAME/KEY: MISC_FEATURE
<222> LOCATION: (1)..(1)
<223> OTHER INFORMATION: optionally absent

<400> SEQUENCE: 7

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu
        195                 200                 205

<210> SEQ ID NO 8
<211> LENGTH: 157
<212> TYPE: PRT
<213> ORGANISM: Artificial Sequence
<220> FEATURE:
<223> OTHER INFORMATION: I53-50B
<220> FEATURE:
<221> NAME/KEY: MISC_FEATURE
<222> LOCATION: (1)..(1)
<223> OTHER INFORMATION: optionally absent

<400> SEQUENCE: 8

Met Asn Gln His Ser His Lys Asp Tyr Glu Thr Val Arg Ile Ala Val
1               5                   10                  15

Val Arg Ala Arg Trp His Ala Glu Ile Val Asp Ala Cys Val Ser Ala
                20                  25                  30

Phe Glu Ala Ala Met Ala Asp Ile Gly Gly Asp Arg Phe Ala Val Asp
            35                  40                  45

Val Phe Asp Val Pro Gly Ala Tyr Glu Ile Pro Leu His Ala Arg Thr
 50                  55                  60

Leu Ala Glu Thr Gly Arg Tyr Gly Ala Val Leu Gly Thr Ala Phe Val
 65                  70                  75                  80

Val Asn Gly Gly Ile Tyr Arg His Glu Phe Val Ala Ser Ala Val Ile
                 85                  90                  95

Asp Gly Met Met Asn Val Gln Leu Ser Thr Gly Val Pro Val Leu Ser
            100                 105                 110

Ala Val Leu Thr Pro His Arg Tyr Arg Asp Ser Asp Ala His Thr Leu
            115                 120                 125

Leu Phe Leu Ala Leu Phe Ala Val Lys Gly Met Glu Ala Ala Arg Ala
130                 135                 140

Cys Val Glu Ile Leu Ala Ala Arg Glu Lys Ile Ala Ala
145                 150                 155

<210> SEQ ID NO 9
<211> LENGTH: 177
<212> TYPE: PRT
<213> ORGANISM: Artificial Sequence
<220> FEATURE:
<223> OTHER INFORMATION: I53-51A
<220> FEATURE:
<221> NAME/KEY: MISC_FEATURE
<222> LOCATION: (1)..(1)
<223> OTHER INFORMATION: optionally absent

<400> SEQUENCE: 9

Met Phe Thr Lys Ser Gly Asp Asp Gly Asn Thr Asn Val Ile Asn Lys
 1                5                  10                  15

Arg Val Gly Lys Asp Ser Pro Leu Val Asn Phe Leu Gly Asp Leu Asp
                 20                  25                  30

Glu Leu Asn Ser Phe Ile Gly Phe Ala Ile Ser Lys Ile Pro Trp Glu
             35                  40                  45

Asp Met Lys Lys Asp Leu Glu Arg Val Gln Val Glu Leu Phe Glu Ile
 50                  55                  60

Gly Glu Asp Leu Ser Thr Gln Ser Ser Lys Lys Lys Ile Asp Glu Ser
 65                  70                  75                  80

Tyr Val Leu Trp Leu Leu Ala Ala Thr Ala Ile Tyr Arg Ile Glu Ser
                 85                  90                  95

Gly Pro Val Lys Leu Phe Val Ile Pro Gly Gly Ser Glu Glu Ala Ser
            100                 105                 110

Val Leu His Val Thr Arg Ser Val Ala Arg Arg Val Glu Arg Asn Ala
            115                 120                 125

Val Lys Tyr Thr Lys Glu Leu Pro Glu Ile Asn Arg Met Ile Ile Val
            130                 135                 140

Tyr Leu Asn Arg Leu Ser Ser Leu Leu Phe Ala Met Ala Leu Val Ala
145                 150                 155                 160

Asn Lys Arg Arg Asn Gln Ser Glu Lys Ile Tyr Glu Ile Gly Lys Ser
                165                 170                 175

Trp

<210> SEQ ID NO 10
<211> LENGTH: 157
<212> TYPE: PRT
<213> ORGANISM: Artificial Sequence
<220> FEATURE:
<223> OTHER INFORMATION: I53-51B
<220> FEATURE:
<221> NAME/KEY: MISC_FEATURE
<222> LOCATION: (1)..(1)
<223> OTHER INFORMATION: optionally absent

<400> SEQUENCE: 10

```
Met Asn Gln His Ser His Lys Asp Tyr Glu Thr Val Arg Ile Ala Val
1               5                   10                  15

Val Arg Ala Arg Trp His Ala Asp Ile Val Asp Gln Cys Val Arg Ala
            20                  25                  30

Phe Glu Glu Ala Met Ala Asp Ala Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Ser Ser Arg Glu His His Glu
        115                 120                 125

Phe Phe Arg Glu His Phe Met Val Lys Gly Val Glu Ala Ala Ala Ala
    130                 135                 140

Cys Ile Thr Ile Leu Ala Ala Arg Glu Lys Ile Ala Ala
145                 150                 155
```

<210> SEQ ID NO 11
<211> LENGTH: 201
<212> TYPE: PRT
<213> ORGANISM: Artificial Sequence
<220> FEATURE:
<223> OTHER INFORMATION: I52-03A
<220> FEATURE:
<221> NAME/KEY: MISC_FEATURE
<222> LOCATION: (1)..(1)
<223> OTHER INFORMATION: optionally absent

<400> SEQUENCE: 11

```
Met Gly His Thr Lys Gly Pro Thr Pro Gln Gln His Asp Gly Ser Ala
1               5                   10                  15

Leu Arg Ile Gly Ile Val His Ala Arg Trp Asn Lys Thr Ile Ile Met
            20                  25                  30

Pro Leu Leu Ile Gly Thr Ile Ala Lys Leu Leu Glu Cys Gly Val Lys
        35                  40                  45

Ala Ser Asn Ile Val Val Gln Ser Val Pro Gly Ser Trp Glu Leu Pro
    50                  55                  60

Ile Ala Val Gln Arg Leu Tyr Ser Ala Ser Gln Leu Gln Thr Pro Ser
65                  70                  75                  80

Ser Gly Pro Ser Leu Ser Ala Gly Asp Leu Leu Gly Ser Ser Thr Thr
                85                  90                  95

Asp Leu Thr Ala Leu Pro Thr Thr Thr Ala Ser Ser Thr Gly Pro Phe
            100                 105                 110

Asp Ala Leu Ile Ala Ile Gly Val Leu Ile Lys Gly Glu Thr Met His
        115                 120                 125

Phe Glu Tyr Ile Ala Asp Ser Val Ser His Gly Leu Met Arg Val Gln
    130                 135                 140

Leu Asp Thr Gly Val Pro Val Ile Phe Gly Val Leu Thr Val Leu Thr
145                 150                 155                 160
```

```
Asp Asp Gln Ala Lys Ala Arg Ala Gly Val Ile Glu Gly Ser His Asn
            165                 170                 175

His Gly Glu Asp Trp Gly Leu Ala Ala Val Glu Met Gly Val Arg Arg
        180                 185                 190

Arg Asp Trp Ala Ala Gly Lys Thr Glu
        195                 200

<210> SEQ ID NO 12
<211> LENGTH: 237
<212> TYPE: PRT
<213> ORGANISM: Artificial Sequence
<220> FEATURE:
<223> OTHER INFORMATION: I52-03B
<220> FEATURE:
<221> NAME/KEY: MISC_FEATURE
<222> LOCATION: (1)..(1)
<223> OTHER INFORMATION: optionally absent

<400> SEQUENCE: 12

Met Tyr Glu Val Asp His Ala Asp Val Tyr Asp Leu Phe Tyr Leu Gly
1               5                  10                  15

Arg Gly Lys Asp Tyr Ala Ala Glu Ala Ser Asp Ile Ala Asp Leu Val
            20                  25                  30

Arg Ser Arg Thr Pro Glu Ala Ser Leu Leu Asp Val Ala Cys Gly
        35                  40                  45

Thr Gly Thr His Leu Glu His Phe Thr Lys Glu Phe Gly Asp Thr Ala
    50                  55                  60

Gly Leu Glu Leu Ser Glu Asp Met Leu Thr His Ala Arg Lys Arg Leu
65                  70                  75                  80

Pro Asp Ala Thr Leu His Gln Gly Asp Met Arg Asp Phe Gln Leu Gly
                85                  90                  95

Arg Lys Phe Ser Ala Val Val Ser Met Phe Ser Ser Val Gly Tyr Leu
            100                 105                 110

Lys Thr Val Ala Glu Leu Gly Ala Ala Val Ala Ser Phe Ala Glu His
        115                 120                 125

Leu Glu Pro Gly Gly Val Val Val Glu Pro Trp Trp Phe Pro Glu
    130                 135                 140

Thr Phe Ala Asp Gly Trp Val Ser Ala Asp Val Val Arg Arg Asp Gly
145                 150                 155                 160

Arg Thr Val Ala Arg Val Ser His Ser Val Arg Glu Gly Asn Ala Thr
                165                 170                 175

Arg Met Glu Val His Phe Thr Val Ala Asp Pro Gly Lys Gly Val Arg
            180                 185                 190

His Phe Ser Asp Val His Leu Ile Thr Leu Phe His Gln Arg Glu Tyr
        195                 200                 205

Glu Ala Ala Phe Met Ala Ala Gly Leu Arg Val Glu Tyr Leu Glu Gly
    210                 215                 220

Gly Pro Ser Gly Arg Gly Leu Phe Val Gly Val Pro Ala
225                 230                 235

<210> SEQ ID NO 13
<211> LENGTH: 138
<212> TYPE: PRT
<213> ORGANISM: Artificial Sequence
<220> FEATURE:
<223> OTHER INFORMATION: I52-32A
<220> FEATURE:
<221> NAME/KEY: MISC_FEATURE
<222> LOCATION: (1)..(1)
<223> OTHER INFORMATION: optionally absent
```

<400> SEQUENCE: 13

Met Gly Met Lys Glu Lys Phe Val Leu Ile Ile Thr His Gly Asp Phe
1               5                   10                  15

Gly Lys Gly Leu Leu Ser Gly Ala Glu Val Ile Ile Gly Lys Gln Glu
            20                  25                  30

Asn Val His Thr Val Gly Leu Asn Leu Gly Asp Asn Ile Glu Lys Val
        35                  40                  45

Ala Lys Glu Val Met Arg Ile Ile Ala Lys Leu Ala Glu Asp Lys
50                  55                  60

Glu Ile Ile Ile Val Val Asp Leu Phe Gly Gly Ser Pro Phe Asn Ile
65                  70                  75                  80

Ala Leu Glu Met Met Lys Thr Phe Asp Val Lys Val Ile Thr Gly Ile
                85                  90                  95

Asn Met Pro Met Leu Val Glu Leu Leu Thr Ser Ile Asn Val Tyr Asp
            100                 105                 110

Thr Thr Glu Leu Leu Glu Asn Ile Ser Lys Ile Gly Lys Asp Gly Ile
        115                 120                 125

Lys Val Ile Glu Lys Ser Ser Leu Lys Met
    130                 135

<210> SEQ ID NO 14
<211> LENGTH: 154
<212> TYPE: PRT
<213> ORGANISM: Artificial Sequence
<220> FEATURE:
<223> OTHER INFORMATION: I52-32B
<220> FEATURE:
<221> NAME/KEY: MISC_FEATURE
<222> LOCATION: (1)..(1)
<223> OTHER INFORMATION: optionally absent

<400> SEQUENCE: 14

Met Lys Tyr Asp Gly Ser Lys Leu Arg Ile Gly Ile Leu His Ala Arg
1               5                   10                  15

Trp Asn Leu Glu Ile Ile Ala Ala Leu Val Ala Gly Ala Ile Lys Arg
            20                  25                  30

Leu Gln Glu Phe Gly Val Lys Ala Glu Asn Ile Ile Ile Glu Thr Val
        35                  40                  45

Pro Gly Ser Phe Glu Leu Pro Tyr Gly Ser Lys Leu Phe Val Glu Lys
    50                  55                  60

Gln Lys Arg Leu Gly Lys Pro Leu Asp Ala Ile Ile Pro Ile Gly Val
65                  70                  75                  80

Leu Ile Lys Gly Ser Thr Met His Phe Glu Tyr Ile Cys Asp Ser Thr
                85                  90                  95

Thr His Gln Leu Met Lys Leu Asn Phe Glu Leu Gly Ile Pro Val Ile
            100                 105                 110

Phe Gly Val Leu Thr Cys Leu Thr Asp Glu Gln Ala Glu Ala Arg Ala
        115                 120                 125

Gly Leu Ile Glu Gly Lys Met His Asn His Gly Glu Asp Trp Gly Ala
    130                 135                 140

Ala Ala Val Glu Met Ala Thr Lys Phe Asn
145                 150

<210> SEQ ID NO 15
<211> LENGTH: 164
<212> TYPE: PRT
<213> ORGANISM: Artificial Sequence

```
<220> FEATURE:
<223> OTHER INFORMATION: I52-33A
<220> FEATURE:
<221> NAME/KEY: MISC_FEATURE
<222> LOCATION: (1)..(1)
<223> OTHER INFORMATION: optionally absent

<400> SEQUENCE: 15

Met Ala Val Lys Gly Leu Gly Glu Val Asp Gln Lys Tyr Asp Gly Ser
1               5                   10                  15

Lys Leu Arg Ile Gly Ile Leu His Ala Arg Trp Asn Arg Lys Ile Ile
            20                  25                  30

Leu Ala Leu Val Ala Gly Ala Val Leu Arg Leu Leu Glu Phe Gly Val
        35                  40                  45

Lys Ala Glu Asn Ile Ile Ile Glu Thr Val Pro Gly Ser Phe Glu Leu
    50                  55                  60

Pro Tyr Gly Ser Lys Leu Phe Val Glu Lys Gln Lys Arg Leu Gly Lys
65              70                  75                  80

Pro Leu Asp Ala Ile Ile Pro Ile Gly Val Leu Ile Lys Gly Ser Thr
                85                  90                  95

Met His Phe Glu Tyr Ile Cys Asp Ser Thr Thr His Gln Leu Met Lys
            100                 105                 110

Leu Asn Phe Glu Leu Gly Ile Pro Val Ile Phe Gly Val Leu Thr Cys
        115                 120                 125

Leu Thr Asp Glu Gln Ala Glu Ala Arg Ala Gly Leu Ile Glu Gly Lys
    130                 135                 140

Met His Asn His Gly Glu Asp Trp Gly Ala Ala Val Glu Met Ala
145                 150                 155                 160

Thr Lys Phe Asn

<210> SEQ ID NO 16
<211> LENGTH: 175
<212> TYPE: PRT
<213> ORGANISM: Artificial Sequence
<220> FEATURE:
<223> OTHER INFORMATION: I52-33B
<220> FEATURE:
<221> NAME/KEY: MISC_FEATURE
<222> LOCATION: (1)..(1)
<223> OTHER INFORMATION: optionally absent

<400> SEQUENCE: 16

Met Gly Ala Asn Trp Tyr Leu Asp Asn Glu Ser Ser Arg Leu Ser Phe
1               5                   10                  15

Thr Ser Thr Lys Asn Ala Asp Ile Ala Glu Val His Arg Phe Leu Val
            20                  25                  30

Leu His Gly Lys Val Asp Pro Lys Gly Leu Ala Glu Val Glu Val Glu
        35                  40                  45

Thr Glu Ser Ile Ser Thr Gly Ile Pro Leu Arg Asp Met Leu Leu Arg
    50                  55                  60

Val Leu Val Phe Gln Val Ser Lys Phe Pro Val Ala Gln Ile Asn Ala
65              70                  75                  80

Gln Leu Asp Met Arg Pro Ile Asn Asn Leu Ala Pro Gly Ala Gln Leu
                85                  90                  95

Glu Leu Arg Leu Pro Leu Thr Val Ser Leu Arg Gly Lys Ser His Ser
            100                 105                 110

Tyr Asn Ala Glu Leu Leu Ala Thr Arg Leu Asp Glu Arg Arg Phe Gln
        115                 120                 125
```

Val Val Thr Leu Glu Pro Leu Val Ile His Ala Gln Asp Phe Asp Met
            130                 135                 140

Val Arg Ala Phe Asn Ala Leu Arg Leu Val Ala Gly Leu Ser Ala Val
145                 150                 155                 160

Ser Leu Ser Val Pro Val Gly Ala Val Leu Ile Phe Thr Ala Arg
                165                 170                 175

<210> SEQ ID NO 17
<211> LENGTH: 208
<212> TYPE: PRT
<213> ORGANISM: Artificial Sequence
<220> FEATURE:
<223> OTHER INFORMATION: I32-06A
<220> FEATURE:
<221> NAME/KEY: MISC_FEATURE
<222> LOCATION: (1)..(1)
<223> OTHER INFORMATION: optionally absent

<400> SEQUENCE: 17

Met Thr Asp Tyr Ile Arg Asp Gly Ser Ala Ile Lys Ala Leu Ser Phe
1               5                   10                  15

Ala Ile Ile Leu Ala Glu Ala Asp Leu Arg His Ile Pro Gln Asp Leu
            20                  25                  30

Gln Arg Leu Ala Val Arg Val Ile His Ala Cys Gly Met Val Asp Val
        35                  40                  45

Ala Asn Asp Leu Ala Phe Ser Glu Gly Ala Gly Lys Ala Gly Arg Asn
    50                  55                  60

Ala Leu Leu Ala Gly Ala Pro Ile Leu Cys Asp Ala Arg Met Val Ala
65                  70                  75                  80

Glu Gly Ile Thr Arg Ser Arg Leu Pro Ala Asp Asn Arg Val Ile Tyr
                85                  90                  95

Thr Leu Ser Asp Pro Ser Val Pro Glu Leu Ala Lys Lys Ile Gly Asn
            100                 105                 110

Thr Arg Ser Ala Ala Ala Leu Asp Leu Trp Leu Pro His Ile Glu Gly
        115                 120                 125

Ser Ile Val Ala Ile Gly Asn Ala Pro Thr Ala Leu Phe Arg Leu Phe
    130                 135                 140

Glu Leu Leu Asp Ala Gly Ala Pro Lys Pro Ala Leu Ile Ile Gly Met
145                 150                 155                 160

Pro Val Gly Phe Val Gly Ala Ala Glu Ser Lys Asp Glu Leu Ala Ala
                165                 170                 175

Asn Ser Arg Gly Val Pro Tyr Val Ile Val Arg Gly Arg Arg Gly Gly
            180                 185                 190

Ser Ala Met Thr Ala Ala Val Asn Ala Leu Ala Ser Glu Arg Glu
        195                 200                 205

<210> SEQ ID NO 18
<211> LENGTH: 128
<212> TYPE: PRT
<213> ORGANISM: Artificial Sequence
<220> FEATURE:
<223> OTHER INFORMATION: I32-06B
<220> FEATURE:
<221> NAME/KEY: MISC_FEATURE
<222> LOCATION: (1)..(1)
<223> OTHER INFORMATION: optionally absent

<400> SEQUENCE: 18

Met Ile Thr Val Phe Gly Leu Lys Ser Lys Leu Ala Pro Arg Arg Glu
1               5                   10                  15

```
Lys Leu Ala Glu Val Ile Tyr Ser Ser Leu His Leu Gly Leu Asp Ile
             20                  25                  30

Pro Lys Gly Lys His Ala Ile Arg Phe Leu Cys Leu Glu Lys Glu Asp
         35                  40                  45

Phe Tyr Tyr Pro Phe Asp Arg Ser Asp Asp Tyr Thr Val Ile Glu Ile
     50                  55                  60

Asn Leu Met Ala Gly Arg Ser Glu Glu Thr Lys Met Leu Leu Ile Phe
 65                  70                  75                  80

Leu Leu Phe Ile Ala Leu Glu Arg Lys Leu Gly Ile Arg Ala His Asp
                 85                  90                  95

Val Glu Ile Thr Ile Lys Glu Gln Pro Ala His Cys Trp Gly Phe Arg
            100                 105                 110

Gly Arg Thr Gly Asp Ser Ala Arg Asp Leu Asp Tyr Asp Ile Tyr Val
        115                 120                 125
```

<210> SEQ ID NO 19
<211> LENGTH: 235
<212> TYPE: PRT
<213> ORGANISM: Artificial Sequence
<220> FEATURE:
<223> OTHER INFORMATION: I32-19A
<220> FEATURE:
<221> NAME/KEY: MISC_FEATURE
<222> LOCATION: (1)..(1)
<223> OTHER INFORMATION: optionally absent

<400> SEQUENCE: 19

```
Met Gly Ser Asp Leu Gln Lys Leu Gln Arg Phe Ser Thr Cys Asp Ile
 1               5                  10                  15

Ser Asp Gly Leu Leu Asn Val Tyr Asn Ile Pro Thr Gly Gly Tyr Phe
             20                  25                  30

Pro Asn Leu Thr Ala Ile Ser Pro Pro Gln Asn Ser Ser Ile Val Gly
         35                  40                  45

Thr Ala Tyr Thr Val Leu Phe Ala Pro Ile Asp Asp Pro Arg Pro Ala
     50                  55                  60

Val Asn Tyr Ile Asp Ser Val Pro Pro Asn Ser Ile Leu Val Leu Ala
 65                  70                  75                  80

Leu Glu Pro His Leu Gln Ser Gln Phe His Pro Phe Ile Lys Ile Thr
                 85                  90                  95

Gln Ala Met Tyr Gly Gly Leu Met Ser Thr Arg Ala Gln Tyr Leu Lys
            100                 105                 110

Ser Asn Gly Thr Val Val Phe Gly Arg Ile Arg Asp Val Asp Glu His
        115                 120                 125

Arg Thr Leu Asn His Pro Val Phe Ala Tyr Gly Val Gly Ser Cys Ala
    130                 135                 140

Pro Lys Ala Val Val Lys Ala Val Gly Thr Asn Val Gln Leu Lys Ile
145                 150                 155                 160

Leu Thr Ser Asp Gly Val Thr Gln Thr Ile Cys Pro Gly Asp Tyr Ile
                165                 170                 175

Ala Gly Asp Asn Asn Gly Ile Val Arg Ile Pro Val Gln Glu Thr Asp
            180                 185                 190

Ile Ser Lys Leu Val Thr Tyr Ile Glu Lys Ser Ile Glu Val Asp Arg
        195                 200                 205

Leu Val Ser Glu Ala Ile Lys Asn Gly Leu Pro Ala Lys Ala Ala Gln
    210                 215                 220

Thr Ala Arg Arg Met Val Leu Lys Asp Tyr Ile
225                 230                 235
```

<210> SEQ ID NO 20
<211> LENGTH: 162
<212> TYPE: PRT
<213> ORGANISM: Artificial Sequence
<220> FEATURE:
<223> OTHER INFORMATION: I32-19B
<220> FEATURE:
<221> NAME/KEY: MISC_FEATURE
<222> LOCATION: (1)..(1)
<223> OTHER INFORMATION: optionally absent

<400> SEQUENCE: 20

Met Ser Gly Met Arg Val Tyr Leu Gly Ala Asp His Ala Gly Tyr Glu
1               5                   10                  15

Leu Lys Gln Ala Ile Ile Ala Phe Leu Lys Met Thr Gly His Glu Pro
            20                  25                  30

Ile Asp Cys Gly Ala Leu Arg Tyr Asp Ala Asp Asp Tyr Pro Ala
        35                  40                  45

Phe Cys Ile Ala Ala Ala Thr Arg Thr Val Ala Asp Pro Gly Ser Leu
    50                  55                  60

Gly Ile Val Leu Gly Gly Ser Gly Asn Gly Glu Gln Ile Ala Ala Asn
65                  70                  75                  80

Lys Val Pro Gly Ala Arg Cys Ala Leu Ala Trp Ser Val Gln Thr Ala
                85                  90                  95

Ala Leu Ala Arg Glu His Asn Asn Ala Gln Leu Ile Gly Ile Gly Gly
            100                 105                 110

Arg Met His Thr Leu Glu Glu Ala Leu Arg Ile Val Lys Ala Phe Val
        115                 120                 125

Thr Thr Pro Trp Ser Lys Ala Gln Arg His Gln Arg Ile Asp Ile
    130                 135                 140

Leu Ala Glu Tyr Glu Arg Thr His Glu Ala Pro Pro Val Pro Gly Ala
145                 150                 155                 160

Pro Ala

<210> SEQ ID NO 21
<211> LENGTH: 157
<212> TYPE: PRT
<213> ORGANISM: Artificial Sequence
<220> FEATURE:
<223> OTHER INFORMATION: I32-28A
<220> FEATURE:
<221> NAME/KEY: MISC_FEATURE
<222> LOCATION: (1)..(1)
<223> OTHER INFORMATION: optionally absent

<400> SEQUENCE: 21

Met Gly Asp Asp Ala Arg Ile Ala Ala Ile Gly Asp Val Asp Glu Leu
1               5                   10                  15

Asn Ser Gln Ile Gly Val Leu Leu Ala Glu Pro Leu Pro Asp Asp Val
            20                  25                  30

Arg Ala Ala Leu Ser Ala Ile Gln His Asp Leu Phe Asp Leu Gly Gly
        35                  40                  45

Glu Leu Cys Ile Pro Gly His Ala Ala Ile Thr Glu Asp His Leu Leu
    50                  55                  60

Arg Leu Ala Leu Trp Leu Val His Tyr Asn Gly Gln Leu Pro Pro Leu
65                  70                  75                  80

Glu Glu Phe Ile Leu Pro Gly Gly Ala Arg Gly Ala Ala Leu Ala His
                85                  90                  95

Val Cys Arg Thr Val Cys Arg Arg Ala Glu Arg Ser Ile Lys Ala Leu
            100                 105                 110

Gly Ala Ser Glu Pro Leu Asn Ile Ala Pro Ala Ala Tyr Val Asn Leu
            115                 120                 125

Leu Ser Asp Leu Leu Phe Val Leu Ala Arg Val Leu Asn Arg Ala Ala
            130                 135                 140

Gly Gly Ala Asp Val Leu Trp Asp Arg Thr Arg Ala His
145                 150                 155

<210> SEQ ID NO 22
<211> LENGTH: 157
<212> TYPE: PRT
<213> ORGANISM: Artificial Sequence
<220> FEATURE:
<223> OTHER INFORMATION: I32-28B
<220> FEATURE:
<221> NAME/KEY: MISC_FEATURE
<222> LOCATION: (1)..(1)
<223> OTHER INFORMATION: optionally absent

<400> SEQUENCE: 22

Met Ile Leu Ser Ala Glu Gln Ser Phe Thr Leu Arg His Pro His Gly
1               5                   10                  15

Gln Ala Ala Ala Leu Ala Phe Val Arg Glu Pro Ala Ala Leu Ala
            20                  25                  30

Gly Val Gln Arg Leu Arg Gly Leu Asp Ser Asp Gly Glu Gln Val Trp
            35                  40                  45

Gly Glu Leu Leu Val Arg Val Pro Leu Leu Gly Glu Val Asp Leu Pro
50                  55                  60

Phe Arg Ser Glu Ile Val Arg Thr Pro Gln Gly Ala Glu Leu Arg Pro
65                  70                  75                  80

Leu Thr Leu Thr Gly Glu Arg Ala Trp Val Ala Val Ser Gly Gln Ala
            85                  90                  95

Thr Ala Ala Glu Gly Gly Glu Met Ala Phe Ala Phe Gln Phe Gln Ala
            100                 105                 110

His Leu Ala Thr Pro Glu Ala Glu Gly Glu Gly Gly Ala Ala Phe Glu
            115                 120                 125

Val Met Val Gln Ala Ala Ala Gly Val Thr Leu Leu Leu Val Ala Met
            130                 135                 140

Ala Leu Pro Gln Gly Leu Ala Ala Gly Leu Pro Pro Ala
145                 150                 155

<210> SEQ ID NO 23
<211> LENGTH: 156
<212> TYPE: PRT
<213> ORGANISM: Artificial Sequence
<220> FEATURE:
<223> OTHER INFORMATION: I53-40A.1
<220> FEATURE:
<221> NAME/KEY: MISC_FEATURE
<222> LOCATION: (1)..(1)
<223> OTHER INFORMATION: optionally absent

<400> SEQUENCE: 23

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
            35                  40                  45

```
Cys Lys Lys Leu Leu Glu Glu Gly Cys Asp Ile Val Met Ala Leu
    50              55                  60

Gly Met Pro Gly Lys Lys Glu Lys Asp Lys Val Cys Ala His Glu Ala
65              70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
            115                 120                 125

Leu Leu Phe Lys Pro Glu Tyr Leu Thr Arg Met Ala Gly Lys Gly Leu
130                 135                 140

Arg Gln Gly Phe Glu Asp Ala Gly Pro Ala Arg Glu
145                 150                 155

<210> SEQ ID NO 24
<211> LENGTH: 209
<212> TYPE: PRT
<213> ORGANISM: Artificial Sequence
<220> FEATURE:
<223> OTHER INFORMATION: I53-40B.1
<220> FEATURE:
<221> NAME/KEY: MISC_FEATURE
<222> LOCATION: (1)..(1)
<223> OTHER INFORMATION: optionally absent

<400> SEQUENCE: 24

Met Asp Asp Ile Asn Asn Gln Leu Lys Arg Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65              70                  75                  80

Glu Ala Gly Ala Asp Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Gln Ala Leu Glu Met Gly Leu Thr Thr Leu
        115                 120                 125

Lys Phe Phe Pro Ala Glu Ala Ser Gly Gly Ile Ser Met Val Lys Ser
130                 135                 140

Leu Val Gly Pro Tyr Gly Asp Ile Arg Leu Met Pro Thr Gly Gly Ile
145                 150                 155                 160

Thr Pro Asp Asn Ile Asp Asn Tyr Leu Ala Ile Pro Gln Val Leu Ala
                165                 170                 175

Cys Gly Gly Thr Trp Met Val Asp Lys Lys Leu Val Arg Asn Gly Glu
            180                 185                 190

Trp Asp Glu Ile Ala Arg Leu Thr Arg Glu Ile Val Glu Gln Val Asn
        195                 200                 205

Pro

<210> SEQ ID NO 25
<211> LENGTH: 114
```

```
<212> TYPE: PRT
<213> ORGANISM: Artificial Sequence
<220> FEATURE:
<223> OTHER INFORMATION: I53-47A.1
<220> FEATURE:
<221> NAME/KEY: MISC_FEATURE
<222> LOCATION: (1)..(1)
<223> OTHER INFORMATION: optionally absent

<400> SEQUENCE: 25
```

Met Pro Ile Phe Thr Leu Asn Thr Asn Ile Lys Ala Asp Asp Val Pro
1               5                   10                  15

Ser Asp Phe Leu Ser Leu Thr Ser Arg Leu Val Gly Leu Ile Leu Ser
            20                  25                  30

Lys Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Asp Lys Asn Arg Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asn Leu Asn Gly Asp Asp Val Gly Trp Asn Gly Thr
            100                 105                 110

Thr Phe

```
<210> SEQ ID NO 26
<211> LENGTH: 114
<212> TYPE: PRT
<213> ORGANISM: Artificial Sequence
<220> FEATURE:
<223> OTHER INFORMATION: I53-47A.1NegT2
<220> FEATURE:
<221> NAME/KEY: MISC_FEATURE
<222> LOCATION: (1)..(1)
<223> OTHER INFORMATION: optionally absent

<400> SEQUENCE: 26
```

Met Pro Ile Phe Thr Leu Asn Thr Asn Ile Lys Ala Asp Asp Val Pro
1               5                   10                  15

Ser Asp Phe Leu Ser Leu Thr Ser Arg Leu Val Gly Leu Ile Leu Ser
            20                  25                  30

Glu Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Asp Lys Asn Glu Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asp Leu Asp Gly Asp Asp Val Gly Trp Asn Gly Thr
            100                 105                 110

Thr Phe

```
<210> SEQ ID NO 27
<211> LENGTH: 157
<212> TYPE: PRT
<213> ORGANISM: Artificial Sequence
<220> FEATURE:
<223> OTHER INFORMATION: I53-47B.1
<220> FEATURE:
```

<221> NAME/KEY: MISC_FEATURE
<222> LOCATION: (1)..(1)
<223> OTHER INFORMATION: optionally absent

<400> SEQUENCE: 27

Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Arg Tyr Arg Asp Ser Asp Glu His His Arg
        115                 120                 125

Phe Phe Ala Ala His Phe Ala Val Lys Gly Val Glu Ala Ala Arg Ala
    130                 135                 140

Cys Ile Glu Ile Leu Asn Ala Arg Glu Lys Ile Ala Ala
145                 150                 155

<210> SEQ ID NO 28
<211> LENGTH: 157
<212> TYPE: PRT
<213> ORGANISM: Artificial Sequence
<220> FEATURE:
<223> OTHER INFORMATION: I53-47B.1NegT2
<220> FEATURE:
<221> NAME/KEY: MISC_FEATURE
<222> LOCATION: (1)..(1)
<223> OTHER INFORMATION: optionally absent

<400> SEQUENCE: 28

Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Glu Tyr Glu Asp Ser Asp Glu Asp His Glu
        115                 120                 125

Phe Phe Ala Ala His Phe Ala Val Lys Gly Val Glu Ala Ala Arg Ala
    130                 135                 140

Cys Ile Glu Ile Leu Asn Ala Arg Glu Lys Ile Ala Ala
145                 150                 155

```
<210> SEQ ID NO 29
<211> LENGTH: 205
<212> TYPE: PRT
<213> ORGANISM: Artificial Sequence
<220> FEATURE:
<223> OTHER INFORMATION: I53-50A.1
<220> FEATURE:
<221> NAME/KEY: MISC_FEATURE
<222> LOCATION: (1)..(1)
<223> OTHER INFORMATION: optionally absent

<400> SEQUENCE: 29

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Asp Ile Leu
            115                 120                 125

Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Asp Ala Leu Val Lys Gly Asp Pro Asp Glu Val Arg Glu Lys
            180                 185                 190

Ala Lys Lys Phe Val Glu Lys Ile Arg Gly Cys Thr Glu
        195                 200                 205

<210> SEQ ID NO 30
<211> LENGTH: 205
<212> TYPE: PRT
<213> ORGANISM: Artificial Sequence
<220> FEATURE:
<223> OTHER INFORMATION: I53-50A.1NegT2
<220> FEATURE:
<221> NAME/KEY: MISC_FEATURE
<222> LOCATION: (1)..(1)
<223> OTHER INFORMATION: optionally absent

<400> SEQUENCE: 30

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60
```

```
Ile Gly Ala Gly Thr Val Thr Ser Val Glu Gln Cys Arg Lys Ala Val
 65                  70                  75                  80

Glu Ser Gly Ala Glu Phe Ile Val Ser Pro His Leu Asp Glu Glu Ile
                 85                  90                  95

Ser Gln Phe Cys Lys Glu Lys Val Phe Tyr Met Pro Gly Val Met
            100                 105                 110

Thr Pro Thr Glu Leu Val Lys Ala Met Lys Leu Gly His Asp Ile Leu
            115                 120                 125

Lys Leu Phe Pro Gly Glu Val Gly Pro Glu Phe Val Glu Ala Met
            130                 135                 140

Lys Gly Pro Phe Pro Asn Val Lys Phe Val Pro Thr Gly Gly Val Asp
145                 150                 155                 160

Leu Asp Asp Val Cys Glu Trp Phe Asp Ala Gly Val Leu Ala Val Gly
                165                 170                 175

Val Gly Asp Ala Leu Val Glu Gly Asp Pro Asp Glu Val Arg Glu Asp
                180                 185                 190

Ala Lys Glu Phe Val Glu Glu Ile Arg Gly Cys Thr Glu
            195                 200                 205

<210> SEQ ID NO 31
<211> LENGTH: 205
<212> TYPE: PRT
<213> ORGANISM: Artificial Sequence
<220> FEATURE:
<223> OTHER INFORMATION: I53-50A.1PosT1
<220> FEATURE:
<221> NAME/KEY: MISC_FEATURE
<222> LOCATION: (1)..(1)
<223> OTHER INFORMATION: optionally absent

<400> SEQUENCE: 31

Met Lys Met Glu Glu Leu Phe Lys Lys His Lys Ile Val Ala Val Leu
 1               5                   10                  15

Arg Ala Asn Ser Val Glu Glu Ala Ile Glu Lys Ala Val Ala Val Phe
                 20                  25                  30

Ala Gly Gly Val His Leu Ile Glu Ile Thr Phe Thr Val Pro Asp Ala
             35                  40                  45

Asp Thr Val Ile Lys Ala Leu Ser Val Leu Lys Glu Lys Gly Ala Ile
         50                  55                  60

Ile Gly Ala Gly Thr Val Thr Ser Val Glu Gln Cys Arg Lys Ala Val
 65                  70                  75                  80

Glu Ser Gly Ala Glu Phe Ile Val Ser Pro His Leu Asp Glu Glu Ile
                 85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
            115                 120                 125

Lys Leu Phe Pro Gly Glu Val Val Gly Pro Gln Phe Val Lys Ala Met
            130                 135                 140

Lys Gly Pro Phe Pro Asn Val Lys Phe Val Pro Thr Gly Gly Val Asn
145                 150                 155                 160

Leu Asp Asn Val Cys Lys Trp Phe Lys Ala Gly Val Leu Ala Val Gly
                165                 170                 175

Val Gly Lys Ala Leu Val Lys Gly Lys Pro Asp Glu Val Arg Glu Lys
                180                 185                 190

Ala Lys Lys Phe Val Lys Lys Ile Arg Gly Cys Thr Glu
            195                 200                 205
```

<210> SEQ ID NO 32
<211> LENGTH: 157
<212> TYPE: PRT
<213> ORGANISM: Artificial Sequence
<220> FEATURE:
<223> OTHER INFORMATION: I53-50B.1
<220> FEATURE:
<221> NAME/KEY: MISC_FEATURE
<222> LOCATION: (1)..(1)
<223> OTHER INFORMATION: optionally absent

<400> SEQUENCE: 32

```
Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Arg Tyr Arg Asp Ser Asp Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155
```

<210> SEQ ID NO 33
<211> LENGTH: 157
<212> TYPE: PRT
<213> ORGANISM: Artificial Sequence
<220> FEATURE:
<223> OTHER INFORMATION: I53-50B.1NegT2
<220> FEATURE:
<221> NAME/KEY: MISC_FEATURE
<222> LOCATION: (1)..(1)
<223> OTHER INFORMATION: optionally absent

<400> SEQUENCE: 33

```
Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                85                  90                  95

Asp Gly Met Met Asn Val Gln Leu Asp Thr Gly Val Pro Val Leu Ser
```

```
                100                 105                 110
Ala Val Leu Thr Pro His Glu Tyr Glu Asp Ser Asp Ala Asp Thr Leu
        115                 120                 125

Leu Phe Leu Ala Leu Phe Ala Val Lys Gly Met Glu Ala Ala Arg Ala
        130                 135                 140

Cys Val Glu Ile Leu Ala Ala Arg Glu Lys Ile Ala Ala
145                 150                 155

<210> SEQ ID NO 34
<211> LENGTH: 157
<212> TYPE: PRT
<213> ORGANISM: Artificial Sequence
<220> FEATURE:
<223> OTHER INFORMATION: I53-50B.4PosT1
<220> FEATURE:
<221> NAME/KEY: MISC_FEATURE
<222> LOCATION: (1)..(1)
<223> OTHER INFORMATION: optionally absent

<400> SEQUENCE: 34

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asn Gly Met Met Asn Val Gln Leu Asn Thr Gly Val Pro Val Leu Ser
            100                 105                 110

Ala Val Leu Thr Pro His Asn Tyr Asp Lys Ser Lys Ala His Thr Leu
        115                 120                 125

Leu Phe Leu Ala Leu Phe Ala Val Lys Gly Met Glu Ala Ala Arg Ala
        130                 135                 140

Cys Val Glu Ile Leu Ala Ala Arg Glu Lys Ile Ala Ala
145                 150                 155

<210> SEQ ID NO 35
<211> LENGTH: 156
<212> TYPE: PRT
<213> ORGANISM: Artificial Sequence
<220> FEATURE:
<223> OTHER INFORMATION: I53-40 A genus
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (70)..(70)
<223> OTHER INFORMATION: Xaa is A or K

<400> SEQUENCE: 35

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30
```

-continued

```
Lys Ile Ile Arg Lys Thr Val Pro Gly Ile Lys Asp Leu Pro Val Ala
             35                  40                  45

Cys Lys Lys Leu Leu Glu Glu Glu Gly Cys Asp Ile Val Met Ala Leu
 50                  55                  60

Gly Met Pro Gly Lys Xaa Glu Lys Asp Lys Val Cys Ala His Glu Ala
 65                  70                  75                  80

Ser Leu Gly Leu Met Leu Ala Gln Leu Met Thr Asn Lys His Ile Ile
                 85                  90                  95

Glu Val Phe Val His Glu Asp Glu Ala Lys Asp Ala Glu Leu Lys
                100                 105                 110

Ile Leu Ala Ala Arg Arg Ala Ile Glu His Ala Leu Asn Val Tyr Tyr
                115                 120                 125

Leu Leu Phe Lys Pro Glu Tyr Leu Thr Arg Met Ala Gly Lys Gly Leu
            130                 135                 140

Arg Gln Gly Phe Glu Asp Ala Gly Pro Ala Arg Glu
145                 150                 155
```

<210> SEQ ID NO 36
<211> LENGTH: 209
<212> TYPE: PRT
<213> ORGANISM: Artificial Sequence
<220> FEATURE:
<223> OTHER INFORMATION: I53-40 B genus
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (2)..(2)
<223> OTHER INFORMATION: Xaa is S or D
<220> FEATURE:
<221> NAME/KEY: MISC_FEATURE
<222> LOCATION: (3)..(3)
<223> OTHER INFORMATION: Xaa is T or D
<220> FEATURE:
<221> NAME/KEY: MISC_FEATURE
<222> LOCATION: (10)..(10)
<223> OTHER INFORMATION: Xaa is A or R
<220> FEATURE:
<221> NAME/KEY: MISC_FEATURE
<222> LOCATION: (85)..(85)
<223> OTHER INFORMATION: Xaa is T or D
<220> FEATURE:
<221> NAME/KEY: MISC_FEATURE
<222> LOCATION: (119)..(119)
<223> OTHER INFORMATION: Xaa is A or Q
<220> FEATURE:
<221> NAME/KEY: MISC_FEATURE
<222> LOCATION: (163)..(163)
<223> OTHER INFORMATION: Xaa is S or D
<220> FEATURE:
<221> NAME/KEY: MISC_FEATURE
<222> LOCATION: (189)..(189)
<223> OTHER INFORMATION: Xaa is T or R

<400> SEQUENCE: 36

```
Met Xaa Xaa Ile Asn Asn Gln Leu Lys Xaa Leu Lys Val Ile Pro Val
 1               5                  10                  15

Ile Ala Ile Asp Asn Ala Glu Asp Ile Ile Pro Leu Gly Lys Val Leu
             20                  25                  30

Ala Glu Asn Gly Leu Pro Ala Ala Glu Ile Thr Phe Arg Ser Ser Ala
         35                  40                  45

Ala Val Lys Ala Ile Met Leu Leu Arg Ser Ala Gln Pro Glu Met Leu
 50                  55                  60

Ile Gly Ala Gly Thr Ile Leu Asn Gly Val Gln Ala Leu Ala Ala Lys
```

```
                65                  70                  75                  80
Glu Ala Gly Ala Xaa Phe Val Val Ser Pro Gly Phe Asn Pro Asn Thr
                    85                  90                  95

Val Arg Ala Cys Gln Ile Ile Gly Ile Asp Ile Val Pro Gly Val Asn
                100                 105                 110

Asn Pro Ser Thr Val Glu Xaa Ala Leu Glu Met Gly Leu Thr Thr Leu
                115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
145                 150                 155                 160

Thr Pro Xaa Asn Ile Asp Asn Tyr Leu Ala Ile Pro Gln Val Leu Ala
            165                 170                 175

Cys Gly Gly Thr Trp Met Val Asp Lys Lys Leu Val Xaa Asn Gly Glu
                180                 185                 190

Trp Asp Glu Ile Ala Arg Leu Thr Arg Glu Ile Val Glu Gln Val Asn
            195                 200                 205

Pro

<210> SEQ ID NO 37
<211> LENGTH: 114
<212> TYPE: PRT
<213> ORGANISM: Artificial Sequence
<220> FEATURE:
<223> OTHER INFORMATION: I53-47A genus
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (13)..(13)
<223> OTHER INFORMATION: Xaa is T or D
<220> FEATURE:
<221> NAME/KEY: MISC_FEATURE
<222> LOCATION: (33)..(33)
<223> OTHER INFORMATION: Xaa is K or E
<220> FEATURE:
<221> NAME/KEY: MISC_FEATURE
<222> LOCATION: (71)..(71)
<223> OTHER INFORMATION: Xaa is S or D
<220> FEATURE:
<221> NAME/KEY: MISC_FEATURE
<222> LOCATION: (74)..(74)
<223> OTHER INFORMATION: Xaa is R or E
<220> FEATURE:
<221> NAME/KEY: MISC_FEATURE
<222> LOCATION: (101)..(101)
<223> OTHER INFORMATION: Xaa is N or D
<220> FEATURE:
<221> NAME/KEY: MISC_FEATURE
<222> LOCATION: (103)..(103)
<223> OTHER INFORMATION: Xaa is N or D

<400> SEQUENCE: 37

Met Pro Ile Phe Thr Leu Asn Thr Asn Ile Lys Ala Xaa Asp Val Pro
1               5                   10                  15

Ser Asp Phe Leu Ser Leu Thr Ser Arg Leu Val Gly Leu Ile Leu Ser
                20                  25                  30

Xaa Pro Gly Ser Tyr Val Ala Val His Ile Asn Thr Asp Gln Gln Leu
            35                  40                  45

Ser Phe Gly Gly Ser Thr Asn Pro Ala Ala Phe Gly Thr Leu Met Ser
        50                  55                  60

Ile Gly Gly Ile Glu Pro Xaa Lys Asn Xaa Asp His Ser Ala Val Leu
```

```
                65                  70                  75                  80
Phe Asp His Leu Asn Ala Met Leu Gly Ile Pro Lys Asn Arg Met Tyr
                    85                  90                  95
Ile His Phe Val Xaa Leu Xaa Gly Asp Asp Val Gly Trp Asn Gly Thr
                100                 105                 110
Thr Phe
```

<210> SEQ ID NO 38
<211> LENGTH: 157
<212> TYPE: PRT
<213> ORGANISM: Artificial Sequence
<220> FEATURE:
<223> OTHER INFORMATION: I53-47B genus
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (9)..(9)
<223> OTHER INFORMATION: Xaa is Y or H
<220> FEATURE:
<221> NAME/KEY: MISC_FEATURE
<222> LOCATION: (82)..(82)
<223> OTHER INFORMATION: Xaa is N or D
<220> FEATURE:
<221> NAME/KEY: MISC_FEATURE
<222> LOCATION: (87)..(87)
<223> OTHER INFORMATION: Xaa is R or D
<220> FEATURE:
<221> NAME/KEY: MISC_FEATURE
<222> LOCATION: (105)..(105)
<223> OTHER INFORMATION: Xaa is S or D
<220> FEATURE:
<221> NAME/KEY: MISC_FEATURE
<222> LOCATION: (119)..(119)
<223> OTHER INFORMATION: Xaa is R or E
<220> FEATURE:
<221> NAME/KEY: MISC_FEATURE
<222> LOCATION: (121)..(121)
<223> OTHER INFORMATION: Xaa is R or E
<220> FEATURE:
<221> NAME/KEY: MISC_FEATURE
<222> LOCATION: (124)..(124)
<223> OTHER INFORMATION: Xaa is A or D
<220> FEATURE:
<221> NAME/KEY: MISC_FEATURE
<222> LOCATION: (126)..(126)
<223> OTHER INFORMATION: Xaa is H or D
<220> FEATURE:
<221> NAME/KEY: MISC_FEATURE
<222> LOCATION: (128)..(128)
<223> OTHER INFORMATION: Xaa is R or E
<220> FEATURE:
<221> NAME/KEY: MISC_FEATURE
<222> LOCATION: (150)..(150)
<223> OTHER INFORMATION: Xaa is A or N

<400> SEQUENCE: 38

```
Met Asn Gln His Ser His Lys Asp Xaa Glu Thr Val Arg Ile Ala Val
1               5                   10                  15

Val Arg Ala Arg Trp His Ala Asp Ile Val Asp Ala Cys Val Glu Ala
                20                  25                  30

Phe Glu Ile Ala Met Ala Ala Ile Gly Gly Asp Arg Phe Ala Val Asp
            35                  40                  45

Val Phe Asp Val Pro Gly Ala Tyr Glu Ile Pro Leu His Ala Arg Thr
        50                  55                  60

Leu Ala Glu Thr Gly Arg Tyr Gly Ala Val Leu Gly Thr Ala Phe Val
65                  70                  75                  80
```

```
Val Xaa Gly Gly Ile Tyr Xaa His Glu Phe Val Ala Ser Ala Val Ile
            85                  90                  95

Asp Gly Met Met Asn Val Gln Leu Xaa Thr Gly Val Pro Val Leu Ser
        100                 105                 110

Ala Val Leu Thr Pro His Xaa Tyr Xaa Asp Ser Xaa Glu Xaa His Xaa
        115                 120                 125

Phe Phe Ala Ala His Phe Ala Val Lys Gly Val Glu Ala Ala Arg Ala
    130                 135                 140

Cys Ile Glu Ile Leu Xaa Ala Arg Glu Lys Ile Ala Ala
145                 150                 155

<210> SEQ ID NO 39
<211> LENGTH: 205
<212> TYPE: PRT
<213> ORGANISM: Artificial Sequence
<220> FEATURE:
<223> OTHER INFORMATION: I53-50A genus
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (126)..(126)
<223> OTHER INFORMATION: Xaa is T or D
<220> FEATURE:
<221> NAME/KEY: MISC_FEATURE
<222> LOCATION: (139)..(139)
<223> OTHER INFORMATION: Xaa is Q or E
<220> FEATURE:
<221> NAME/KEY: MISC_FEATURE
<222> LOCATION: (142)..(142)
<223> OTHER INFORMATION: Xaa is K or E
<220> FEATURE:
<221> NAME/KEY: MISC_FEATURE
<222> LOCATION: (160)..(160)
<223> OTHER INFORMATION: Xaa is N or D
<220> FEATURE:
<221> NAME/KEY: MISC_FEATURE
<222> LOCATION: (163)..(163)
<223> OTHER INFORMATION: Xaa is N or D
<220> FEATURE:
<221> NAME/KEY: MISC_FEATURE
<222> LOCATION: (166)..(166)
<223> OTHER INFORMATION: Xaa is E or K
<220> FEATURE:
<221> NAME/KEY: MISC_FEATURE
<222> LOCATION: (169)..(169)
<223> OTHER INFORMATION: Xaa is D or K
<220> FEATURE:
<221> NAME/KEY: MISC_FEATURE
<222> LOCATION: (179)..(179)
<223> OTHER INFORMATION: Xaa is S, D or K
<220> FEATURE:
<221> NAME/KEY: MISC_FEATURE
<222> LOCATION: (183)..(183)
<223> OTHER INFORMATION: Xaa is K or E
<220> FEATURE:
<221> NAME/KEY: MISC_FEATURE
<222> LOCATION: (185)..(185)
<223> OTHER INFORMATION: Xaa is T, D, or K
<220> FEATURE:
<221> NAME/KEY: MISC_FEATURE
<222> LOCATION: (192)..(192)
<223> OTHER INFORMATION: Xaa is D or K
<220> FEATURE:
<221> NAME/KEY: MISC_FEATURE
<222> LOCATION: (195)..(195)
<223> OTHER INFORMATION: Xaa is A, E, or K
<220> FEATURE:
<221> NAME/KEY: MISC_FEATURE
<222> LOCATION: (198)..(198)
<223> OTHER INFORMATION: Xaa is E or K
<220> FEATURE:
```

<221> NAME/KEY: MISC_FEATURE
<222> LOCATION: (199)..(199)
<223> OTHER INFORMATION: Xaa is E or K

<400> SEQUENCE: 39

```
Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Xaa Ile Leu
        115                 120                 125

Lys Leu Phe Pro Gly Glu Val Val Gly Pro Xaa Phe Val Xaa Ala Met
    130                 135                 140

Lys Gly Pro Phe Pro Asn Val Lys Phe Val Pro Thr Gly Gly Val Xaa
145                 150                 155                 160

Leu Asp Xaa Val Cys Xaa Trp Phe Xaa Ala Gly Val Leu Ala Val Gly
                165                 170                 175

Val Gly Xaa Ala Leu Val Xaa Gly Xaa Pro Asp Glu Val Arg Glu Xaa
            180                 185                 190

Ala Lys Xaa Phe Val Xaa Xaa Ile Arg Gly Cys Thr Glu
        195                 200                 205
```

<210> SEQ ID NO 40
<211> LENGTH: 157
<212> TYPE: PRT
<213> ORGANISM: Artificial Sequence
<220> FEATURE:
<223> OTHER INFORMATION: I53-50B genus
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (9)..(9)
<223> OTHER INFORMATION: Xaa is Y or H
<220> FEATURE:
<221> NAME/KEY: MISC_FEATURE
<222> LOCATION: (38)..(38)
<223> OTHER INFORMATION: Xaa is A or R
<220> FEATURE:
<221> NAME/KEY: MISC_FEATURE
<222> LOCATION: (82)..(82)
<223> OTHER INFORMATION: Xaa is N or D
<220> FEATURE:
<221> NAME/KEY: MISC_FEATURE
<222> LOCATION: (87)..(87)
<223> OTHER INFORMATION: Xaa is R or D
<220> FEATURE:
<221> NAME/KEY: MISC_FEATURE
<222> LOCATION: (97)..(97)
<223> OTHER INFORMATION: Xaa is N or D
<220> FEATURE:
<221> NAME/KEY: MISC_FEATURE
<222> LOCATION: (105)..(105)

```
<223> OTHER INFORMATION: Xaa is S, N, or D
<220> FEATURE:
<221> NAME/KEY: MISC_FEATURE
<222> LOCATION: (119)..(119)
<223> OTHER INFORMATION: Xaa is R, E, or N
<220> FEATURE:
<221> NAME/KEY: MISC_FEATURE
<222> LOCATION: (121)..(121)
<223> OTHER INFORMATION: Xaa is R, E, or D
<220> FEATURE:
<221> NAME/KEY: MISC_FEATURE
<222> LOCATION: (122)..(122)
<223> OTHER INFORMATION: Xaa is K or D
<220> FEATURE:
<221> NAME/KEY: MISC_FEATURE
<222> LOCATION: (124)..(124)
<223> OTHER INFORMATION: Xaa is K or D
<220> FEATURE:
<221> NAME/KEY: MISC_FEATURE
<222> LOCATION: (126)..(126)
<223> OTHER INFORMATION: Xaa is H or D

<400> SEQUENCE: 40

Met Asn Gln His Ser His Lys Asp Xaa Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Xaa Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
                85                  90                  95

Xaa Gly Met Met Asn Val Gln Leu Xaa Thr Gly Val Pro Val Leu Ser
            100                 105                 110

Ala Val Leu Thr Pro His Xaa Tyr Xaa Xaa Ser Xaa Ala Xaa Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 41
<211> LENGTH: 159
<212> TYPE: PRT
<213> ORGANISM: Artificial Sequence
<220> FEATURE:
<223> OTHER INFORMATION: T32-28A
<220> FEATURE:
<221> NAME/KEY: MISC_FEATURE
<222> LOCATION: (1)..(1)
<223> OTHER INFORMATION: optionally absent

<400> SEQUENCE: 41

Met Gly Glu Val Pro Ile Gly Asp Pro Lys Glu Leu Asn Gly Met Glu
1               5                   10                  15

Ile Ala Ala Val Tyr Leu Gln Pro Ile Glu Met Glu Pro Arg Gly Ile
            20                  25                  30

Asp Leu Ala Ala Ser Leu Ala Asp Ile His Leu Glu Ala Asp Ile His
        35                  40                  45

Ala Leu Lys Asn Asn Pro Asn Gly Phe Pro Glu Gly Phe Trp Met Pro
    50                  55                  60
```

```
Tyr Leu Thr Ile Ala Tyr Ala Leu Ala Asn Ala Asp Thr Gly Ala Ile
 65                  70                  75                  80

Lys Thr Gly Thr Leu Met Pro Met Val Ala Asp Asp Gly Pro His Tyr
                 85                  90                  95

Gly Ala Asn Ile Ala Met Glu Lys Asp Lys Lys Gly Gly Phe Gly Val
                100                 105                 110

Gly Thr Tyr Ala Leu Thr Phe Leu Ile Ser Asn Pro Glu Lys Gln Gly
            115                 120                 125

Phe Gly Arg His Val Asp Glu Glu Thr Gly Val Gly Lys Trp Phe Glu
130                 135                 140

Pro Phe Val Val Thr Tyr Phe Phe Lys Tyr Thr Gly Thr Pro Lys
145                 150                 155
```

<210> SEQ ID NO 42
<211> LENGTH: 184
<212> TYPE: PRT
<213> ORGANISM: Artificial Sequence
<220> FEATURE:
<223> OTHER INFORMATION: T32-28B
<220> FEATURE:
<221> NAME/KEY: MISC_FEATURE
<222> LOCATION: (1)..(1)
<223> OTHER INFORMATION: optionally absent

<400> SEQUENCE: 42

```
Met Ser Gln Ala Ile Gly Ile Leu Glu Leu Thr Ser Ile Ala Lys Gly
  1               5                  10                  15

Met Glu Leu Gly Asp Ala Met Leu Lys Ser Ala Asn Val Asp Leu Leu
                 20                  25                  30

Val Ser Lys Thr Ile Ser Pro Gly Lys Phe Leu Leu Met Leu Gly Gly
                 35                  40                  45

Asp Ile Gly Ala Ile Gln Gln Ala Ile Glu Thr Gly Thr Ser Gln Ala
            50                  55                  60

Gly Glu Met Leu Val Asp Ser Leu Val Leu Ala Asn Ile His Pro Ser
 65                  70                  75                  80

Val Leu Pro Ala Ile Ser Gly Leu Asn Ser Val Asp Lys Arg Gln Ala
                 85                  90                  95

Val Gly Ile Val Glu Thr Trp Ser Val Ala Ala Cys Ile Ser Ala Ala
                100                 105                 110

Asp Leu Ala Val Lys Gly Ser Asn Val Thr Leu Val Arg Val His Met
            115                 120                 125

Ala Phe Gly Ile Gly Gly Lys Cys Tyr Met Val Ala Gly Asp Val
130                 135                 140

Leu Asp Val Ala Ala Val Ala Thr Ala Ser Leu Ala Ala Gly Ala
145                 150                 155                 160

Lys Gly Leu Leu Val Tyr Ala Ser Ile Ile Pro Arg Pro His Glu Ala
                165                 170                 175

Met Trp Arg Gln Met Val Glu Gly
            180
```

<210> SEQ ID NO 43
<211> LENGTH: 103
<212> TYPE: PRT
<213> ORGANISM: Artificial Sequence
<220> FEATURE:
<223> OTHER INFORMATION: T33-09A
<220> FEATURE:
<221> NAME/KEY: MISC_FEATURE
<222> LOCATION: (1)..(1)

<223> OTHER INFORMATION: optionally absent

<400> SEQUENCE: 43

Met Glu Glu Val Val Leu Ile Thr Val Pro Ser Ala Leu Val Ala Val
1               5                   10                  15

Lys Ile Ala His Ala Leu Val Glu Glu Arg Leu Ala Ala Cys Val Asn
            20                  25                  30

Ile Val Pro Gly Leu Thr Ser Ile Tyr Arg Trp Gln Gly Ser Val Val
        35                  40                  45

Ser Asp His Glu Leu Leu Leu Val Lys Thr Thr Thr His Ala Phe
    50                  55                  60

Pro Lys Leu Lys Glu Arg Val Lys Ala Leu His Pro Tyr Thr Val Pro
65                  70                  75                  80

Glu Ile Val Ala Leu Pro Ile Ala Glu Gly Asn Arg Glu Tyr Leu Asp
                85                  90                  95

Trp Leu Arg Glu Asn Thr Gly
            100

<210> SEQ ID NO 44
<211> LENGTH: 122
<212> TYPE: PRT
<213> ORGANISM: Artificial Sequence
<220> FEATURE:
<223> OTHER INFORMATION: T33-09B
<220> FEATURE:
<221> NAME/KEY: MISC_FEATURE
<222> LOCATION: (1)..(1)
<223> OTHER INFORMATION: optionally absent

<400> SEQUENCE: 44

Met Val Arg Gly Ile Arg Gly Ala Ile Thr Val Glu Glu Asp Thr Pro
1               5                   10                  15

Ala Ala Ile Leu Ala Ala Thr Ile Glu Leu Leu Leu Lys Met Leu Glu
            20                  25                  30

Ala Asn Gly Ile Gln Ser Tyr Glu Glu Leu Ala Ala Val Ile Phe Thr
        35                  40                  45

Val Thr Glu Asp Leu Thr Ser Ala Phe Pro Ala Glu Ala Ala Arg Leu
    50                  55                  60

Ile Gly Met His Arg Val Pro Leu Leu Ser Ala Arg Glu Val Pro Val
65                  70                  75                  80

Pro Gly Ser Leu Pro Arg Val Ile Arg Val Leu Ala Leu Trp Asn Thr
                85                  90                  95

Asp Thr Pro Gln Asp Arg Val Arg His Val Tyr Leu Asn Glu Ala Val
            100                 105                 110

Arg Leu Arg Pro Asp Leu Glu Ser Ala Gln
        115                 120

<210> SEQ ID NO 45
<211> LENGTH: 177
<212> TYPE: PRT
<213> ORGANISM: Artificial Sequence
<220> FEATURE:
<223> OTHER INFORMATION: T33-15A
<220> FEATURE:
<221> NAME/KEY: MISC_FEATURE
<222> LOCATION: (1)..(1)
<223> OTHER INFORMATION: optionally absent

<400> SEQUENCE: 45

Met Ser Lys Ala Lys Ile Gly Ile Val Thr Val Ser Asp Arg Ala Ser
1               5                   10                  15

```
Ala Gly Ile Thr Ala Asp Ile Ser Gly Lys Ala Ile Ile Leu Ala Leu
            20                  25                  30

Asn Leu Tyr Leu Thr Ser Glu Trp Glu Pro Ile Tyr Gln Val Ile Pro
        35                  40                  45

Asp Glu Gln Asp Val Ile Glu Thr Thr Leu Ile Lys Met Ala Asp Glu
50                  55                  60

Gln Asp Cys Cys Leu Ile Val Thr Thr Gly Thr Gly Pro Ala Lys
65                  70                  75                  80

Arg Asp Val Thr Pro Glu Ala Thr Glu Ala Val Cys Asp Arg Met Met
                85                  90                  95

Pro Gly Phe Gly Glu Leu Met Arg Ala Glu Ser Leu Lys Glu Val Pro
            100                 105                 110

Thr Ala Ile Leu Ser Arg Gln Thr Ala Gly Leu Arg Gly Asp Ser Leu
        115                 120                 125

Ile Val Asn Leu Pro Gly Asp Pro Ala Ser Ile Ser Asp Cys Leu Leu
130                 135                 140

Ala Val Phe Pro Ala Ile Pro Tyr Cys Ile Asp Leu Met Glu Gly Pro
145                 150                 155                 160

Tyr Leu Glu Cys Asn Glu Ala Met Ile Lys Pro Phe Arg Pro Lys Ala
                165                 170                 175

Lys

<210> SEQ ID NO 46
<211> LENGTH: 122
<212> TYPE: PRT
<213> ORGANISM: Artificial Sequence
<220> FEATURE:
<223> OTHER INFORMATION: T33-15B
<220> FEATURE:
<221> NAME/KEY: MISC_FEATURE
<222> LOCATION: (1)..(1)
<223> OTHER INFORMATION: optionally absent

<400> SEQUENCE: 46

Met Val Arg Gly Ile Arg Gly Ala Ile Thr Val Asn Ser Asp Thr Pro
1               5                   10                  15

Thr Ser Ile Ile Ile Ala Thr Ile Leu Leu Glu Lys Met Leu Glu
            20                  25                  30

Ala Asn Gly Ile Gln Ser Tyr Glu Glu Leu Ala Ala Val Ile Phe Thr
        35                  40                  45

Val Thr Glu Asp Leu Thr Ser Ala Phe Pro Ala Glu Ala Ala Arg Gln
    50                  55                  60

Ile Gly Met His Arg Val Pro Leu Leu Ser Ala Arg Glu Val Pro Val
65                  70                  75                  80

Pro Gly Ser Leu Pro Arg Val Ile Arg Val Leu Ala Leu Trp Asn Thr
                85                  90                  95

Asp Thr Pro Gln Asp Arg Val Arg His Val Tyr Leu Ser Glu Ala Val
            100                 105                 110

Arg Leu Arg Pro Asp Leu Glu Ser Ala Gln
        115                 120

<210> SEQ ID NO 47
<211> LENGTH: 172
<212> TYPE: PRT
<213> ORGANISM: Artificial Sequence
<220> FEATURE:
<223> OTHER INFORMATION: T33-21A
<220> FEATURE:
```

<221> NAME/KEY: MISC_FEATURE
<222> LOCATION: (1)..(1)
<223> OTHER INFORMATION: optionally absent

<400> SEQUENCE: 47

Met Arg Ile Thr Thr Lys Val Gly Asp Lys Gly Ser Thr Arg Leu Phe
1               5                   10                  15

Gly Gly Glu Glu Val Trp Lys Asp Ser Pro Ile Ile Glu Ala Asn Gly
            20                  25                  30

Thr Leu Asp Glu Leu Thr Ser Phe Ile Gly Ala Lys His Tyr Val
        35                  40                  45

Asp Glu Glu Met Lys Gly Ile Leu Glu Ile Gln Asn Asp Ile Tyr
50                  55                  60

Lys Ile Met Gly Glu Ile Gly Ser Lys Gly Lys Ile Glu Gly Ile Ser
65                  70                  75                  80

Glu Glu Arg Ile Ala Trp Leu Leu Lys Leu Ile Leu Arg Tyr Met Glu
                85                  90                  95

Met Val Asn Leu Lys Ser Phe Val Leu Pro Gly Gly Thr Leu Glu Ser
            100                 105                 110

Ala Lys Leu Asp Val Cys Arg Thr Ile Ala Arg Arg Ala Leu Arg Lys
        115                 120                 125

Val Leu Thr Val Thr Arg Glu Phe Gly Ile Gly Ala Glu Ala Ala
130                 135                 140

Tyr Leu Leu Ala Leu Ser Asp Leu Leu Phe Leu Leu Ala Arg Val Ile
145                 150                 155                 160

Glu Ile Glu Lys Asn Lys Leu Lys Glu Val Arg Ser
                165                 170

<210> SEQ ID NO 48
<211> LENGTH: 123
<212> TYPE: PRT
<213> ORGANISM: Artificial Sequence
<220> FEATURE:
<223> OTHER INFORMATION: T33-21B
<220> FEATURE:
<221> NAME/KEY: MISC_FEATURE
<222> LOCATION: (1)..(1)
<223> OTHER INFORMATION: optionally absent

<400> SEQUENCE: 48

Met Pro His Leu Val Ile Glu Ala Thr Ala Asn Leu Arg Leu Glu Thr
1               5                   10                  15

Ser Pro Gly Glu Leu Leu Glu Gln Ala Asn Lys Ala Leu Phe Ala Ser
            20                  25                  30

Gly Gln Phe Gly Glu Ala Asp Ile Lys Ser Arg Phe Val Thr Leu Glu
        35                  40                  45

Ala Tyr Arg Gln Gly Thr Ala Ala Val Glu Arg Ala Tyr Leu His Ala
    50                  55                  60

Cys Leu Ser Ile Leu Asp Gly Arg Asp Ile Ala Thr Arg Thr Leu Leu
65                  70                  75                  80

Gly Ala Ser Leu Cys Ala Val Leu Ala Glu Val Ala Gly Gly Gly
                85                  90                  95

Glu Glu Gly Val Gln Val Ser Val Glu Val Arg Glu Met Glu Arg Leu
            100                 105                 110

Ser Tyr Ala Lys Arg Val Val Ala Arg Gln Arg
        115                 120

<210> SEQ ID NO 49

```
<211> LENGTH: 158
<212> TYPE: PRT
<213> ORGANISM: Artificial Sequence
<220> FEATURE:
<223> OTHER INFORMATION: T33-28A
<220> FEATURE:
<221> NAME/KEY: MISC_FEATURE
<222> LOCATION: (1)..(1)
<223> OTHER INFORMATION: optionally absent

<400> SEQUENCE: 49

Met Glu Ser Val Asn Thr Ser Phe Leu Ser Pro Ser Leu Val Thr Ile
1               5                   10                  15

Arg Asp Phe Asp Asn Gly Gln Phe Ala Val Leu Arg Ile Gly Arg Thr
            20                  25                  30

Gly Phe Pro Ala Asp Lys Gly Asp Ile Asp Leu Cys Leu Asp Lys Met
        35                  40                  45

Ile Gly Val Arg Ala Ala Gln Ile Phe Leu Gly Asp Asp Thr Glu Asp
50                  55                  60

Gly Phe Lys Gly Pro His Ile Arg Ile Arg Cys Val Asp Ile Asp Asp
65                  70                  75                  80

Lys His Thr Tyr Asn Ala Met Val Tyr Val Asp Leu Ile Val Gly Thr
                85                  90                  95

Gly Ala Ser Glu Val Glu Arg Glu Thr Ala Glu Glu Glu Ala Lys Leu
            100                 105                 110

Ala Leu Arg Val Ala Leu Gln Val Asp Ile Ala Asp Glu His Ser Cys
        115                 120                 125

Val Thr Gln Phe Glu Met Lys Leu Arg Glu Glu Leu Leu Ser Ser Asp
    130                 135                 140

Ser Phe His Pro Asp Lys Asp Glu Tyr Tyr Lys Asp Phe Leu
145                 150                 155

<210> SEQ ID NO 50
<211> LENGTH: 113
<212> TYPE: PRT
<213> ORGANISM: Artificial Sequence
<220> FEATURE:
<223> OTHER INFORMATION: T33-28B
<220> FEATURE:
<221> NAME/KEY: MISC_FEATURE
<222> LOCATION: (1)..(1)
<223> OTHER INFORMATION: optionally absent

<400> SEQUENCE: 50

Met Pro Val Ile Gln Thr Phe Val Ser Thr Pro Leu Asp His His Lys
1               5                   10                  15

Arg Leu Leu Leu Ala Ile Ile Tyr Arg Ile Val Thr Arg Val Val Leu
            20                  25                  30

Gly Lys Pro Glu Asp Leu Val Met Met Thr Phe His Asp Ser Thr Pro
        35                  40                  45

Met His Phe Phe Gly Ser Thr Asp Pro Val Ala Cys Val Arg Val Glu
    50                  55                  60

Ala Leu Gly Gly Tyr Gly Pro Ser Glu Pro Glu Lys Val Thr Ser Ile
65                  70                  75                  80

Val Thr Ala Ala Ile Thr Ala Val Cys Gly Ile Val Ala Asp Arg Ile
                85                  90                  95

Phe Val Leu Tyr Phe Ser Pro Leu His Cys Gly Trp Asn Gly Thr Asn
            100                 105                 110

Phe
```

-continued

<210> SEQ ID NO 51
<211> LENGTH: 103
<212> TYPE: PRT
<213> ORGANISM: Artificial Sequence
<220> FEATURE:
<223> OTHER INFORMATION: T33-31A
<220> FEATURE:
<221> NAME/KEY: MISC_FEATURE
<222> LOCATION: (1)..(1)
<223> OTHER INFORMATION: optionally absent

<400> SEQUENCE: 51

```
Met Glu Glu Val Val Leu Ile Thr Val Pro Ser Ala Leu Val Ala Val
1               5                   10                  15

Lys Ile Ala His Ala Leu Val Glu Glu Arg Leu Ala Ala Cys Val Asn
            20                  25                  30

Ile Val Pro Gly Leu Thr Ser Ile Tyr Arg Glu Glu Gly Ser Val Val
        35                  40                  45

Ser Asp His Glu Leu Leu Leu Val Lys Thr Thr Thr Asp Ala Phe
    50                  55                  60

Pro Lys Leu Lys Glu Arg Val Lys Glu Leu His Pro Tyr Glu Val Pro
65                  70                  75                  80

Glu Ile Val Ala Leu Pro Ile Ala Glu Gly Asn Arg Glu Tyr Leu Asp
                85                  90                  95

Trp Leu Arg Glu Asn Thr Gly
            100
```

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

```
Gln Asn Ile Thr Glu Glu Phe
1               5
```

<210> SEQ ID NO 53
<211> LENGTH: 513
<212> TYPE: PRT
<213> ORGANISM: Artificial Sequence
<220> FEATURE:
<223> OTHER INFORMATION: DS-Cav1
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
<222> LOCATION: (508)..(513)
<223> OTHER INFORMATION: optionally absent

<400> SEQUENCE: 53

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
```

```
                65                  70                  75                  80

Gln Glu Leu Asp Lys Tyr Lys Asn Ala Val Thr Glu Leu Gln Leu Leu
                        85                  90                  95

Met Gln Ser Thr Pro Ala Thr Asn Asn Arg Ala Arg Arg Glu Leu Pro
                    100                 105                 110

Arg Phe Met Asn Tyr Thr Leu Asn Asn Ala Lys Lys Thr Asn Val Thr
                    115                 120                 125

Leu Ser Lys Lys Arg Lys Arg Arg Phe Leu Gly Phe Leu Leu Gly Val
                130                 135                 140

Gly Ser Ala Ile Ala Ser Gly Val Ala Val Cys Lys Val Leu His Leu
        145                 150                 155                 160

Glu Gly Glu Val Asn Lys Ile Lys Ser Ala Leu Leu Ser Thr Asn Lys
                        165                 170                 175

Ala Val Val Ser Leu Ser Asn Gly Val Ser Val Leu Thr Phe Lys Val
                    180                 185                 190

Leu Asp Leu Lys Asn Tyr Ile Asp Lys Gln Leu Leu Pro Ile Leu Asn
                    195                 200                 205

Lys Gln Ser Cys Ser Ile Ser Asn Ile Glu Thr Val Ile Glu Phe Gln
                210                 215                 220

Gln Lys Asn Asn Arg Leu Leu Glu Ile Thr Arg Glu Phe Ser Val Asn
        225                 230                 235                 240

Ala Gly Val Thr Thr Pro Val Ser Thr Tyr Met Leu Thr Asn Ser Glu
                        245                 250                 255

Leu Leu Ser Leu Ile Asn Asp Met Pro Ile Thr Asn Asp Gln Lys Lys
                    260                 265                 270

Leu Met Ser Asn Asn Val Gln Ile Val Arg Gln Gln Ser Tyr Ser Ile
                    275                 280                 285

Met Cys Ile Ile Lys Glu Glu Val Leu Ala Tyr Val Val Gln Leu Pro
                290                 295                 300

Leu Tyr Gly Val Ile Asp Thr Pro Cys Trp Lys Leu His Thr Ser Pro
        305                 310                 315                 320

Leu Cys Thr Thr Asn Thr Lys Glu Gly Ser Asn Ile Cys Leu Thr Arg
                        325                 330                 335

Thr Asp Arg Gly Trp Tyr Cys Asp Asn Ala Gly Ser Val Ser Phe Phe
                    340                 345                 350

Pro Gln Ala Glu Thr Cys Lys Val Gln Ser Asn Arg Val Phe Cys Asp
                    355                 360                 365

Thr Met Asn Ser Leu Thr Leu Pro Ser Glu Val Asn Leu Cys Asn Val
                370                 375                 380

Asp Ile Phe Asn Pro Lys Tyr Asp Cys Lys Ile Met Thr Ser Lys Thr
        385                 390                 395                 400

Asp Val Ser Ser Ser Val Ile Thr Ser Leu Gly Ala Ile Val Ser Cys
                        405                 410                 415

Tyr Gly Lys Thr Lys Cys Thr Ala Ser Asn Lys Asn Arg Gly Ile Ile
                    420                 425                 430

Lys Thr Phe Ser Asn Gly Cys Asp Tyr Val Ser Asn Lys Gly Val Asp
                    435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
        465                 470                 475                 480

Leu Val Phe Pro Ser Asp Glu Phe Asp Ala Ser Ile Ser Gln Val Asn
                        485                 490                 495
```

```
Glu Lys Ile Asn Gln Ser Leu Ala Phe Ile Arg Lys Ser Asp Glu Leu
                500                 505                 510

Leu

<210> SEQ ID NO 54
<211> LENGTH: 27
<212> TYPE: PRT
<213> ORGANISM: Artificial Sequence
<220> FEATURE:
<223> OTHER INFORMATION: T4 fibritin foldon domain

<400> SEQUENCE: 54

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 55
<211> LENGTH: 15
<212> TYPE: PRT
<213> ORGANISM: Artificial Sequence
<220> FEATURE:
<223> OTHER INFORMATION: Linker

<400> SEQUENCE: 55

Gly Ser Gly Gly Ser Gly Ser Gly Ser Gly Ser Gly Ser Gly
1               5                   10                  15

<210> SEQ ID NO 56
<211> LENGTH: 8
<212> TYPE: PRT
<213> ORGANISM: Artificial Sequence
<220> FEATURE:
<223> OTHER INFORMATION: Linker

<400> SEQUENCE: 56

Gly Gly Ser Gly Gly Ser Gly Ser
1               5

<210> SEQ ID NO 57
<211> LENGTH: 8
<212> TYPE: PRT
<213> ORGANISM: Artificial Sequence
<220> FEATURE:
<223> OTHER INFORMATION: Linker

<400> SEQUENCE: 57

Gly Ser Gly Gly Ser Gly Ser Gly
1               5

<210> SEQ ID NO 58
<211> LENGTH: 11
<212> TYPE: PRT
<213> ORGANISM: Artificial Sequence
<220> FEATURE:
<223> OTHER INFORMATION: Helical extension

<400> SEQUENCE: 58

Glu Lys Ala Ala Lys Ala Glu Glu Ala Ala Arg
1               5                   10

<210> SEQ ID NO 59
<211> LENGTH: 25
<212> TYPE: PRT
<213> ORGANISM: Artificial Sequence
```

```
<220> FEATURE:
<223> OTHER INFORMATION: Signal peptide

<400> SEQUENCE: 59

Met Glu Leu Leu Ile Leu Lys Ala Asn Ala Ile Thr Thr Ile Leu Thr
1               5                   10                  15

Ala Val Thr Phe Cys Phe Ala Ser Gly
            20                  25

<210> SEQ ID NO 60
<211> LENGTH: 540
<212> TYPE: PRT
<213> ORGANISM: Artificial Sequence
<220> FEATURE:
<223> OTHER INFORMATION: DS-Cav1-foldon
<220> FEATURE:
<221> NAME/KEY: MISC_FEATURE
<222> LOCATION: (1)..(25)
<223> OTHER INFORMATION: optionally absent

<400> SEQUENCE: 60

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285
```

```
Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Gly Tyr Ile Pro Glu Ala Pro Arg Asp Gly Gln Ala Tyr Val Arg
        515                 520                 525

Lys Asp Gly Glu Trp Val Leu Leu Ser Thr Phe Leu
530                 535                 540

<210> SEQ ID NO 61
<211> LENGTH: 474
<212> TYPE: PRT
<213> ORGANISM: Artificial Sequence
<220> FEATURE:
<223> OTHER INFORMATION: sc9-10 DS-Cav1 A149C Y458C
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
<222> LOCATION: (468)..(474)
<223> OTHER INFORMATION: optionally absent

<400> SEQUENCE: 61

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
```

```
            65                  70                  75                  80

Gln Glu Leu Asp Lys Tyr Lys Asn Ala Val Thr Glu Leu Gln Leu Leu
                        85                  90                  95

Met Gln Ser Thr Pro Ala Thr Gly Ser Gly Ser Ala Ile Cys Ser Gly
                        100                 105                 110

Val Ala Val Cys Lys Val Leu His Leu Glu Gly Glu Val Asn Lys Ile
                        115                 120                 125

Lys Ser Ala Leu Leu Ser Thr Asn Lys Ala Val Val Ser Leu Ser Asn
        130                 135                 140

Gly Val Ser Val Leu Thr Phe Lys Val Leu Asp Leu Lys Asn Tyr Ile
        145                 150                 155                 160

Asp Lys Gln Leu Leu Pro Ile Leu Asn Lys Gln Ser Cys Ser Ile Ser
                        165                 170                 175

Asn Ile Glu Thr Val Ile Glu Phe Gln Gln Lys Asn Asn Arg Leu Leu
                        180                 185                 190

Glu Ile Thr Arg Glu Phe Ser Val Asn Ala Gly Val Thr Thr Pro Val
                        195                 200                 205

Ser Thr Tyr Met Leu Thr Asn Ser Glu Leu Leu Ser Leu Ile Asn Asp
                        210                 215                 220

Met Pro Ile Thr Asn Asp Gln Lys Lys Leu Met Ser Asn Asn Val Gln
        225                 230                 235                 240

Ile Val Arg Gln Gln Ser Tyr Ser Ile Met Cys Ile Ile Lys Glu Glu
                        245                 250                 255

Val Leu Ala Tyr Val Val Gln Leu Pro Leu Tyr Gly Val Ile Asp Thr
                        260                 265                 270

Pro Cys Trp Lys Leu His Thr Ser Pro Leu Cys Thr Thr Asn Thr Lys
                        275                 280                 285

Glu Gly Ser Asn Ile Cys Leu Thr Arg Thr Asp Arg Gly Trp Tyr Cys
                        290                 295                 300

Asp Asn Ala Gly Ser Val Ser Phe Phe Pro Gln Ala Glu Thr Cys Lys
        305                 310                 315                 320

Val Gln Ser Asn Arg Val Phe Cys Asp Thr Met Asn Ser Arg Thr Leu
                        325                 330                 335

Pro Ser Glu Val Asn Leu Cys Asn Val Asp Ile Phe Asn Pro Lys Tyr
                        340                 345                 350

Asp Cys Lys Ile Met Thr Ser Lys Thr Asp Val Ser Ser Ser Val Ile
                        355                 360                 365

Thr Ser Leu Gly Ala Ile Val Ser Cys Tyr Gly Lys Thr Lys Cys Thr
                        370                 375                 380

Ala Ser Asn Lys Asn Arg Gly Ile Ile Lys Thr Phe Ser Asn Gly Cys
        385                 390                 395                 400

Asp Tyr Val Ser Asn Lys Gly Val Asp Thr Val Ser Val Gly Asn Thr
                        405                 410                 415

Leu Tyr Cys Val Asn Lys Gln Glu Gly Lys Ser Leu Tyr Val Lys Gly
                        420                 425                 430

Glu Pro Ile Ile Asn Phe Tyr Asp Pro Leu Val Phe Pro Ser Asp Glu
                        435                 440                 445

Phe Asp Ala Ser Ile Ser Gln Val Asn Glu Lys Ile Asn Gln Ser Leu
                        450                 455                 460

Ala Phe Ile Arg Lys Ser Asp Glu Leu Leu
        465                 470

<210> SEQ ID NO 62
```

```
<211> LENGTH: 474
<212> TYPE: PRT
<213> ORGANISM: Artificial Sequence
<220> FEATURE:
<223> OTHER INFORMATION: sc9-10 DS-Cav1 A149C Y458C S46G K465Q S215P
      E92D
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
<222> LOCATION: (468)..(474)
<223> OTHER INFORMATION: optionally absent

<400> SEQUENCE: 62
```

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

-continued

```
Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu
465                 470
```

<210> SEQ ID NO 63
<211> LENGTH: 522
<212> TYPE: PRT
<213> ORGANISM: Artificial Sequence
<220> FEATURE:
<223> OTHER INFORMATION: SC-DM (N67I, S215P)
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
<222> LOCATION: (486)..(522)
<223> OTHER INFORMATION: optionally absent

<400> SEQUENCE: 63

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175
```

```
Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
        260                 265                 270

Glu Val Leu Ala Tyr Val Val Gln Leu Pro Leu Tyr Gly Val Ile Asp
    275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
            325                 330                 335

Lys Val Gln Ser Asn Arg Val Phe Cys Asp Thr Met Asn Ser Leu Thr
        340                 345                 350

Leu Pro Ser Glu Val Asn Leu Cys Asn Val Asp Ile Phe Asn Pro Lys
    355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
        420                 425                 430

Thr Leu Tyr Tyr Val Asn Lys Gln Glu Gly Lys Ser Leu Tyr Val Lys
    435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
            485                 490                 495

Tyr Ile Pro Glu Ala Pro Arg Asp Gly Gln Ala Tyr Val Arg Lys Asp
        500                 505                 510

Gly Glu Trp Val Leu Leu Ser Thr Phe Leu
    515                 520

<210> SEQ ID NO 64
<211> LENGTH: 522
<212> TYPE: PRT
<213> ORGANISM: Artificial Sequence
<220> FEATURE:
<223> OTHER INFORMATION: SC-TM (N67I, S215P, and E487Q)
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
```

<222> LOCATION: (486)..(522)
<223> OTHER INFORMATION: optionally absent

<400> SEQUENCE: 64

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

-continued

```
Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
        450                 455                 460

Gln Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu
            515                 520

<210> SEQ ID NO 65
<211> LENGTH: 490
<212> TYPE: PRT
<213> ORGANISM: Artificial Sequence
<220> FEATURE:
<223> OTHER INFORMATION: HMPV F protein, strain CAN97-83 (A2)
<220> FEATURE:
<221> NAME/KEY: MISC_FEATURE
<222> LOCATION: (1)..(18)
<223> OTHER INFORMATION: optionally absent

<400> SEQUENCE: 65

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
```

```
                    210                 215                 220
Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                    245                 250                 255

Gly Ile Leu Ile Gly Val Tyr Gly Ser Ser Val Ile Tyr Met Val Gln
                    260                 265                 270

Leu Pro Ile Phe Gly Val Ile Asp Thr Pro Cys Trp Ile Val Lys Ala
                275                 280                 285

Ala Pro Ser Cys Ser Gly Lys Lys Gly Asn Tyr Ala Cys Leu Leu Arg
            290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                    325                 330                 335

Thr Ala Ala Gly Ile Asn Val Ala Glu Gln Ser Lys Glu Cys Asn Ile
                340                 345                 350

Asn Ile Ser Thr Thr Asn Tyr Pro Cys Lys Val Ser Thr Gly Arg His
            355                 360                 365

Pro Ile Ser Met Val Ala Leu Ser Pro Leu Gly Ala Leu Val Ala Cys
        370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                    405                 410                 415

Thr Val Thr Ile Asp Asn Thr Val Tyr Gln Leu Ser Lys Val Glu Gly
                420                 425                 430

Glu Gln His Val Ile Lys Gly Arg Pro Val Ser Ser Phe Asp Pro
            435                 440                 445

Ile Lys Phe Pro Glu Asp Gln Phe Asn Val Ala Leu Asp Gln Val Phe
        450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly
                485                 490

<210> SEQ ID NO 66
<211> LENGTH: 490
<212> TYPE: PRT
<213> ORGANISM: Artificial Sequence
<220> FEATURE:
<223> OTHER INFORMATION: HMPVF with A113C, A339C, T160F, I177L
<220> FEATURE:
<221> NAME/KEY: MISC_FEATURE
<222> LOCATION: (1)

```
Ser Leu Ile Lys Thr Glu Leu Asp Leu Thr Lys Ser Ala Leu Arg Glu
 65                  70                  75                  80

Leu Lys Thr Val Ser Ala Asp Gln Leu Ala Arg Glu Glu Gln Ile Glu
                 85                  90                  95

Asn Pro Arg Gln Ser Arg Phe Val Leu Gly Ala Ile Ala Leu Gly Val
            100                 105                 110

Cys Thr Ala Ala Ala Val Thr Ala Gly Val Ala Ile Ala Lys Thr Ile
            115                 120                 125

Arg Leu Glu Ser Glu Val Thr Ala Ile Lys Asn Ala Leu Lys Thr Thr
        130                 135                 140

Asn Glu Ala Val Ser Thr Leu Gly Asn Gly Val Arg Val Leu Ala Phe
145                 150                 155                 160

Ala Val Arg Glu Leu Lys Asp Phe Val Ser Lys Asn Leu Thr Arg Ala
                165                 170                 175

Leu Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Cys Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly
```

-continued

```
                485                 490

<210> SEQ ID NO 67
<211> LENGTH: 490
<212> TYPE: PRT
<213> ORGANISM: Artificial Sequence
<220> FEATURE:
<223> OTHER INFORMATION: HMPV- F with A113C, A120C, A339C, T160F, I177L,
      and Q426C
<220> FEATURE:
<221> NAME/KEY: MISC_FEATURE
<222> LOCATION: (1)..(18)
<223> OTHER INFORMATION: optionally absent

<400> SEQUENCE: 67

Met

-continued

```
Thr Ala Cys Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Cys Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly
                485                 490
```

<210> SEQ ID NO 68
<211> LENGTH: 542
<212> TYPE: PRT
<213> ORGANISM: Artificial Sequence
<220> FEATURE:
<223> OTHER INFORMATION: 115-BV (A185P)
<220> FEATURE:
<221> NAME/KEY: MISC_FEATURE
<222> LOCATION: (1)..(18)
<223> OTHER INFORMATION: optionally absent
<220> FEATURE:
<221> NAME/KEY: MISC_FEATURE
<222> LOCATION: (490)..(542)
<223> OTHER INFORMATION: optionally absent

<400> SEQUENCE: 68

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Arg Arg Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160
```

Ala Val Arg Glu Leu Lys Asp Phe Val Ser Lys Asn Leu Thr Arg Ala
            165                 170                 175

Ile Asn Lys Asn Lys Cys Asp Ile Pro Asp Leu Lys Met Ala Val Ser
        180                 185                 190

Phe Ser Gln Phe Asn Arg Arg Phe Leu Asn Val Val Arg Gln Phe Ser
    195                 200                 205

Asp Asn Ala Gly Ile Thr Pro Ala Ile Ser Leu Asp Leu Met Thr Asp
210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
            245                 250                 255

Gly Ile Leu Ile Gly Val Tyr Gly Ser Ser Val Ile Tyr Met Val Gln
        260                 265                 270

Leu Pro Ile Phe Gly Val Ile Asp Thr Pro Cys Trp Ile Val Lys Ala
    275                 280                 285

Ala Pro Ser Cys Ser Glu Lys Lys Gly Asn Tyr Ala Cys Leu Leu Arg
290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
            325                 330                 335

Thr Ala Ala Gly Ile Asn Val Ala Glu Gln Ser Lys Glu Cys Asn Ile
        340                 345                 350

Asn Ile Ser Thr Thr Asn Tyr Pro Cys Lys Val Ser Thr Gly Arg His
    355                 360                 365

Pro Ile Ser Met Val Ala Leu Ser Pro Leu Gly Ala Leu Val Ala Cys
370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
            405                 410                 415

Thr Val Thr Ile Asp Asn Thr Val Tyr Gln Leu Ser Lys Val Glu Gly
        420                 425                 430

Glu Gln His Val Ile Lys Gly Arg Pro Val Ser Ser Phe Asp Pro
    435                 440                 445

Val Lys Phe Pro Glu Asp Gln Phe Asn Val Ala Leu Asp Gln Val Phe
450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Ser Gly Arg Glu Asn Leu Tyr
            485                 490                 495

Phe Gln Gly Gly Gly Ser Gly Tyr Ile Pro Glu Ala Pro Arg Asp
        500                 505                 510

Gly Gln Ala Tyr Val Arg Lys Asp Gly Glu Trp Val Leu Leu Ser Thr
    515                 520                 525

Phe Leu Gly Gly Ile Glu Gly Arg His His His His His
    530                 535                 540

<210> SEQ ID NO 69
<211> LENGTH: 646
<212> TYPE: PRT
<213> ORGANISM: Artificial Sequence
<220> FEATURE:
<223> OTHER INFORMATION: DS-Cav1-foldon-T33-31A

```
<220> FEATURE:
<221> NAME/KEY: MISC_FEATURE
<222> LOCATION: (1)..(26)
<223> OTHER INFORMATION: optionally absent

<400> SEQUENCE: 69
```

| | | | | | | | | | | | | | |
|---|---|---|---|---|---|---|---|---|---|---|---|---|---|
| Met | Glu | Leu | Leu | Ile | Leu | Lys | Ala | Asn | Val | Ile | Ala | Thr | Ile | Leu | Thr |
| 1 | | | | 5 | | | | | 10 | | | | | 15 | |
| Ala | Val | Thr | Phe | Cys | Phe | Ala | Ser | Ser | Gln | Asn | Ile | Thr | Glu | Glu | Phe |
| | | | 20 | | | | | 25 | | | | | 30 | | |
| Tyr | Gln | Ser | Thr | Cys | Ser | Ala | Val | Ser | Lys | Gly | Tyr | Leu | Ser | Ala | Leu |
| | | 35 | | | | | 40 | | | | | 45 | | | |
| Arg | Thr | Gly | Trp | Tyr | Thr | Ser | Val | Ile | Thr | Ile | Glu | Leu | Ser | Asn | Ile |
| | 50 | | | | | 55 | | | | | 60 | | | | |
| Lys | Glu | Asn | Lys | Cys | Asn | Gly | Thr | Asp | Ala | Lys | Val | Lys | Leu | Ile | Lys |
| 65 | | | | | 70 | | | | | 75 | | | | | 80 |
| Gln | Glu | Leu | Asp | Lys | Tyr | Lys | Asn | Ala | Val | Thr | Glu | Leu | Gln | Leu | Leu |
| | | | | 85 | | | | | 90 | | | | | 95 | |
| Met | Gln | Ser | Thr | Pro | Ala | Thr | Asn | Asn | Arg | Ala | Arg | Arg | Glu | Leu | Pro |
| | | | 100 | | | | | 105 | | | | | 110 | | |
| Arg | Phe | Met | Asn | Tyr | Thr | Leu | Asn | Asn | Ala | Lys | Lys | Thr | Asn | Val | Thr |
| | | 115 | | | | | 120 | | | | | 125 | | | |
| Leu | Ser | Lys | Lys | Arg | Lys | Arg | Arg | Phe | Leu | Gly | Phe | Leu | Leu | Gly | Val |
| | 130 | | | | | 135 | | | | | 140 | | | | |
| Gly | Ser | Ala | Ile | Ala | Ser | Gly | Val | Ala | Val | Cys | Lys | Val | Leu | His | Leu |
| 145 | | | | | 150 | | | | | 155 | | | | | 160 |
| Glu | Gly | Glu | Val | Asn | Lys | Ile | Lys | Ser | Ala | Leu | Leu | Ser | Thr | Asn | Lys |
| | | | | 165 | | | | | 170 | | | | | 175 | |
| Ala | Val | Val | Ser | Leu | Ser | Asn | Gly | Val | Ser | Val | Leu | Thr | Phe | Lys | Val |
| | | | 180 | | | | | 185 | | | | | 190 | | |
| Leu | Asp | Leu | Lys | Asn | Tyr | Ile | Asp | Lys | Gln | Leu | Leu | Pro | Ile | Leu | Asn |
| | | 195 | | | | | 200 | | | | | 205 | | | |
| Lys | Gln | Ser | Cys | Ser | Ile | Ser | Asn | Ile | Glu | Thr | Val | Ile | Glu | Phe | Gln |
| 210 | | | | | 215 | | | | | 220 | | | | | |
| Gln | Lys | Asn | Asn | Arg | Leu | Leu | Glu | Ile | Thr | Arg | Glu | Phe | Ser | Val | Asn |
| 225 | | | | | 230 | | | | | 235 | | | | | 240 |
| Ala | Gly | Val | Thr | Thr | Pro | Val | Ser | Thr | Tyr | Met | Leu | Thr | Asn | Ser | Glu |
| | | | | 245 | | | | | 250 | | | | | 255 | |
| Leu | Leu | Ser | Leu | Ile | Asn | Asp | Met | Pro | Ile | Thr | Asn | Asp | Gln | Lys | Lys |
| | | | 260 | | | | | 265 | | | | | 270 | | |
| Leu | Met | Ser | Asn | Asn | Val | Gln | Ile | Val | Arg | Gln | Ser | Tyr | Ser | Ile |
| | | 275 | | | | | 280 | | | | | 285 | | | |
| Met | Cys | Ile | Ile | Lys | Glu | Glu | Val | Leu | Ala | Tyr | Val | Val | Gln | Leu | Pro |
| | 290 | | | | | 295 | | | | | 300 | | | | |
| Leu | Tyr | Gly | Val | Ile | Asp | Thr | Pro | Cys | Trp | Lys | Leu | His | Thr | Ser | Pro |
| 305 | | | | | 310 | | | | | 315 | | | | | 320 |
| Leu | Cys | Thr | Thr | Asn | Thr | Lys | Glu | Gly | Ser | Asn | Ile | Cys | Leu | Thr | Arg |
| | | | | 325 | | | | | 330 | | | | | 335 | |
| Thr | Asp | Arg | Gly | Trp | Tyr | Cys | Asp | Asn | Ala | Gly | Ser | Val | Ser | Phe | Phe |
| | | | 340 | | | | | 345 | | | | | 350 | | |
| Pro | Gln | Ala | Glu | Thr | Cys | Lys | Val | Gln | Ser | Asn | Arg | Val | Phe | Cys | Asp |
| | | 355 | | | | | 360 | | | | | 365 | | | |
| Thr | Met | Asn | Ser | Leu | Thr | Leu | Pro | Ser | Glu | Val | Asn | Leu | Cys | Asn | Val |
| | 370 | | | | | 375 | | | | | 380 | | | | |

```
Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Gly Tyr Ile Pro Glu Ala Pro Arg Asp Gly Gln Ala Tyr Val Arg
            515                 520                 525

Lys Asp Gly Glu Trp Val Leu Leu Ser Thr Phe Leu Gly Gly Ser Met
530                 535                 540

Glu Glu Val Val Leu Ile Thr Val Pro Ser Ala Leu Val Ala Val Lys
545                 550                 555                 560

Ile Ala His Ala Leu Val Glu Glu Arg Leu Ala Ala Cys Val Asn Ile
            565                 570                 575

Val Pro Gly Leu Thr Ser Ile Tyr Arg Glu Glu Gly Ser Val Val Ser
            580                 585                 590

Asp His Glu Leu Leu Leu Val Lys Thr Thr Asp Ala Phe Pro
            595                 600                 605

Lys Leu Lys Glu Arg Val Lys Glu Leu His Pro Tyr Glu Val Pro Glu
610                 615                 620

Ile Val Ala Leu Pro Ile Ala Glu Gly Asn Arg Glu Tyr Leu Asp Trp
625                 630                 635                 640

Leu Arg Glu Asn Thr Gly
                645
```

<210> SEQ ID NO 70
<211> LENGTH: 619
<212> TYPE: PRT
<213> ORGANISM: Artificial Sequence
<220> FEATURE:
<223> OTHER INFORMATION: DS-Cav1-T33-31A
<220> FEATURE:
<221> NAME/KEY: MISC_FEATURE
<222> LOCATION: (1)..(25)
<223> OTHER INFORMATION: optionally absent

<400> SEQUENCE: 70

```
Met Glu Leu Leu Ile Leu Lys Ala Asn Val Ile Ala Thr Ile Leu Thr
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80
```

```
Gln Glu Leu Asp Lys Tyr Lys Asn Ala Val Thr Leu Gln Leu Leu
                 85                  90                  95

Met Gln Ser Thr Pro Ala Thr Asn Arg Ala Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495
```

-continued

```
Glu Lys Ile Asn Gln Ser Leu Ala Phe Ile Arg Lys Ser Asp Glu Leu
                500                 505                 510
Leu Gly Gly Ser Met Glu Val Val Leu Ile Thr Val Pro Ser Ala
        515                 520                 525
Leu Val Ala Val Lys Ile Ala His Ala Leu Val Glu Glu Arg Leu Ala
    530                 535                 540
Ala Cys Val Asn Ile Val Pro Gly Leu Thr Ser Ile Tyr Arg Glu Glu
545                 550                 555                 560
Gly Ser Val Val Ser Asp His Glu Leu Leu Leu Val Lys Thr Thr
                565                 570                 575
Thr Asp Ala Phe Pro Lys Leu Lys Glu Arg Val Lys Glu Leu His Pro
            580                 585                 590
Tyr Glu Val Pro Glu Ile Val Ala Leu Pro Ile Ala Glu Gly Asn Arg
        595                 600                 605
Glu Tyr Leu Asp Trp Leu Arg Glu Asn Thr Gly
    610                 615
```

<210> SEQ ID NO 71
<211> LENGTH: 665
<212> TYPE: PRT
<213> ORGANISM: Artificial Sequence
<220> FEATURE:
<223> OTHER INFORMATION: DS-Cav1-foldon-T33-15B
<220> FEATURE:
<221> NAME/KEY: MISC_FEATURE
<222> LOCATION: (1)..(25)
<223> OTHER INFORMATION: optionally absent

<400> SEQUENCE: 71

```
Met Glu Leu Leu Ile Leu Lys Ala Asn Val Ile Ala Thr Ile Leu Thr
1               5                   10                  15
Ala Val Thr Phe Cys Phe Ala Ser Ser Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Glu Asn Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Arg Ala Arg Arg Glu Leu Pro
            100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
    130                 135                 140
Gly Ser Ala Ile Ala Ser Gly Val Ala Val Cys Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Phe Lys Val
            180                 185                 190
Leu Asp Leu Lys Asn Tyr Ile Asp Lys Gln Leu Leu Pro Ile Leu Asn
        195                 200                 205
Lys Gln Ser Cys Ser Ile Ser Asn Ile Glu Thr Val Ile Glu Phe Gln
    210                 215                 220
```

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
            275                 280                 285

Met Cys Ile Ile Lys Glu Glu Val Leu Ala Tyr Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Gly Tyr Ile Pro Glu Ala Pro Arg Asp Gly Gln Ala Tyr Val Arg
            515                 520                 525

Lys Asp Gly Glu Trp Val Leu Leu Ser Thr Phe Leu Gly Gly Ser Met
            530                 535                 540

Val Arg Gly Ile Arg Gly Ala Ile Thr Val Asn Ser Asp Thr Pro Thr
545                 550                 555                 560

Ser Ile Ile Ile Ala Thr Ile Leu Leu Leu Glu Lys Met Leu Glu Ala
                565                 570                 575

Asn Gly Ile Gln Ser Tyr Glu Glu Leu Ala Ala Val Ile Phe Thr Val
            580                 585                 590

Thr Glu Asp Leu Thr Ser Ala Phe Pro Ala Glu Ala Ala Arg Gln Ile
            595                 600                 605

Gly Met His Arg Val Pro Leu Leu Ser Ala Arg Glu Val Pro Val Pro
            610                 615                 620

Gly Ser Leu Pro Arg Val Ile Arg Val Leu Ala Leu Trp Asn Thr Asp
625                 630                 635                 640
```

```
Thr Pro Gln Asp Arg Val Arg His Val Tyr Leu Ser Glu Ala Val Arg
                645                 650                 655

Leu Arg Pro Asp Leu Glu Ser Ala Gln
        660                 665

<210> SEQ ID NO 72
<211> LENGTH: 638
<212> TYPE: PRT
<213> ORGANISM: Artificial Sequence
<220> FEATURE:
<223> OTHER INFORMATION: DS-Cav1-T33-15B
<220> FEATURE:
<221> NAME/KEY: MISC_FEATURE
<222> LOCATION: (1)..(25)
<223> OTHER INFORMATION: optionally absent

<400> SEQUENCE: 72

Met Glu Leu Leu Ile Leu Lys Ala Asn Val Ile Ala Thr Ile Leu Thr
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320
```

```
Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Gly Gly Ser Met Val Arg Gly Ile Arg Gly Ala Ile Thr Val Asn
            515                 520                 525

Ser Asp Thr Pro Thr Ser Ile Ile Ile Ala Thr Ile Leu Leu Leu Glu
        530                 535                 540

Lys Met Leu Glu Ala Asn Gly Ile Gln Ser Tyr Glu Leu Ala Ala
545                 550                 555                 560

Val Ile Phe Thr Val Thr Glu Asp Leu Thr Ser Ala Phe Pro Ala Glu
                565                 570                 575

Ala Ala Arg Gln Ile Gly Met His Arg Val Pro Leu Leu Ser Ala Arg
            580                 585                 590

Glu Val Pro Val Pro Gly Ser Leu Pro Arg Val Ile Arg Val Leu Ala
        595                 600                 605

Leu Trp Asn Thr Asp Thr Pro Gln Asp Arg Val Arg His Val Tyr Leu
    610                 615                 620

Ser Glu Ala Val Arg Leu Arg Pro Asp Leu Glu Ser Ala Gln
625                 630                 635

<210> SEQ ID NO 73
<211> LENGTH: 769
<212> TYPE: PRT
<213> ORGANISM: Artificial Sequence
<220> FEATURE:
<223> OTHER INFORMATION: DS-Cav1-foldon-I53-50A
<220> FEATURE:
<221> NAME/KEY: MISC_FEATURE
<222> LOCATION: (1)..(25)
<223> OTHER INFORMATION: optionally absent

<400> SEQUENCE: 73

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
```

-continued

```
                20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
        50                  55                  60
Lys Glu Asn Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Arg Ala Arg Arg Glu Leu Pro
            100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
            130                 135                 140
Gly Ser Ala Ile Ala Ser Gly Val Ala Val Cys Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Phe Lys Val
            180                 185                 190
Leu Asp Leu Lys Asn Tyr Ile Asp Lys Gln Leu Leu Pro Ile Leu Asn
        195                 200                 205
Lys Gln Ser Cys Ser Ile Ser Asn Ile Glu Thr Val Ile Glu Phe Gln
        210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Cys Ile Ile Lys Glu Glu Val Leu Ala Tyr Val Val Gln Leu Pro
        290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
        370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
```

```
Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Gly Tyr Ile Pro Glu
                500                 505                 510

Ala Pro Arg Asp Gly Gln Ala Tyr Val Arg Lys Asp Gly Glu Trp Val
        515                 520                 525

Leu Leu Ser Thr Phe Leu Gly Ser Gly Ser His His His His His
        530                 535                 540

His His Gly Gly Ser Gly Ser Gly Ser Glu Lys Ala Ala Lys Ala
545                 550                 555                 560

Glu Glu Ala Ala Arg Lys Met Glu Glu Leu Phe Lys Lys His Lys Ile
                565                 570                 575

Val Ala Val Leu Arg Ala Asn Ser Val Glu Ala Ile Glu Lys Ala
                580                 585                 590

Val Ala Val Phe Ala Gly Gly Val His Leu Ile Glu Ile Thr Phe Thr
                595                 600                 605

Val Pro Asp Ala Asp Thr Val Ile Lys Ala Leu Ser Val Leu Lys Glu
        610                 615                 620

Lys Gly Ala Ile Ile Gly Ala Gly Thr Val Thr Ser Val Glu Gln Cys
625                 630                 635                 640

Arg Lys Ala Val Glu Ser Gly Ala Glu Phe Ile Val Ser Pro His Leu
                645                 650                 655

Asp Glu Glu Ile Ser Gln Phe Cys Lys Glu Lys Gly Val Phe Tyr Met
                660                 665                 670

Pro Gly Val Met Thr Pro Thr Glu Leu Val Lys Ala Met Lys Leu Gly
        675                 680                 685

His Thr Ile Leu Lys Leu Phe Pro Gly Glu Val Val Gly Pro Gln Phe
        690                 695                 700

Val Lys Ala Met Lys Gly Pro Phe Pro Asn Val Lys Phe Val Pro Thr
705                 710                 715                 720

Gly Gly Val Asn Leu Asp Asn Val Cys Glu Trp Phe Lys Ala Gly Val
                725                 730                 735

Leu Ala Val Gly Val Gly Ser Ala Leu Val Lys Gly Thr Pro Asp Glu
                740                 745                 750

Val Arg Glu Lys Ala Lys Ala Phe Val Glu Lys Ile Arg Gly Cys Thr
        755                 760                 765

Glu

<210> SEQ ID NO 74
<211> LENGTH: 730
<212> TYPE: PRT
<213> ORGANISM: Artificial Sequence
<220> FEATURE:
<223> OTHER INFORMATION: DS-Cav1-I53-50A
<220> FEATURE:
<221> NAME/KEY: MISC_FEATURE
<222> LOCATION: (1)..(25)
<223> OTHER INFORMATION: optionally absent

<400> SEQUENCE: 74

Met Glu Leu Leu Ile Leu Lys Ala Asn Val Ile Ala Thr Ile Leu Thr
1               5                   10                  15
```

-continued

```
Ala Val Thr Phe Cys Phe Ala Ser Ser Gln Asn Ile Thr Glu Glu Phe
             20                  25                  30

Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
             85                  90                  95

Met Gln Ser Thr Pro Ala Thr Asn Asn Arg Ala Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
            195                 200                 205

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430
```

```
Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Gly Ser Gly Gly
                500                 505                 510

Ser Gly Ser Glu Lys Ala Ala Lys Ala Glu Ala Ala Arg Lys Met
    515                 520                 525

Glu Glu Leu Phe Lys Lys His Lys Ile Val Ala Val Leu Arg Ala Asn
            530                 535                 540

Ser Val Glu Glu Ala Ile Glu Lys Ala Val Ala Val Phe Ala Gly Gly
545                 550                 555                 560

Val His Leu Ile Glu Ile Thr Phe Thr Val Pro Asp Ala Asp Thr Val
                565                 570                 575

Ile Lys Ala Leu Ser Val Leu Lys Glu Lys Gly Ala Ile Ile Gly Ala
            580                 585                 590

Gly Thr Val Thr Ser Val Glu Gln Cys Arg Lys Ala Val Glu Ser Gly
    595                 600                 605

Ala Glu Phe Ile Val Ser Pro His Leu Asp Glu Glu Ile Ser Gln Phe
            610                 615                 620

Cys Lys Glu Lys Gly Val Phe Tyr Met Pro Gly Val Met Thr Pro Thr
625                 630                 635                 640

Glu Leu Val Lys Ala Met Lys Leu Gly His Thr Ile Leu Lys Leu Phe
                645                 650                 655

Pro Gly Glu Val Val Gly Pro Gln Phe Val Lys Ala Met Lys Gly Pro
            660                 665                 670

Phe Pro Asn Val Lys Phe Val Pro Thr Gly Gly Val Asn Leu Asp Asn
            675                 680                 685

Val Cys Glu Trp Phe Lys Ala Gly Val Leu Ala Val Gly Val Gly Ser
    690                 695                 700

Ala Leu Val Lys Gly Thr Pro Asp Glu Val Arg Glu Lys Ala Lys Ala
705                 710                 715                 720

Phe Val Glu Lys Ile Arg Gly Cys Thr Glu
                725                 730

<210> SEQ ID NO 75
<211> LENGTH: 676
<212> TYPE: PRT
<213> ORGANISM: Artificial Sequence
<220> FEATURE:
<223> OTHER INFORMATION: DS-Cav1-I32-28A
<220> FEATURE:
<221> NAME/KEY: MISC_FEATURE
<222> LOCATION: (1)..(25)
<223> OTHER INFORMATION: optionally absent

<400> SEQUENCE: 75

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45
```

```
Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460
```

-continued

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Gly Gly Ser Gly Gly Ser Gly Ser Asp Asp Ala Arg Ile Ala Ala
        515                 520                 525

Ile Gly Asp Val Asp Glu Leu Asn Ser Gln Ile Gly Val Leu Leu Ala
    530                 535                 540

Glu Pro Leu Pro Asp Asp Val Arg Ala Ala Leu Ser Ala Ile Gln His
545                 550                 555                 560

Asp Leu Phe Asp Leu Gly Gly Glu Leu Cys Ile Pro Gly His Ala Ala
                565                 570                 575

Ile Thr Glu Asp His Leu Leu Arg Leu Ala Leu Trp Leu Val His Tyr
            580                 585                 590

Asn Gly Gln Leu Pro Pro Leu Glu Glu Phe Ile Leu Pro Gly Gly Ala
        595                 600                 605

Arg Gly Ala Ala Leu Ala His Val Cys Arg Thr Val Cys Arg Arg Ala
610                 615                 620

Glu Arg Ser Ile Lys Ala Leu Gly Ala Ser Glu Pro Leu Asn Ile Ala
625                 630                 635                 640

Pro Ala Ala Tyr Val Asn Leu Leu Ser Asp Leu Leu Phe Val Leu Ala
                645                 650                 655

Arg Val Leu Asn Arg Ala Ala Gly Gly Ala Asp Val Leu Trp Asp Arg
            660                 665                 670

Thr Arg Ala His
            675

<210> SEQ ID NO 76
<211> LENGTH: 730
<212> TYPE: PRT
<213> ORGANISM: Artificial Sequence
<220> FEATURE:
<223> OTHER INFORMATION: DS-Cav1-8GS-HelExt-I53-50A (F10)
<220> FEATURE:
<221> NAME/KEY: MISC_FEATURE
<222> LOCATION: (1)..(25)
<223> OTHER INFORMATION: optionally absent

<400> SEQUENCE: 76

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125
```

```
Leu Ser Lys Lys Arg Lys Arg Arg Phe Leu Gly Phe Leu Gly Val
    130                 135                 140
Gly Ser Ala Ile Ala Ser Gly Val Ala Val Cys Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Phe Lys Val
            180                 185                 190
Leu Asp Leu Lys Asn Tyr Ile Asp Lys Gln Leu Leu Pro Ile Leu Asn
        195                 200                 205
Lys Gln Ser Cys Ser Ile Ser Asn Ile Glu Thr Val Ile Glu Phe Gln
210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Cys Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Gly Ser Gly Gly Ser
            500                 505                 510
Gly Ser Gly Glu Lys Ala Ala Lys Ala Glu Glu Ala Ala Arg Lys Met
        515                 520                 525
Glu Glu Leu Phe Lys Lys His Lys Ile Val Ala Val Leu Arg Ala Asn
530                 535                 540
```

```
Ser Val Glu Glu Ala Ile Glu Lys Ala Val Ala Val Phe Ala Gly Gly
545                 550                 555                 560

Val His Leu Ile Glu Ile Thr Phe Thr Val Pro Asp Ala Asp Thr Val
                565                 570                 575

Ile Lys Ala Leu Ser Val Leu Lys Glu Lys Gly Ala Ile Ile Gly Ala
            580                 585                 590

Gly Thr Val Thr Ser Val Glu Gln Cys Arg Lys Ala Val Glu Ser Gly
        595                 600                 605

Ala Glu Phe Ile Val Ser Pro His Leu Asp Glu Glu Ile Ser Gln Phe
    610                 615                 620

Cys Lys Glu Lys Gly Val Phe Tyr Met Pro Gly Val Met Thr Pro Thr
625                 630                 635                 640

Glu Leu Val Lys Ala Met Lys Leu Gly His Thr Ile Leu Lys Leu Phe
                645                 650                 655

Pro Gly Glu Val Val Gly Pro Gln Phe Val Lys Ala Met Lys Gly Pro
            660                 665                 670

Phe Pro Asn Val Lys Phe Val Pro Thr Gly Gly Val Asn Leu Asp Asn
        675                 680                 685

Val Cys Glu Trp Phe Lys Ala Gly Val Leu Ala Val Gly Val Gly Ser
    690                 695                 700

Ala Leu Val Lys Gly Thr Pro Asp Glu Val Arg Glu Lys Ala Lys Ala
705                 710                 715                 720

Phe Val Glu Lys Ile Arg Gly Cys Thr Glu
                725                 730

<210> SEQ ID NO 77
<211> LENGTH: 764
<212> TYPE: PRT
<213> ORGANISM: Artificial Sequence
<220> FEATURE:
<223> OTHER INFORMATION: DS-Cav1-foldon-15GS-HelExt-I53-50A (F14)
<220> FEATURE:
<221> NAME/KEY: MISC_FEATURE
<222> LOCATION: (1)..(25)
<223> OTHER INFORMATION: optionally absent

<400> SEQUENCE: 77

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160
```

```
Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Gly Tyr Ile Pro Glu
            500                 505                 510

Ala Pro Arg Asp Gly Gln Ala Tyr Val Arg Lys Asp Gly Glu Trp Val
        515                 520                 525

Leu Leu Ser Thr Phe Leu Gly Ser Gly Ser Gly Ser Gly Ser Gly
    530                 535                 540

Gly Ser Gly Ser Gly Glu Lys Ala Ala Lys Ala Glu Ala Ala Arg
545                 550                 555                 560

Lys Met Glu Glu Leu Phe Lys Lys His Lys Ile Val Ala Val Leu Arg
                565                 570                 575
```

```
Ala Asn Ser Val Glu Glu Ala Ile Glu Lys Ala Val Ala Val Phe Ala
            580                 585                 590

Gly Gly Val His Leu Ile Glu Ile Thr Phe Thr Val Pro Asp Ala Asp
        595                 600                 605

Thr Val Ile Lys Ala Leu Ser Val Leu Lys Glu Lys Gly Ala Ile Ile
    610                 615                 620

Gly Ala Gly Thr Val Thr Ser Val Glu Gln Cys Arg Lys Ala Val Glu
625                 630                 635                 640

Ser Gly Ala Glu Phe Ile Val Ser Pro His Leu Asp Glu Glu Ile Ser
                645                 650                 655

Gln Phe Cys Lys Glu Lys Gly Val Phe Tyr Met Pro Gly Val Met Thr
            660                 665                 670

Pro Thr Glu Leu Val Lys Ala Met Lys Leu Gly His Thr Ile Leu Lys
        675                 680                 685

Leu Phe Pro Gly Glu Val Val Gly Pro Gln Phe Val Lys Ala Met Lys
    690                 695                 700

Gly Pro Phe Pro Asn Val Lys Phe Val Pro Thr Gly Gly Val Asn Leu
705                 710                 715                 720

Asp Asn Val Cys Glu Trp Phe Lys Ala Gly Val Leu Ala Val Gly Val
                725                 730                 735

Gly Ser Ala Leu Val Lys Gly Thr Pro Asp Glu Val Arg Glu Lys Ala
            740                 745                 750

Lys Ala Phe Val Glu Lys Ile Arg Gly Cys Thr Glu
        755                 760

<210> SEQ ID NO 78
<211> LENGTH: 774
<212> TYPE: PRT
<213> ORGANISM: Artificial Sequence
<220> FEATURE:
<223> OTHER INFORMATION: HMPV F wt_CAN97-83 strain-I53-50A
<220> FEATURE:
<221> NAME/KEY: MISC_FEATURE
<222> LOCATION: (1)..(18)
<223> OTHER INFORMATION: optionally absent
<400> SEQUENCE: 78

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160
```

```
Ala Val Arg Glu Leu Lys Asp Phe Val Ser Lys Asn Leu Thr Arg Ala
                165                 170                 175

Ile Asn Lys Asn Lys Cys Asp Ile Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
                260                 265                 270

Leu Pro Ile Phe Gly Val Ile Asp Thr Pro Cys Trp Ile Val Lys Ala
            275                 280                 285

Ala Pro Ser Cys Ser Gly Lys Lys Gly Asn Tyr Ala Cys Leu Leu Arg
        290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
                340                 345                 350

Asn Ile Ser Thr Thr Asn Tyr Pro Cys Lys Val Ser Thr Gly Arg His
            355                 360                 365

Pro Ile Ser Met Val Ala Leu Ser Pro Leu Gly Ala Leu Val Ala Cys
        370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
                420                 425                 430

Glu Gln His Val Ile Lys Gly Arg Pro Val Ser Ser Ser Phe Asp Pro
            435                 440                 445

Ile Lys Phe Pro Glu Asp Gln Phe Asn Val Ala Leu Asp Gln Val Phe
        450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Ser Gly Ser Gly Ser His
530                 535                 540

His His His His His His Gly Gly Ser Gly Gly Ser Gly Ser Glu
545                 550                 555                 560

Lys Ala Ala Lys Ala Glu Glu Ala Ala Arg Lys Met Glu Glu Leu Phe
                565                 570                 575
```

-continued

```
Lys Lys His Lys Ile Val Ala Val Leu Arg Ala Asn Ser Val Glu Glu
            580                 585                 590

Ala Ile Glu Lys Ala Val Ala Val Phe Ala Gly Gly Val His Leu Ile
        595                 600                 605

Glu Ile Thr Phe Thr Val Pro Asp Ala Asp Thr Val Ile Lys Ala Leu
    610                 615                 620

Ser Val Leu Lys Glu Lys Gly Ala Ile Ile Gly Ala Gly Thr Val Thr
625                 630                 635                 640

Ser Val Glu Gln Cys Arg Lys Ala Val Glu Ser Gly Ala Glu Phe Ile
                645                 650                 655

Val Ser Pro His Leu Asp Glu Glu Ile Ser Gln Phe Cys Lys Glu Lys
            660                 665                 670

Gly Val Phe Tyr Met Pro Gly Val Met Thr Pro Thr Glu Leu Val Lys
        675                 680                 685

Ala Met Lys Leu Gly His Thr Ile Leu Lys Leu Phe Pro Gly Glu Val
    690                 695                 700

Val Gly Pro Gln Phe Val Lys Ala Met Lys Gly Pro Phe Pro Asn Val
705                 710                 715                 720

Lys Phe Val Pro Thr Gly Gly Val Asn Leu Asp Asn Val Cys Glu Trp
                725                 730                 735

Phe Lys Ala Gly Val Leu Ala Val Gly Val Gly Ser Ala Leu Val Lys
            740                 745                 750

Gly Thr Pro Asp Glu Val Arg Glu Lys Ala Lys Ala Phe Val Glu Lys
        755                 760                 765

Ile Arg Gly Cys Thr Glu
    770

<210> SEQ ID NO 79
<211> LENGTH: 725
<212> TYPE: PRT
<213> ORGANISM: Artificial Sequence
<220> FEATURE:
<223> OTHER INFORMATION: HMPV F A113C_A339C_T160F_I177L-I53-50A
<220> FEATURE:
<221> NAME/KEY: MISC_FEATURE
<222> LOCATION: (1)..(18)
<223> OTHER INFORMATION: optionally absent

<400> SEQUENCE: 79

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Cys Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140
```

```
Asn Glu Ala Val Ser Thr Leu Gly Asn Gly Val Arg Val Leu Ala Phe
145                 150                 155                 160

Ala Val Arg Glu Leu Lys Asp Phe Val Ser Lys Asn Leu Thr Arg Ala
                165                 170                 175

Leu Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Cys Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Gly Ser Gly Ser His His
                485                 490                 495

His His His His His Gly Gly Ser Gly Gly Ser Gly Ser Glu Lys
            500                 505                 510

Ala Ala Lys Ala Glu Glu Ala Ala Arg Lys Met Glu Glu Leu Phe Lys
        515                 520                 525

Lys His Lys Ile Val Ala Val Leu Arg Ala Asn Ser Val Glu Glu Ala
    530                 535                 540

Ile Glu Lys Ala Val Ala Val Phe Ala Gly Gly Val His Leu Ile Glu
545                 550                 555                 560
```

```
Ile Thr Phe Thr Val Pro Asp Ala Asp Thr Val Ile Lys Ala Leu Ser
            565                 570                 575

Val Leu Lys Glu Lys Gly Ala Ile Ile Gly Ala Gly Thr Val Thr Ser
        580                 585                 590

Val Glu Gln Cys Arg Lys Ala Val Glu Ser Gly Ala Glu Phe Ile Val
    595                 600                 605

Ser Pro His Leu Asp Glu Glu Ile Ser Gln Phe Cys Lys Glu Lys Gly
610                 615                 620

Val Phe Tyr Met Pro Gly Val Met Thr Pro Thr Glu Leu Val Lys Ala
625                 630                 635                 640

Met Lys Leu Gly His Thr Ile Leu Lys Leu Phe Pro Gly Glu Val Val
                645                 650                 655

Gly Pro Gln Phe Val Lys Ala Met Lys Gly Pro Phe Pro Asn Val Lys
            660                 665                 670

Phe Val Pro Thr Gly Gly Val Asn Leu Asp Asn Val Cys Glu Trp Phe
        675                 680                 685

Lys Ala Gly Val Leu Ala Val Gly Val Gly Ser Ala Leu Val Lys Gly
    690                 695                 700

Thr Pro Asp Glu Val Arg Glu Lys Ala Lys Ala Phe Val Glu Lys Ile
705                 710                 715                 720

Arg Gly Cys Thr Glu
                725

<210> SEQ ID NO 80
<211> LENGTH: 725
<212> TYPE: PRT
<213> ORGANISM: Artificial Sequence
<220> FEATURE:
<223> OTHER INFORMATION: HMPV F A113C_A339C_T160F_I177L_A120C, Q426C -
      I53-50A
<220> FEATURE:
<221> NAME/KEY: MISC_FEATURE

```
                 165                 170                 175
Leu Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
            245                 250                 255

Gly Ile Leu Ile Gly Val Tyr Gly Ser Ser Val Ile Tyr Met Val Gln
        260                 265                 270

Leu Pro Ile Phe Gly Val Ile Asp Thr Pro Cys Trp Ile Val Lys Ala
    275                 280                 285

Ala Pro Ser Cys Ser Gly Lys Lys Gly Asn Tyr Ala Cys Leu Leu Arg
290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
            325                 330                 335

Thr Ala Cys Gly Ile Asn Val Ala Glu Gln Ser Lys Glu Cys Asn Ile
        340                 345                 350

Asn Ile Ser Thr Thr Asn Tyr Pro Cys Lys Val Ser Thr Gly Arg His
    355                 360                 365

Pro Ile Ser Met Val Ala Leu Ser Pro Leu Gly Ala Leu Val Ala Cys
370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
            405                 410                 415

Thr Val Thr Ile Asp Asn Thr Val Tyr Cys Leu Ser Lys Val Glu Gly
        420                 425                 430

Glu Gln His Val Ile Lys Gly Arg Pro Val Ser Ser Phe Asp Pro
    435                 440                 445

Ile Lys Phe Pro Glu Asp Gln Phe Asn Val Ala Leu Asp Gln Val Phe
450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Ser Gly Ser His His
            485                 490                 495

His His His His His Gly Gly Ser Gly Gly Ser Gly Ser Glu Lys
        500                 505                 510

Ala Ala Lys Ala Glu Glu Ala Arg Lys Met Glu Glu Leu Phe Lys
    515                 520                 525

Lys His Lys Ile Val Ala Val Leu Arg Ala Asn Ser Val Glu Glu Ala
    530                 535                 540

Ile Glu Lys Ala Val Ala Val Phe Ala Gly Gly Val His Leu Ile Glu
545                 550                 555                 560

Ile Thr Phe Thr Val Pro Asp Ala Asp Thr Val Ile Lys Ala Leu Ser
            565                 570                 575

Val Leu Lys Glu Lys Gly Ala Ile Ile Gly Ala Gly Thr Val Thr Ser
        580                 585                 590
```

```
Val Glu Gln Cys Arg Lys Ala Val Glu Ser Gly Ala Glu Phe Ile Val
            595                 600                 605

Ser Pro His Leu Asp Glu Glu Ile Ser Gln Phe Cys Lys Glu Lys Gly
    610                 615                 620

Val Phe Tyr Met Pro Gly Val Met Thr Pro Thr Glu Leu Val Lys Ala
625                 630                 635                 640

Met Lys Leu Gly His Thr Ile Leu Lys Leu Phe Pro Gly Glu Val Val
                645                 650                 655

Gly Pro Gln Phe Val Lys Ala Met Lys Gly Pro Phe Pro Asn Val Lys
            660                 665                 670

Phe Val Pro Thr Gly Gly Val Asn Leu Asp Asn Val Cys Glu Trp Phe
            675                 680                 685

Lys Ala Gly Val Leu Ala Val Gly Val Gly Ser Ala Leu Val Lys Gly
            690                 695                 700

Thr Pro Asp Glu Val Arg Glu Lys Ala Lys Ala Phe Val Glu Lys Ile
705                 710                 715                 720

Arg Gly Cys Thr Glu
            725

<210> SEQ ID NO 81
<211> LENGTH: 703
<212> TYPE: PRT
<213> ORGANISM: Artificial Sequence
<220> FEATURE:
<223> OTHER INFORMATION: sc-DS2-I53-50A
<220> FEATURE:
<221> NAME/KEY: MISC_FEATURE
<222> LOCATION: (1)..(25)
<223> OTHER INFORMATION: optionally absent

<400> SEQUENCE: 81

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Cys Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
```

```
            195                 200                 205
Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                    245                 250                 255

Val Leu Ala Tyr Val Val Gln Leu Pro Leu Tyr Gly Val Ile Asp Thr
                260                 265                 270

Pro Cys Trp Lys Leu His Thr Ser Pro Leu Cys Thr Thr Asn Thr Lys
            275                 280                 285

Glu Gly Ser Asn Ile Cys Leu Thr Arg Thr Asp Arg Gly Trp Tyr Cys
        290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Leu Thr Leu
                    325                 330                 335

Pro Ser Glu Val Asn Leu Cys Asn Val Asp Ile Phe Asn Pro Lys Tyr
                340                 345                 350

Asp Cys Lys Ile Met Thr Ser Lys Thr Asp Val Ser Ser Ser Val Ile
            355                 360                 365

Thr Ser Leu Gly Ala Ile Val Ser Cys Tyr Gly Lys Thr Lys Cys Thr
        370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                    405                 410                 415

Leu Tyr Cys Val Asn Lys Gln Glu Gly Lys Ser Leu Tyr Val Lys Gly
                420                 425                 430

Glu Pro Ile Ile Asn Phe Tyr Asp Pro Leu Val Phe Pro Ser Asp Glu
            435                 440                 445

Phe Asp Ala Ser Ile Ser Gln Val Asn Glu Lys Ile Asn Gln Ser Leu
        450                 455                 460

Ala Phe Ile Arg Gly Ser Gly Ser His His His His His His His His
465                 470                 475                 480

Gly Gly Ser Gly Gly Ser Gly Ser Glu Lys Ala Ala Lys Ala Glu Glu
                    485                 490                 495

Ala Ala Arg Lys Met Glu Glu Leu Phe Lys Lys His Lys Ile Val Ala
                500                 505                 510

Val Leu Arg Ala Asn Ser Val Glu Glu Ala Ile Glu Lys Ala Val Ala
            515                 520                 525

Val Phe Ala Gly Gly Val His Leu Ile Glu Ile Thr Phe Thr Val Pro
        530                 535                 540

Asp Ala Asp Thr Val Ile Lys Ala Leu Ser Val Leu Lys Glu Lys Gly
545                 550                 555                 560

Ala Ile Ile Gly Ala Gly Thr Val Thr Ser Val Glu Gln Cys Arg Lys
                    565                 570                 575

Ala Val Glu Ser Gly Ala Glu Phe Ile Val Ser Pro His Leu Asp Glu
                580                 585                 590

Glu Ile Ser Gln Phe Cys Lys Glu Lys Gly Val Phe Tyr Met Pro Gly
            595                 600                 605

Val Met Thr Pro Thr Glu Leu Val Lys Ala Met Lys Leu Gly His Thr
        610                 615                 620
```

-continued

```
Ile Leu Lys Leu Phe Pro Gly Glu Val Val Gly Pro Gln Phe Val Lys
625                 630                 635                 640

Ala Met Lys Gly Pro Phe Pro Asn Val Lys Phe Val Pro Thr Gly Gly
                645                 650                 655

Val Asn Leu Asp Asn Val Cys Glu Trp Phe Lys Ala Gly Val Leu Ala
                660                 665                 670

Val Gly Val Gly Ser Ala Leu Val Lys Gly Thr Pro Asp Glu Val Arg
            675                 680                 685

Glu Lys Ala Lys Ala Phe Val Glu Lys Ile Arg Gly Cys Thr Glu
        690                 695                 700

<210> SEQ ID NO 82
<211> LENGTH: 742
<212> TYPE: PRT
<213> ORGANISM: Artificial Sequence
<220> FEATURE:
<223> OTHER INFORMATION: tc-DS2-I53-50A
<220> FEATURE:
<221> NAME/KEY: MISC_FEATURE
<222> LOCATION: (1)..(25)
<223> OTHER INFORMATION: optionally absent

<400> SEQUENCE: 82

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Cys Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
```

```
              260                 265                 270
Leu Met Ser Asn Asn Val Gln Ile Val Arg Gln Gln Ser Tyr Ser Ile
            275                 280                 285
Met Cys Ile Ile Lys Glu Glu Val Leu Ala Tyr Val Val Gln Leu Pro
        290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
        370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Cys Val Asn Lys Gln Glu Gly
        450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Gly Ser Gly Ser His
                500                 505                 510
His His His His His His Gly Gly Ser Gly Gly Ser Gly Ser Glu
            515                 520                 525
Lys Ala Ala Lys Ala Glu Glu Ala Arg Lys Met Glu Glu Leu Phe
        530                 535                 540
Lys Lys His Lys Ile Val Ala Val Leu Arg Ala Asn Ser Val Glu Glu
545                 550                 555                 560
Ala Ile Glu Lys Ala Val Ala Val Phe Ala Gly Gly Val His Leu Ile
                565                 570                 575
Glu Ile Thr Phe Thr Val Pro Asp Ala Asp Thr Val Ile Lys Ala Leu
            580                 585                 590
Ser Val Leu Lys Glu Lys Gly Ala Ile Ile Gly Ala Gly Thr Val Thr
        595                 600                 605
Ser Val Glu Gln Cys Arg Lys Ala Val Glu Ser Gly Ala Glu Phe Ile
        610                 615                 620
Val Ser Pro His Leu Asp Glu Glu Ile Ser Gln Phe Cys Lys Glu Lys
625                 630                 635                 640
Gly Val Phe Tyr Met Pro Gly Val Met Thr Pro Thr Glu Leu Val Lys
                645                 650                 655
Ala Met Lys Leu Gly His Thr Ile Leu Lys Leu Phe Pro Gly Glu Val
                660                 665                 670
Val Gly Pro Gln Phe Val Lys Ala Met Lys Gly Pro Phe Pro Asn Val
            675                 680                 685
```

```
Lys Phe Val Pro Thr Gly Gly Val Asn Leu Asp Asn Val Cys Glu Trp
            690                 695                 700

Phe Lys Ala Gly Val Leu Ala Val Gly Val Gly Ser Ala Leu Val Lys
705                 710                 715                 720

Gly Thr Pro Asp Glu Val Arg Glu Lys Ala Lys Ala Phe Val Glu Lys
                725                 730                 735

Ile Arg Gly Cys Thr Glu
            740
```

```
<210> SEQ ID NO 83
<211> LENGTH: 734
<212> TYPE: PRT
<213> ORGANISM: Artificial Sequence
<220> FEATURE:
<223> OTHER INFORMATION: DS-Cav1-12GS-HelExt-I53-50A (F11)
<220> FEATURE:
<221> NAME/KEY: MISC_FEATURE
<222> LOCATION: (1)..(25)
<223> OTHER INFORMATION: optionally absent

<400> SEQUENCE: 83
```

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
```

```
              275                 280                 285
Met Cys Ile Ile Lys Glu Glu Val Leu Ala Tyr Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Gly Ser Gly Gly Ser
            500                 505                 510

Gly Ser Gly Ser Gly Gly Ser Glu Lys Ala Ala Lys Ala Glu Glu Ala
        515                 520                 525

Ala Arg Lys Met Glu Glu Leu Phe Lys Lys His Lys Ile Val Ala Val
    530                 535                 540

Leu Arg Ala Asn Ser Val Glu Glu Ala Ile Glu Lys Ala Val Ala Val
545                 550                 555                 560

Phe Ala Gly Gly Val His Leu Ile Glu Ile Thr Phe Thr Val Pro Asp
                565                 570                 575

Ala Asp Thr Val Ile Lys Ala Leu Ser Val Leu Lys Glu Lys Gly Ala
            580                 585                 590

Ile Ile Gly Ala Gly Thr Val Thr Ser Val Glu Gln Cys Arg Lys Ala
        595                 600                 605

Val Glu Ser Gly Ala Glu Phe Ile Val Ser Pro His Leu Asp Glu Glu
    610                 615                 620

Ile Ser Gln Phe Cys Lys Glu Lys Gly Val Phe Tyr Met Pro Gly Val
625                 630                 635                 640

Met Thr Pro Thr Glu Leu Val Lys Ala Met Lys Leu Gly His Thr Ile
                645                 650                 655

Leu Lys Leu Phe Pro Gly Glu Val Val Gly Pro Gln Phe Val Lys Ala
            660                 665                 670

Met Lys Gly Pro Phe Pro Asn Val Lys Phe Val Pro Thr Gly Gly Val
        675                 680                 685

Asn Leu Asp Asn Val Cys Glu Trp Phe Lys Ala Gly Val Leu Ala Val
    690                 695                 700
```

```
Gly Val Gly Ser Ala Leu Val Lys Gly Thr Pro Asp Glu Val Arg Glu
705                 710                 715                 720

Lys Ala Lys Ala Phe Val Glu Lys Ile Arg Gly Cys Thr Glu
                725                 730
```

<210> SEQ ID NO 84
<211> LENGTH: 738
<212> TYPE: PRT
<213> ORGANISM: Artificial Sequence
<220> FEATURE:
<223> OTHER INFORMATION: DS-Cav1-16GS-HelExt-I53-50A (F12)
<220> FEATURE:
<221> NAME/KEY: MISC_FEATURE
<222> LOCATION: (1)..(25)
<223> OTHER INFORMATION: optionally absent

<400> SEQUENCE: 84

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
```

```
                305                 310                 315                 320
Leu Cys Thr Thr Asn Thr Lys Glu Gly Ser Asn Ile Cys Leu Thr Arg
                    325                 330                 335

Thr Asp Arg Gly Trp Tyr Cys Asp Asn Ala Gly Ser Val Ser Phe Phe
                    340                 345                 350

Pro Gln Ala Glu Thr Cys Lys Val Gln Ser Asn Arg Val Phe Cys Asp
                    355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
                    420                 425                 430

Lys Thr Phe Ser Asn Gly Cys Asp Tyr Val Ser Asn Lys Gly Val Asp
                    435                 440                 445

Thr Val Ser Val Gly Asn Thr Leu Tyr Tyr Val Asn Lys Gln Glu Gly
                    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                    485                 490                 495

Glu Lys Ile Asn Gln Ser Leu Ala Phe Ile Arg Gly Ser Gly Gly Ser
                    500                 505                 510

Gly Ser Gly Ser Gly Gly Ser Gly Gly Glu Lys Ala Ala Lys
                    515                 520                 525

Ala Glu Glu Ala Ala Arg Lys Met Glu Glu Leu Phe Lys Lys His Lys
                    530                 535                 540

Ile Val Ala Val Leu Arg Ala Asn Ser Val Glu Glu Ala Ile Glu Lys
545                 550                 555                 560

Ala Val Ala Val Phe Ala Gly Gly Val His Leu Ile Glu Ile Thr Phe
                    565                 570                 575

Thr Val Pro Asp Ala Asp Thr Val Ile Lys Ala Leu Ser Val Leu Lys
                    580                 585                 590

Glu Lys Gly Ala Ile Ile Gly Ala Gly Thr Val Thr Ser Val Glu Gln
                    595                 600                 605

Cys Arg Lys Ala Val Glu Ser Gly Ala Glu Phe Ile Val Ser Pro His
                    610                 615                 620

Leu Asp Glu Glu Ile Ser Gln Phe Cys Lys Glu Lys Gly Val Phe Tyr
625                 630                 635                 640

Met Pro Gly Val Met Thr Pro Thr Glu Leu Val Lys Ala Met Lys Leu
                    645                 650                 655

Gly His Thr Ile Leu Lys Leu Phe Pro Gly Glu Val Val Gly Pro Gln
                    660                 665                 670

Phe Val Lys Ala Met Lys Gly Pro Phe Pro Asn Val Lys Phe Val Pro
                    675                 680                 685

Thr Gly Gly Val Asn Leu Asp Asn Val Cys Glu Trp Phe Lys Ala Gly
                    690                 695                 700

Val Leu Ala Val Gly Val Gly Ser Ala Leu Val Lys Gly Thr Pro Asp
705                 710                 715                 720

Glu Val Arg Glu Lys Ala Lys Ala Phe Val Glu Lys Ile Arg Gly Cys
                    725                 730                 735
```

Thr Glu

<210> SEQ ID NO 85
<211> LENGTH: 759
<212> TYPE: PRT
<213> ORGANISM: Artificial Sequence
<220> FEATURE:
<223> OTHER INFORMATION: DS-Cav1-foldon-10GS-HelExt-I53-50A (F13)
<220> FEATURE:
<221> NAME/KEY: MISC_FEATURE
<222> LOCATION: (1)..(25)
<223> OTHER INFORMATION: optionally absent

<400> SEQUENCE: 85

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

```
Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Gly Tyr Ile Pro Glu
            500                 505                 510

Ala Pro Arg Asp Gly Gln Ala Tyr Val Arg Lys Asp Gly Glu Trp Val
        515                 520                 525

Leu Leu Ser Thr Phe Leu Gly Ser Gly Ser Gly Ser Gly Ser Gly
    530                 535                 540

Glu Lys Ala Ala Lys Ala Glu Ala Ala Arg Lys Met Glu Glu Leu
545                 550                 555                 560

Phe Lys Lys His Lys Ile Val Ala Val Leu Arg Ala Asn Ser Val Glu
                565                 570                 575

Glu Ala Ile Glu Lys Ala Val Ala Val Phe Ala Gly Gly Val His Leu
            580                 585                 590

Ile Glu Ile Thr Phe Thr Val Pro Asp Ala Asp Thr Val Ile Lys Ala
        595                 600                 605

Leu Ser Val Leu Lys Glu Lys Gly Ala Ile Ile Gly Ala Gly Thr Val
    610                 615                 620

Thr Ser Val Glu Gln Cys Arg Lys Ala Val Glu Ser Gly Ala Glu Phe
625                 630                 635                 640

Ile Val Ser Pro His Leu Asp Glu Glu Ile Ser Gln Phe Cys Lys Glu
                645                 650                 655

Lys Gly Val Phe Tyr Met Pro Gly Val Met Thr Pro Thr Glu Leu Val
            660                 665                 670

Lys Ala Met Lys Leu Gly His Thr Ile Leu Lys Leu Phe Pro Gly Glu
        675                 680                 685

Val Val Gly Pro Gln Phe Val Lys Ala Met Lys Gly Pro Phe Pro Asn
    690                 695                 700

Val Lys Phe Val Pro Thr Gly Gly Val Asn Leu Asp Asn Val Cys Glu
705                 710                 715                 720

Trp Phe Lys Ala Gly Val Leu Ala Val Gly Val Gly Ser Ala Leu Val
                725                 730                 735

Lys Gly Thr Pro Asp Glu Val Arg Glu Lys Ala Lys Ala Phe Val Glu
            740                 745                 750
```

```
Lys Ile Arg Gly Cys Thr Glu
        755
```

<210> SEQ ID NO 86
<211> LENGTH: 769
<212> TYPE: PRT
<213> ORGANISM: Artificial Sequence
<220> FEATURE:
<223> OTHER INFORMATION: DS-Cav1-foldon-20GS-HelExt-I53-50A (F15)
<220> FEATURE:
<221> NAME/KEY: MISC_FEATURE
<222> LOCATION: (1)..(25)
<223> OTHER INFORMATION: optionally absent

<400> SEQUENCE: 86

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335
```

```
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
            370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
            450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Gly Tyr Ile Pro Glu
            500                 505                 510
Ala Pro Arg Asp Gly Gln Ala Tyr Val Arg Lys Asp Gly Glu Trp Val
            515                 520                 525
Leu Leu Ser Thr Phe Leu Gly Ser Gly Ser Gly Ser Gly Ser Gly Gly
            530                 535                 540
Gly Ser Gly Ser Gly Gly Ser Ser Gly Ser Glu Lys Ala Ala Lys Ala
545                 550                 555                 560
Glu Glu Ala Ala Arg Lys Met Glu Glu Leu Phe Lys Lys His Lys Ile
                565                 570                 575
Val Ala Val Leu Arg Ala Asn Ser Val Glu Glu Ala Ile Glu Lys Ala
            580                 585                 590
Val Ala Val Phe Ala Gly Gly Val His Leu Ile Glu Ile Thr Phe Thr
            595                 600                 605
Val Pro Asp Ala Asp Thr Val Ile Lys Ala Leu Ser Val Leu Lys Glu
            610                 615                 620
Lys Gly Ala Ile Ile Gly Ala Gly Thr Val Thr Ser Val Glu Gln Cys
625                 630                 635                 640
Arg Lys Ala Val Glu Ser Gly Ala Glu Phe Ile Val Ser Pro His Leu
                645                 650                 655
Asp Glu Glu Ile Ser Gln Phe Cys Lys Glu Lys Gly Val Phe Tyr Met
            660                 665                 670
Pro Gly Val Met Thr Pro Thr Glu Leu Val Lys Ala Met Lys Leu Gly
            675                 680                 685
His Thr Ile Leu Lys Leu Phe Pro Gly Glu Val Val Gly Pro Gln Phe
            690                 695                 700
Val Lys Ala Met Lys Gly Pro Phe Pro Asn Val Lys Phe Val Pro Thr
705                 710                 715                 720
Gly Gly Val Asn Leu Asp Asn Val Cys Glu Trp Phe Lys Ala Gly Val
                725                 730                 735
Leu Ala Val Gly Val Gly Ser Ala Leu Val Lys Gly Thr Pro Asp Glu
            740                 745                 750
```

```
Val Arg Glu Lys Ala Lys Ala Phe Val Glu Lys Ile Arg Gly Cys Thr
        755                 760                 765

Glu

<210> SEQ ID NO 87
<211> LENGTH: 736
<212> TYPE: PRT
<213> ORGANISM: Artificial Sequence
<220> FEATURE:
<223> OTHER INFORMATION: sc9-10 DS-Cav1 A149C Y458C-foldon-I53-50A
      embodiment
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
<222> LOCATION: (469)..(474)
<223> OTHER INFORMATION: optionally absent

<400> SEQUENCE: 87

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
```

```
                290                 295                 300
Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Val Ile
        355                 360                 365

Thr Ser Leu Gly Ala Ile Val Ser Cys Tyr Gly Lys Thr Lys Cys Thr
370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
450                 455                 460

Ala Phe Ile Arg Lys Ser Asp Glu Leu Leu Gly Tyr Ile Pro Glu Ala
465                 470                 475                 480

Pro Arg Asp Gly Gln Ala Tyr Val Arg Lys Asp Gly Glu Trp Val Leu
                485                 490                 495

Leu Ser Thr Phe Leu Gly Ser Gly Ser His His His His His His
            500                 505                 510

His Gly Gly Ser Gly Gly Ser Gly Ser Glu Lys Ala Ala Lys Ala Glu
        515                 520                 525

Glu Ala Ala Arg Lys Met Glu Glu Leu Phe Lys Lys His Lys Ile Val
530                 535                 540

Ala Val Leu Arg Ala Asn Ser Val Glu Glu Ala Ile Glu Lys Ala Val
545                 550                 555                 560

Ala Val Phe Ala Gly Gly Val His Leu Ile Glu Ile Thr Phe Thr Val
                565                 570                 575

Pro Asp Ala Asp Thr Val Ile Lys Ala Leu Ser Val Leu Lys Glu Lys
            580                 585                 590

Gly Ala Ile Ile Gly Ala Gly Thr Val Thr Ser Val Glu Gln Cys Arg
        595                 600                 605

Lys Ala Val Glu Ser Gly Ala Glu Phe Ile Val Ser Pro His Leu Asp
610                 615                 620

Glu Glu Ile Ser Gln Phe Cys Lys Glu Lys Gly Val Phe Tyr Met Pro
625                 630                 635                 640

Gly Val Met Thr Pro Thr Glu Leu Val Lys Ala Met Lys Leu Gly His
                645                 650                 655

Thr Ile Leu Lys Leu Phe Pro Gly Glu Val Val Gly Pro Gln Phe Val
            660                 665                 670

Lys Ala Met Lys Gly Pro Phe Pro Asn Val Lys Phe Val Pro Thr Gly
        675                 680                 685

Gly Val Asn Leu Asp Asn Val Cys Glu Trp Phe Lys Ala Gly Val Leu
690                 695                 700

Ala Val Gly Val Gly Ser Ala Leu Val Lys Gly Thr Pro Asp Glu Val
705                 710                 715                 720
```

```
Arg Glu Lys Ala Lys Ala Phe Val Glu Lys Ile Arg Gly Cys Thr Glu
                725                 730                 735

<210> SEQ ID NO 88
<211> LENGTH: 697
<212> TYPE: PRT
<213> ORGANISM: Artificial Sequence
<220> FEATURE:
<223> OTHER INFORMATION: sc9-10 DS-Cav1 A149C Y458C - F10 embodiment
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
<222> LOCATION: (469)..(474)
<223> OTHER INFORMATION: optionally absent

<400> SEQUENCE: 88

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300
```

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
            325                 330                 335

Pro Ser Glu Val Asn Leu Cys Asn Val Asp Ile Phe Asn Pro Lys Tyr
        340                 345                 350

Asp Cys Lys Ile Met Thr Ser Lys Thr Asp Val Ser Ser Ser Val Ile
    355                 360                 365

Thr Ser Leu Gly Ala Ile Val Ser Cys Tyr Gly Lys Thr Lys Cys Thr
370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
            405                 410                 415

Leu Tyr Cys Val Asn Lys Gln Glu Gly Lys Ser Leu Tyr Val Lys Gly
        420                 425                 430

Glu Pro Ile Ile Asn Phe Tyr Asp Pro Leu Val Phe Pro Ser Asp Glu
    435                 440                 445

Phe Asp Ala Ser Ile Ser Gln Val Asn Glu Lys Ile Asn Gln Ser Leu
450                 455                 460

Ala Phe Ile Arg Lys Ser Asp Glu Leu Leu Gly Ser Gly Ser Gly Ser
465                 470                 475                 480

Ser Gly Glu Lys Ala Ala Lys Ala Glu Ala Ala Arg Lys Met Glu
            485                 490                 495

Glu Leu Phe Lys Lys His Lys Ile Val Ala Val Leu Arg Ala Asn Ser
        500                 505                 510

Val Glu Glu Ala Ile Glu Lys Ala Val Ala Val Phe Ala Gly Gly Val
    515                 520                 525

His Leu Ile Glu Ile Thr Phe Thr Val Pro Asp Ala Asp Thr Val Ile
530                 535                 540

Lys Ala Leu Ser Val Leu Lys Glu Lys Gly Ala Ile Ile Gly Ala Gly
545                 550                 555                 560

Thr Val Thr Ser Val Glu Gln Cys Arg Lys Ala Val Glu Ser Gly Ala
            565                 570                 575

Glu Phe Ile Val Ser Pro His Leu Asp Glu Glu Ile Ser Gln Phe Cys
        580                 585                 590

Lys Glu Lys Gly Val Phe Tyr Met Pro Gly Val Met Thr Pro Thr Glu
    595                 600                 605

Leu Val Lys Ala Met Lys Leu Gly His Thr Ile Leu Lys Leu Phe Pro
610                 615                 620

Gly Glu Val Val Gly Pro Gln Phe Val Lys Ala Met Lys Gly Pro Phe
625                 630                 635                 640

Pro Asn Val Lys Phe Val Pro Thr Gly Gly Val Asn Leu Asp Asn Val
            645                 650                 655

Cys Glu Trp Phe Lys Ala Gly Val Leu Ala Val Gly Val Gly Ser Ala
        660                 665                 670

Leu Val Lys Gly Thr Pro Asp Glu Val Arg Glu Lys Ala Lys Ala Phe
    675                 680                 685

Val Glu Lys Ile Arg Gly Cys Thr Glu
    690                 695

<210> SEQ ID NO 89
<211> LENGTH: 736
<212> TYPE: PRT

<213> ORGANISM: Artificial Sequence
<220> FEATURE:
<223> OTHER INFORMATION: sc9-10 DS-Cav1 A149C Y458C S46G K465Q S215P
      E92D -foldon-I53-50A embodiment
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
<222> LOCATION: (469)..(474)
<223> OTHER INFORMATION: optionally absent

<400> SEQUENCE: 89

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr

```
                340             345             350
Asp Cys Lys Ile Met Thr Ser Lys Thr Asp Val Ser Ser Val Ile
                355             360             365

Thr Ser Leu Gly Ala Ile Val Ser Cys Tyr Gly Lys Thr Cys Thr
    370             375             380

Ala Ser Asn Lys Asn Arg Gly Ile Ile Lys Thr Phe Ser Asn Gly Cys
385             390             395             400

Asp Tyr Val Ser Asn Lys Gly Val Asp Thr Val Ser Val Gly Asn Thr
                405             410             415

Leu Tyr Cys Val Asn Lys Gln Glu Gly Gln Ser Leu Tyr Val Lys Gly
            420             425             430

Glu Pro Ile Ile Asn Phe Tyr Asp Pro Leu Val Phe Pro Ser Asp Glu
            435             440             445

Phe Asp Ala Ser Ile Ser Gln Val Asn Glu Lys Ile Asn Gln Ser Leu
        450             455             460

Ala Phe Ile Arg Lys Ser Asp Glu Leu Leu Gly Tyr Ile Pro Glu Ala
465             470             475             480

Pro Arg Asp Gly Gln Ala Tyr Val Arg Lys Asp Gly Glu Trp Val Leu
                485             490             495

Leu Ser Thr Phe Leu Gly Ser Gly Ser His His His His His His
                500             505             510

His Gly Gly Ser Gly Gly Ser Gly Ser Glu Lys Ala Ala Lys Ala Glu
            515             520             525

Glu Ala Ala Arg Lys Met Glu Glu Leu Phe Lys Lys His Lys Ile Val
        530             535             540

Ala Val Leu Arg Ala Asn Ser Val Glu Glu Ala Ile Glu Lys Ala Val
545             550             555             560

Ala Val Phe Ala Gly Gly Val His Leu Ile Glu Ile Thr Phe Thr Val
                565             570             575

Pro Asp Ala Asp Thr Val Ile Lys Ala Leu Ser Val Leu Lys Glu Lys
            580             585             590

Gly Ala Ile Ile Gly Ala Gly Thr Val Thr Ser Val Glu Gln Cys Arg
        595             600             605

Lys Ala Val Glu Ser Gly Ala Glu Phe Ile Val Ser Pro His Leu Asp
    610             615             620

Glu Glu Ile Ser Gln Phe Cys Lys Glu Lys Gly Val Phe Tyr Met Pro
625             630             635             640

Gly Val Met Thr Pro Thr Glu Leu Val Lys Ala Met Lys Leu Gly His
                645             650             655

Thr Ile Leu Lys Leu Phe Pro Gly Glu Val Val Gly Pro Gln Phe Val
            660             665             670

Lys Ala Met Lys Gly Pro Phe Pro Asn Val Lys Phe Val Pro Thr Gly
        675             680             685

Gly Val Asn Leu Asp Asn Val Cys Glu Trp Phe Lys Ala Gly Val Leu
        690             695             700

Ala Val Gly Val Gly Ser Ala Leu Val Lys Gly Thr Pro Asp Glu Val
705             710             715             720

Arg Glu Lys Ala Lys Ala Phe Val Glu Lys Ile Arg Gly Cys Thr Glu
                725             730             735

<210> SEQ ID NO 90
<211> LENGTH: 697
<212> TYPE: PRT
<213> ORGANISM: Artificial Sequence
```

```
<220> FEATURE:
<223> OTHER INFORMATION: sc9-10 DS-Cav1 A149C Y458C S46G K465Q S215P
      E92D - F10 embodiment
<220> FEATURE:
<221> NAME/KEY: M Asp Cys Lys Ile Met Thr Ser Lys Thr Asp Val Ser Ser Val Ile
            355                 360                 365

Thr Ser Leu Gly Ala Ile Val Ser Cys Tyr Gly Lys Thr Lys Cys Thr
370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Gly Ser Gly Gly Ser Gly
465                 470                 475                 480

Ser Gly Glu Lys Ala Ala Lys Ala Glu Ala Ala Arg Lys Met Glu
                485                 490                 495

Glu Leu Phe Lys Lys His Lys Ile Val Ala Val Leu Arg Ala Asn Ser
                500                 505                 510

Val Glu Glu Ala Ile Glu Lys Ala Val Ala Val Phe Ala Gly Gly Val
            515                 520                 525

His Leu Ile Glu Ile Thr Phe Thr Val Pro Asp Ala Asp Thr Val Ile
        530                 535                 540

Lys Ala Leu Ser Val Leu Lys Glu Lys Gly Ala Ile Ile Gly Ala Gly
545                 550                 555                 560

Thr Val Thr Ser Val Glu Gln Cys Arg Lys Ala Val Glu Ser Gly Ala
                565                 570                 575

Glu Phe Ile Val Ser Pro His Leu Asp Glu Glu Ile Ser Gln Phe Cys
                580                 585                 590

Lys Glu Lys Gly Val Phe Tyr Met Pro Gly Val Met Thr Pro Thr Glu
            595                 600                 605

Leu Val Lys Ala Met Lys Leu Gly His Thr Ile Leu Lys Leu Phe Pro
        610                 615                 620

Gly Glu Val Val Gly Pro Gln Phe Val Lys Ala Met Lys Gly Pro Phe
625                 630                 635                 640

Pro Asn Val Lys Phe Val Pro Thr Gly Gly Val Asn Leu Asp Asn Val
                645                 650                 655

Cys Glu Trp Phe Lys Ala Gly Val Leu Ala Val Gly Val Gly Ser Ala
            660                 665                 670

Leu Val Lys Gly Thr Pro Asp Glu Val Arg Glu Lys Ala Lys Ala Phe
        675                 680                 685

Val Glu Lys Ile Arg Gly Cys Thr Glu
    690                 695

<210> SEQ ID NO 91
<211> LENGTH: 753
<212> TYPE: PRT
<213> ORGANISM: Artificial Sequence
<220> FEATURE:
<223> OTHER INFORMATION: SC-DM (N67I, S215P) - foldon-I53-50A embodiment
<220> FEATURE:
<221> NAME/KEY: MISC_FEATURE
<222> LOCATION: (1)..(25)
<223> OTHER INFORMATION: optionally absent
<220> FEATURE:

```
<221> NAME/KEY: MISC_FEATURE
<222> LOCATION: (486)..(491)
<223> OTHER INFORMATION: optionally absent

<400> SEQUENCE: 91

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
```

```
            385                 390                 395                 400
        Thr Ala Ser Asn Lys Asn Arg Gly Ile Ile Lys Thr Phe Ser Asn Gly
                        405                 410                 415

Cys Asp Tyr Val Ser Asn Lys Gly Val Asp Thr Val Ser Val Gly Asn
                        420                 425                 430

Thr Leu Tyr Tyr Val Asn Lys Gln Glu Gly Lys Ser Leu Tyr Val Lys
                        435                 440                 445

Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
        465                 470                 475                 480

Leu Ala Phe Ile Arg Lys Ser Asp Glu Leu Leu Gly Tyr Ile Pro Glu
                        485                 490                 495

Ala Pro Arg Asp Gly Gln Ala Tyr Val Arg Lys Asp Gly Glu Trp Val
                        500                 505                 510

Leu Leu Ser Thr Phe Leu Gly Ser Gly Ser His His His His His His
                        515                 520                 525

His His Gly Gly Ser Gly Gly Ser Gly Ser Glu Lys Ala Ala Lys Ala
        530                 535                 540

Glu Glu Ala Ala Arg Lys Met Glu Glu Leu Phe Lys Lys His Lys Ile
        545                 550                 555                 560

Val Ala Val Leu Arg Ala Asn Ser Val Glu Glu Ala Ile Glu Lys Ala
                        565                 570                 575

Val Ala Val Phe Ala Gly Gly Val His Leu Ile Glu Ile Thr Phe Thr
                        580                 585                 590

Val Pro Asp Ala Asp Thr Val Ile Lys Ala Leu Ser Val Leu Lys Glu
                        595                 600                 605

Lys Gly Ala Ile Ile Gly Ala Gly Thr Val Thr Ser Val Glu Gln Cys
        610                 615                 620

Arg Lys Ala Val Glu Ser Gly Ala Glu Phe Ile Val Ser Pro His Leu
        625                 630                 635                 640

Asp Glu Glu Ile Ser Gln Phe Cys Lys Glu Lys Gly Val Phe Tyr Met
                        645                 650                 655

Pro Gly Val Met Thr Pro Thr Glu Leu Val Lys Ala Met Lys Leu Gly
                        660                 665                 670

His Thr Ile Leu Lys Leu Phe Pro Gly Glu Val Val Gly Pro Gln Phe
                        675                 680                 685

Val Lys Ala Met Lys Gly Pro Phe Pro Asn Val Lys Phe Val Pro Thr
        690                 695                 700

Gly Gly Val Asn Leu Asp Asn Val Cys Glu Trp Phe Lys Ala Gly Val
        705                 710                 715                 720

Leu Ala Val Gly Val Gly Ser Ala Leu Val Lys Gly Thr Pro Asp Glu
                        725                 730                 735

Val Arg Glu Lys Ala Lys Ala Phe Val Glu Lys Ile Arg Gly Cys Thr
                        740                 745                 750

Glu

<210> SEQ ID NO 92
<211> LENGTH: 714
<212> TYPE: PRT
<213> ORGANISM: Artificial Sequence
<220> FEATURE:
<223> OTHER INFORMATION: SC-DM (N67I, S215P) - F10 embodiment
<220> FEATURE:
<221> NAME/KEY: M
<222> LOCATION: (1)..(25)
<223> OTHER INFORMATION: optionally absent
<220> FEATURE:
<221> NAME/KEY: MISC_FEATURE
<222> LOCATION: (486)..(491)
<223> OTHER INFORMATION: optionally absent

<400> SEQUENCE: 92

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
```

```
                370                 375                 380
Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
                435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Gly Ser Gly Gly Ser
                485                 490                 495

Gly Ser Gly Glu Lys Ala Ala Lys Ala Glu Ala Ala Arg Lys Met
                500                 505                 510

Glu Glu Leu Phe Lys Lys His Lys Ile Val Ala Val Leu Arg Ala Asn
                515                 520                 525

Ser Val Glu Glu Ala Ile Glu Lys Ala Val Ala Val Phe Ala Gly Gly
                530                 535                 540

Val His Leu Ile Glu Ile Thr Phe Thr Val Pro Asp Ala Asp Thr Val
545                 550                 555                 560

Ile Lys Ala Leu Ser Val Leu Lys Glu Lys Gly Ala Ile Ile Gly Ala
                565                 570                 575

Gly Thr Val Thr Ser Val Glu Gln Cys Arg Lys Ala Val Glu Ser Gly
                580                 585                 590

Ala Glu Phe Ile Val Ser Pro His Leu Asp Glu Glu Ile Ser Gln Phe
                595                 600                 605

Cys Lys Glu Lys Gly Val Phe Tyr Met Pro Gly Val Met Thr Pro Thr
                610                 615                 620

Glu Leu Val Lys Ala Met Lys Leu Gly His Thr Ile Leu Lys Leu Phe
625                 630                 635                 640

Pro Gly Glu Val Val Gly Pro Gln Phe Val Lys Ala Met Lys Gly Pro
                645                 650                 655

Phe Pro Asn Val Lys Phe Val Pro Thr Gly Gly Val Asn Leu Asp Asn
                660                 665                 670

Val Cys Glu Trp Phe Lys Ala Gly Val Leu Ala Val Gly Val Gly Ser
                675                 680                 685

Ala Leu Val Lys Gly Thr Pro Asp Glu Val Arg Glu Lys Ala Lys Ala
                690                 695                 700

Phe Val Glu Lys Ile Arg Gly Cys Thr Glu
705                 710
```

<210> SEQ ID NO 93
<211> LENGTH: 753
<212> TYPE: PRT
<213> ORGANISM: Artificial Sequence
<220> FEATURE:
<223> OTHER INFORMATION: SC-TM (N67I, S215P, and E487Q) - foldon-I53-50A
      embodiment
<220> FEATURE:
<221> NAME/KEY: MISC_FEATURE
<222> LOCATION: (1)..(25)
<223> OTHER INFORMATION: optionally absent
<220> FEATURE:
<221> NAME/KEY: MISC_FEATURE
<222> LOCATION: (486)..(491)
<223> OTHER INFORMATION: optionally absent

<400> SEQUENCE: 93

| | | | | | | | | | | | | | | |
|---|---|---|---|---|---|---|---|---|---|---|---|---|---|---|
| Met | Glu | Leu | Leu | Ile | Leu | Lys | Ala | Asn | Ala | Ile | Thr | Thr | Ile | Leu | Thr |
| 1 | | | | 5 | | | | | 10 | | | | | 15 | |

Ala Val Thr Phe Cys Phe Ala Ser Gly Gln Asn Ile Thr Glu Phe
            20             25            30

Tyr Gln Ser Thr Cys Ser Ala Val Ser Lys Gly Tyr Leu Ser Ala Leu
            35            40            45

Arg Thr Gly Trp Tyr Thr Ser Val Ile Thr Ile Glu Leu Ser Asn Ile
50                  55            60

Lys Lys Ile Lys Cys Asn Gly Thr Asp Ala Lys Ile Lys Leu Ile Lys
65            70            75            80

Gln Glu Leu Asp Lys Tyr Lys Asn Ala Val Thr Glu Leu Gln Leu Leu
            85            90            95

Met Gln Ser Thr Pro Ala Thr Asn Asn Gln Ala Arg Gly Ser Gly Ser
            100          105          110

Gly Arg Ser Leu Gly Phe Leu Leu Gly Val Gly Ser Ala Ile Ala Ser
      115            120          125

Gly Val Ala Val Ser Lys Val Leu His Leu Glu Gly Glu Val Asn Lys
130               135          140

Ile Lys Ser Ala Leu Leu Ser Thr Asn Lys Ala Val Val Ser Leu Ser
145               150          155        160

Asn Gly Val Ser Val Leu Thr Ser Lys Val Leu Asp Leu Lys Asn Tyr
            165          170          175

Ile Asp Lys Gln Leu Leu Pro Ile Val Asn Lys Gln Ser Cys Ser Ile
         180           185           190

Pro Asn Ile Glu Thr Val Ile Glu Phe Gln Gln Lys Asn Asn Arg Leu
         195           200           205

Leu Glu Ile Thr Arg Glu Phe Ser Val Asn Ala Gly Val Thr Thr Pro
      210            215          220

Val Ser Thr Tyr Met Leu Thr Asn Ser Glu Leu Leu Ser Leu Ile Asn
225               230          235        240

Asp Met Pro Ile Thr Asn Asp Gln Lys Lys Leu Met Ser Asn Asn Val
            245          250          255

Gln Ile Val Arg Gln Gln Ser Tyr Ser Ile Met Ser Ile Ile Lys Glu
         260           265           270

Glu Val Leu Ala Tyr Val Val Gln Leu Pro Leu Tyr Gly Val Ile Asp
         275           280           285

Thr Pro Cys Trp Lys Leu His Thr Ser Pro Leu Cys Thr Thr Asn Thr
      290            295          300

Lys Glu Gly Ser Asn Ile Cys Leu Thr Arg Thr Asp Arg Gly Trp Tyr
305               310          315        320

Cys Asp Asn Ala Gly Ser Val Ser Phe Phe Pro Gln Ala Glu Thr Cys
            325          330          335

Lys Val Gln Ser Asn Arg Val Phe Cys Asp Thr Met Asn Ser Leu Thr
         340           345           350

Leu Pro Ser Glu Val Asn Leu Cys Asn Val Asp Ile Phe Asn Pro Lys
         355           360           365

Tyr Asp Cys Lys Ile Met Thr Ser Lys Thr Asp Val Ser Ser Ser Val
      370            375          380

Ile Thr Ser Leu Gly Ala Ile Val Ser Cys Tyr Gly Lys Thr Lys Cys
385               390          395        400

Thr Ala Ser Asn Lys Asn Arg Gly Ile Ile Lys Thr Phe Ser Asn Gly
            405                 410                 415
Cys Asp Tyr Val Ser Asn Lys Gly Val Asp Thr Val Ser Val Gly Asn
        420                 425                 430
Thr Leu Tyr Tyr Val Asn Lys Gln Glu Gly Lys Ser Leu Tyr Val Lys
    435                 440                 445
Gly Glu Pro Ile Ile Asn Phe Tyr Asp Pro Leu Val Phe Pro Ser Asp
450                 455                 460
Gln Phe Asp Ala Ser Ile Ser Gln Val Asn Glu Lys Ile Asn Gln Ser
465                 470                 475                 480
Leu Ala Phe Ile Arg Lys Ser Asp Glu Leu Leu Gly Tyr Ile Pro Glu
                485                 490                 495
Ala Pro Arg Asp Gly Gln Ala Tyr Val Arg Lys Asp Gly Glu Trp Val
            500                 505                 510
Leu Leu Ser Thr Phe Leu Gly Ser Gly Ser His His His His His His
        515                 520                 525
His His Gly Gly Ser Gly Gly Ser Gly Ser Glu Lys Ala Ala Lys Ala
    530                 535                 540
Glu Glu Ala Ala Arg Lys Met Glu Glu Leu Phe Lys Lys His Lys Ile
545                 550                 555                 560
Val Ala Val Leu Arg Ala Asn Ser Val Glu Glu Ala Ile Glu Lys Ala
                565                 570                 575
Val Ala Val Phe Ala Gly Gly Val His Leu Ile Glu Ile Thr Phe Thr
            580                 585                 590
Val Pro Asp Ala Asp Thr Val Ile Lys Ala Leu Ser Val Leu Lys Glu
        595                 600                 605
Lys Gly Ala Ile Ile Gly Ala Gly Thr Val Thr Ser Val Glu Gln Cys
    610                 615                 620
Arg Lys Ala Val Glu Ser Gly Ala Glu Phe Ile Val Ser Pro His Leu
625                 630                 635                 640
Asp Glu Glu Ile Ser Gln Phe Cys Lys Glu Lys Gly Val Phe Tyr Met
                645                 650                 655
Pro Gly Val Met Thr Pro Thr Glu Leu Val Lys Ala Met Lys Leu Gly
            660                 665                 670
His Thr Ile Leu Lys Leu Phe Pro Gly Glu Val Val Gly Pro Gln Phe
        675                 680                 685
Val Lys Ala Met Lys Gly Pro Phe Pro Asn Val Lys Phe Val Pro Thr
    690                 695                 700
Gly Gly Val Asn Leu Asp Asn Val Cys Glu Trp Phe Lys Ala Gly Val
705                 710                 715                 720
Leu Ala Val Gly Val Gly Ser Ala Leu Val Lys Gly Thr Pro Asp Glu
                725                 730                 735
Val Arg Glu Lys Ala Lys Ala Phe Val Glu Lys Ile Arg Gly Cys Thr
            740                 745                 750
Glu

<210> SEQ ID NO 94
<211> LENGTH: 714
<212> TYPE: PRT
<213> ORGANISM: Artificial Sequence
<220> FEATURE:
<223> OTHER INFORMATION: SC-TM (N67I, S215P, and E487Q)-I53-50A - F10
      embodiment
<220> FEATURE:
<221> NAME/KEY: MISC_FEATURE

```
<222> LOCATION: (1)..(25)
<223> OTHER INFORMATION: optionally absent
<220> FEATURE:
<221> NAME/KEY: MISC_FEATURE
<222> LOCATION: (486)..(491)
<223> OTHER INFORMATION: optionally absent

<400> SEQUENCE: 94
```

| | | | | | | | | | | | | | | |
|---|---|---|---|---|---|---|---|---|---|---|---|---|---|---|
| Met | Glu | Leu | Leu | Ile | Leu | Lys | Ala | Asn | Ala | Ile | Thr | Thr | Ile | Leu | Thr |
| 1 | | | | 5 | | | | | 10 | | | | | 15 | |

| Ala | Val | Thr | Phe | Cys | Phe | Ala | Ser | Gly | Gln | Asn | Ile | Thr | Glu | Glu | Phe |
|---|---|---|---|---|---|---|---|---|---|---|---|---|---|---|---|
| | | | 20 | | | | | 25 | | | | | 30 | | |

| Tyr | Gln | Ser | Thr | Cys | Ser | Ala | Val | Ser | Lys | Gly | Tyr | Leu | Ser | Ala | Leu |
|---|---|---|---|---|---|---|---|---|---|---|---|---|---|---|---|
| | | | 35 | | | | | 40 | | | | | 45 | | |

| Arg | Thr | Gly | Trp | Tyr | Thr | Ser | Val | Ile | Thr | Ile | Glu | Leu | Ser | Asn | Ile |
|---|---|---|---|---|---|---|---|---|---|---|---|---|---|---|---|
| | 50 | | | | | 55 | | | | | 60 | | | | |

| Lys | Lys | Ile | Lys | Cys | Asn | Gly | Thr | Asp | Ala | Lys | Ile | Lys | Leu | Ile | Lys |
|---|---|---|---|---|---|---|---|---|---|---|---|---|---|---|---|
| 65 | | | | | 70 | | | | | 75 | | | | | 80 |

| Gln | Glu | Leu | Asp | Lys | Tyr | Lys | Asn | Ala | Val | Thr | Glu | Leu | Gln | Leu | Leu |
|---|---|---|---|---|---|---|---|---|---|---|---|---|---|---|---|
| | | | | 85 | | | | | 90 | | | | | 95 | |

| Met | Gln | Ser | Thr | Pro | Ala | Thr | Asn | Asn | Gln | Ala | Arg | Gly | Ser | Gly | Ser |
|---|---|---|---|---|---|---|---|---|---|---|---|---|---|---|---|
| | | | 100 | | | | | 105 | | | | | 110 | | |

| Gly | Arg | Ser | Leu | Gly | Phe | Leu | Leu | Gly | Val | Gly | Ser | Ala | Ile | Ala | Ser |
|---|---|---|---|---|---|---|---|---|---|---|---|---|---|---|---|
| | | 115 | | | | | 120 | | | | | 125 | | | |

| Gly | Val | Ala | Val | Ser | Lys | Val | Leu | His | Leu | Glu | Gly | Glu | Val | Asn | Lys |
|---|---|---|---|---|---|---|---|---|---|---|---|---|---|---|---|
| | 130 | | | | | 135 | | | | | 140 | | | | |

| Ile | Lys | Ser | Ala | Leu | Leu | Ser | Thr | Asn | Lys | Ala | Val | Val | Ser | Leu | Ser |
|---|---|---|---|---|---|---|---|---|---|---|---|---|---|---|---|
| 145 | | | | | 150 | | | | | 155 | | | | | 160 |

| Asn | Gly | Val | Ser | Val | Leu | Thr | Ser | Lys | Val | Leu | Asp | Leu | Lys | Asn | Tyr |
|---|---|---|---|---|---|---|---|---|---|---|---|---|---|---|---|
| | | | | 165 | | | | | 170 | | | | | 175 | |

| Ile | Asp | Lys | Gln | Leu | Leu | Pro | Ile | Val | Asn | Lys | Gln | Ser | Cys | Ser | Ile |
|---|---|---|---|---|---|---|---|---|---|---|---|---|---|---|---|
| | | | 180 | | | | | 185 | | | | | 190 | | |

| Pro | Asn | Ile | Glu | Thr | Val | Ile | Glu | Phe | Gln | Gln | Lys | Asn | Asn | Arg | Leu |
|---|---|---|---|---|---|---|---|---|---|---|---|---|---|---|---|
| | | 195 | | | | | 200 | | | | | 205 | | | |

| Leu | Glu | Ile | Thr | Arg | Glu | Phe | Ser | Val | Asn | Ala | Gly | Val | Thr | Thr | Pro |
|---|---|---|---|---|---|---|---|---|---|---|---|---|---|---|---|
| | 210 | | | | | 215 | | | | | 220 | | | | |

| Val | Ser | Thr | Tyr | Met | Leu | Thr | Asn | Ser | Glu | Leu | Leu | Ser | Leu | Ile | Asn |
|---|---|---|---|---|---|---|---|---|---|---|---|---|---|---|---|
| 225 | | | | | 230 | | | | | 235 | | | | | 240 |

| Asp | Met | Pro | Ile | Thr | Asn | Asp | Gln | Lys | Lys | Leu | Met | Ser | Asn | Asn | Val |
|---|---|---|---|---|---|---|---|---|---|---|---|---|---|---|---|
| | | | | 245 | | | | | 250 | | | | | 255 | |

| Gln | Ile | Val | Arg | Gln | Gln | Ser | Tyr | Ser | Ile | Met | Ser | Ile | Ile | Lys | Glu |
|---|---|---|---|---|---|---|---|---|---|---|---|---|---|---|---|
| | | | 260 | | | | | 265 | | | | | 270 | | |

| Glu | Val | Leu | Ala | Tyr | Val | Val | Gln | Leu | Pro | Leu | Tyr | Gly | Val | Ile | Asp |
|---|---|---|---|---|---|---|---|---|---|---|---|---|---|---|---|
| | | 275 | | | | | 280 | | | | | 285 | | | |

| Thr | Pro | Cys | Trp | Lys | Leu | His | Thr | Ser | Pro | Leu | Cys | Thr | Thr | Asn | Thr |
|---|---|---|---|---|---|---|---|---|---|---|---|---|---|---|---|
| | 290 | | | | | 295 | | | | | 300 | | | | |

| Lys | Glu | Gly | Ser | Asn | Ile | Cys | Leu | Thr | Arg | Thr | Asp | Arg | Gly | Trp | Tyr |
|---|---|---|---|---|---|---|---|---|---|---|---|---|---|---|---|
| 305 | | | | | 310 | | | | | 315 | | | | | 320 |

| Cys | Asp | Asn | Ala | Gly | Ser | Val | Ser | Phe | Phe | Pro | Gln | Ala | Glu | Thr | Cys |
|---|---|---|---|---|---|---|---|---|---|---|---|---|---|---|---|
| | | | | 325 | | | | | 330 | | | | | 335 | |

| Lys | Val | Gln | Ser | Asn | Arg | Val | Phe | Cys | Asp | Thr | Met | Asn | Ser | Leu | Thr |
|---|---|---|---|---|---|---|---|---|---|---|---|---|---|---|---|
| | | | 340 | | | | | 345 | | | | | 350 | | |

| Leu | Pro | Ser | Glu | Val | Asn | Leu | Cys | Asn | Val | Asp | Ile | Phe | Asn | Pro | Lys |
|---|---|---|---|---|---|---|---|---|---|---|---|---|---|---|---|
| | | 355 | | | | | 360 | | | | | 365 | | | |

| Tyr | Asp | Cys | Lys | Ile | Met | Thr | Ser | Lys | Thr | Asp | Val | Ser | Ser | Ser | Val |

-continued

```
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Gln Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Gly Ser Gly Gly Ser
                485                 490                 495

Gly Ser Gly Glu Lys Ala Ala Lys Ala Glu Glu Ala Ala Arg Lys Met
            500                 505                 510

Glu Glu Leu Phe Lys Lys His Lys Ile Val Ala Val Leu Arg Ala Asn
        515                 520                 525

Ser Val Glu Glu Ala Ile Glu Lys Ala Val Ala Val Phe Ala Gly Gly
    530                 535                 540

Val His Leu Ile Glu Ile Thr Phe Thr Val Pro Asp Ala Asp Thr Val
545                 550                 555                 560

Ile Lys Ala Leu Ser Val Leu Lys Glu Lys Gly Ala Ile Ile Gly Ala
                565                 570                 575

Gly Thr Val Thr Ser Val Glu Gln Cys Arg Lys Ala Val Glu Ser Gly
            580                 585                 590

Ala Glu Phe Ile Val Ser Pro His Leu Asp Glu Glu Ile Ser Gln Phe
        595                 600                 605

Cys Lys Glu Lys Gly Val Phe Tyr Met Pro Gly Val Met Thr Pro Thr
    610                 615                 620

Glu Leu Val Lys Ala Met Lys Leu Gly His Thr Ile Leu Lys Leu Phe
625                 630                 635                 640

Pro Gly Glu Val Val Gly Pro Gln Phe Val Lys Ala Met Lys Gly Pro
                645                 650                 655

Phe Pro Asn Val Lys Phe Val Pro Thr Gly Gly Val Asn Leu Asp Asn
            660                 665                 670

Val Cys Glu Trp Phe Lys Ala Gly Val Leu Ala Val Gly Val Gly Ser
        675                 680                 685

Ala Leu Val Lys Gly Thr Pro Asp Glu Val Arg Glu Lys Ala Lys Ala
    690                 695                 700

Phe Val Glu Lys Ile Arg Gly Cys Thr Glu
705                 710
```

<210> SEQ ID NO 95
<211> LENGTH: 752
<212> TYPE: PRT
<213> ORGANISM: Artificial Sequence
<220> FEATURE:
<223> OTHER INFORMATION: HMPV-F with A113C, A339C, T160F, I177L - foldon-I53-50A embodiment
<220> FEATURE:
<221> NAME/KEY: MISC_FEATURE
<222> LOCATION: (1)..(18)
<223> OTHER INFORMATION: optionally absent

<400> SEQUENCE: 95

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
                20                  25                  30

Glu Gly Tyr Leu Ser Val Leu Arg Thr Gly Trp Tyr Thr Asn Val Phe
            35                  40                  45

Thr Leu Glu Val Gly Asp Val Glu Asn Leu Thr Cys Ser Asp Gly Pro
        50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
                100                 105                 110

Cys Thr Ala Ala Ala Val Thr Ala Gly Val Ala Ile Ala Lys Thr Ile
            115                 120                 125

Arg Leu Glu Ser Glu Val Thr Ala Ile Lys Asn Ala Leu Lys Thr Thr
        130                 135                 140

Asn Glu Ala Val Ser Thr Leu Gly Asn Gly Val Arg Val Leu Ala Phe
145                 150                 155                 160

Ala Val Arg Glu Leu Lys Asp Phe Val Ser Lys Asn Leu Thr Arg Ala
                165                 170                 175

Leu Asn Lys Asn Lys Cys Asp Ile Asp Asp Leu Lys Met Ala Val Ser
                180                 185                 190

Phe Ser Gln Phe Asn Arg Arg Phe Leu Asn Val Val Arg Gln Phe Ser
            195                 200                 205

Asp Asn Ala Gly Ile Thr Pro Ala Ile Ser Leu Asp Leu Met Thr Asp
        210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
                260                 265                 270

Leu Pro Ile Phe Gly Val Ile Asp Thr Pro Cys Trp Ile Val Lys Ala
            275                 280                 285

Ala Pro Ser Cys Ser Gly Lys Lys Gly Asn Tyr Ala Cys Leu Leu Arg
        290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Cys Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415
```

-continued

```
Thr Val Thr Ile Asp Asn Thr Val Tyr Gln Leu Ser Lys Val Gly
            420                 425                 430
Glu Gln His Val Ile Lys Gly Arg Pro Val Ser Ser Phe Asp Pro
        435                 440                 445
Ile Lys Phe Pro Glu Asp Gln Phe Asn Val Ala Leu Asp Gln Val Phe
450                 455                 460
Glu Asn Ile Glu Asn Ser Gln Ala Leu Val Asp Gln Ser Asn Arg Ile
465                 470                 475                 480
Leu Ser Ser Ala Glu Lys Gly Asn Thr Gly Tyr Ile Pro Glu Ala
            485                 490                 495
Pro Arg Asp Gly Gln Ala Tyr Val Arg Lys Asp Gly Glu Trp Val Leu
                500                 505                 510
Leu Ser Thr Phe Leu Gly Ser Gly Ser His His His His His His
            515                 520                 525
His Gly Gly Ser Gly Gly Ser Gly Ser Glu Lys Ala Ala Lys Ala Glu
            530                 535                 540
Glu Ala Ala Arg Lys Met Glu Glu Leu Phe Lys Lys His Lys Ile Val
545                 550                 555                 560
Ala Val Leu Arg Ala Asn Ser Val Glu Ala Ile Glu Lys Ala Val
                565                 570                 575
Ala Val Phe Ala Gly Gly Val His Leu Ile Glu Ile Thr Phe Thr Val
                580                 585                 590
Pro Asp Ala Asp Thr Val Ile Lys Ala Leu Ser Val Leu Lys Glu Lys
                595                 600                 605
Gly Ala Ile Ile Gly Ala Gly Thr Val Thr Ser Val Glu Gln Cys Arg
610                 615                 620
Lys Ala Val Glu Ser Gly Ala Glu Phe Ile Val Ser Pro His Leu Asp
625                 630                 635                 640
Glu Glu Ile Ser Gln Phe Cys Lys Glu Lys Gly Val Phe Tyr Met Pro
                645                 650                 655
Gly Val Met Thr Pro Thr Glu Leu Val Lys Ala Met Lys Leu Gly His
                660                 665                 670
Thr Ile Leu Lys Leu Phe Pro Gly Glu Val Val Gly Pro Gln Phe Val
            675                 680                 685
Lys Ala Met Lys Gly Pro Phe Pro Asn Val Lys Phe Val Pro Thr Gly
690                 695                 700
Gly Val Asn Leu Asp Asn Val Cys Glu Trp Phe Lys Ala Gly Val Leu
705                 710                 715                 720
Ala Val Gly Val Gly Ser Ala Leu Val Lys Gly Thr Pro Asp Glu Val
                725                 730                 735
Arg Glu Lys Ala Lys Ala Phe Val Glu Lys Ile Arg Gly Cys Thr Glu
            740                 745                 750
```

<210> SEQ ID NO 96
<211> LENGTH: 713
<212> TYPE: PRT
<213> ORGANISM: Artificial Sequence
<220> FEATURE:
<223> OTHER INFORMATION: HMPV-F with A113C, A339C, T160F, I177L-I53-50A
      F10 embodiment
<220> FEATURE:
<221> NAME/KEY: MISC_FEATURE
<222> LOCATION: (1)..(18)
<223> OTHER INFORMATION: optionally absent

<400> SEQUENCE: 96

```
Met Ser Trp Lys Val Val Ile Ile Phe Ser Leu Leu Ile Thr Pro Gln
```

-continued

```
1               5                   10                  15
His Gly Leu Lys Glu Ser Tyr Leu Glu Ser Cys Ser Thr Ile Thr
                20                  25                  30
Glu Gly Tyr Leu Ser Val Leu Arg Thr Gly Trp Tyr Thr Asn Val Phe
                35                  40                  45
Thr Leu Glu Val Gly Asp Val Glu Asn Leu Thr Cys Ser Asp Gly Pro
                50                  55                  60
Ser Leu Ile Lys Thr Glu Leu Asp Leu Thr Lys Ser Ala Leu Arg Glu
65                  70                  75                  80
Leu Lys Thr Val Ser Ala Asp Gln Leu Ala Arg Glu Glu Gln Ile Glu
                85                  90                  95
Asn Pro Arg Gln Ser Arg Phe Val Leu Gly Ala Ile Ala Leu Gly Val
                100                 105                 110
Cys Thr Ala Ala Ala Val Thr Ala Gly Val Ala Ile Ala Lys Thr Ile
                115                 120                 125
Arg Leu Glu Ser Glu Val Thr Ala Ile Lys Asn Ala Leu Lys Thr Thr
                130                 135                 140
Asn Glu Ala Val Ser Thr Leu Gly Asn Gly Val Arg Val Leu Ala Phe
145                 150                 155                 160
Ala Val Arg Glu Leu Lys Asp Phe Val Ser Lys Asn Leu Thr Arg Ala
                165                 170                 175
Leu Asn Lys Asn Lys Cys Asp Ile Asp Asp Leu Lys Met Ala Val Ser
                180                 185                 190
Phe Ser Gln Phe Asn Arg Arg Phe Leu Asn Val Val Arg Gln Phe Ser
                195                 200                 205
Asp Asn Ala Gly Ile Thr Pro Ala Ile Ser Leu Asp Leu Met Thr Asp
                210                 215                 220
Ala Glu Leu Ala Arg Ala Val Ser Asn Met Pro Thr Ser Ala Gly Gln
225                 230                 235                 240
Ile Lys Leu Met Leu Glu Asn Arg Ala Met Val Arg Arg Lys Gly Phe
                245                 250                 255
Gly Ile Leu Ile Gly Val Tyr Gly Ser Ser Val Ile Tyr Met Val Gln
                260                 265                 270
Leu Pro Ile Phe Gly Val Ile Asp Thr Pro Cys Trp Ile Val Lys Ala
                275                 280                 285
Ala Pro Ser Cys Ser Gly Lys Lys Gly Asn Tyr Ala Cys Leu Leu Arg
                290                 295                 300
Glu Asp Gln Gly Trp Tyr Cys Gln Asn Ala Gly Ser Thr Val Tyr Tyr
305                 310                 315                 320
Pro Asn Glu Lys Asp Cys Glu Thr Arg Gly Asp His Val Phe Cys Asp
                325                 330                 335
Thr Ala Cys Gly Ile Asn Val Ala Glu Gln Ser Lys Glu Cys Asn Ile
                340                 345                 350
Asn Ile Ser Thr Thr Asn Tyr Pro Cys Lys Val Ser Thr Gly Arg His
                355                 360                 365
Pro Ile Ser Met Val Ala Leu Ser Pro Leu Gly Ala Leu Val Ala Cys
                370                 375                 380
Tyr Lys Gly Val Ser Cys Ser Ile Gly Ser Asn Arg Val Gly Ile Ile
385                 390                 395                 400
Lys Gln Leu Asn Lys Gly Cys Ser Tyr Ile Thr Asn Gln Asp Ala Asp
                405                 410                 415
Thr Val Thr Ile Asp Asn Thr Val Tyr Gln Leu Ser Lys Val Glu Gly
                420                 425                 430
```

```
Glu Gln His Val Ile Lys Gly Arg Pro Val Ser Ser Ser Phe Asp Pro
            435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Ser Gly Gly Ser Gly
                485                 490                 495

Ser Gly Glu Lys Ala Ala Lys Ala Glu Ala Ala Arg Lys Met Glu
                500                 505                 510

Glu Leu Phe Lys Lys His Lys Ile Val Ala Val Leu Arg Ala Asn Ser
            515                 520                 525

Val Glu Glu Ala Ile Glu Lys Ala Val Ala Val Phe Ala Gly Gly Val
        530                 535                 540

His Leu Ile Glu Ile Thr Phe Thr Val Pro Asp Ala Asp Thr Val Ile
545                 550                 555                 560

Lys Ala Leu Ser Val Leu Lys Glu Lys Gly Ala Ile Ile Gly Ala Gly
                565                 570                 575

Thr Val Thr Ser Val Glu Gln Cys Arg Lys Ala Val Glu Ser Gly Ala
                580                 585                 590

Glu Phe Ile Val Ser Pro His Leu Asp Glu Glu Ile Ser Gln Phe Cys
        595                 600                 605

Lys Glu Lys Gly Val Phe Tyr Met Pro Gly Val Met Thr Pro Thr Glu
        610                 615                 620

Leu Val Lys Ala Met Lys Leu Gly His Thr Ile Leu Lys Leu Phe Pro
625                 630                 635                 640

Gly Glu Val Val Gly Pro Gln Phe Val Lys Ala Met Lys Gly Pro Phe
                645                 650                 655

Pro Asn Val Lys Phe Val Pro Thr Gly Gly Val Asn Leu Asp Asn Val
            660                 665                 670

Cys Glu Trp Phe Lys Ala Gly Val Leu Ala Val Gly Val Gly Ser Ala
            675                 680                 685

Leu Val Lys Gly Thr Pro Asp Glu Val Arg Glu Lys Ala Lys Ala Phe
        690                 695                 700

Val Glu Lys Ile Arg Gly Cys Thr Glu
705                 710

<210> SEQ ID NO 97
<211> LENGTH: 752
<212> TYPE: PRT
<213> ORGANISM: Artificial Sequence
<220> FEATURE:
<223> OTHER INFORMATION: HMPV-F with A113C, A120C, A339C, T160F, I177L,
      and Q426C - foldon-I53-50A embodiment
<220> FEATURE:
<221> NAME/KEY: MISC_FEATURE
<222> LOCATION: (1)..(18)
<223> OTHER INFORMATION: optionally absent

<400> SEQUENCE: 97

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45
```

```
Thr Leu Glu Val Gly Asp Val Glu Asn Leu Thr Cys Ser Asp Gly Pro
    50              55                  60

Ser Leu Ile Lys Thr Glu Leu Asp Leu Thr Lys Ser Ala Leu Arg Glu
65              70                  75                      80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Cys Thr Ala Ala Ala Val Thr Cys Gly Val Ala Ile Ala Lys Thr Ile
            115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Phe
145                 150                 155                 160

Ala Val Arg Glu Leu Lys Asp Phe Val Ser Lys Asn Leu Thr Arg Ala
                165                 170                 175

Leu Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
    195                 200                 205

Asp Asn Ala Gly Ile Thr Pro Ala Ile Ser Leu Asp Leu Met Thr Asp
210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
    275                 280                 285

Ala Pro Ser Cys Ser Gly Lys Lys Gly Asn Tyr Ala Cys Leu Leu Arg
290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
            325                 330                 335

Thr Ala Cys Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
    355                 360                 365

Pro Ile Ser Met Val Ala Leu Ser Pro Leu Gly Ala Leu Val Ala Cys
370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Cys Leu Ser Lys Val Glu Gly
            420                 425                 430

Glu Gln His Val Ile Lys Gly Arg Pro Val Ser Ser Ser Phe Asp Pro
    435                 440                 445

Ile Lys Phe Pro Glu Asp Gln Phe Asn Val Ala Leu Asp Gln Val Phe
450                 455                 460

Glu Asn Ile Glu Asn Ser Gln Ala Leu Val Asp Gln Ser Asn Arg Ile
```

```
            465                 470                 475                 480

Leu Ser Ser Ala Glu Lys Gly Asn Thr Gly Gly Tyr Ile Pro Glu Ala
                485                 490                 495

Pro Arg Asp Gly Gln Ala Tyr Val Arg Lys Asp Gly Glu Trp Val Leu
                500                 505                 510

Leu Ser Thr Phe Leu Gly Ser Gly Ser His His His His His His
                515                 520                 525

His Gly Gly Ser Gly Gly Ser Gly Ser Glu Lys Ala Ala Lys Ala Glu
                530                 535                 540

Glu Ala Ala Arg Lys Met Glu Glu Leu Phe Lys Lys His Lys Ile Val
545                 550                 555                 560

Ala Val Leu Arg Ala Asn Ser Val Glu Glu Ala Ile Glu Lys Ala Val
                565                 570                 575

Ala Val Phe Ala Gly Gly Val His Leu Ile Glu Ile Thr Phe Thr Val
                580                 585                 590

Pro Asp Ala Asp Thr Val Ile Lys Ala Leu Ser Val Leu Lys Glu Lys
                595                 600                 605

Gly Ala Ile Ile Gly Ala Gly Thr Val Thr Ser Val Glu Gln Cys Arg
610                 615                 620

Lys Ala Val Glu Ser Gly Ala Glu Phe Ile Val Ser Pro His Leu Asp
625                 630                 635                 640

Glu Glu Ile Ser Gln Phe Cys Lys Glu Lys Gly Val Phe Tyr Met Pro
                645                 650                 655

Gly Val Met Thr Pro Thr Glu Leu Val Lys Ala Met Lys Leu Gly His
                660                 665                 670

Thr Ile Leu Lys Leu Phe Pro Gly Glu Val Val Gly Pro Gln Phe Val
                675                 680                 685

Lys Ala Met Lys Gly Pro Phe Pro Asn Val Lys Phe Val Pro Thr Gly
                690                 695                 700

Gly Val Asn Leu Asp Asn Val Cys Glu Trp Phe Lys Ala Gly Val Leu
705                 710                 715                 720

Ala Val Gly Val Gly Ser Ala Leu Val Lys Gly Thr Pro Asp Glu Val
                725                 730                 735

Arg Glu Lys Ala Lys Ala Phe Val Glu Lys Ile Arg Gly Cys Thr Glu
                740                 745                 750

<210> SEQ ID NO 98
<211> LENGTH: 713
<212> TYPE: PRT
<213> ORGANISM: Artificial Sequence
<220> FEATURE:
<223> OTHER INFORMATION: HMPV-F with A113C, A120C, A339C, T160F, I177L,
      and Q426C - F10 emb -continued Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Cys Thr Ala Ala Ala Val Thr Cys Gly Val Ala Ile Ala Lys Thr Ile
        115                 120                 125

Arg Leu Glu Ser Glu Val Thr Ala Ile Lys Asn Ala Leu Lys Thr Thr
130                 135                 140

Asn Glu Ala Val Ser Thr Leu Gly Asn Gly Val Arg Val Leu Ala Phe
145                 150                 155                 160

Ala Val Arg Glu Leu Lys Asp Phe Val Ser Lys Asn Leu Thr Arg Ala
                165                 170                 175

Leu Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Cys Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Cys Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
450                 455                 460

Glu Asn Ile Glu Asn Ser Gln Ala Leu Val Asp Gln Ser Asn Arg Ile
465                 470                 475                 480

-continued

```
Leu Ser Ser Ala Glu Lys Gly Asn Thr Gly Ser Gly Gly Ser Gly
                485                 490                 495

Ser Gly Glu Lys Ala Ala Lys Ala Glu Glu Ala Ala Arg Lys Met Glu
            500                 505                 510

Glu Leu Phe Lys Lys His Lys Ile Val Ala Val Leu Arg Ala Asn Ser
            515                 520                 525

Val Glu Glu Ala Ile Glu Lys Ala Val Ala Val Phe Ala Gly Gly Val
            530                 535                 540

His Leu Ile Glu Ile Thr Phe Thr Val Pro Asp Ala Asp Thr Val Ile
545                 550                 555                 560

Lys Ala Leu Ser Val Leu Lys Glu Lys Gly Ala Ile Ile Gly Ala Gly
                565                 570                 575

Thr Val Thr Ser Val Glu Gln Cys Arg Lys Ala Val Glu Ser Gly Ala
            580                 585                 590

Glu Phe Ile Val Ser Pro His Leu Asp Glu Glu Ile Ser Gln Phe Cys
            595                 600                 605

Lys Glu Lys Gly Val Phe Tyr Met Pro Gly Val Met Thr Pro Thr Glu
            610                 615                 620

Leu Val Lys Ala Met Lys Leu Gly His Thr Ile Leu Lys Leu Phe Pro
625                 630                 635                 640

Gly Glu Val Val Gly Pro Gln Phe Val Lys Ala Met Lys Gly Pro Phe
                645                 650                 655

Pro Asn Val Lys Phe Val Pro Thr Gly Gly Val Asn Leu Asp Asn Val
            660                 665                 670

Cys Glu Trp Phe Lys Ala Gly Val Leu Ala Val Gly Val Gly Ser Ala
            675                 680                 685

Leu Val Lys Gly Thr Pro Asp Glu Val Arg Glu Lys Ala Lys Ala Phe
            690                 695                 700

Val Glu Lys Ile Arg Gly Cys Thr Glu
705                 710

<210> SEQ ID NO 99
<211> LENGTH: 751
<212> TYPE: PRT
<213> ORGANISM: Artificial Sequence
<220> FEATURE:
<223> OTHER INFORMATION: HMPV-F 115-BV (A185P)-foldon-I53-50A
      embodiment
<220> FEATURE:
<221> NAME/KEY: MISC_FEATURE
<222> LOCATION: (1)..(18)
<223> OTHER INFORMATION: optionally absent

<400> SEQUENCE: 99

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
                20                  25                  30

Glu Gly Tyr Leu Ser Val Leu Arg Thr Gly Trp Tyr Thr Asn Val Phe
            35                  40                  45

Thr Leu Glu Val Gly Asp Val Glu Asn Leu Thr Cys Ala Asp Gly Pro
        50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Arg Arg Arg Phe Val Leu Gly Ala Ile Ala Leu Gly Val
```

```
            100                 105                 110
Ala Thr Ala Ala Val Thr Ala Gly Val Ala Ile Ala Lys Thr Ile
            115                 120                 125
Arg Leu Glu Ser Glu Val Thr Ala Ile Lys Asn Ala Leu Lys Lys Thr
            130                 135             140
Asn Glu Ala Val Ser Thr Leu Gly Asn Gly Val Arg Val Leu Ala Thr
145                 150                 155                 160
Ala Val Arg Glu Leu Lys Asp Phe Val Ser Lys Asn Leu Thr Arg Ala
                165                 170                 175
Ile Asn Lys Asn Lys Cys Asp Ile Pro Asp Leu Lys Met Ala Val Ser
                180                 185                 190
Phe Ser Gln Phe Asn Arg Arg Phe Leu Asn Val Val Arg Gln Phe Ser
                195                 200                 205
Asp Asn Ala Gly Ile Thr Pro Ala Ile Ser Leu Asp Leu Met Thr Asp
            210                 215                 220
Ala Glu Leu Ala Arg Ala Val Ser Asn Met Pro Thr Ser Ala Gly Gln
225                 230                 235                 240
Ile Lys Leu Met Leu Glu Asn Arg Ala Met Val Arg Arg Lys Gly Phe
                245                 250                 255
Gly Ile Leu Ile Gly Val Tyr Gly Ser Ser Val Ile Tyr Met Val Gln
                260                 265                 270
Leu Pro Ile Phe Gly Val Ile Asp Thr Pro Cys Trp Ile Val Lys Ala
                275                 280                 285
Ala Pro Ser Cys Ser Glu Lys Lys Gly Asn Tyr Ala Cys Leu Leu Arg
            290                 295                 300
Glu Asp Gln Gly Trp Tyr Cys Gln Asn Ala Gly Ser Thr Val Tyr Tyr
305                 310                 315                 320
Pro Asn Glu Lys Asp Cys Glu Thr Arg Gly Asp His Val Phe Cys Asp
                325                 330                 335
Thr Ala Ala Gly Ile Asn Val Ala Glu Gln Ser Lys Glu Cys Asn Ile
                340                 345                 350
Asn Ile Ser Thr Thr Asn Tyr Pro Cys Lys Val Ser Thr Gly Arg His
            355                 360                 365
Pro Ile Ser Met Val Ala Leu Ser Pro Leu Gly Ala Leu Val Ala Cys
            370                 375                 380
Tyr Lys Gly Val Ser Cys Ser Ile Gly Ser Asn Arg Val Gly Ile Ile
385                 390                 395                 400
Lys Gln Leu Asn Lys Gly Cys Ser Tyr Ile Thr Asn Gln Asp Ala Asp
                405                 410                 415
Thr Val Thr Ile Asp Asn Thr Val Tyr Gln Leu Ser Lys Val Glu Gly
                420                 425                 430
Glu Gln His Val Ile Lys Gly Arg Pro Val Ser Ser Phe Asp Pro
            435                 440                 445
Val Lys Phe Pro Glu Asp Gln Phe Asn Val Ala Leu Asp Gln Val Phe
            450                 455                 460
Glu Ser Ile Glu Asn Ser Gln Ala Leu Val Asp Gln Ser Asn Arg Ile
465                 470                 475                 480
Leu Ser Ser Ala Glu Lys Gly Asn Thr Gly Tyr Ile Pro Glu Ala Pro
                485                 490                 495
Arg Asp Gly Gln Ala Tyr Val Arg Lys Asp Gly Glu Trp Val Leu Leu
            500                 505                 510
Ser Thr Phe Leu Gly Ser Gly Ser His His His His His His
            515                 520                 525
```

Gly Gly Ser Gly Gly Ser Gly Ser Glu Lys Ala Ala Lys Ala Glu
            530                 535                 540

Ala Ala Arg Lys Met Glu Glu Leu Phe Lys Lys His Lys Ile Val Ala
545                 550                 555                 560

Val Leu Arg Ala Asn Ser Val Glu Glu Ala Ile Glu Lys Ala Val Ala
                565                 570                 575

Val Phe Ala Gly Gly Val His Leu Ile Glu Ile Thr Phe Thr Val Pro
            580                 585                 590

Asp Ala Asp Thr Val Ile Lys Ala Leu Ser Val Leu Lys Glu Lys Gly
                595                 600                 605

Ala Ile Ile Gly Ala Gly Thr Val Thr Ser Val Glu Gln Cys Arg Lys
            610                 615                 620

Ala Val Glu Ser Gly Ala Glu Phe Ile Val Ser Pro His Leu Asp Glu
625                 630                 635                 640

Glu Ile Ser Gln Phe Cys Lys Glu Lys Gly Val Phe Tyr Met Pro Gly
                645                 650                 655

Val Met Thr Pro Thr Glu Leu Val Lys Ala Met Lys Leu Gly His Thr
            660                 665                 670

Ile Leu Lys Leu Phe Pro Gly Glu Val Val Gly Pro Gln Phe Val Lys
                675                 680                 685

Ala Met Lys Gly Pro Phe Pro Asn Val Lys Phe Val Pro Thr Gly Gly
            690                 695                 700

Val Asn Leu Asp Asn Val Cys Glu Trp Phe Lys Ala Gly Val Leu Ala
705                 710                 715                 720

Val Gly Val Gly Ser Ala Leu Val Lys Gly Thr Pro Asp Glu Val Arg
                725                 730                 735

Glu Lys Ala Lys Ala Phe Val Glu Lys Ile Arg Gly Cys Thr Glu
            740                 745                 750

<210> SEQ ID NO 100
<211> LENGTH: 712
<212> TYPE: PRT
<213> ORGANISM: Artificial Sequence
<220> FEATURE:
<223> OTHER INFORMATION: HMPV-F 115-BV (A185P)-I53-50A - F10 embodiment
<220> FEATURE:
<221> NAME/KEY: MISC_FEATURE
<222> LOCATION: (1)..(18)
<223> OTHER INFORMATION: optionally absent

<400> SEQUENCE: 100

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
                20                  25                  30

Glu Gly Tyr Leu Ser Val Leu Arg Thr Gly Trp Tyr Thr Asn Val Phe
            35                  40                  45

Thr Leu Glu Val Gly Asp Val Glu Asn Leu Thr Cys Ala Asp Gly Pro
        50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Arg Arg Arg Phe Val Leu Gly Ala Ile Ala Leu Gly Val
            100                 105                 110

Ala Thr Ala Ala Ala Val Thr Ala Gly Val Ala Ile Ala Lys Thr Ile

```
            115                 120                 125
Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Pro Asp Leu Lys Met Ala Val Ser
                180                 185                 190

Phe Ser Gln Phe Asn Arg Arg Phe Leu Asn Val Val Arg Gln Phe Ser
                195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
                260                 265                 270

Leu Pro Ile Phe Gly Val Ile Asp Thr Pro Cys Trp Ile Val Lys Ala
                275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
                340                 345                 350

Asn Ile Ser Thr Thr Asn Tyr Pro Cys Lys Val Ser Thr Gly Arg His
                355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
                420                 425                 430

Glu Gln His Val Ile Lys Gly Arg Pro Val Ser Ser Ser Phe Asp Pro
                435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Ser Gly Ser Gly Ser Gly
                485                 490                 495

Gly Glu Lys Ala Ala Lys Ala Glu Glu Ala Ala Arg Lys Met Glu Glu
                500                 505                 510

Leu Phe Lys Lys His Lys Ile Val Ala Val Leu Arg Ala Asn Ser Val
                515                 520                 525

Glu Glu Ala Ile Glu Lys Ala Val Ala Val Phe Ala Gly Gly Val His
    530                 535                 540
```

```
Leu Ile Glu Ile Thr Phe Thr Val Pro Asp Ala Asp Thr Val Ile Lys
545                 550                 555                 560

Ala Leu Ser Val Leu Lys Glu Lys Gly Ala Ile Ile Gly Ala Gly Thr
                565                 570                 575

Val Thr Ser Val Glu Gln Cys Arg Lys Ala Val Glu Ser Gly Ala Glu
            580                 585                 590

Phe Ile Val Ser Pro His Leu Asp Glu Glu Ile Ser Gln Phe Cys Lys
        595                 600                 605

Glu Lys Gly Val Phe Tyr Met Pro Gly Val Met Thr Pro Thr Glu Leu
    610                 615                 620

Val Lys Ala Met Lys Leu Gly His Thr Ile Leu Lys Leu Phe Pro Gly
625                 630                 635                 640

Glu Val Val Gly Pro Gln Phe Val Lys Ala Met Lys Gly Pro Phe Pro
                645                 650                 655

Asn Val Lys Phe Val Pro Thr Gly Gly Val Asn Leu Asp Asn Val Cys
            660                 665                 670

Glu Trp Phe Lys Ala Gly Val Leu Ala Val Gly Val Gly Ser Ala Leu
        675                 680                 685

Val Lys Gly Thr Pro Asp Glu Val Arg Glu Lys Ala Lys Ala Phe Val
    690                 695                 700

Glu Lys Ile Arg Gly Cys Thr Glu
705                 710

<210> SEQ ID NO 101
<211> LENGTH: 490
<212> TYPE: PRT
<213> ORGANISM: Artificial Sequence
<220> FEATURE:
<223> OTHER INFORMATION: HMPV F >AAK62968.2 fusion protein [Human
      metapneumovirus]
<220> FEATURE:
<221> NAME/KEY: MISC_FEATURE
<222> LOCATION: (1)..(18)
<223> OTHER INFORMATION: optionally absent

<400> SEQUENCE: 101

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160
```

-continued

```
Ala Val Arg Glu Leu Lys Asp Phe Val Ser Lys Asn Leu Thr Arg Ala
            165                 170                 175
Ile Asn Lys Asn Lys Cys Asp Ile Ala Asp Leu Lys Met Ala Val Ser
            180                 185                 190
Phe Ser Gln Phe Asn Arg Arg Phe Leu Asn Val Val Arg Gln Phe Ser
            195                 200                 205
Asp Asn Ala Gly Ile Thr Pro Ala Ile Ser Leu Asp Leu Met Thr Asp
            210                 215                 220
Ala Glu Leu Ala Arg Ala Val Ser Asn Met Pro Thr Ser Ala Gly Gln
225                 230                 235                 240
Ile Lys Leu Met Leu Glu Asn Arg Ala Met Val Arg Arg Lys Gly Phe
                    245                 250                 255
Gly Phe Leu Ile Gly Val Tyr Gly Ser Ser Val Ile Tyr Met Val Gln
                    260                 265                 270
Leu Pro Ile Phe Gly Val Ile Asp Thr Pro Cys Trp Ile Val Lys Ala
                275                 280                 285
Ala Pro Ser Cys Ser Gly Lys Lys Gly Asn Tyr Ala Cys Leu Leu Arg
290                 295                 300
Glu Asp Gln Gly Trp Tyr Cys Gln Asn Ala Gly Ser Thr Val Tyr Tyr
305                 310                 315                 320
Pro Asn Glu Lys Asp Cys Glu Thr Arg Gly Asp His Val Phe Cys Asp
                325                 330                 335
Thr Ala Ala Gly Ile Asn Val Ala Glu Gln Ser Lys Glu Cys Asn Ile
                340                 345                 350
Asn Ile Ser Thr Thr Asn Tyr Pro Cys Lys Val Ser Thr Gly Arg His
                355                 360                 365
Pro Ile Ser Met Val Ala Leu Ser Pro Leu Gly Ala Leu Val Ala Cys
                370                 375                 380
Tyr Lys Gly Val Ser Cys Ser Ile Gly Ser Asn Arg Val Gly Ile Ile
385                 390                 395                 400
Lys Gln Leu Asn Lys Gly Cys Ser Tyr Ile Thr Asn Gln Asp Ala Asp
                405                 410                 415
Thr Val Thr Ile Asp Asn Thr Val Tyr Gln Leu Ser Lys Val Glu Gly
                420                 425                 430
Glu Gln His Val Ile Lys Gly Arg Pro Val Ser Ser Ser Phe Asp Pro
            435                 440                 445
Val Lys Phe Pro Glu Asp Gln Phe Asn Val Ala Leu Asp Gln Val Phe
        450                 455                 460
Glu Ser Ile Glu Asn Ser Gln Ala Leu Val Asp Gln Ser Asn Arg Ile
465                 470                 475                 480
Leu Ser Ser Ala Glu Lys Gly Asn Thr Gly
                485                 490
```